(12) United States Patent
Smith et al.

(10) Patent No.: US 11,891,514 B2
(45) Date of Patent: *Feb. 6, 2024

(54) COMPOSITE MATERIAL, AND METHODS FOR PRODUCTION THEREOF

(71) Applicant: Bolt Threads, Inc., Emeryville, CA (US)

(72) Inventors: Matthew Jordan Smith, Emeryville, CA (US); Julian Goldman, Oakland, CA (US); Maxime Boulet-Audet, El Cerrito, CA (US); Steven Joseph Tom, El Cerrito, CA (US); Hua Li, Davis, CA (US); Tyler John Hurlburt, Oakland, CA (US)

(73) Assignee: BOLT THREADS, INC., Emeryville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/226,861

(22) Filed: Apr. 9, 2021

(65) Prior Publication Data

US 2021/0292706 A1  Sep. 23, 2021

Related U.S. Application Data

(63) Continuation of application No. 16/943,581, filed on Jul. 30, 2020, now Pat. No. 11,015,059, which is a continuation of application No. PCT/US2020/034354, filed on May 22, 2020.

(60) Provisional application No. 63/024,368, filed on May 13, 2020, provisional application No. 62/851,867, filed on May 23, 2019.

(51) Int. Cl.
| | |
|---|---|
| C08L 89/00 | (2006.01) |
| C08L 33/06 | (2006.01) |
| C08L 23/08 | (2006.01) |
| C08L 31/04 | (2006.01) |
| C08J 5/04 | (2006.01) |
| C08J 5/10 | (2006.01) |
| C12N 1/14 | (2006.01) |
| C08J 5/24 | (2006.01) |

(52) U.S. Cl.
CPC .............. *C08L 89/00* (2013.01); *C08J 5/045* (2013.01); *C08J 5/046* (2013.01); *C08J 5/10* (2013.01); *C08J 5/245* (2021.05); *C08J 5/249* (2021.05); *C08L 23/0853* (2013.01); *C08L 31/04* (2013.01); *C08L 33/062* (2013.01); *C12N 1/14* (2013.01); *C08J 2323/08* (2013.01); *C08J 2331/04* (2013.01); *C08J 2333/06* (2013.01); *C08J 2389/00* (2013.01); *C08J 2399/00* (2013.01); *C08J 2423/08* (2013.01); *C08J 2431/04* (2013.01); *C08J 2433/06* (2013.01); *C08J 2489/00* (2013.01); *C08L 2205/03* (2013.01); *C08L 2205/06* (2013.01); *C08L 2207/322* (2013.01)

(58) Field of Classification Search
CPC ........ C08L 31/04; C08L 33/062; C08L 89/00; C08J 5/24

See application file for complete search history.

(56) References Cited

U.S. PATENT DOCUMENTS

| | | |
|---|---|---|
| 2,850,841 A | 9/1958 | Szuecs |
| 3,034,927 A | 5/1962 | Fairclough et al. |
| 3,616,246 A | 10/1971 | Cherry |
| 4,018,647 A | 4/1977 | Wietsma |
| 4,939,016 A | 7/1990 | Radwanski et al. |
| 4,960,413 A | 10/1990 | Sagar et al. |
| 5,854,056 A | 12/1998 | Dschida |
| 6,942,711 B2 | 9/2005 | Faulkner et al. |
| 7,132,024 B2 | 11/2006 | Wang et al. |
| 7,708,214 B2 | 5/2010 | Medoff |
| 7,951,388 B2 | 5/2011 | Stamets |
| 7,971,809 B2 | 7/2011 | Medoff |
| 8,001,719 B2 | 8/2011 | Bayer et al. |
| 8,074,910 B2 | 12/2011 | Medoff |
| 8,202,379 B1 | 6/2012 | DeLong et al. |
| 8,227,224 B2 | 7/2012 | Kalisz et al. |
| 8,227,225 B2 | 7/2012 | Rocco et al. |
| 8,227,233 B2 | 7/2012 | Kalisz et al. |
| 8,283,153 B2 | 10/2012 | Rocco et al. |
| 8,298,809 B2 | 10/2012 | Kalisz et al. |
| 8,298,810 B2 | 10/2012 | Rocco et al. |

(Continued)

FOREIGN PATENT DOCUMENTS

| | | |
|---|---|---|
| AU | 2013251269 B2 | 10/2015 |
| AU | 2015271910 B2 | 9/2019 |

(Continued)

OTHER PUBLICATIONS

Haneef, M., et al., "Advanced Materials From Funcal Mycelium: Fabrication and Tuning of Physical Properties", Scientific Reports, Jan. 24, 2017, vol. 7, Article No. 41292, pp. 1-11.
International Preliminary Report on Patentability for PCT/US2019/061500, dated May 18, 2021, 10 pages.
Haverhals et al., "Natural fiber welding." Macromolecular Materials and Engineering 295, No. 5 (2010): 425-430.
Haverhals et al., "Process variables that control natural fiber welding: time, temperature, and amount of ionic liquid." Cellulose 19, No. 1 (2012): 13-22.
Suskind, "Man-Made Leather Substrates: I0. Nonwoven Assemblies." Journal of Coated Fibrous Materials 2, No. 4 (1973): 187-195.
Hole et al., "Structure and properties of natural and artificial leathers." Journal of materials science 6, No. 1 (1971): 1-15.

(Continued)

*Primary Examiner* — Edward J Cain
(74) *Attorney, Agent, or Firm* — MARSHALL, GERSTEIN & BORUN LLP

(57) ABSTRACT

Provided herein are mycelium materials and methods for production thereof. In some embodiments, a mycelium material includes: a cultivated mycelium material including one or more masses of branching hyphae, wherein the one or more masses of branching hyphae may be disrupted or pressed and/or a bonding agent may be combined with the cultivated mycelium material. Methods of producing a mycelium material are also provided.

23 Claims, 62 Drawing Sheets

(56) References Cited

U.S. PATENT DOCUMENTS

| | | | |
|---|---|---|---|
| 8,313,939 B2 | 11/2012 | Kalisz et al. |
| 8,544,773 B2 | 10/2013 | Medoff |
| 8,562,731 B2 | 10/2013 | Yang et al. |
| 8,757,525 B2 | 6/2014 | Medoff |
| 8,999,667 B2 | 4/2015 | Otte et al. |
| 8,999,687 B2 | 4/2015 | Bayer et al. |
| 9,085,763 B2 | 7/2015 | Winiski et al. |
| 9,253,889 B2 | 2/2016 | Bayer et al. |
| 9,303,357 B2 | 4/2016 | Clark et al. |
| 9,332,779 B2 | 5/2016 | Marga |
| 9,394,512 B2 | 7/2016 | Bayer et al. |
| 9,410,116 B2 | 8/2016 | Ross |
| 9,469,838 B2 | 10/2016 | Schaak et al. |
| 9,485,917 B2 | 11/2016 | Bayer et al. |
| 9,555,395 B2 | 1/2017 | Araldi et al. |
| 9,617,685 B2 | 4/2017 | Clark et al. |
| 9,714,180 B2 | 7/2017 | McIntyre et al. |
| 9,745,223 B2 | 8/2017 | Hojaji |
| 9,867,337 B2 | 1/2018 | Babcock et al. |
| 9,879,219 B2 | 1/2018 | McIntyre et al. |
| 9,914,906 B2 | 3/2018 | Winiski et al. |
| 9,951,307 B2 | 4/2018 | Ross |
| 10,011,931 B2 | 7/2018 | Haverhals et al. |
| 10,125,347 B2 | 11/2018 | Winiski |
| 10,138,595 B1 | 11/2018 | Tymon |
| 10,144,149 B2 | 12/2018 | McIntyre et al. |
| 10,154,627 B2 | 12/2018 | McIntyre et al. |
| 10,266,695 B2 | 4/2019 | Lucht et al. |
| 10,301,440 B2 | 5/2019 | Purcell et al. |
| 10,400,061 B1 | 9/2019 | Amstutz et al. |
| 10,407,675 B2 | 9/2019 | Bayer et al. |
| 10,525,662 B2 | 1/2020 | Bayer et al. |
| 10,537,070 B2 | 1/2020 | Betts et al. |
| 10,583,626 B2 | 3/2020 | Bayer et al. |
| 10,589,489 B2 | 3/2020 | Bayer et al. |
| 10,687,482 B2 | 6/2020 | Ross et al. |
| 10,842,089 B2 | 11/2020 | Ross et al. |
| 10,947,496 B2 | 3/2021 | Ross |
| 11,013,189 B2 | 5/2021 | Ross et al. |
| 11,015,059 B2 * | 5/2021 | Smith ............... C08L 31/04 |
| 11,032,982 B2 | 6/2021 | Ross et al. |
| 2004/0263598 A1 | 12/2004 | Watanabe |
| 2011/0266831 A1 | 11/2011 | Kalisz et al. |
| 2011/0268980 A1 | 11/2011 | Kalisz et al. |
| 2012/0148995 A1 | 6/2012 | Cheung et al. |
| 2012/0225471 A1 | 9/2012 | McIntyre et al. |
| 2013/0095560 A1 | 4/2013 | McIntyre et al. |
| 2013/0309755 A1 | 11/2013 | McIntyre et al. |
| 2014/0031810 A1 | 1/2014 | Mahvi et al. |
| 2014/0056653 A1 | 2/2014 | Scully et al. |
| 2014/0186927 A1 | 7/2014 | Winiski et al. |
| 2015/0033620 A1 | 2/2015 | Greetham et al. |
| 2015/0038619 A1 | 2/2015 | McIntyre et al. |
| 2015/0101509 A1 | 4/2015 | McIntyre et al. |
| 2016/0168563 A1 | 6/2016 | Kojoh et al. |
| 2017/0190850 A1 | 7/2017 | Haverhals et al. |
| 2017/0233537 A1 | 8/2017 | Purcell et al. |
| 2017/0253852 A1 | 9/2017 | Bayer et al. |
| 2018/0146627 A1 | 5/2018 | Ross et al. |
| 2018/0148682 A1 | 5/2018 | Ross |
| 2018/0282529 A1 | 10/2018 | Kaplan-Bie |
| 2018/0339428 A1 | 11/2018 | Medoff |
| 2018/0368337 A1 | 12/2018 | McIntyre et al. |
| 2019/0024303 A1 | 1/2019 | Lee et al. |
| 2019/0055675 A1 | 2/2019 | Haverhals et al. |
| 2019/0099474 A1 | 4/2019 | Jung et al. |
| 2019/0144957 A1 | 5/2019 | Purcell et al. |
| 2019/0284307 A1 | 9/2019 | Chase et al. |
| 2019/0322799 A1 | 10/2019 | Amstutz et al. |
| 2019/0322997 A1 | 10/2019 | Schaak |
| 2019/0338240 A1 | 11/2019 | Carlton et al. |
| 2019/0357454 A1 | 11/2019 | Mueller et al. |
| 2019/0358913 A1 | 11/2019 | Haverhals et al. |
| 2019/0359931 A1 | 11/2019 | Mueller et al. |
| 2019/0390156 A1 | 12/2019 | Bayer et al. |
| 2019/0390399 A1 | 12/2019 | Chase et al. |
| 2020/0024577 A1 | 1/2020 | Carlton et al. |
| 2020/0025672 A1 | 1/2020 | Scullin et al. |
| 2020/0055274 A1 | 2/2020 | Bayer et al. |
| 2020/0102530 A1 | 4/2020 | Winiski et al. |
| 2020/0120880 A1 | 4/2020 | Ross et al. |
| 2020/0128763 A1 | 4/2020 | Ross |
| 2020/0131694 A1 | 4/2020 | Scullin et al. |
| 2020/0146224 A1 | 5/2020 | Kaplan-Bie et al. |
| 2020/0157506 A1 | 5/2020 | Bayer et al. |
| 2020/0173063 A1 | 6/2020 | Haverhals et al. |
| 2020/0196541 A1 | 6/2020 | Ross et al. |
| 2020/0208097 A1 | 7/2020 | Winiski |
| 2020/0231805 A1 | 7/2020 | Teglia et al. |
| 2020/0239830 A1 | 7/2020 | O'Brien et al. |

FOREIGN PATENT DOCUMENTS

| | | |
|---|---|---|
| AU | 2015271912 B2 | 2/2020 |
| AU | 2018229517 B2 | 8/2020 |
| CA | 2915182 A1 | 6/2017 |
| CA | 2915179 C | 3/2020 |
| CN | 102329512 A | 1/2012 |
| EP | 2831291 A1 | 2/2015 |
| EP | 3205754 A1 | 8/2017 |
| EP | 3215670 A1 | 9/2017 |
| EP | 3215670 B1 | 9/2017 |
| EP | 3709791 A1 | 9/2020 |
| GB | 2148959 A | 6/1985 |
| GB | 2165865 A | 4/1986 |
| HK | 262244 B | 11/2010 |
| IN | 2009MN01111 | 11/2010 |
| KR | 102045830 B1 | 11/2019 |
| WO | 1999/024555 A2 | 5/1999 |
| WO | 2006/102543 A2 | 9/2006 |
| WO | 2007/146922 A2 | 12/2007 |
| WO | 2010/138514 A2 | 12/2010 |
| WO | 2012/148995 A1 | 11/2012 |
| WO | 2013/149083 A1 | 10/2013 |
| WO | 2013/161939 A1 | 10/2013 |
| WO | 2014/031810 A3 | 4/2014 |
| WO | 2016/073453 A1 | 5/2016 |
| WO | 2016/168563 A1 | 10/2016 |
| WO | 2017/132523 A1 | 8/2017 |
| WO | 2018/068455 A1 | 4/2018 |
| WO | 2018/068456 A1 | 4/2018 |
| WO | 2019/094971 A1 | 5/2019 |
| WO | 2019/099474 A1 | 5/2019 |
| WO | 2019246636 A9 | 12/2019 |
| WO | 2020/018516 A1 | 1/2020 |
| WO | 2020072140 A1 | 4/2020 |
| WO | 2020082043 A1 | 4/2020 |
| WO | 2020/102552 A1 | 5/2020 |
| WO | 2020186068 A1 | 9/2020 |
| WO | 2021092051 A1 | 5/2021 |

OTHER PUBLICATIONS

Katsumi, "Leather Like Materials." Kirk-Othmer Encyclopedia of Chemical Technology (2000), 15 pages.
Yu, "The mechanical properties of leather in relation to softness." Thesis submitted for degree of Doctor of Philosophy, University of Leicester, May 1999, 217 pages.
Backer et al., "Some principles of nonwoven fabrics1." Textile Research Journal 30, No. 9 (1960): 704-711.
Lamb et al., "Properties and potential applications of nonwoven crepe fabrics." Textile Research Journal 45, No. 10 (1975): 722-728.
Liu et al., "Physical property studies for leather lubricated with various types of fatliquors." Journal of the American Leather Chemists Association 97, No. 11 (2002): 431-440.
Termonia, "Lattice model for the drape and bending properties of nonwoven fabrics." Textile research journal 73, No. 1 (2003): 74-78.
Fan et al., Engineering apparel fabrics and garments, Chapter 7—Garment Drape, Elsevier, 2009, pp. 115-134.

(56) References Cited

OTHER PUBLICATIONS

Kocik et al., "Evaluating the bending rigidity of flat textiles with the use of an Instron tensile tester." Fibres & Textiles in Eastern Europe 2 (50) (2005): 31-34.
Tao et al., "Carding kenaf for nonwovens." Textile research journal 68, No. 6 (1998): 402-406.
Adams, "Test Methods for Composites," Sampe Long Beach 2016 Conference, Long Beach CA, Adams, Donald F., speaker, Wyoming Test Fixtures, Inc., May 23, 2016, 100 pages.
Albrecht et al., eds. Nonwoven fabrics: raw materials, manufacture, applications, characteristics, testing processes. WILEY-VCH Verlag GmbH & Co. KGaA, Weinheim, 2003.
Das et al., eds., Composite nonwoven materials: structure, properties and applications. Woodhead Publishing Limited, 2014, 253 pages.
Platt, Biodegradable polymers: market report. Smithers Rapra Limited, 2006, 170 pages.
Biopreferred, "Understanding Biobased Content," U.S. Department of Agriculture, 2017, 6 pages.
Nen, Bio-based content certification scheme, NCS 16785 (en), Nov. 2016, 32 pages.
Society of the Plastics Industry Bioplastics Council, "Life Cycle Analysis Primer What, Why and How," Feb. 2012, 9 pages.
Stevens et al., "How green are green plastics?." Biocycle 43, No. 12 (2002): 42-45.
Boethling et al., "Designing small molecules for biodegradability." Chemical reviews 107, No. 6 (2007): 2207-2227.
Din Certco, Certification Scheme, Biobased Product, Nov. 2019, 20 pages.
ASTM International, "Standard Specification for Labeling of Plastics Designed to be Aerobically Composted in Municipal or Industrial Facilities," D6400-19, Mar. 23, 2020, pp. 1-3.
Afirm Group, Restricted Substances List, Version 05, 2020, 38 pages.
Balada et al., "Whey protein isolate: A potential filler for the leather industry." (2009), pp. 122-130.
Taylor et al., "Effect of fillers prepared from enzymatically modified proteins on mechanical properties of leather." (2008), pp. 128-137.
Qian, "Development of a New Non-woven Composite and its Properties." Textile Research Journal 77, No. 6 (2007): 397-402.
PCT/US19/61500—International Search Report and Written Opionion, dated Apr. 14, 2020.
PCT/US20/34354—Invitation to Pay Additional Fees, dated Aug. 7, 2020, 2 pages.
PCT/US2020/034354—International Search Report and Wirtten Opinion, dated Oct. 6, 2020, 11 pages.
Appels et al., Fabrication factors influencing mechanical, moisture- and water-related properties of mycelium-based composites, Materials and Design, 161:64-71 (2019).
European Patent Application No. 20809724.6, Extended European Search Report, dated May 9, 2023.
European Patent Application No. 20809724.6, Third Party Observations against EP3973055 (Bolt Threads, Inc.), submitted Apr. 9, 2023.
Harris, Hyphal branching in filamentous fungi, Dev. Biol., 451(1):35-39 (2019).
He et al., Study on the mechanical properties of the latex-mycelium composite, Applied Mechanics and Materials, 507:415-20 (2014).
Lee et al., A Review on Citric Acid as Green Modifying Agent and Binder for Wood, Polymers, 12(8):1692 (2020).
Shi et al., Evaluation of biodegradable films made of waste mycelium and poly (vinyl alcohol) on the yield of Pak-Choi, J. Polym. Environ., 20:492-500 (2012).
Canadian Patent Application No. 3137693, Office Action, dated Aug. 3, 2023.
Indonesian Office Action corresponding to Indonesian Patent Application No. P00202111889 dated Jun. 26, 2023.
Chinese Patent Application No. 2020800376776, Office Action and Search Report dated Dec. 1, 2023.

\* cited by examiner

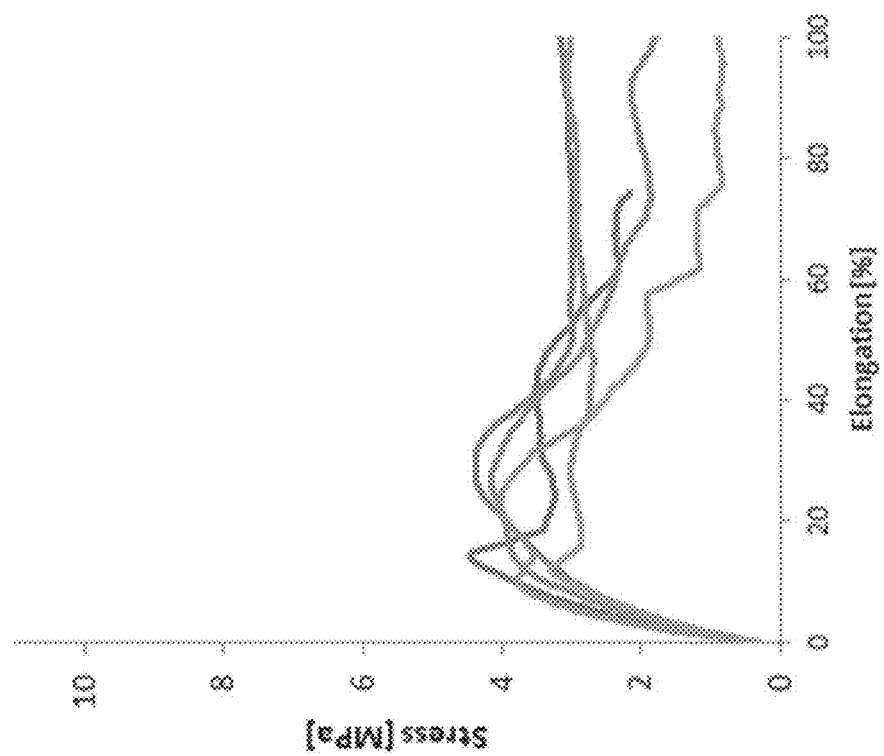
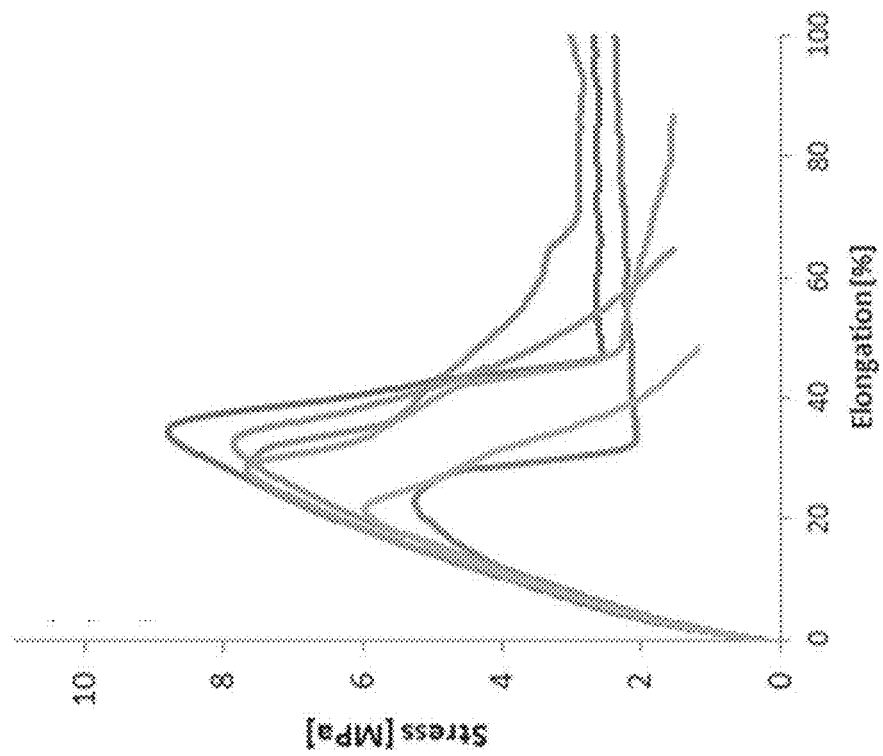
FIG. 12A
FIG. 12B

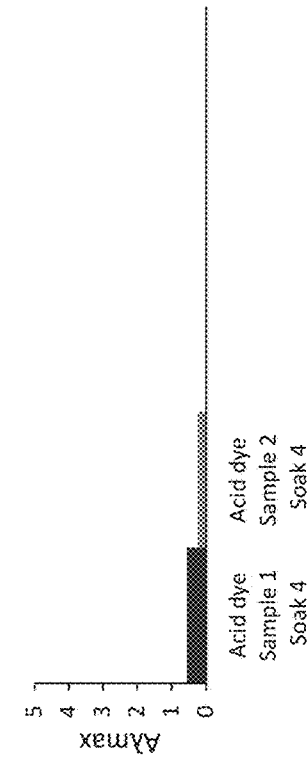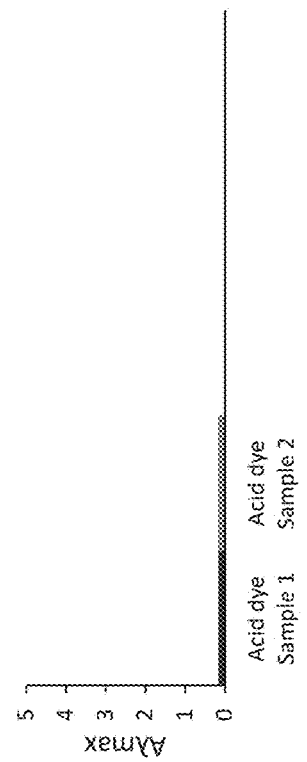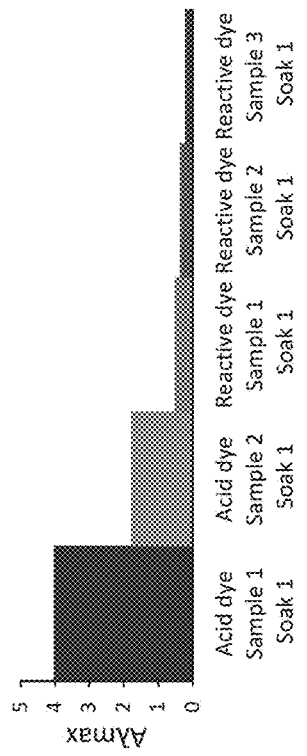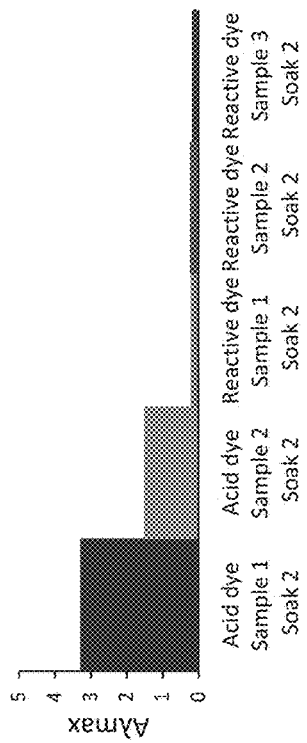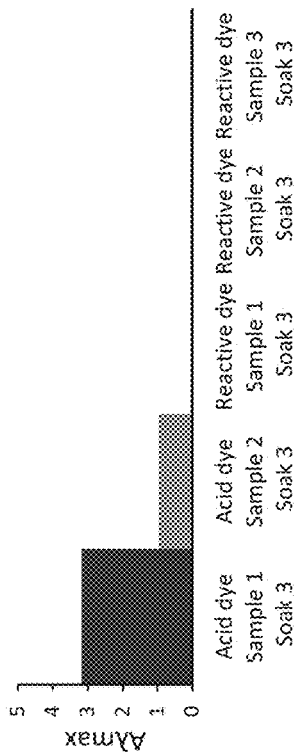

FIG. 74
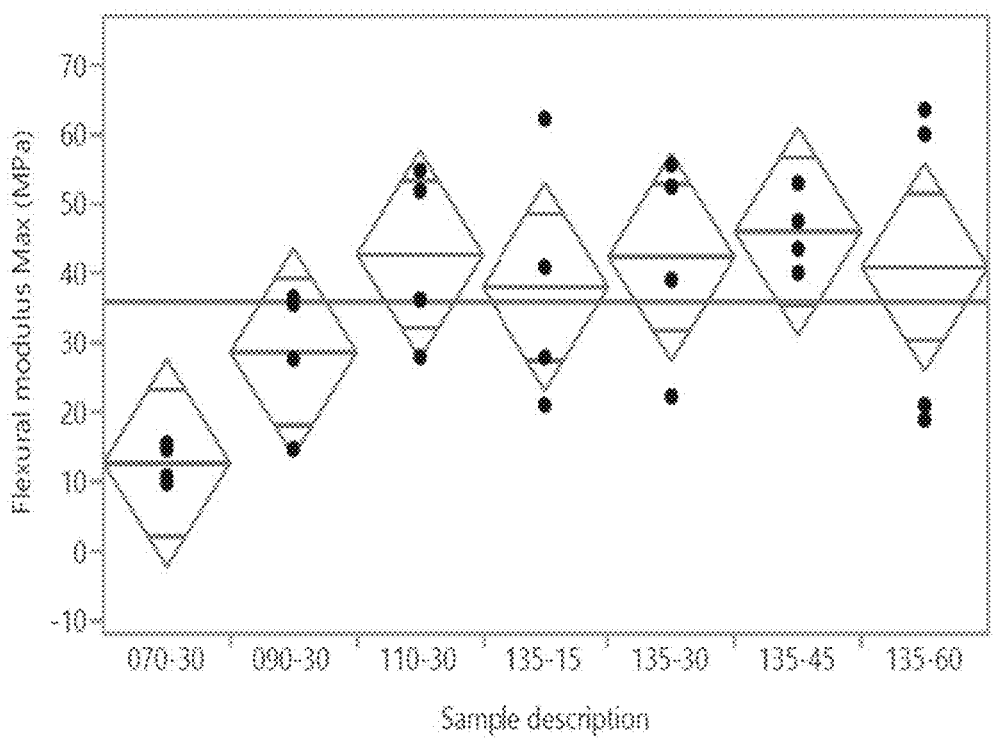
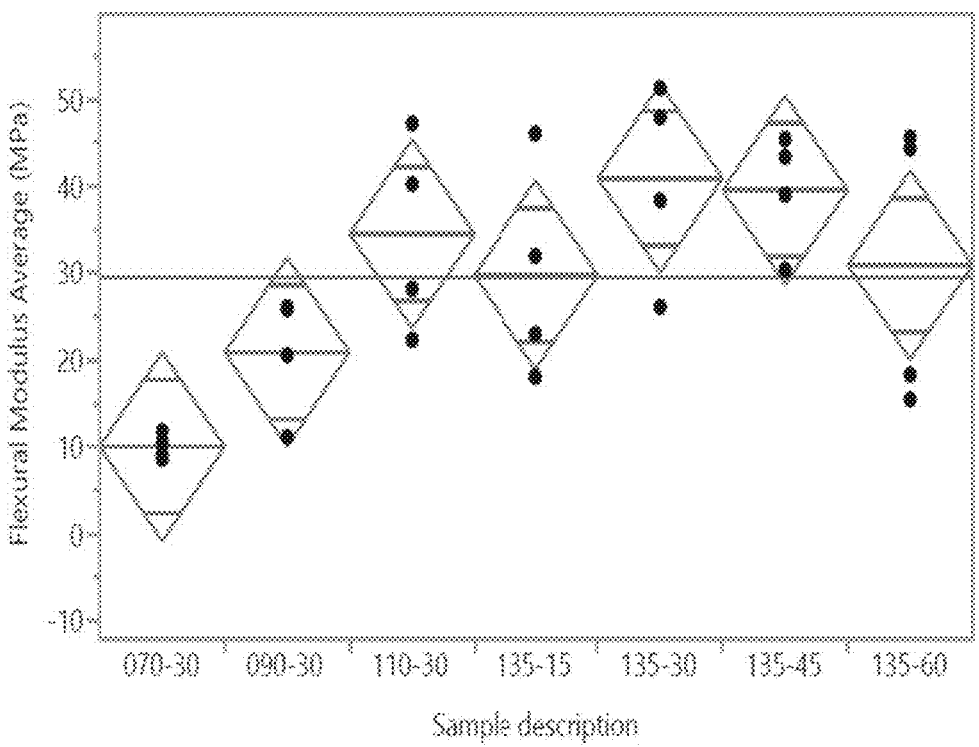

FIG. 75
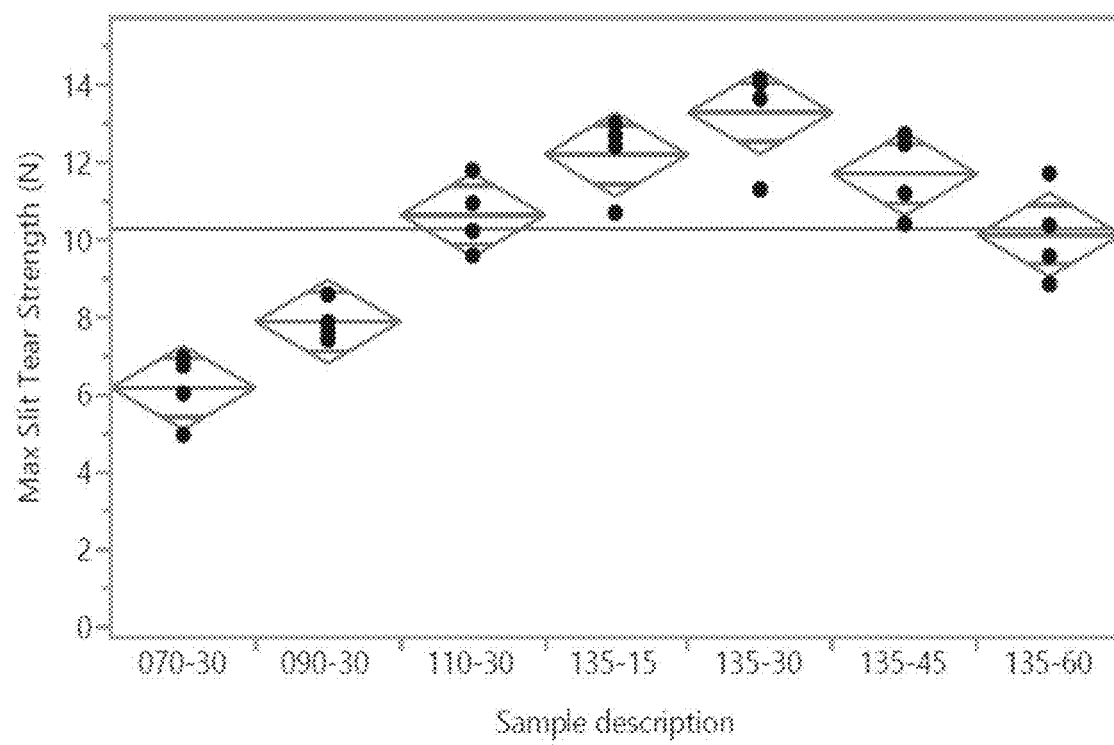
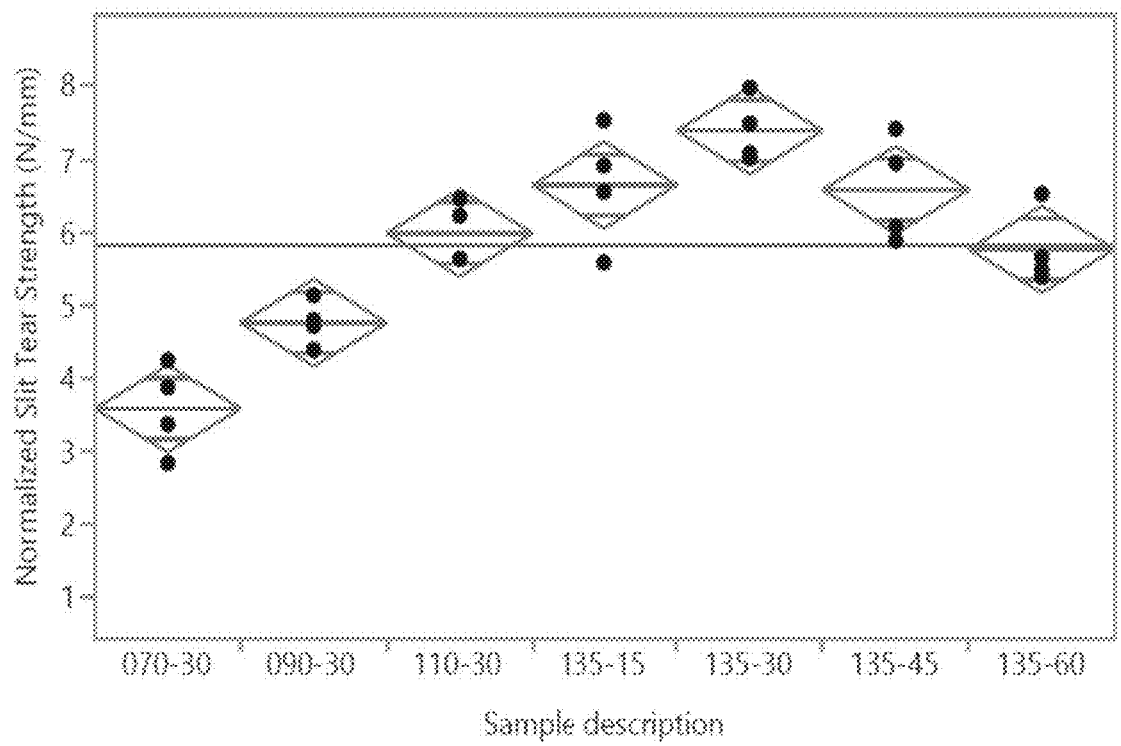

FIG. 85
| | 15 min | 30 min | 45 min |
|---|---|---|---|
| Dried at 40 °C | 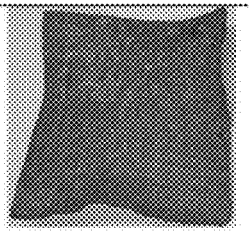 *4 h, not 15 min | | |
| Cured at 70 °C | 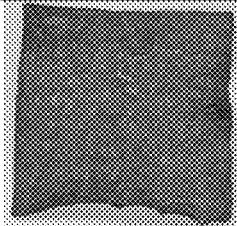 | 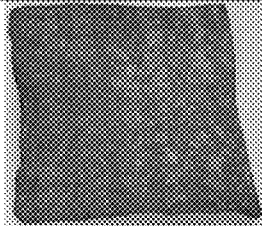 | |
| Cured at 90 °C | 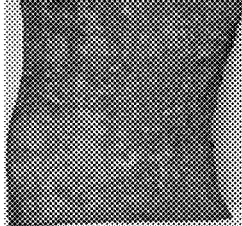 | 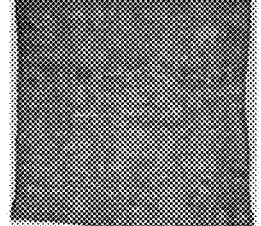 | 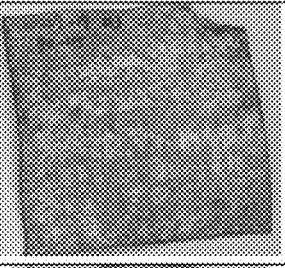 |
| Cured at 110 °C | 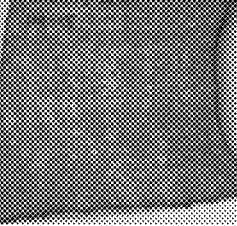 | 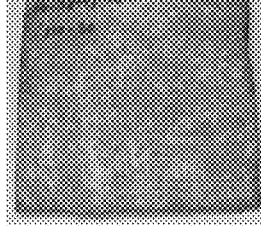 | 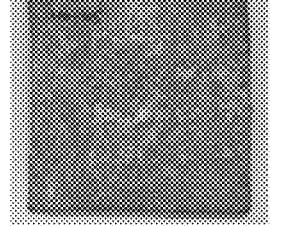 |
| Cured at 130 °C | 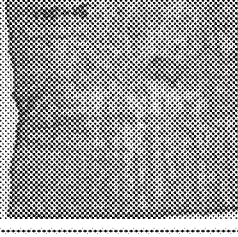 | | |

COMPOSITE MATERIAL, AND METHODS FOR PRODUCTION THEREOF

CROSS REFERENCE TO RELATED APPLICATIONS

This application is a continuation of Ser. No. 16/943,581, filed on Jul. 30, 2020, which is a continuation of International application PCT/US2020/034354 filed May 22, 2020, which claims the benefit of U.S. Provisional Application No. 62/851,867, filed May 23, 2019; and U.S. Provisional Application No. 63/024,368, filed May 13, 2020; each of which are hereby incorporated in their entirety by reference.

FIELD

The present disclosure generally relates to various mycelium materials having a grown mycelium component and methods for production thereof to provide favorable mechanical and aesthetic qualities.

BACKGROUND

Due to its bioefficiency, strength, and low environmental footprint, mycelium is of increasing interest in the next generation of sustainable materials. To this end, various applications have discussed methods of growing networks of enmeshed mycelium both on its own and as a composite material (e.g. enmeshed with particles, fibers, networks of fibers, solid matrix bonding agent, or nonwoven lamina). However, the mycelium materials currently undergoing development have poor mechanical qualities, including susceptibility to delamination and tearing under stress, and non-uniform aesthetic qualities. What is needed, therefore, are improved mycelium materials with favorable mechanical properties, aesthetic properties, and other advantages, as well as materials and methods for making improved mycelium materials.

SUMMARY

Provided herein, according to some embodiments, are various mycelium materials and methods for production thereof to provide mycelium materials and composite mycelium materials with favorable mechanical and aesthetic qualities, and related advantages.

In one aspect, provided herein is a composite mycelium material. In one aspect, provided herein are composite mycelium materials, comprising: a cultivated mycelium material comprising one or more masses of branching hyphae, wherein the one or more masses of branching hyphae is disrupted; and a bonding agent.

In some embodiments, the cultivated mycelium material has been generated on a solid substrate.

In some embodiments, the cultivated mycelium material comprises one or more masses of disrupted branching hyphae. In some embodiments, the one or more masses of disrupted branching hyphae has a length of 0.1 mm to 5 mm. In some embodiments, the one or more masses of disrupted branching hyphae has a length of 2 mm.

In some embodiments, the one or more masses of branching hyphae are entangled, wherein the entangling the hyphae comprises needle punching, felting, or hydroentangling. In some embodiments, the entangling hyphae are hydroentangled.

In some embodiments, the bonding agent comprises one or more reactive groups. In some embodiments, the one or more reactive groups react with active hydrogen containing groups. In some embodiments, the active hydrogen containing groups comprise amine, hydroxyl, and carboxyl groups. In some embodiments, the bonding agent comprises an adhesive, a resin, a crosslinking agent, and/or a matrix. In some embodiments, the bonding agent is selected from the group consisting of a vinyl acetate-ethylene (VAE) copolymer, a vinyl acetate-acrylic copolymer, a polyamide-epichlorohydrin resin (PAE), a copolymer, transglutaminase, citric acid, genipin, alginate, gum arabic, latex, a natural adhesive, and a synthetic adhesive. In some embodiments, the bonding agent is a copolymer with a property selected from the group consisting of: a particle size of less than or equal to 1 µm, a sub-zero glass transition temperature, and self-crosslinking function. In some embodiments, the bonding agent is a vinyl acetate-ethylene (VAE) copolymer. In some embodiments, the bonding agent is a vinyl acetate-acrylic copolymer. In some embodiments, the bonding agent is PAE. In some embodiments, the PAE comprises cationic azetidinium groups that react with active hydrogen containing groups comprising amine, hydroxyl, and carboxyl groups, in the one or more branches of hyphae.

In some embodiments, the natural adhesive comprises a natural latex-based adhesive. In some embodiments, the natural latex-based adhesive is leather glue or weld.

In some embodiments, the composite mycelium material further comprises a supporting material. In some embodiments, the supporting material has a pore size of 1/16th of an inch.

In some embodiments, the supporting material comprises a reinforcing material. In some embodiments, the reinforcing material is entangled within the composite mycelium material. In some embodiments, the supporting material comprises a base material. In some embodiments, the base material is positioned on one or more surfaces of the composite mycelium material. In some embodiments, the supporting material is selected from the group consisting of a mesh, a cheesecloth, a fabric, a knit textile, a woven textile, and a non-woven textile.

In some embodiments, the one or more masses of branching hyphae is disrupted by a mechanical action. In some embodiments, the mechanical action comprises blending the one or more masses of branching hyphae. In some embodiments, the mechanical action comprises breaking the one or more masses of branching hyphae. In some embodiments, the mechanical action comprises applying a physical force to the one or more masses of branching hyphae such that at least some of the masses of branching hyphae are aligned in a parallel formation. In some embodiments, the physical force is a pulling force.

In some embodiments, the mechanical action comprises applying the physical force in one or more directions such that the at least some of the masses of branching hyphae are aligned in parallel in one or more directions, wherein the physical force is applied repeatedly.

In some embodiments, the one or more masses of branching hyphae is disrupted by chemical treatment. In some embodiments, the chemical treatment comprises contacting the one or more masses of branching hyphae with a base or other chemical agent in an amount sufficient to cause a disruption. In some embodiments, the base comprises alkaline peroxide.

In some embodiments, the composite mycelium material comprises one or more proteins that are from a species other than a fungal species from which the cultivated mycelium material is generated. In some embodiments, the one or more proteins is from a plant source. In some embodiments, the plant source is a pea plant. In some embodiments, the plant source is a soybean plant.

In some embodiments, the composite mycelium material further comprises a dye. In some embodiments, the dye is selected from the group consisting of an acid dye, a direct dye, a synthetic dye, a natural dye, and a reactive dye. In some embodiments, the dye is a reactive dye. In some embodiments, the composite mycelium material is colored with the dye and the color of the composite mycelium material is substantially uniform on one or more surfaces of the composite mycelium material. In some embodiments, the dye is present throughout the interior of the composite mycelium material.

In some embodiments, the composite mycelium material further comprises a plasticizer. In some embodiments, the plasticizer is selected from the group consisting of oil, glycerin, fatliquor, sorbitol, diethyloxyester dimethyl ammonium chloride, Tween 20, Tween 80, m-erythritol, water, glycol, triethyl citrate, water, acetylated monoglycerides, and epoxidized soybean oil. In some embodiments, the plasticizer is a fatliquor.

In some embodiments, the composite mycelium material is flexible.

In some embodiments, an external element is applied to the cultivated mycelium material. In some embodiments, the external element is applied via heating and/or pressing. In some embodiments, the external element is hot pressing.

In some embodiments, the composite mycelium material further comprises a tannin.

In some embodiments, the composite mycelium material further comprises a finishing agent. In some embodiments, the finishing agent is selected from the group consisting of urethane, wax, nitrocellulose, and a plasticizer.

In some embodiments, the composite mycelium material comprises a mechanical property.

In some embodiments, the mechanical property comprises a wet tensile strength, an initial modulus, an elongation percentage at the break, a thickness, and/or a slit tear strength.

In some embodiments, the composite mycelium material has a wet tensile strength of 0.05 MPa to 10 MPa. In some embodiments, the composite mycelium material has a wet tensile strength of 5 MPa to 20 MPa. In some embodiments, the composite mycelium material has a wet tensile strength of 7 MPa. In some embodiments, the composite mycelium material has an initial modulus of 1 MPa to 100 MPa. In some embodiments, the composite mycelium material has an elongation percentage at the break of 1% to 25%. In some embodiments, the composite mycelium material has a thickness of 0.5 mm to 3.5 mm. In some embodiments, the composite mycelium material has a thickness of 2 mm. In some embodiments, the composite mycelium material has a slit tear strength of 5 N to 100 N. In some embodiments, the composite mycelium material has a slit tear strength of 50 N.

In some embodiments, the composite mycelium material is produced using traditional paper milling equipment.

In another aspect, provided herein are composite mycelium materials, comprising: a cultivated mycelium material comprising one or more masses of branching hyphae, wherein the one or more masses of branching hyphae is disrupted; a bonding agent comprising a vinyl acetate-ethylene copolymer; and a reactive dye.

In another aspect, provided herein are methods of producing a composite mycelium material, the method comprising: generating a cultivated mycelium material comprising one or more masses of branching hyphae; disrupting the cultivated mycelium material comprising the one or more masses of branching hyphae; and adding a bonding agent to the cultivated mycelium material; thus producing the composite mycelium material.

In some embodiments, the bonding agent is added before the masses of branching hyphae are disrupted, during disruption of the masses of branching hyphae, or after the disruption of the masses of branching hyphae.

In some embodiments, the generating comprises generating cultivated mycelium material on a solid substrate.

In some embodiments, the cultivated mycelium material comprises one or more masses of disrupted branching hyphae.

In some embodiments, the one or more masses of disrupted branching hyphae has a length of 0.1 mm to 5 mm.

In some embodiments, the one or more masses of disrupted branching hyphae has a length of 2 mm.

In some embodiments, the method further comprises entangling the one or more masses of branching hyphae, wherein the entangling the hyphae comprises needle punching, felting, or hydroentangling.

In some embodiments, the entangling the hyphae comprises hydroentangling.

In some embodiments, the hydroentangling the one or more masses of branching hyphae comprises hydroentangling using a liquid jet configured to spray liquid at a pressure of from about 700 psi to about 1000 psi.

In some embodiments, the hydroentangling comprises using a liquid jet configured to spray liquid at a flow rate of from about 100 mL/min. to 300 mL/min.

In some embodiments, the disrupting comprises disrupting the one or more masses of branching hyphae by a mechanical action.

In some embodiments, the mechanical action comprises blending the one or more masses of branching hyphae.

In some embodiments, the mechanical action comprises breaking the one or more masses of branching hyphae.

In some embodiments, the mechanical action comprises applying a physical force to the one or more masses of branching hyphae such that at least some of the masses of branching hyphae are aligned in a parallel formation.

In some embodiments, the physical force is a pulling force.

In some embodiments, the mechanical action comprises applying the physical force in one or more directions such that the at least some of the masses of branching hyphae are aligned in parallel in one or more directions, wherein the physical force is applied repeatedly.

In some embodiments, the one or more masses of branching hyphae is disrupted by chemical treatment.

In some embodiments, the chemical treatment comprises contacting the one or more masses of branching hyphae with a base or other chemical agent in an amount sufficient to cause a disruption.

In some embodiments, the base comprises alkaline peroxide.

In some embodiments, the bonding agent comprises one or more reactive groups.

In some embodiments, the one or more reactive groups react with active hydrogen containing groups.

In some embodiments, the active hydrogen containing groups comprise amine, hydroxyl, and carboxyl groups.

In some embodiments, the bonding agent comprises an adhesive, a resin, a crosslinking agent, and/or a matrix.

In some embodiments, the bonding agent is selected from the group consisting of a vinyl acetate-ethylene copolymer, a vinyl acetate-acrylic copolymer, a polyamide-epichlorohydrin resin (PAE), a copolymer, transglutaminase, citric acid, genipin, alginate, gum arabic, latex, a natural adhesive, and a synthetic adhesive.

In some embodiments, the bonding agent is a copolymer with a property selected from the group consisting of: a particle size of less than or equal to 1 µm, a sub-zero glass transition temperature, and self-crosslinking function.

In some embodiments, the bonding agent is a vinyl acetate-ethylene copolymer.

In some embodiments, the bonding agent is a vinyl acetate-acrylic copolymer.

In some embodiments, the bonding agent is PAE.

In some embodiments, the PAE comprises cationic azetidinium groups that react with active hydrogen containing groups comprising amine, hydroxyl, and carboxyl groups, in the one or more branches of hyphae.

In some embodiments, the natural adhesive comprises a natural latex-based adhesive.

In some embodiments, the natural latex-based adhesive is leather glue or weld.

In some embodiments, the method further comprises incorporating a supporting material into the composite mycelium material.

In some embodiments, the supporting material has a pore size of 1/16th of an inch.

In some embodiments, the supporting material comprises a reinforcing material.

In some embodiments, the reinforcing material is entangled within the composite mycelium material.

In some embodiments, the supporting material comprises a base material.

In some embodiments, the base material is positioned on one or more surfaces of the composite mycelium material.

In some embodiments, the supporting material is selected from the group consisting of a mesh, a cheesecloth, a fabric, a knit textile, a woven textile, and a non-woven textile.

In some embodiments, the method further comprises perforating, sonicating, and/or vacuum-processing the cultivated mycelium material.

In some embodiments, the method further comprises perforating and sonicating the cultivated mycelium material.

In some embodiments, the method further comprises adding one or more proteins that are from a species other than a fungal species from which the cultivated mycelium material is generated.

In some embodiments, the one or more proteins is from a plant source.

In some embodiments, the plant source is a pea plant.

In some embodiments, the plant source is a soybean plant.

In some embodiments, the method further comprises adding a dye to the cultivated mycelium material or the composite mycelium material.

In some embodiments, the dye is selected from the group consisting of an acid dye, a direct dye, a synthetic dye, a natural dye, and a reactive dye.

In some embodiments, the dye is a reactive dye.

In some embodiments, the composite mycelium material is colored with the dye and the color of the composite mycelium material is substantially uniform on one or more surfaces of the composite mycelium material.

In some embodiments, the dye is present throughout the interior of the composite mycelium material.

In some embodiments, the method further comprises adding a plasticizer to the cultivated mycelium material or the composite mycelium material.

In some embodiments, the plasticizer is selected from the group consisting of oil, glycerin, fatliquor, sorbitol, diethyloxyester dimethyl ammonium chloride, Tween 20, Tween 80, m-erythritol, water, glycol, triethyl citrate, water, acetylated monoglycerides, and epoxidized soybean oil.

In some embodiments, the plasticizer is a fatliquor.

In some embodiments, the composite mycelium material is flexible.

In some embodiments, the method further comprises applying an external element to the cultivated mycelium material.

In some embodiments, the external element is applied via heating and/or pressing.

In some embodiments, the external element is hot pressing.

In some embodiments, the method further comprises adding a tannin to the cultivated mycelium material or the composite mycelium material.

In some embodiments, the method further comprises adding a finishing agent to the composite mycelium material.

In some embodiments, the finishing agent is selected from the group consisting of urethane, wax, nitrocellulose, and a plasticizer.

In some embodiments, the method further comprises determining a mechanical property of the composite mycelium material.

In some embodiments, the mechanical property comprises a wet tensile strength, an initial modulus, an elongation percentage at the break, a thickness, and/or a slit tear strength.

In some embodiments, the composite mycelium material has a wet tensile strength of 0.05 MPa to 10 MPa.

In some embodiments, the composite mycelium material has a wet tensile strength of 5 MPa to 20 MPa.

In some embodiments, the composite mycelium material has a wet tensile strength of 7 MPa.

In some embodiments, the composite mycelium material has an initial modulus of 1 MPa to 100 MPa.

In some embodiments, the composite mycelium material has an elongation percentage at the break of 1% to 25%.

In some embodiments, the composite mycelium material has a thickness of 0.5 mm to 3.5 mm.

In some embodiments, the composite mycelium material has a thickness of 2 mm.

In some embodiments, the composite mycelium material has a slit tear strength of 5 N to 100 N.

In some embodiments, the composite mycelium material has a slit tear strength of 50 N.

In some embodiments, the composite mycelium material is produced using traditional paper milling equipment.

In another aspect, provided herein are methods, comprising: generating a cultivated mycelium material; pressing the cultivated mycelium material; and contacting the pressed cultivated mycelium material with a solution comprising a bonding agent.

In some embodiments, the bonding agent is added before the pressing step, during the pressing step, or after the pressing step.

In some embodiments, the generating comprises generating cultivated mycelium material on a solid substrate.

In some embodiments, the method further comprises incorporating a supporting material into the composite mycelium material.

In some embodiments, the supporting material has a pore size of 1/16th of an inch.

In some embodiments, the supporting material comprises a reinforcing material.

In some embodiments, the reinforcing material is entangled within the composite mycelium material.

In some embodiments, the supporting material comprises a base material.

In some embodiments, the base material is positioned on one or more surfaces of the composite mycelium material.

In some embodiments, the supporting material is selected from the group consisting of a mesh, a cheesecloth, a fabric, a knit textile, a woven textile, and a non-woven textile.

In some embodiments, the bonding agent comprises one or more reactive groups.

In some embodiments, the one or more reactive groups react with active hydrogen containing groups.

In some embodiments, the active hydrogen containing groups comprise amine, hydroxyl, and carboxyl groups.

In some embodiments, the bonding agent comprises an adhesive, a resin, a crosslinking agent, and/or a matrix.

In some embodiments, the bonding agent is selected from the group consisting of a vinyl acetate-ethylene copolymer, a vinyl acetate-acrylic copolymer, a polyamide-epichlorohydrin resin (PAE), a copolymer, transglutaminase, citric acid, genipin, alginate, gum arabic, latex, a natural adhesive, and a synthetic adhesive.

In some embodiments, the bonding agent is a copolymer with a property selected from the group consisting of: a particle size of less than or equal to 1 μm, a sub-zero glass transition temperature, and self-crosslinking function.

In some embodiments, the bonding agent is a vinyl acetate-ethylene copolymer.

In some embodiments, the bonding agent is a vinyl acetate-acrylic copolymer.

In some embodiments, the bonding agent is PAE.

In some embodiments, the PAE comprises cationic azetidinium groups that react with active hydrogen containing groups comprising amine, hydroxyl, and carboxyl groups, in the one or more branches of hyphae.

In some embodiments, the natural adhesive comprises a natural latex-based adhesive.

In some embodiments, the natural latex-based adhesive is leather glue or weld.

In some embodiments, the method further comprises perforating, sonicating, and/or vacuum-processing the cultivated mycelium material.

In some embodiments, the method further comprises perforating and sonicating the cultivated mycelium material.

In some embodiments, the method further comprises adding one or more proteins that are from a species other than a fungal species from which the cultivated mycelium material is generated.

In some embodiments, the one or more proteins is from a plant source.

In some embodiments, the plant source is a pea plant.

In some embodiments, the plant source is a soybean plant.

In some embodiments, the method further comprises adding a dye to the cultivated mycelium material or the composite mycelium material.

In some embodiments, the dye is selected from the group consisting of an acid dye, a direct dye, a synthetic dye, a natural dye, and a reactive dye.

In some embodiments, the dye is a reactive dye.

In some embodiments, the composite mycelium material is colored with the dye and the color of the composite mycelium material is substantially uniform on one or more surfaces of the composite mycelium material.

In some embodiments, the dye is present throughout the interior of the composite mycelium material.

In some embodiments, the method further comprises adding a plasticizer to the cultivated mycelium material or the composite mycelium material.

In some embodiments, the plasticizer is selected from the group consisting of oil, glycerin, fatliquor, sorbitol, diethyloxyester dimethyl ammonium chloride, Tween 20, Tween 80, m-erythritol, water, glycol, triethyl citrate, water, acetylated monoglycerides, and epoxidized soybean oil.

In some embodiments, the plasticizer is a fatliquor.

In some embodiments, the composite mycelium material is flexible.

In some embodiments, the method further comprises applying an external element to the cultivated mycelium material.

In some embodiments, the external element is applied via heating and/or pressing.

In some embodiments, the external element is hot pressing.

In some embodiments, the method further comprises adding a tannin to the cultivated mycelium material or the composite mycelium material.

In some embodiments, the method further comprises adding a finishing agent to the composite mycelium material.

In some embodiments, the finishing agent is selected from the group consisting of urethane, wax, nitrocellulose, and a plasticizer.

In some embodiments, the method further comprises determining a mechanical property of the composite mycelium material.

In some embodiments, the mechanical property comprises a wet tensile strength, an initial modulus, an elongation percentage at the break, a thickness, and/or a slit tear strength.

In some embodiments, the composite mycelium material has a wet tensile strength of 0.05 MPa to 10 MPa.

In some embodiments, the composite mycelium material has a wet tensile strength of 5 MPa to 20 MPa.

In some embodiments, the composite mycelium material has a wet tensile strength of 7 MPa.

In some embodiments, the composite mycelium material has an initial modulus of 1 MPa to 100 MPa.

In some embodiments, the composite mycelium material has an elongation percentage at the break of 1% to 25%.

In some embodiments, the composite mycelium material has a thickness of 0.5 mm to 3.5 mm.

In some embodiments, the composite mycelium material has a thickness of 2 mm.

In some embodiments, the composite mycelium material has a slit tear strength of 5 N to 100 N.

In some embodiments, the composite mycelium material has a slit tear strength of 50 N.

In some embodiments, the composite mycelium material is produced using traditional paper milling equipment.

In another aspect, provided herein are composite mycelium materials, comprising: a pressed cultivated mycelium material; and a bonding agent.

In some embodiments, the cultivated mycelium material has been generated on a solid substrate.

In some embodiments, the bonding agent comprises one or more reactive groups.

In some embodiments, the one or more reactive groups react with active hydrogen containing groups.

In some embodiments, the active hydrogen containing groups comprise amine, hydroxyl, and carboxyl groups.

In some embodiments, the bonding agent comprises an adhesive, a resin, a crosslinking agent, and/or a matrix.

In some embodiments, the bonding agent is selected from the group consisting of a vinyl acetate-ethylene (VAE) copolymer, a vinyl acetate-acrylic copolymer, a polyamide-epichlorohydrin resin (PAE), a copolymer, transglutaminase, citric acid, genipin, alginate, gum arabic, latex, a natural adhesive, and a synthetic adhesive.

In some embodiments, the bonding agent is a copolymer with a property selected from the group consisting of: a particle size of less than or equal to 1 μm, a sub-zero glass transition temperature, and self-crosslinking function.

In some embodiments, the bonding agent is a vinyl acetate-ethylene (VAE) copolymer.

In some embodiments, the bonding agent is a vinyl acetate-acrylic copolymer.

In some embodiments, the bonding agent is PAE.

In some embodiments, the PAE comprises cationic azetidinium groups that react with active hydrogen containing groups comprising amine, hydroxyl, and carboxyl groups, in the one or more branches of hyphae.

In some embodiments, the natural adhesive comprises a natural latex-based adhesive.

In some embodiments, the natural latex-based adhesive is leather glue or weld.

In some embodiments, the composite mycelium material further comprises a supporting material.

In some embodiments, the supporting material has a pore size of 1/16th of an inch.

In some embodiments, the supporting material comprises a reinforcing material.

In some embodiments, the reinforcing material is entangled within the composite mycelium material.

In some embodiments, the supporting material comprises a base material.

In some embodiments, the base material is positioned on one or more surfaces of the composite mycelium material.

In some embodiments, the supporting material is selected from the group consisting of a mesh, a cheesecloth, a fabric, a knit textile, a woven textile, and a non-woven textile.

In some embodiments, the composite mycelium material comprises one or more proteins that are from a species other than a fungal species from which the cultivated mycelium material is generated.

In some embodiments, the one or more proteins is from a plant source.

In some embodiments, the plant source is a pea plant.

In some embodiments, the plant source is a soybean plant.

In some embodiments, the composite mycelium material further comprises a dye.

In some embodiments, the dye is selected from the group consisting of an acid dye, a direct dye, a synthetic dye, a natural dye, and a reactive dye.

In some embodiments, the dye is a reactive dye.

In some embodiments, the composite mycelium material is colored with the dye and the color of the composite mycelium material is substantially uniform on one or more surfaces of the composite mycelium material.

In some embodiments, the dye is present throughout the interior of the composite mycelium material.

In some embodiments, the composite mycelium material further comprises a plasticizer.

In some embodiments, the plasticizer is selected from the group consisting of oil, glycerin, fatliquor, sorbitol, diethyloxyester dimethyl ammonium chloride, Tween 20, Tween 80, m-erythritol, water, glycol, triethyl citrate, water, acetylated monoglycerides, and epoxidized soybean oil.

In some embodiments, the plasticizer is a fatliquor.

In some embodiments, the composite mycelium material is flexible.

In some embodiments, an external element is applied to the cultivated mycelium material.

In some embodiments, the external element is applied via heating and/or pressing.

In some embodiments, the external element is hot pressing.

In some embodiments, the composite mycelium material further comprises a tannin.

In some embodiments, the composite mycelium material further comprises a finishing agent.

In some embodiments, the finishing agent is selected from the group consisting of urethane, wax, nitrocellulose, and a plasticizer.

In some embodiments, the composite mycelium material comprises a mechanical property.

In some embodiments, the mechanical property comprises a wet tensile strength, an initial modulus, an elongation percentage at the break, a thickness, and/or a slit tear strength.

In some embodiments, the composite mycelium material has a wet tensile strength of 0.05 MPa to 10 MPa.

In some embodiments, the composite mycelium material has a wet tensile strength of 5 MPa to 20 MPa.

In some embodiments, the composite mycelium material has a wet tensile strength of 7 MPa.

In some embodiments, the composite mycelium material has an initial modulus of 1 MPa to 100 MPa.

In some embodiments, the composite mycelium material has an elongation percentage at the break of 1% to 25%.

In some embodiments, the composite mycelium material has a thickness of 0.5 mm to 3.5 mm.

In some embodiments, the composite mycelium material has a thickness of 2 mm.

In some embodiments, the composite mycelium material has a slit tear strength of 5 N to 100 N.

In some embodiments, the composite mycelium material has a slit tear strength of 50 N.

In some embodiments, the composite mycelium material is produced using traditional paper milling equipment.

BRIEF DESCRIPTION OF THE FIGURES

FIG. 12A depicts stress-strain curves of aligned mycelium bonded with polyurethane hot melt adhesive tested after conditioning at 65% relative humidity (RH) in a dry state. FIG. 12B depicts stress-strain curves of aligned mycelium bonded with polyurethane hot melt adhesive tested after conditioning at 65% relative humidity (RH) in a wet state.

FIG. 55A shows the light absorbance of a dyed mycelium panel after 1 round of soaking.

FIG. 55B shows the light absorbance of a dyed mycelium panel after 2 rounds of soaking. FIG. 55C shows the light absorbance of a dyed mycelium panel after 3 rounds of soaking. FIG. 55D shows the light absorbance of a dyed mycelium panel after 4 rounds of soaking. FIG. 55E shows the light absorbance after 5 rounds of soaking.

FIG. 74 shows flexural modulus of mycelium material samples with different curing conditions.

FIG. 75 shows slit tear strength of mycelium material samples with different curing conditions.

FIG. 85 shows images of spunlace samples dyed after binder application and curing at various temperatures and times.

DETAILED DESCRIPTION

Definitions

Figure 1:
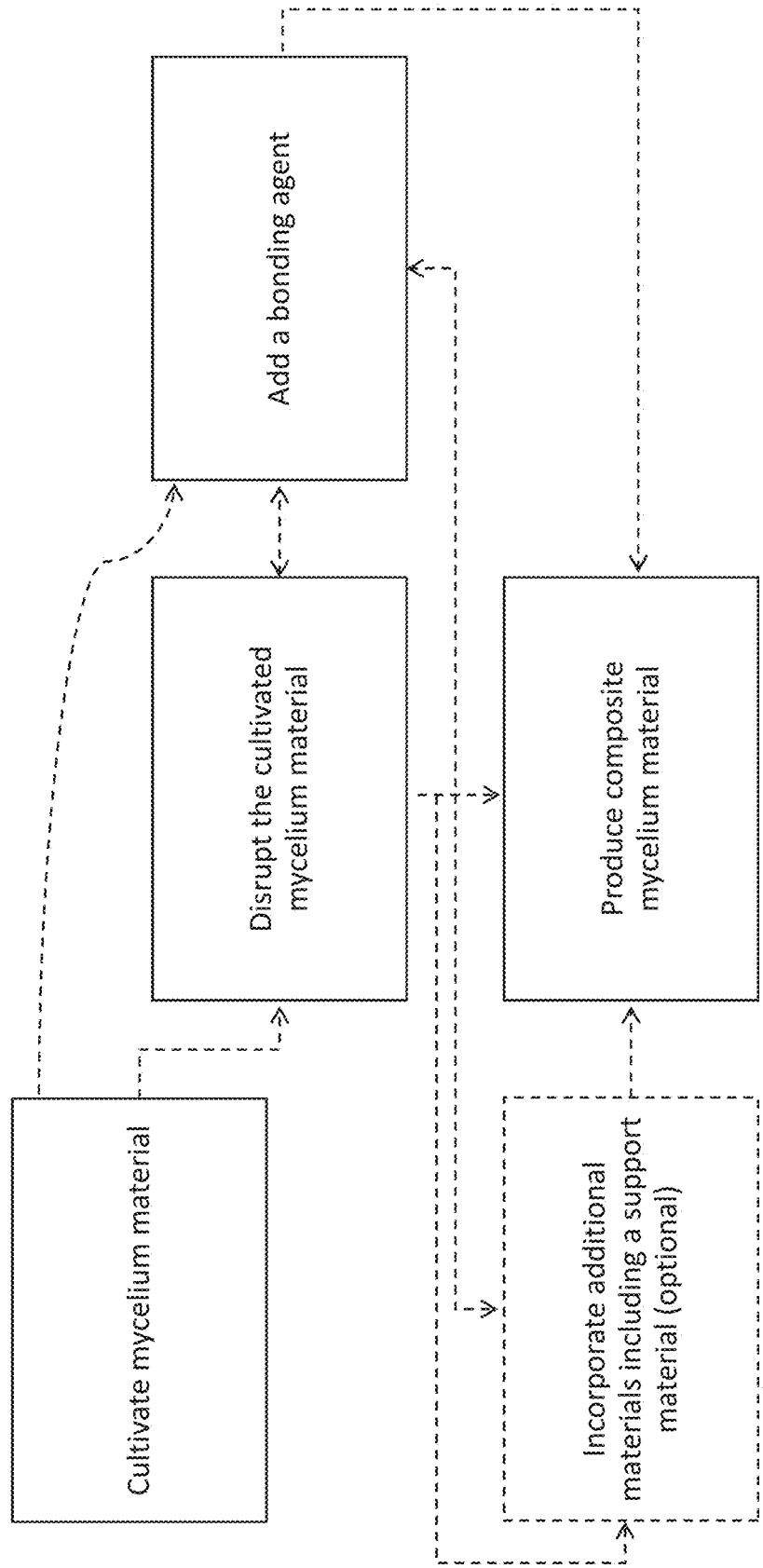
FIG. 1 depicts a schematic diagram of methods of producing a composite mycelium material according to some embodiments described herein. A box having a solid line indicates a required step and a box having a dashed line indicates an optional step.

The details of various embodiments of the disclosure are set forth in the description below. Other features, objects, and advantages of the disclosure will be apparent from the description. Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. The terms "a" and "an" includes plural references unless the context dictates otherwise. Generally, nomenclatures used in connection with, and techniques of, biochemistry, enzymology, molecular and cellular biology, microbiology, genetics and protein and nucleic acid chemistry and hybridization described herein are those well-known and commonly used in the art.

The following terms, unless otherwise indicated, shall be understood to have the following meanings:

The term "hyphae" refers to a morphological structure of a fungus that is characterized by a branching filamentous shape.

The term "hyphal" refers to an object having a component thereof comprised of hyphae.

The term "mycelium" refers to a structure formed by one or more masses of branching hyphae. A "mass" refers to a quantity of matter. Mycelium is a distinct and separate structure from a fruiting body of a fungus or sporocarp.

The terms "cultivate" and "cultivated" refer to the use of defined techniques to deliberately grow a fungus or other organism.

The term "cultivated mycelium material" refers to material that includes one or more masses of cultivated mycelium, or includes solely of cultivated mycelium. In some embodiments, the one or more masses of cultivated mycelium is disrupted as described herein. In most cases, the cultivated mycelium material has been generated on a solid substrate, as described below.

The term "composite mycelium material" refers to any material including cultivated mycelium material combined with another material, such as a bonding agent or a supporting material as described herein, such as a crosslinking agent, natural adhesive, or a synthetic adhesive. In some embodiments, the mycelium comprises a supporting material. Suitable supporting materials include, but are not limited to, a mass of contiguous, disordered fibers (e.g. nonwoven fibers), a perforated material (e.g. metal mesh, perforated plastic), a mass of discontiguous particles (e.g. pieces of woodchip) or any combination thereof. In specific embodiments, the supporting material is selected from the group consisting of a mesh, a cheesecloth, a fabric, a knit, a woven, and a non-woven textile. In some embodiments, the mycelium comprises a reinforcing material. A reinforcing material is a supporting material that is entangled within a mycelium or composite mycelium material. In some embodiments, the mycelium comprises a base material. A base material is a supporting material that is positioned on one or more surfaces of the mycelium or composite mycelium material.

The term "incorporate" refers to any substance, e.g., cultivated mycelium material, composite mycelium material, or a bonding agent, that can be combined with or contacted with another substance. In a specific embodiment, a mycelium or composite mycelium material can be combined with, contacted with, or incorporated into a supporting material, e.g., woven, twisted, wound, folded, entwined, entangled, or braided together, to produce a mycelium material that has become incorporated with the supporting material. In another embodiment, one or more bonding agents may be incorporated within the cultivated mycelium material to be bonded, either in its disrupted or undisrupted state, e.g., embedded throughout the material, or added as a thin coating layer, such as by spraying, saturation, dipping, nip rolling, coating, and the like, to produce a mycelium material.

As used herein, the term "disrupted" with respect to one or more masses of branching hyphae refer to one or more masses of branching hyphae of which one or more disruptions have been applied. A "disruption," as described herein, may be mechanical or chemical, or a combination thereof. In some embodiments, the one or more masses of branching hyphae is disrupted by a mechanical action. A "mechanical action" as used herein refers to a manipulation of or relating to machinery or tools. Exemplary mechanical actions include, but are not limited to, blending, chopping, impacting, compacting, bounding, shredding, grinding, compressing, high-pressure, shearing, laser cutting, hammer milling, and waterjet forces. In some embodiments, a mechanical action may include applying a physical force, e.g., in one or more directions such that the at least some of the masses of branching hyphae are aligned in parallel in one or more directions, wherein the physical force is applied repeatedly. In some other embodiments, the one or more masses of branching hyphae is disrupted by chemical treatment. "Chemical treatment" as used herein refers to contacting the cultivated mycelium material or composite mycelium material with a chemical agent, e.g., a base or other chemical agent, in an amount sufficient to cause a disruption. In various embodiments, a combination of mechanical actions and chemical treatments may be used herein. The amount of mechanical action (for example, the amount of pressure) and/or chemical agent applied, the period of time for which the mechanical action and/or chemical treatment is applied, and the temperature at which the mechanical action and/or chemical agent is applied, depends, in part, on the components of the cultivated mycelium material or composite mycelium material, and are selected to provide an optimal disruption on the cultivated mycelium material or composite mycelium material.

The term "plasticizer" as used herein refers to any molecule that interacts with a structure to increase mobility of the structure.

The term "processed mycelium material" as used herein refers to a mycelium that has been post-processed by any combination of treatments with preserving agents, plasticizers, finishing agents, dyes, and/or protein treatments.

The term "web" as used herein refers to a mycelium material or composite mycelium material that has been disrupted, converted into a slurry, and arranged in a formation (e.g. drylaid, airlaid and/or wetlaid).

The term "spunlace" as used herein refers to a mycelium material or composite mycelium material that has been disrupted and hydroentangled, wherein one or more masses of branching hyphae are entangled using jets of water or the like.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range, is encompassed within the aspects of the present disclosure. The upper and lower limits of these smaller ranges may independently be included in the smaller ranges, and are also encompassed within the aspects of the present disclosure, subject to any specifically excluded limit in the stated range. Where the stated range includes one or both of the limits, ranges excluding either or both of those included limits are also included in the aspects of the present disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Exemplary methods and materials are described below, although methods and materials similar or equivalent to those described herein can also be used in the practice of the present disclosure and will be apparent to those of skill in the art. All publications and other references mentioned herein are incorporated by reference in their entirety. In case of conflict, the present specification, including definitions, will control. The materials, methods, and examples are illustrative only and not intended to be limiting.

Mycelium Compositions and Methods of Production

Provided herein are cultivated mycelium materials and composite mycelium materials and scalable methods of producing the cultivated mycelium materials and composite mycelium materials. In some or most embodiments, the composite mycelium materials include a cultivated mycelium material having one or more masses of branching hyphae, wherein the one or more masses of branching hyphae is disrupted, and a bonding agent. Methods of producing the cultivated mycelium material and composite mycelium material are also provided.

Exemplary patents and applications discussing methods of growing mycelium include, but are not limited to: WIPO Patent Publication No. 1999/024555; G.B. Patent No. 2,148, 959; G.B. Patent No. 2,165,865; U.S. Pat. Nos. 5,854,056; 2,850,841; 3,616,246; 9,485,917; 9,879,219; 9,469,838; 9,914,906; 9,555,395; U.S. Patent Publication No. 2015/0101509; U.S. Patent Publication No. 2015/0033620, all of which are incorporated herein by reference in their entirety. U.S. Patent Publication No. 2018/0282529, published on Oct. 4, 2018 discusses various mechanisms of solution-based post-processing mycelium material to produce a material that has favorable mechanical characteristics for processing into a textile or leather alternative.

As shown in FIG. 1, exemplary methods of producing mycelium materials according to some embodiments described herein include cultivating mycelium material, optionally disrupting cultivated mycelium material, optionally adding a bonding agent, optionally incorporating additional materials such as a support material, and combinations thereof. In various embodiments, traditional paper milling equipment may be adapted or used to perform some, or all, of the steps presented herein. In such embodiments, the mycelium material is produced using traditional paper milling equipment.

A description of an embodiment with several components in communication with each other does not imply that all such components are required. To the contrary, a variety of optional components may be described to illustrate a wide variety of possible embodiments of one or more aspects of the present disclosure and in order to more fully illustrate one or more aspects of the present disclosure. Similarly, although process steps, method steps, algorithms or the like may be described in sequential order, such processes, methods, and algorithms may generally be configured to work in alternate orders, unless specifically stated to the contrary. In other words, any sequence or order of steps that may be described herein does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more embodiments, and does not imply that the illustrated process is preferred. Also, steps are generally described once per embodiment, but this does not mean they must occur once, or that they may only occur once each time a process, method, or algorithm is carried out or executed. Some steps may be omitted in some embodiments or some occurrences, or some steps may be executed more than once in a given embodiment or occurrence.

Cultivated Mycelium Material

Embodiments of the present disclosure include various types of cultivated mycelium materials. Depending on the particular embodiment and requirements of the material sought, various known methods of cultivating mycelium may be used. Any fungus that can be cultivated as mycelium may be used. Suitable fungus species for use include but are not limited to: *Agaricus arvensis; Agrocybe brasiliensis; Amylomyces rouxii; Amylomyces* sp.; *Armillaria mellea; Aspergillus nidulans; Aspergillus niger; Aspergillus oryzae; Ceriporia lacerata; Coprinus comatus; Fibroporia vaillantii; Fistulina hepatica; Flammulina velutipes; Fomitopsis officinalis; Ganoderma sessile; Ganoderma tsugae; Hericium erinaceus; Hypholoma capnoides; Hypholoma sublaterium; Inonotus obliquus; Lactarius chrysorrheus; Macrolepiota procera; Morchella angusticeps; Myceliophthora thermophila; Neurospora crassa; Penicillium camembertii; Penicillium chrysogenum; Penicillium rubens; Phycomyces blakesleeanus; Pleurotus djamor; Pleurotus ostreatus; Polyporus squamosus; Psathyrella aquatica; Rhizopus microspores; Rhizopus oryzae; Schizophyllum commune; Streptomyces venezuelae; Stropharia rugosoannulata; Thielavia terrestris*; and *Ustilago maydis*. In some embodiments, the fungus used includes *Ganoderma sessile, Neurospora crassa*, and/or *Phycomyces blakesleeanus*.

In some embodiments, the strain or species of fungus may be bred to produce cultivated mycelium material with specific characteristics, such as a dense network of hyphae, a highly-branched network of hyphae, hyphal fusion within the network of hyphae, and other characteristics that may alter the properties of the cultivated mycelium material. In some embodiments, the strain or species of fungus may be genetically modified to produce cultivated mycelium material with specific characteristics.

In most embodiments, the cultivated mycelium may be grown by first inoculating a solid or liquid substrate with an inoculum of the mycelium from the selected species of fungus. In some embodiments, the substrate is pasteurized or sterilized prior to inoculation to prevent contamination or competition from other organisms. For example, a standard method of cultivating mycelium includes inoculating a sterilized solid substrate (e.g. grain) with an inoculum of mycelium. Other standard methods of cultivating mycelium include inoculating a sterilized liquid medium (e.g. liquid potato dextrose) with an inoculum of mycelium or a pure cultured spawn. In some embodiments, the solid and/or liquid substrate will include lignocellulose as a carbon source for mycelium. In some embodiments, the solid and/or liquid substrate will contain simple or complex sugars as a carbon source for the mycelium.

Figure 13:
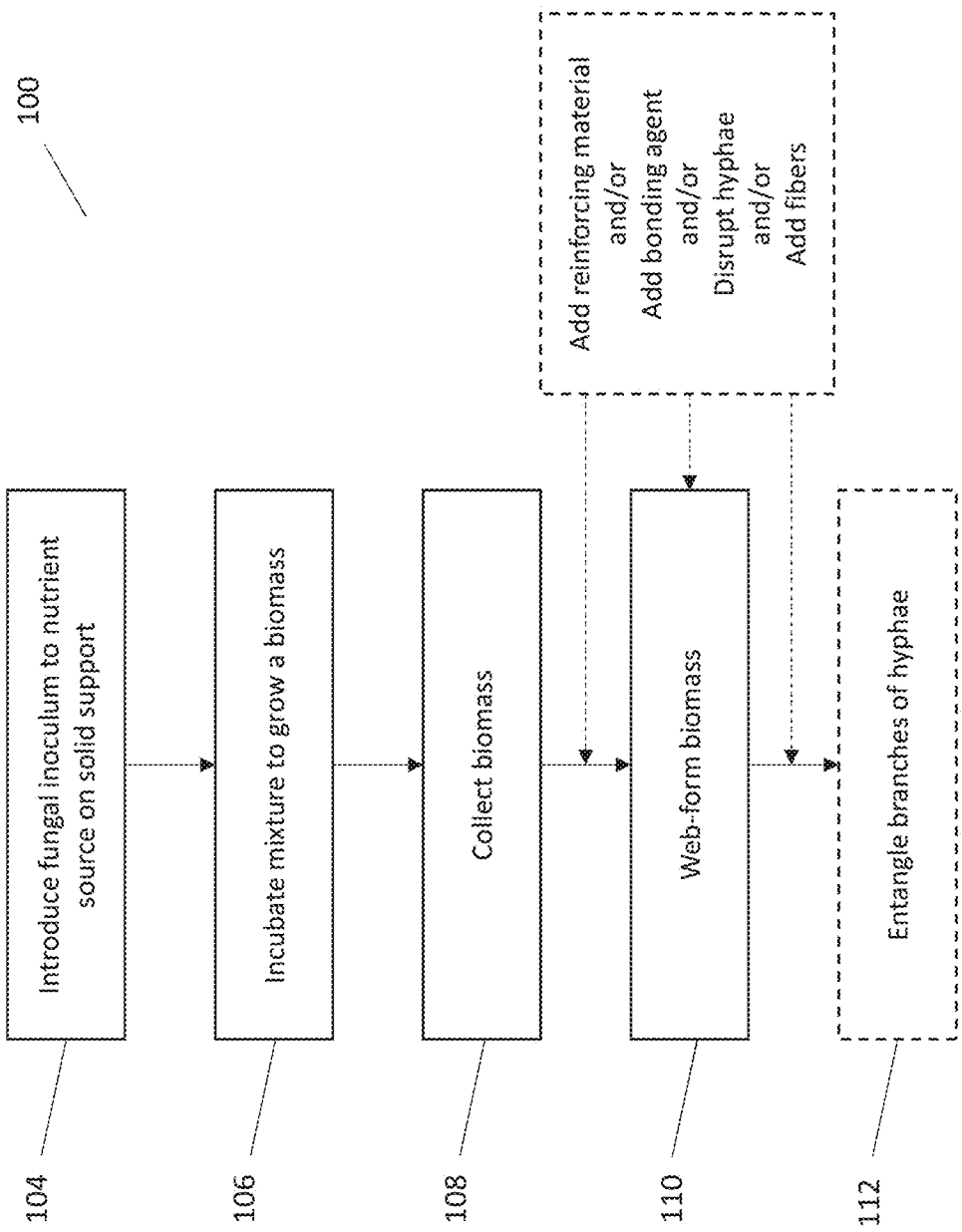
FIG. 13 shows a flowchart of a method of producing a material comprising mycelium

Referring now to FIG. 13, a method 100 for producing a mycelium material is illustrated. The method 100 includes inoculating a nutrient source on a solid support 104, and incubating the mixture to grow a biomass of mycelium at 106, collecting the cultivated biomass of mycelium at 108, web-forming the biomass of mycelium at 110 to form a hyphal network, and entangling branches of hyphae in the hyphal network at 112.

At step 106, the inoculated nutrient source is incubated to promote growth of the mycelium biomass. The conditions of the nutrient source and solid support can be selected to promote growth of a mycelium biomass having a plurality of branches of hyphae having sufficient morphological characteristics for entanglement in a downstream process. Exemplary morphological characteristics include a minimum length of hyphae branches, a desired density of the hyphae network, a desired degree of branching of the hyphae, a desired aspect ratio, and/or a desired degree of hyphal fusion of the hyphae network. According to one aspect of the present disclosure, the conditions of the solid support in the incubating step at 106 are selected to promote growth of a biomass of mycelium having a plurality of branches of hyphae having a length of at least about 0.1 mm. For example, the hyphae can have a length of from about 0.1 mm to about 5 mm, about 0.1 mm to about 4 mm, about 0.1 mm to about 3 mm, about 0.1 mm to about 2 mm, about 0.1 mm to about 1 mm, about 1 mm to about 5 mm, about 1 mm to about 4 mm, about 1 mm to about 3 mm, about 1 mm to about 2 mm, about 2 mm to about 5 mm, about 2 mm to about 4 mm, or about 2 mm to about 3 mm.

The incubation step 106 can occur under aerobic conditions in the presence of oxygen. Optionally, the solid support can be sealed into a chamber during all or a portion of the incubation step. In some examples, oxygen may be introduced into the chamber. The incubation temperature can be selected based on the specific fungal species. In some examples, the temperature of the chamber during incubation is from about 20° C. to about 40° C., about 25° C. to about 40° C., about 30° C. to about 40° C., about 35° C. to about 40° C., about 20° C. to about 35° C., about 25° C. to about 35° C., about 30° C. to about 35° C., about 20° C. to about 30° C., or about 25° C. to about 30° C.

The incubation step 106 is configured to promote the growth of a biomass of mycelium that includes a plurality of branches of hyphae. The incubation step 106 can be ended when the cultivated biomass of mycelium is collected at step 108. The incubation step 106 may be ended at a predetermined time or when a predetermined concentration of mycelium biomass is reached. There may be some continued growth of the mycelium after the cultivated biomass is collected at step 108. Optionally, the mycelium biomass may be treated to stop growth of the mycelium.

At step 108 the cultivated mycelium biomass is collected. The collected biomass can be made into a slurry by adding the dry mycelium biomass to an aqueous solution. At step 108 a concentration of the collected biomass of mycelium in such a slurry may be adjusted based on the subsequent web-forming process at step 110. In some examples, the cultivated biomass of mycelium is in the form of slurry. The concentration of the biomass of mycelium may be adjusted by increasing a volume of the slurry or concentrating the mycelium biomass by removing at least a portion of the liquid from the slurry. In some examples, the concentration of the mycelium biomass may be adjusted to a concentration of from about 10 g/L to about 30 g/L, about 10 g/L to about 25 g/L, or about 10 g/L to about 20 g/L. In other examples, the cultivated biomass of mycelium may be collected and dried.

In some aspects, a bonding agent can optionally be added to the cultivated biomass of mycelium before, during, or after the web-forming process at step 110. The bonding agent can be added before, during, or after collecting the cultivated biomass of mycelium and/or adjusting the concentration of the cultivated biomass of mycelium. The bonding agent can include any adhesive, resin, cross-linking agent, or polymeric matrix material described herein and combinations thereof.

In some aspects, the plurality of branches of hyphae can optionally be disrupted, before, during, or after the web-forming process at step 110. The plurality of branches of hyphae can be disrupted according to any of the mechanical and/or chemical methods described herein for disrupting hyphae. For example, prior to the web-forming process at step 110, the hyphae can mechanically disrupted by a mechanical action such as blending, chopping, impacting, compacting, bounding, shredding, grinding, compressing, high-pressure waterjet, or shearing forces. The hyphae can be disrupted before, during, or after adjusting the concentration of the cultivated biomass of mycelium.

In some aspects, the collected biomass of mycelium can optionally be combined with natural and/or synthetic fibers, before, during, or after the web-forming process at step 110. In one aspect, the fibers can be combined with the mycelium before, during, or after disrupting the plurality of branches of hyphae. The fibers can have any suitable dimension. Non-limiting examples of suitable fibers include cellulosic fibers, cotton fibers, rayon fibers, Lyocell fibers, TENCEL™ fibers, polypropylene fibers, and combinations thereof. In one aspect, the fibers can have a length of less than about 25 mm, less than about 20 mm, less than about 15 mm, or less than about 10 mm. For example, the fibers can have a length of from about 1 mm to about 25 mm, about 1 mm to about 20 mm, about 1 mm to about 15 mm, about 1 mm to about 10 mm, about 1 mm to about 5 mm, about 5 mm to about 25 mm, about 5 mm to about 20 mm, about 5 mm to about 15 mm, about 5 mm to about 10 mm, about 10 mm to about 25 mm, about 10 mm to about 20 mm, or about 10 mm to about 15 mm. The fibers may be combined with the mycelium in a desired concentration. In one example, the fibers may be combined with the mycelium in an amount of from about 1 wt % to about 25 wt %, about 1 wt % to about 20 wt %, about 1 wt % to about 15 wt %, about 1 wt % to about 10 wt %, about 1 wt % to about 5 wt %, about 5 wt % to about 25 wt %, about 5 wt % to about 20 wt %, about 5 wt % to about 15 wt %, about 5 wt % to about 10 wt %, about 10 wt % to about 25 wt %, about 10 wt % to about 20 wt %, or about 10 wt % to about 15 wt %.

At step 110, the biomass of mycelium collected in step 108 can be treated according to a web-forming process to form a hyphal network. The web-forming process can include any of the wet-lay, dry array, or air-lay techniques described herein. The hyphae of the web formed in step 110 can optionally be chemically and/or thermally bonded using any of the bonding agents described herein.

Optionally, the web-forming at step 110 can include laying the branches of hyphae on a supporting material. As described herein, in some aspects the supporting material is a reinforcing material. Non-limiting examples of a suitable supporting material include a woven fiber, a mass of contiguous, disordered fibers (e.g., non-woven fibers), perforated material (e.g., a metal mesh or perforated plastic), a mass of discontiguous particles (e.g., pieces of woodchip), a cheesecloth, a fabric, a knot fiber, a scrim, and a textile. The hyphae can be combined with, contacted with, and/or incorporated into the supporting material. For example, in some aspects, the hyphae can be woven, twisted, would, folded, entwined, entangled, and/or braided together with the supporting material to form a mycelium material, as described herein. In some aspects, the fibers can be laid on the supporting material before, during, and/or after adding a chemical bonding agent. In some aspects, a reinforcing material can be combined with the branches of hyphae before, during, or after the web-forming step 110.

At step 112, the hyphal network formed at step 110 can undergo an entanglement process to entangle the plurality of branches of hyphae in the hyphal network. The entanglement process can include needle punching (also referred to as felting) and/or hydroentangling. When a supporting material is present, the entanglement process optionally includes entangling at least a portion of the plurality of hyphae branches with the supporting material. The entanglement process can form mechanical interactions between hyphae and optionally between hyphae and a supporting material (when present). In some embodiments, the hyphae are not entangled with a supporting material.

In some aspects, the entanglement at step 112 is achieved through a needle punching or needle felting process in which one or more needles are passed into and out of the hyphal network. Movement of the needles in and out of the hyphal network facilitate entangling the hyphae and optionally orienting the hyphae. A needle punch having an array of needles can be used to punch the hyphal network at a plurality of locations with each pass of the needle array. The number of needles, spacing of needles, shape of the needles, and size of the needles (i.e., needle gauge) can be selected to provide the desired degree of entanglement of the hyphal network. For example, the needles may be barbed and have any suitable shape, non-limiting examples of which include a pinch blade, a star blade, and a conical blade. The number of needle punches per area and the punching rate can also be selected to provide the desired degree of entanglement of the hyphal network. The parameters of the needle punching or needle felting process can be selected at least based in part on the fungal species, the morphology and dimensions of the hyphae forming the hyphal network, the desired degree of entanglement, and/or end-use applications of the mycelium material.

In some aspects, the entanglement at step 112 is achieved through a hydroentanglement process. The hydroentanglement process directs high pressure liquid jets into the hyphal network to facilitate entangling the hyphae. The liquid may be any suitable liquid, an example of which includes water. The entanglement process can include a spinneret having an array of holes configured to direct a stream of liquid at a specific location in the hyphal network. The diameter of the holes can be selected to provide a jet of liquid having the desired diameter to direct at the hyphal network. Additional aspects of the spinneret, such as the number of holes in the array and the spacing of the holes in the array can be selected to provide the desired degree of entanglement of the hyphal network. The hyphal network and the spinneret may move relative to one another such that the liquid jets are directed at the hyphal network in a pattern. For example, the spinneret may move relative to the hyphal network in a generally "Z" or "N" shaped pattern to provide multiple passes of the spinneret over the hyphal network. The number of passes and the application pattern can be selected to provide the desired degree of entanglement of the hyphal network. The parameters of the hydroentanglement process can be selected based at least in part on the fungal species, the morphology and dimensions of the hyphae forming the hyphal network, the desired degree of entanglement, and/or end-use applications of the mycelium material. In some examples, the hydroentanglement process occurs in phases in which a portion of the mycelium material is web-formed (e.g., wet-laying), the hydroentanglement process proceeds, and then a second portion of the mycelium material is web-formed on top of the first portion and the hydroentanglement process is repeated. This process of web-forming a portion of the mycelium material and hydroentangling the web-formed portion can be repeated any number of times until a final thickness of material is web-formed.

The liquid pressure, the diameter of the openings in the spinneret, and/or the flow rate of liquid can be selected to provide the desired degree of entanglement of the hyphal network and optionally entanglement of the hyphal network and a supporting material. For example, the liquid pressure during the hydroentanglement process can be at least 100 psi, at least 200 psi, at least 300 psi, at least 400 psi, at least 500 psi, at least 600 psi, at least 700 psi, at least 800 psi, at least 900 psi, or at least 1000 psi. In some examples, the liquid jet pressure is from about 700 to about 900 psi. In some examples, the diameter of the openings in the spinneret is at least about 10 microns, at least about 30 microns, at least about 50 microns, at least about 70 microns, at least about 90 microns, at least about 110 microns, at least about 130 microns, or at least about 150 microns. For example, the diameter of the openings in the spinneret can be from about 10 microns to about 150 microns, from 20 microns to about 70 microns, about 30 microns to about 80 microns, about 40 microns to about 90 microns, about 50 microns to about 100 microns, about 60 microns to about 110 microns, or about 70 microns to about 120 microns. In some examples, the openings have a diameter of about 50 microns. The flow rate of liquid can be from about 100 mL/min. to about 300 mL/min. in some examples. In some examples, the belt speed during the entanglement process is about 1 meter/minute.

After completion of the entanglement process at 112, the mycelium material can be processed according to any of the post-processing methods and/or treatments described herein. Non-limiting examples of post-processing methods and treatments include treatment with a plasticizer, treatment with a tannin and/or dye, treatment with a preservative, treatment with a protein source, treatment with a coating and/or finishing agent, a drying process, a rolling or pressing process, and treatment in an embossing process.

In various embodiments, the liquid or solid substrate may be supplemented with one or more different nutritional sources. The nutritional sources may contain lignocellulose, simple sugars (e.g. dextrose, glucose), complex sugars, agar, malt extract, a nitrogen source (e.g. ammonium nitrate, ammonium chloride, amino acids) and other minerals (e.g. magnesium sulfate, phosphate). In some embodiments, one or more of the nutritional sources may be present in lumber waste (e.g. sawdust including from hardwoods, beeches, and hickory) and/or agricultural waste (e.g. livestock feces, straw, corn stover). Once the substrate has been inoculated and, optionally, supplemented with one or more different nutritional sources, cultivated mycelium may be grown. Methods of growing mycelium have been well established in the art. Exemplary methods of growing mycelium include but are not limited to U.S. Pat. Nos. 5,854,056; 4,960,413; and 7,951,388.

In some embodiments, the growth of the cultivated mycelium will be controlled to prevent the formation of fruiting bodies. Various methods of preventing fruiting body formation as discussed in detail in U.S. Patent Publication No. 2015/0033620; U.S. Pat. Nos. 9,867,337; and 7,951,388. In other embodiments, the cultivated mycelium may be grown so that it is devoid of any morphological or structural variations. Depending on the embodiment sought, growing conditions such as exposure to light (e.g. sunlight or a growing lamp), temperature, carbon dioxide may be controlled during growth.

In some embodiments, the cultivated mycelium may be grown on an agar medium. Nutrients may be added to the agar/water base. Standard agar media commonly used to cultivate mycelium material include, but are not limited to, a fortified version of Malt Extract Agar (MEA), Potato Dextrose Agar (PDA), Oatmeal Agar (OMA), and Dog Food Agar (DFA).

In most embodiments, the cultivated mycelium material may be grown as a solid mass and may later be disrupted. Cultivated mycelium material that is disrupted may be a live mat, preserved, or otherwise treated to kill the mycelium (i.e., stop mycelium growth) as described below.

In some embodiments, cultivated mycelium material may be grown to include elongate hyphae defining fine filaments that interconnect with one another, and further may interconnect with various supporting materials provided in a growing procedure, as further described below. The fine filaments may be analyzed using an optical magnifying or imaging device to determine if a grown length of the fine filaments is adequate to support sufficient network interconnection between the fine filaments and various additives. The fine filaments should not only be of a sufficient length, but also flexible to provide adequate interconnection therebetween.

In some embodiments, cultivated mycelium material may be processed using a dry array, a wet-lay, or an air-lay technique. In dry-lay or dry array, an inert or growing mycelium network of branched hyphae may be pulled apart and detangled to expand the volume of the network. Similarly, in a wet-lay technique, an inert or growing mycelium network of branched hyphae may be saturated in a liquid medium to detangle and expand the volume of the network. Further, in an air-lay technique, an inert or growing mycelium network of branched hyphae may be suspended in air to create a web that expands the volume of the network. After such a technique, the expanded network can be compressed to provide a dense or compacted network. The web can be densified to include an overall density profile of at least 6 gm per cubic meter. A compacted web can be embossed with a replicated leather pattern for providing a leather alternative material.

In some embodiments, the method comprises a step of web-forming the collected biomass of the mycelium. In some embodiments, the step of web-forming the collected biomass of mycelium comprises depositing the biomass of mycelium on a supporting material.

In some embodiments, the supporting material comprises a woven fiber, a non-woven fiber, a mesh, a perforated plastic, woodchips, a cheesecloth, a fabric, a knot fiber, a scrim, a textile, or combinations thereof.

In some embodiments, the entangling the plurality of branches of hyphae comprises entangling at least a portion of the plurality of branches of hyphae with the sup-porting material.

In some embodiments, the method further comprises combining a reinforcing material with the biomass of mycelium one of prior to the web-forming step, during the web-forming step, or after the web-forming step. In some embodiments, web-forming comprises wet-laying, air-laying, or dry-laying.

In some embodiments, the method further comprises combining one of natural fibers, synthetic fibers, or a combination thereof with the biomass of mycelium one of prior to the web-forming step, during the web-forming step, or after the web-forming step.

In some embodiments, the fibers have a length of less than 25 millimeters.

Disrupted Cultivated Mycelium Material

Various types of cultivated mycelium material including one or more masses of branching hyphae may be disrupted at a variety of points during the production process, thus generating one or more masses of disrupted branching hyphae. In such embodiments, the cultivated mycelium material comprises one or more masses of disrupted branching hyphae. The cultivated mycelium material may be disrupted before or after adding a bonding agent. In one aspect, the cultivated mycelium material may be disrupted at the same time as adding a bonding agent. Exemplary embodiments of disruptions include, but are not limited to, mechanical action, chemical treatment, or a combination thereof. For example, the one or more masses of branching hyphae may be disrupted by both a mechanical action and chemical treatment, a mechanical action alone, or chemical treatment alone.

In some embodiments, the one or more masses of branching hyphae is disrupted by a mechanical action. Mechanical actions may include blending, chopping, impacting, compacting, bounding, shredding, grinding, compressing, high-pressure, waterjet, and shearing forces. In some embodiments, the mechanical action includes blending the one or more masses of branching hyphae. Exemplary methods of achieving such a disruption include use of a blender, a mill, a hammer mill, a drum carder, heat, pressure, liquid such as water, a grinder, a beater, and a refiner. In an exemplary production process, a cultivated mycelium material is mechanically disrupted by a conventional unit operation, such as homogenization, grinding, coacervation, milling, jet milling, waterjet and the like.

According to a further aspect, the mechanical action includes applying a physical force to the one or more masses of branching hyphae such that at least some of the masses of branching hyphae are aligned in a particular formation, e.g., aligned in a parallel formation, or along or against the stress direction. The physical force can be applied to one or more layers of a cultivated mycelium material or composite mycelium material. Such disrupted mycelia material can typically be constructed with layers with varying orientation. Exemplary physical forces include, but are not limited to, pulling and aligning forces. Exemplary methods of achieving such a disruption include use of rollers and drafting equipment. In some embodiments, a physical force is applied in one or more directions such that the at least some of the masses of branching hyphae are aligned in parallel in one or more directions, wherein the physical force is applied repeatedly. In such embodiments, the physical force may be applied at least two times, e.g., at least three times, at least four times, or at least five times.

In some other embodiments, the one or more masses of branching hyphae is disrupted by chemical treatment. In such embodiments, the chemical treatment includes contacting the one or more masses of branching hyphae with a base or other chemical agent sufficient to cause a disruption including, but not limited to alkaline peroxide, beta-glucanase, surfactants, acids, and bases such as sodium hydroxide and sodium carbonate (or soda ash). The pH of the cultivated mycelium material in solution can be monitored for the purpose of maintaining the optimal pH.

In some embodiments, the disruptions described herein generate one or more masses of disrupted branching hyphae, e.g., sub-networks. As used herein, a "sub-network" refers to discrete masses of branching hyphae that are produced after disruption, e.g., a mechanical action or chemical treatment. A sub-network may come in a wide assortment of shapes, e.g., sphere-, square-, rectangular-, diamond-, and odd-shaped sub-networks, etc., and each sub-network may come in varied sizes. The cultivated mycelium material may be disrupted sufficiently to produce one or more masses of disrupted branching hyphae, e.g., sub-networks, having a size in the desired ranges. In many instances, the disruption can be controlled sufficiently to obtain both the size and size distribution of the sub-network within a desired range. In other embodiments, where more precise size distributions of sub-networks are required, the disrupted cultivated mycelium material can be further treated or selected to provide the desired size distribution, e.g. by sieving, aggregation, or the like. For example, a sub-network may have a size represented by, e.g., length, of about 0.1 mm to about 5 mm, inclusive, e.g., of about 0.1 mm to about 2 mm, about 1 mm to about 3 mm, about 2 mm to about 4 mm, and about 3 mm to about 5 mm. In some embodiments, a sub-network may have a size represented by a length of about 2 mm. The "length" of a sub-network is a measure of distance equivalent to the most extended dimension of the sub-network. Other measurable dimensions include, but are not limited to, length, width, height, area, and volume.

In various embodiments, physical force may be used to create new physical interactions (i.e. re-entangle) between the one or more masses of branching hyphae after disruption. Various known methods of creating entanglements between fiber may be used, including methods of creating non-woven materials by creating mechanical interactions between fibers. In some embodiments described below, hydroentanglement may be used to create mechanical interactions between the hyphae after the hyphae have disrupted.

Preserved Cultivated Mycelium Material

Once the cultivated mycelium material has been grown, it may be optionally separated from the substrate in any manner known in the art, and optionally subjected to post-processing in order to prevent further growth by killing the mycelium and otherwise rendering the mycelium imputrescible, referred to herein as "preserved mycelium material". Suitable methods of generating preserved mycelium material can include drying or desiccating the cultivated mycelium material (e.g. pressing the cultivated mycelium material to expel moisture) and/or heat treating the cultivated mycelium material.

In a specific embodiment, the cultivated mycelium material is pressed at 190,000 pounds force to 0.25 inches for 30 minutes. The cultivated mycelium material can be pressed by at least 100, 1000, 10,000, 100,000, 110,000, 120,000, 130,000, 140,000, 150,000, 160,000, 170,000, 180,000, 190,000, 200,000, or 300,00 or more pounds force. The cultivated mycelium material can be pressed to at least 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, or 1 inch or more. The cultivated mycelium material can be pressed to at least 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, or 1 centimeter or more. The cultivated mycelium material can be pressed for at least 1 min, 5 min, 10 min, 15 min, 20 min, 25 min, 30 min, 35 min, 40 min, 45 min, 50 min, 55 min, or 60 min or more.

Suitable methods of drying organic matter to render it imputrescible are well known in the art. In one specific embodiment, the cultivated mycelium material is dried in an oven at a temperature of 100° F. or higher. In another specific embodiment, the cultivated mycelium material is heat pressed.

In other instances, living or dried cultivated mycelium material is processed using one or more solutions that function to remove waste material and water from the mycelium. In some embodiments, the solutions include a solvent such as ethanol, methanol or isopropyl alcohol. In some embodiments, the solutions include a salt such as calcium chloride. Depending on the embodiments, the cultivated mycelium material may be submerged in the solution for various durations of time with and without pressure. In some embodiments the cultivated mycelium material may be submerged in several solutions consecutively. In a specific embodiment, the cultivated mycelium material may first be submerged in one or more first solutions including an alcohol and a salt, then submerged in a second solution including alcohol. In another specific embodiment, the cultivated mycelium material may first be submerged in one or more first solutions including an alcohol and a salt, then submerged in a second solution including water. After treatment with solution, the cultivated mycelium material may be pressed using a hot or cold process and/or dried using various methods including air drying and/or vacuum drying. U.S. Patent Publication No. 2018/0282529, the entirety of which is incorporated herein by reference, describes these embodiments in detail.

In one aspect, the cultivated mycelium material may be fixated by adjusting pH using an acid such as formic acid. In specific embodiments, the pH will be at least 2, 3, 4 or 5. In some embodiments, the pH of the cultivated mycelium material will be adjusted to an acidic pH of 3 in order to fix the cultivated mycelium material using various agents such as formic acid. In specific embodiments, the pH will be adjusted to a pH less than 6, 5, 4 or 3 in order to fix the cultivated mycelium material. In one embodiment, the pH will be adjusted to a pH of 5.5.

Bonding Agents

Various aspects of the present disclosure include a bonding agent. A "bonding agent" as used herein may include any suitable agent that provides added strength and/or other properties such as additional softness, strength, durability, and compatibility. A bonding agent may be an agent that reacts with some portion of the cultivated mycelium material, enhances the treatment of the cultivated mycelium material, co-treated with the cultivated mycelium material or treated separately, but as a network with the cultivated mycelium material, to produce a composite mycelium material. In some aspects, a bonding agent is added prior to the disruption. In other aspects, a bonding agent is added after the disruption. In some other aspects, a bonding agent is added while the sample is being disrupted. Bonding agents include an adhesive, a resin, a crosslinking agent, and/or a matrix. A composite mycelium material described herein includes cultivated mycelium material and bonding agents that may be water-based, 100% solids, UV and moisture cure, two-component reactive blend, pressure sensitive, self-crosslinking hot melt, and the like.

In some embodiments, the bonding agent is selected from the group including a natural adhesive or a synthetic adhesive. In such embodiments, the natural adhesive may include a natural latex-based adhesive. In specific embodiments, the natural latex-based adhesive is leather glue or weld. The bonding agents may include anionic, cationic, and/or non-ionic agents. In one aspect, the bonding agents may include crosslinking agents.

In some embodiments, the bonding agent has a particle size of less than or equal to 1 µm, a sub-zero glass transition temperature, or a self-crosslinking function. In some embodiments, the bonding agent has a particle size of less than or equal to 1 µm, a sub-zero glass transition temperature, and a self-crosslinking function. In some embodiments, the bonding agent has a particle size of less than or equal to 1 µm. In some embodiments, the bonding agent has a sub-zero glass transition temperature. In some embodiments, the bonding agent has a self-crosslinking function. In some embodiments, the bonding agent has a particle size of less than or equal to 500 nanometers. Specific exemplary bonding agents include vinyl acetate ethylene copolymers such as Dur-O-Set® Elite Plus and Dur-O-Set® Elite 22.

In some embodiments, the bonding agent has a glass transition temperature of $-100$--$10°$ C., $-100$--$90°$ C., $-90$--$80°$ C., $-80$--$70°$ C., $-70$--$60°$ C., $-60$--$50°$ C., $-50$--$40°$ C., $-40$--$30°$ C., $-30$--$20°$ C., $-20$--$10°$ C., $-10$--$10°$ C., $-30$--$25°$ C., $-25$--$20°$ C., $-20$--$15°$ C., $-15$--$10°$ C., $-10$--$5°$ C., $-5$--$0°$ C., $-90°$ C., $-80°$ C., $-70°$ C., $-60°$ C., $-50°$ C., $-40°$ C., $-35°$ C., $-30°$ C., $-25°$ C., $-20°$ C., $-15°$ C., $-10°$ C., $-5°$ C., or $0°$ C. In some embodiments, the bonding agent has a glass transition temperature of $-15°$ C.

Other exemplary bonding agents include, but are not limited to transglutaminase, polyamide-epichlorohydrin resin (PAE), citric acid, genipin, alginate, vinyl acetate-ethylene copolymers, and vinyl acetate-acrylic copolymers. In some embodiments, the binder is polyamide-epichlorohydrin resin (PAE). In some embodiments, the binder is a vinyl acetate-ethylene copolymer. In some embodiments, the binder is a vinyl acetate-acrylic copolymer.

In some embodiments, the bonding agent includes one or more reactive groups. For example, the bonding agent reacts with active hydrogen containing groups such as amine, hydroxyl, and carboxyl groups. In a specific embodiment, the bonding agent crosslinks one or more masses of branching hyphae via the one or more reactive groups. In some instances, amines are present on chitin, and hydroxyl and carboxyl groups are present on the polysaccharides and proteins surrounding the chitin. In a specific embodiment, PAE includes cationic azetidinium groups. In such embodiments, the cationic azetidinium groups on PAE act as reactive sites in the polyamideamine backbone, and react with active hydrogen containing groups such as amine, hydroxyl, and carboxyl groups, in the one or more branches of hyphae.

Further examples of bonding agents include, but are not limited to, citric acid in combination with sodium hypophosphite or monosodium phosphate or sodium dichloroacetate, alginate in combination with sodium hypophosphite or monosodium phosphate or sodium dichloroacetate, epoxidized soybean oil, N-(3-Dimethylaminopropyl)-N'-ethylcarbodiimide hydrochloride (EDC), polyamide epichlorohydrin resin (PAE), and ammonium persulfate. Some examples of bonding agents include epoxies, isocyanates, sulfur compounds, aldehydes, anhydrides, silanes, aziridines, and azetidinium compounds and compounds with all such functional groups. Possible formaldehyde-containing bonding agents include formaldehyde, phenol formaldehyde, urea formaldehyde, melamine urea formaldehyde, melamine formaldehyde, phenol resorcinol and any combinations of them.

Additional examples of suitable bonding agents include latex materials, such as butadiene copolymers, acrylates, vinyl-acrylics, styrene-acrylics, styrene-butadiene, nitrile-butadiene, polyvinyl acetates, olefin containing polymers, e.g., vinyl acetate-ethylene copolymers, vinyl ester copolymers, halogenated copolymers, e.g., vinylidene chloride polymers. Latex-based agents, when used, can contain functionality. Any kind of latex can be used, including acrylics. Representative acrylics include those formed from ethyl acrylate, butyl acrylate methyl (meth)acrylate, carboxylated versions thereof, glycosylated versions thereof, self-cross-linking versions thereof (for example, those including N-methyl acrylamide), and copolymers and blends thereof, including copolymers with other monomers such as acrylonitrile. Natural polymers such as starch, natural rubber latex, dextrin, lignin, cellulosic polymers, saccharide gums, and the like can also be used. In addition, other synthetic polymers, such as epoxies, urethanes, phenolics, neoprene, butyl rubber, polyolefins, polyamides, polypropylene, polyesters, polyvinyl alcohol, and polyester amides can also be used. The term "polypropylene" as used herein includes polymers of propylene or polymerizing propylene with other aliphatic polyolefins, such as ethylene, 1-butene, 1-pentene, 3-methyl-1-butene, 4-methyl-1-pentene, 4-methyl-1-hexene, 5-methyl-1-hexene and mixtures thereof. In specific embodiments, bonding agents include, but are not limited to, natural adhesives (e.g. natural latex-based adhesives such as leather glue or weld, latex, soy protein-based adhesives), synthetic adhesives (polyurethane), neoprene (PCP), acrylic copolymer, styrene-butadiene copolymer, ethylene-vinyl acetate-b, nitrocellulose, polyvinyl acetate (PVA), and vinyl acetate ethylene (VAE). In other embodiments, the bonding agent is VAE.

In one aspect, one or more bonding agents may be incorporated within the cultivated mycelium material to be bonded, either in its disrupted or undisrupted state, e.g., embedded throughout the material, or added as a thin coating layer, such as by spraying, dipping, rolling, coating, and the like, to produce a composite mycelium material. In one other aspect, one or more bonding agents may be incorporated at the same time the disruption occurs. Any suitable method of bonding may be used according to the present disclosure. Bonding of the surfaces may occur on drying, and a strong cured bond can be developed. The bonding of one or more bonding agents may include the use of open or closed-cell foam materials like urethane, olefinic rubber, and vinyl foam materials, as well as textiles, metal and fabrics in various lamination arrangements.

A bonded assembly (i.e., a laminate) may be prepared by uniformly applying the aqueous adhesive to the cultivated mycelium material. In some embodiments, the lamina includes two successive layers. In some embodiments, the lamina includes three successive layers. Various coating methods may be used such as spraying, roll coating, saturation, and the like. The coated substrate can be dried before bonding.

A composite mycelium material may be chemically bonded by impregnating the composite mycelium material with a chemical binder to link fibers to one another, including linking cellulosic fibers to one another. Non-limiting examples of suitable binders include gum arabic, vinyl acetate-ethylene (VAE), and adhesives. Examples of suitable adhesive include S-10, available from US Adhesives, U.S.A., and Bish's Original Tear Mender Instant Fabric & Leather Adhesive, available from Tear Mender, U.S.A. One example of a suitable VAE-based binder is Dur-O-Set® Elite 22, which is available from Celanese Emulsions, U.S.A. One other example of a suitable VAE-based binder is Dur-O-Set® Elite Plus, which is available from Celanese Emulsions, U.S.A. Another exemplary binder includes X-LINK® 2833, available from Celanese Emulsions, U.S.A., and which is described as a self-crosslinking vinyl acetate acrylic. In a web of interconnected hyphae, a chemical binder will have to saturate the web to diffuse through the web and reach the core of the network. Thus, a composite mycelium material may be immersed in a binder solution to fully impregnate the material. A spray application of a chemical binder may also be provided to a composite mycelium material. A spray application of a chemical binder may be aided by capillary action for dispersal, or may be aided by a vacuum application to draw the chemical binder through the material. A coater may also be used for coating a composite mycelium material.

A composite mycelium material may be bonded using a thermal bonding technique, wherein an additive is provided along with the composite mycelium material. This additive may be a "meltable" material that melts at a known heat level. The cellulosic material of the composite mycelium material does not melt, such that the composite mycelium material along with the additive can be heated to the additive's melting point. As melted, the additive can disperse within the composite mycelium material and then be cooled to harden the overall material.

The present disclosure is not limited to the above lists of suitable bonding agents. Other bonding agents are known in the art. The role of a bonding agent, regardless of type, is to, in part, provide several reactive sites per molecule. The type and amount of bonding agent used in the present disclosure depend on what properties are desired. In various embodiments, an effective amount of bonding agent may be used. As used herein, an "effective amount" with respect to a bonding agent refers to the amount of agent that is sufficient to provide added strength and/or other properties such as additional softness, strength, durability, and compatibility.

The bonding agent can be added to cultivated mycelium material that has been pressed, had one or more masses of hyphae disrupted, and/or hydroentangled. The bonding agent can be added to cultivated mycelium material before disruption of the one or more masses of branching hyphae or pressing. The bonding agent can be added to cultivated mycelium material during disruption of the one or more masses of branching hyphae or pressing. The bonding agent can be added to cultivated mycelium material after disruption of the one or more masses of branching hyphae or pressing.

In some embodiments, a pressed cultivated mycelium material is contacted with a bonding agent. In some embodiments, a disrupted cultivated mycelium material is contacted with a bonding agent. In some embodiments, the bonding agent is added before the masses of branching hyphae are disrupted. In some embodiments, the bonding agent is added during the disruption of the one or more masses of branching hyphae. In some embodiments, the bonding agent is added after the masses of branching hyphae are disrupted. In some embodiments, the bonding agent is added before the cultivated mycelium material is pressed. In some embodiments, the bonding agent is added during the pressing of the cultivated mycelium material. In some embodiments, the bonding agent is added after the cultivated mycelium material is pressed.

Supporting Materials

According to one aspect, the cultivated mycelium material or composite mycelium material may further include a supporting material, e.g., to form a bonded assembly, i.e., a laminate. As used herein, the term "supporting material" refers to any material, or combination of one or more materials, that provide support to the cultivated mycelium material or composite mycelium material. In some embodiments, the support material is a scaffold. In some embodiments, the support material is a scrim.

In some embodiments, the supporting material is entangled within the cultivated mycelium material or composite mycelium material, e.g., a reinforcing material. In some other embodiments, the supporting material is positioned on a surface of the cultivated mycelium material or composite mycelium material, e.g., a base material. In some embodiments, the supporting material includes, but is not limited to, a mesh, a cheesecloth, a fabric, a plurality of fibers, a knit textile, a woven textile, a non-woven textile, a knit fiber, a woven fiber, a non-woven fiber, a film, a surface spray coating, and a fiber additive. In some embodiments, a knit textile is a knit fiber. In some embodiments, a woven textile is a woven fiber. In some embodiments, a non-woven textile is a non-woven fiber. In some embodiments, the supporting material may be constructed in whole or in part of any combination of synthetic fiber, natural fiber (e.g. lignocellulosic fiber), metal, or plastic. The supporting material may be entangled, in part, within the cultivated mycelium material or composite mycelium material, e.g., using known methods of entanglement like felting or needle punching. In some aspects, the supporting material is not entangled within the cultivated mycelium material or composite mycelium material. Various methods known in the art may be used to form a laminate as described herein. In some other embodiments, the supporting material includes a base material that is, e.g., applied to a top or bottom surface of a cultivated mycelium material or composite mycelium material. The supporting material may be attached through any means known in the art, including, but not limited to, chemical attachment, e.g., a suitable spray coating material, in particular, a suitable adhesive, or alternatively, e.g., due to their inherent tackiness.

A laminate according to the present disclosure may include at least one supporting material. If more than one supporting material is used, the cultivated mycelium material or composite mycelium material can include an inner layer of a sandwich of multiple layers, with the inner layer, e.g., being a supporting material such as a knit or woven or scaffold. In this instance, the supporting material would be embedded within the cultivated mycelium material or composite mycelium material.

Figure 11B:
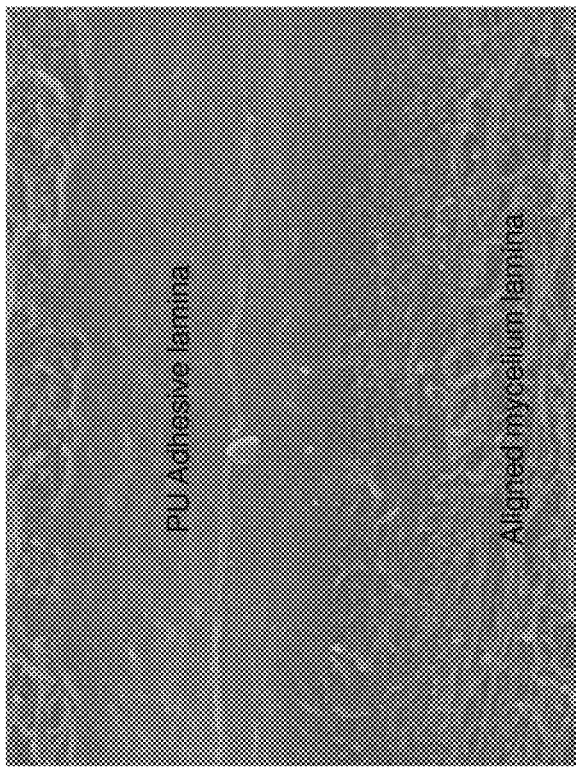
FIG. 11B depicts scanning electron microscope (SEM) micrographs of two aligned mycelium lamina bonded with polyurethane hot melt adhesive at 500× magnification.
Figure 11A:
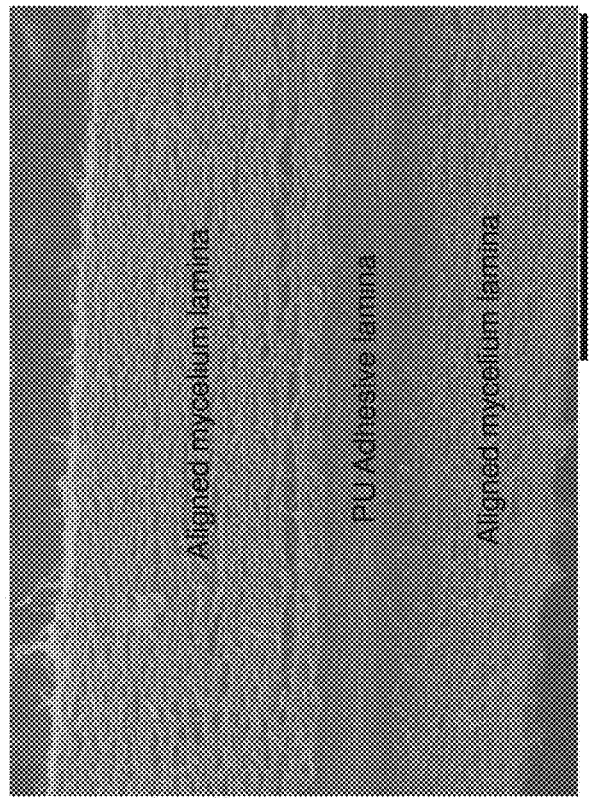
FIG. 11A depicts scanning electron microscope (SEM) micrographs of two aligned mycelium lamina bonded with polyurethane hot melt adhesive at 150×

Supporting materials as used herein can include scaffolds or textiles. A "scaffold" as used herein refers to any material known in the art that is distinct from the cultivated mycelium material and provides support to the cultivated mycelium material or composite mycelium material. A "scaffold" may be embedded within the cultivated mycelium material or composite mycelium material or layered on, under, or within the cultivated mycelium material or composite mycelium material. In the present disclosure, all kinds and types of scaffolds may be used, including, but not limited to films, textiles, scrims, and polymers. A "textile" as used herein refers to a type of scaffold that may be any woven, knitted, or non-woven fibrous structure. Where multiple layers are included in the cultivated mycelium material or composite mycelium material, such as shown in FIGS. 11A and 11B, the two or more layers may include a scaffold; or in other embodiments, the two or more layers may include a cheesecloth. Useful scaffolds include woven and non-woven scaffolds, directional and non-directional scaffolds, and orthogonal and non-orthogonal scaffolds. Useful scaffolds may include conventional scaffolds, which include a plurality of yarns oriented in the machine direction, or along the length of the scaffold, and a plurality of yarns oriented in the cross-machine direction, or across the width of the scaffold. These yarns may be referred to as the warp yarns and weft yarns, respectively. Numerous yarns can be employed including, but not limited to, fibrous materials and polymers. For example, the yarns can include, but are not limited to, fiberglass, aluminum, or aromatic polyamide polymers. In one embodiment, the scaffold includes fiberglass yarns. The scaffolds may be adhered together or locked into position using conventional bonding agents such as cross-linkable acrylic resins, polyvinyl alcohol, or similar adhesives. The scaffolds may also be mechanically entangled by employing techniques such as, but not limited to, needle punching. In yet another embodiment, the scaffolds can be locked into place by weaving. A combination of supporting materials may be used according to the present disclosure.

In some embodiments, supporting materials may be incorporated into a cultivated mycelium material or composite mycelium material as described herein according to methods known in the art, including but not limited to the methods described in U.S. Pat. Nos. 4,939,016 and 6,942,711, the entirety of which are incorporated herein by reference. For example, supporting materials may be incorporated into a cultivated mycelium material or composite mycelium material via hydroentanglement. In such embodiments, supporting materials may be incorporated into a cultivated mycelium material or composite mycelium material before or after adding a bonding agent and/or a crosslinking agent. In some embodiments, a liquid such as water directed to the cultivated mycelium material or composite mycelium material through one or more pores for hydroentanglement can pass through the cultivated mycelium material or composite mycelium material. In some embodiments, the liquid is a high-pressure liquid. In some embodiments, the pressure and water flow may vary depending, in part, on the type of supporting material and pore size. In various embodiments, the water pressure is at least 100 psi, e.g., at least 200 psi, at least 300 psi, at least 400 psi, at least 500 psi, at least 600 psi, at least 700 psi, at least 800 psi, at least 900 psi, and at least 1000 psi. In various embodiments, the water pressure is about 100 psi to about 5000 psi, inclusive, e.g., about 200 psi to about 1000 psi, about 300 psi to about 2000 psi, about 400 psi to about 3000 psi, about 500 psi to about 4000 psi, and about 600 psi to about 5000 psi. In some embodiments, the water pressure is about 750 psi. In various embodiments, the one or more pores has a diameter of at least 10 microns, e.g., at least 30 microns, at least 50 microns, at least 70 microns, at least 90 microns, at least 110 microns, at least 130 microns, and at least 150 microns. In various embodiments, the one or more pores has a diameter of about 10 microns to about 150 microns, inclusive, e.g., about 20 microns to about 70 microns, about 30 microns to about 80 microns, about 40 microns to about 90 microns, about 50 microns to about 100 microns, about 60 microns to about 110 microns, and about 70 microns to about 120 microns. In some embodiments, the one or more pores has a diameter of about 50 microns.

The cultivated mycelium material or composite mycelium material may also include auxiliary agents that are used in foam materials. Auxiliary agents or additives include cross-linking agents, processing aids (e.g., drainage aid), dispersing agent, flocculent, viscosity reducers, flame retardants, dispersing agents, plasticizers, antioxidants, compatibility agents, fillers, pigments, UV protectors, fibers such as abaca fibers, and the like. It is further contemplated that a foaming agent can be used to introduce a chemical bonding agent to a composite mycelium material. Such a foaming agent can make a web of composite mycelium material more porous by introducing air to the web.

Plasticizers

Various plasticizers may be applied to the cultivated mycelium material or composite mycelium material to alter the mechanical properties of the cultivated mycelium material or composite mycelium material. In such embodiments, the cultivated mycelium material or composite mycelium material further includes a plasticizer. U.S. Pat. No. 9,555,395 discusses adding a variety of humectants and plasticization agents. Specifically, the U.S. Pat. No. 9,555,395 discusses using glycerol, sorbitol, triglyceride plasticizers, oils such as linseed oils, castor oils, drying oils, ionic and/or nonionic glycols, and polyethylene oxides. U.S. Patent Publication No. 2018/0282529 further discusses treating cultivated mycelium material or composite mycelium material with plasticizers such as glycerol, sorbitol or another humectant to retain moisture and otherwise enhance the mechanical properties of the cultivated mycelium material or composite mycelium material such as the elasticity and flexibility of the cultivated mycelium material or composite mycelium material. In such embodiments, the cultivated mycelium material or composite mycelium material is flexible.

Other similar plasticizers and humectants are well-known in the art, such as polyethylene glycol and fatliquors obtained by emulsifying natural oil with a liquid that is immiscible with oil (e.g. water) such that the micro-droplets of oil may penetrate the material. Various fatliquors contain emulsified oil in water with the addition of other compounds such as ionic and non-ionic emulsifying agents, surfactants, soap, and sulfate. Fatliquors may include various types of oil such as mineral, animal and plant-based oils. Appropriate fatliquors include, but are not limited to, Truposol® LEX fatliquour (Trumpler, Germany), Trupon® DXV fatliquor (Trumpler, Germany), Diethyloxyester dimethyl ammonium chloride (DEEDMAC), Downy fabric softener, sorbitol, m-erythritol, Tween 20 and Tween 80.

Tannins and Dyes

In various embodiments of the present disclosure, it may be ideal to impart color to the cultivated mycelium material or composite mycelium material. As discussed in U.S. Patent Publication No. 2018/0282529, tannins may be used to impart a color to cultivated mycelium material, composite mycelium material, or preserved composite mycelium material.

As cultivated mycelium material and/or composite mycelium material includes, in part, of chitin, it lacks the functional sites that are abundant in protein-based materials. Therefore, it may be necessary to functionalize the chitin in the cultivated mycelium material or composite mycelium material in order to create binding sites for acid and direct dyes. Methods of functionalizing chitin are discussed above.

Various dyes may be used to impart color to the cultivated mycelium material or composite mycelium material such as acid dyes, direct dyes, disperse dyes, sulfur dyes, synthetic dyes, reactive dyes, pigments (e.g. iron oxide black and cobalt blue) and natural dyes. In some embodiments, the cultivated mycelium material or composite mycelium material is submerged in an alkaline solution to facilitate dye uptake and penetration into the material prior to application of a dye solution. In some embodiments, the cultivated mycelium material or composite mycelium material is pre-soaked in ammonium chloride, ammonium hydroxide, and/or formic acid prior to application of a dye solution to facilitate dye uptake and penetration into the material. In some embodiments, tannins may be added to the dye solution. In various embodiments, the cultivated mycelium material or composite mycelium material may be preserved as discussed above before dye treatment or pre-treatment.

Depending on the embodiment, the dye solution may be applied to the cultivated mycelium material or composite mycelium material using different application techniques. In some embodiments, the dye solution may be applied to the one or more exterior surfaces of the cultivated mycelium material or composite mycelium material. In other embodiments, the cultivated mycelium material or composite mycelium material may be submerged in the dye solution.

In addition to pre-soaking with various solutions, agents may be added to the dye solution to facilitate dye uptake and penetration into the material. In some embodiments, ammonium hydroxide and/or formic acid with an acid or direct dye to facilitate dye uptake and penetration into the material. In some embodiments, an ethoxylated fatty amine is used to facilitate dye uptake and penetration into the processed material.

In various embodiments, a plasticization agent is added after or during the addition of the dye. In various embodiments, the plasticization agent may be added with the dye solution. In specific embodiments, the plasticization agent may be coconut oil, vegetable glycerol, or a sulfited or sulfated fatliquor.

In some embodiments, the dye solution may be maintained at a basic pH using a base such as ammonium hydroxide. In specific embodiments, the pH will be at least 9, 10, 11 or 12. In some embodiments, the pH of the dye solution will be adjusted to an acidic pH in order to fix the dye using various agents such as formic acid. In specific embodiments, the pH will be adjusted to a pH less than 6, 5, 4 or 3 in order to fix the dye.

In various methods, the cultivated mycelium material, composite mycelium material, and/or preserved composite mycelium material may be subject to mechanical working or agitation while the dye solution is being applied in order to facilitate dye uptake and penetration into the material. In some embodiments, subjecting the cultivated mycelium material, composite mycelium material, and/or preserved composite mycelium material to squeezing or other forms of pressure while in a dye solution enhanced dye uptake and penetration. In some embodiments, the cultivated mycelium material, composite mycelium material, and/or preserved composite mycelium material may be subject to sonication.

Using the methods described herein, the cultivated mycelium material or composite mycelium material may be dyed or colored such that the color of the processed cultivated mycelium material or composite mycelium material is substantially uniform. In some embodiments, the cultivated mycelium material or composite mycelium material is colored with the dye and the color of the cultivated mycelium material or composite mycelium material is substantially uniform on one or more surfaces of the cultivated mycelium material or composite mycelium material. Using the methods described above, the cultivated mycelium material or composite mycelium material may be dyed or colored such that dye and color is not just present in the surfaces of the cultivated mycelium material or composite mycelium material but instead penetrated through the surface to the inner core of the material. In such embodiments, the dye is present throughout the interior of the cultivated mycelium material or composite mycelium material.

In various embodiments of the present disclosure, the cultivated mycelium material or composite mycelium material may be dyed so that the cultivated mycelium material or composite mycelium material is colorfast. Colorfastness may be measured using various techniques such as ISO 11640:2012: Tests for Color Fastness—Tests for color fastness—Color fastness to cycles of to-and-fro rubbing or ISO 11640:2018 which is an update of ISO 11640:2012. In a specific embodiment, colorfastness will be measured according to the above using a Grey Scale Rating as a metric to determine rub fastness and change to sample. In some embodiments, the cultivated mycelium material or composite mycelium material will demonstrate strong colorfastness indicated by a Grey Scale Rating of at least 3, at least 4 or at least 5.

Protein Sources

In various embodiments, it may be beneficial to optionally treat the cultivated mycelium material or composite mycelium material with one or more protein sources that are not naturally occurring in the cultivated mycelium material or composite mycelium material (i.e. exogenous protein sources). In some embodiments, the one or more proteins are from a species other than a fungal species from which the cultivated mycelium material is generated. In some embodiments, the cultivated mycelium material or composite mycelium material may be optionally treated with a plant protein source such as pea protein, rice protein, hemp protein and soy protein. In some embodiments, the protein source will be an animal protein such as an insect protein or a mammalian protein. In some embodiments, the protein will be a recombinant protein produced by a microorganism. In some embodiments, the protein will be a fibrous protein such as silk or collagen. In some embodiments, the protein will be an elastomeric protein such as elastin or resilin. In some embodiments, the protein will have one or more chitin-binding domains. Exemplary proteins with chitin-binding domains include resilin and various bacterial chitin-binding proteins. In some embodiments, the protein will be an engineered or fusion protein including one or more chitin-binding domains. Depending on the embodiment, the cultivated mycelium material or composite mycelium material may be preserved, as described above, before treatment or treated without prior preservation.

In a specific embodiment of the disclosure, the cultivated mycelium material or composite mycelium material is submerged in a solution including the protein source. In a specific embodiment, the solution including the protein source is aqueous. In other embodiments, the solution including the protein source includes a buffer such as a phosphate buffered saline.

In some embodiments, the solution including the protein source will include an agent that functions to crosslink the protein source. Depending on the embodiment, various known agents that interact with functional groups of amino acids can be used. In a specific embodiment, the agent that functions to crosslink the protein source is transglutaminase. Other suitable agents that crosslink amino acid functional groups include tyrosinases, genipin, sodium borate, and lactases. In other embodiments, traditional tanning agents may be used to crosslink proteins including chromium, vegetable tannins, tanning oils, epoxies, aldehydes and syntans. As discussed above, due to toxicity and environmental concerns with chromium, PAE other minerals may be used such as aluminum, titanium, zirconium, iron and combinations thereof with and without chromium.

In various embodiments, treatment with a protein source may occur before, after or concurrently with preserving the cultivated mycelium material or composite mycelium material, plasticizing the cultivated mycelium material or composite mycelium material and/or dyeing the cultivated mycelium material or composite mycelium material. In some embodiments, treatment with a protein source may occur before or during preservation of the cultivated mycelium material or composite mycelium material using a solution including alcohol and salt. In some embodiments, treatment with a protein source occurs before or concurrently with dyeing the cultivated mycelium material or composite mycelium material. In some of these embodiments, the protein source is dissolved in the dye solution. In a specific embodiment, the protein source will be dissolved in a basic dye solution optionally including one or more agents to facilitate dye uptake.

In some embodiments, a plasticizer will be added to the dye solution including the dissolved protein source to concurrently plasticize the cultivated mycelium material or composite mycelium material. In a specific embodiment, the plasticizer may be a fatliquor. In a specific embodiment, a plasticizer will be added to a protein source that is dissolved in a basic dye solution including one or more agents to facilitate dye uptake.

Coating and Finishing Agents

After a cultivated mycelium material or composite mycelium material has been processed using any combination of methods as described above, the cultivated mycelium material or composite mycelium material may be treated with a finishing agent or coating. Various finishing agents common to the leather industry such as proteins in binder solutions, nitrocellulose, synthetic waxes, natural waxes, waxes with protein dispersions, oils, polyurethane, acrylic polymers, acrylic resins, emulsion polymers, water-resistant polymers and various combinations thereof may be used. In a specific embodiment, a finishing agent including nitrocellulose may be applied to the cultivated mycelium material or composite mycelium material. In another specific embodiment, a finishing agent including conventional polyurethane finish will be applied to the cultivated mycelium material or composite mycelium material. In various embodiments, one or more finishing agents will be applied to the cultivated mycelium material or composite mycelium material sequentially. In some instances, the finishing agents will be combined with a dye or pigment. In some instances, the finishing agents will be combined with a handle modifier (i.e. feel modifier or touch) including one or more of natural and synthetic waxes, silicone, paraffins, saponified fatty substances, amides of fatty acids, amides esters, stearic amides, emulsions thereof, and any combination of the foregoing. In some instances, the finishing agents will be combined with an antifoam agent. In some embodiments, an external element or force is applied to the cultivated mycelium material or composite mycelium material. In such embodiments, the external element or force includes heating and/or pressing. In some embodiments, the external element or force is hot pressing. In some embodiments, an external force is applied to the cultivated mycelium material or composite mycelium material. In such embodiments, the external force includes heating and/or pressing. In some embodiments, the external force is hot pressing.

Processed Mycelium Material

In various embodiments of the present disclosure, the cultivated mycelium material or composite mycelium material is sonicated, perforated, or vacuum-processed. Perforation may include needle-punching, air-punching, or water-punching.

In various embodiments of the present disclosure, the cultivated mycelium material or composite mycelium material may be mechanically processed and/or chemically processed in different ways both in solution (i.e. dye solution, protein solution or plasticizer) and after the cultivated mycelium material or composite mycelium material has been removed from the solution. In such embodiments, the method includes mechanically processing and/or chemically processing the cultivated mycelium material or composite mycelium material, wherein a processed mycelium material is produced.

While the cultivated mycelium material or composite mycelium material is in a solution or dispersion it may be agitated, sonicated, squeezed or pressed to ensure uptake of the solution. The degree of mechanical processing will depend on the specific treatment being applied and the level of fragility of the cultivated mycelium material or composite mycelium material at its stage in processing. Squeezing or pressing of the cultivated mycelium material or composite mycelium material may be accomplished by hand wringing, mechanical wringing, a platen press, a lino roller or a calendar roller.

Similarly, as discussed above, the cultivated mycelium material or composite mycelium material may be pressed or otherwise worked to remove solution from the composite mycelium material after it is removed from solution. Treating with a solution and pressing the material may be repeated several times. In some embodiments, the material is pressed at least two times, at least three times, at least four times, or at least five times.

Once the cultivated mycelium material or composite mycelium material is fully dried (e.g. using heat, pressing or other desiccation techniques described above), the cultivated mycelium material or composite mycelium material may be subject to additional mechanical- and/or chemical-processing. Depending on the technique used to treat the cultivated mycelium material or composite mycelium material and the resultant toughness of the cultivated mycelium material or composite mycelium material, different types of mechanical processing may be applied including but not limited to sanding, brushing, plating, staking, tumbling, vibration and cross-rolling.

In some embodiments, the cultivated mycelium material or composite mycelium material may be embossed with any heat source or through the application of chemicals. In some embodiments, the cultivated mycelium material or composite mycelium material in solution may be subjected to additional chemical processing, such as, e.g., being maintained at a basic pH using a base such as ammonium hydroxide. In specific embodiments, the pH will be at least 9, 10, 11 or 12. In some embodiments, the pH of the cultivated mycelium material or composite mycelium material in solution will be adjusted to an acidic pH in order to fix the composite mycelium material using various agents such as formic acid. In specific embodiments, the pH will be adjusted to a pH less than 6, 5, 4 or 3 in order to fix the cultivated mycelium material or composite mycelium material.

Finishing, coating and other steps may be performed after or before mechanical processing and/or chemical processing of the dried cultivated mycelium material or composite mycelium material. Similarly, final pressing steps, including ornamental steps such as embossing or engraving, may be performed after or before mechanical processing and/or chemical processing of the dried cultivated mycelium material or composite mycelium material.

Figure 14:
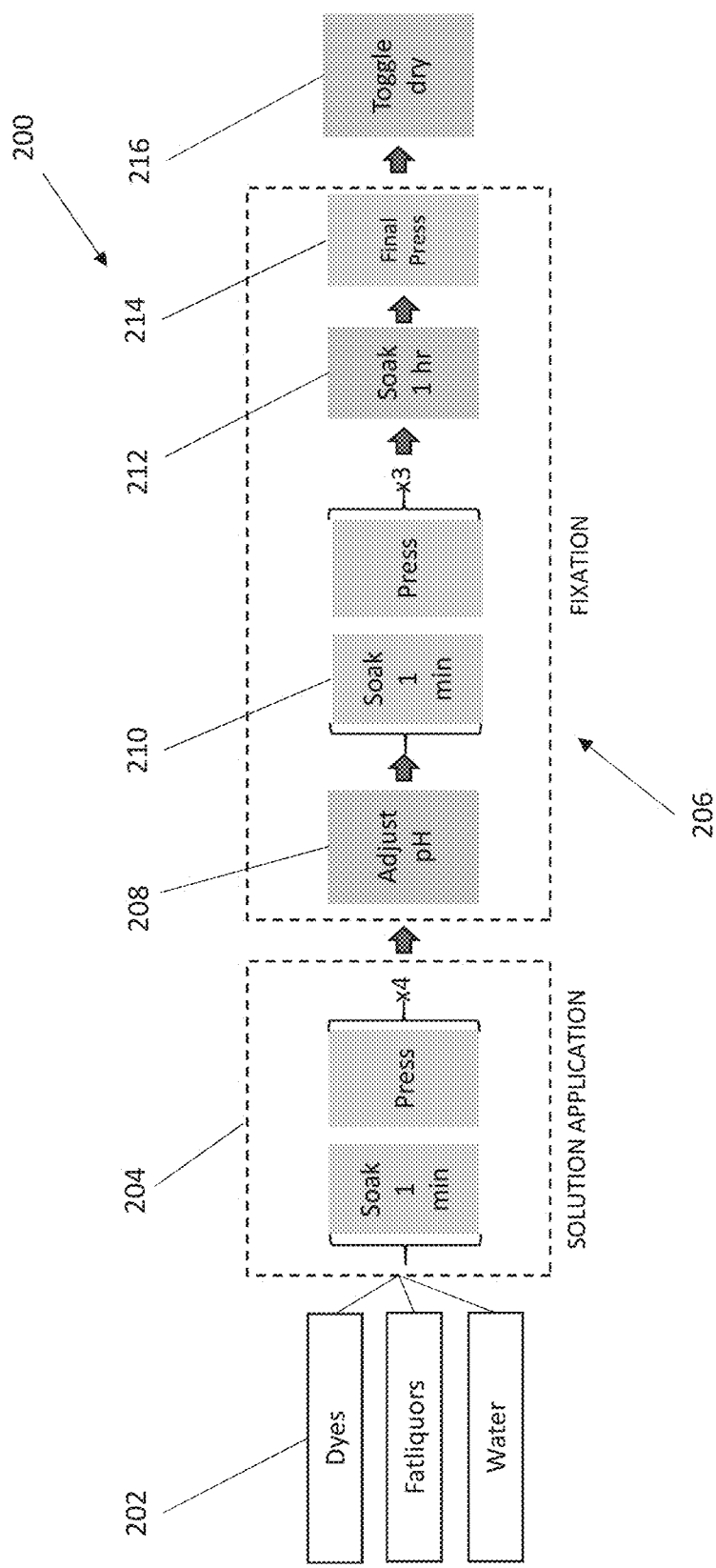
FIG. 14 shows depicts a flowchart of a method for converting raw mycelium material into a processed material.

FIG. 14 illustrates a flow chart of a method 200 for converting raw mycelium material into a crust material that can be treated according to a desired finishing process (e.g., finishing coatings, ornamental steps, final pressing steps) based on the end-use application of the material. The raw mycelium material can be dried, refrigerated, or frozen material made according to any of the processes described herein. The raw material may optionally be split on the top and/or bottom to provide a mycelium panel having the desired thickness. Splitting can also provide a smoother surface at the cut. The crust material can be dyed, plasticized, dried and/or otherwise post-processed as described herein.

Still referring to FIG. 14, at step 202 a pre-finishing treatment solution can be prepared based on the dimensions and mass of the mycelium material. In one example, the pre-finishing treatment solution can be prepared at a volume of about 6 mL per gram of wet mycelium material or 20 mL per gram of dried mycelium material. The pre-finishing treatment solution can include one or more dyes, tannins, and/or plasticizers (e.g. fatliquors) in a suitable solvent, such as water. In one example, the pre-finishing treatment solution includes one or more dyes and/or tannins and one or more fatliquors. The amount of dye added can be based on the particular type of dye and the desired color of the resulting product. An exemplary pre-finishing treatment solution includes: one or more acid dyes at a concentration to produce the desired color; about 25 g/L vegetable tannins; about 6.25 g/L Truposol® LEX fatliquour (Trumpler, Germany); and about 18 g/L to about 19 g/L Trupon® DXV fatliquor (Trumpler, Germany).

At step 204, the pre-finishing treatment solution can be applied to the mycelium material through a combination of soaking and pressing processes. In one example, the material is soaked in the pre-finishing treatment solution for a predetermined period of time (e.g., 1 minute) and then moved through a pressing system. An example of a suitable pressing system includes moving the soaked material through a pair of rollers that are spaced to provide the desired degree of pressing to the material with each pass between the rollers. The material can be pushed and/or pulled through the rollers. The rate at which the material is passed through the rollers can vary. According to one aspect of the present disclosure, the soaking and pressing process at step 204 can be repeated one or more times (e.g., 1, 2, 3, 4, 5 or more times).

Following the pre-finishing treatment application at 204, the material can proceed to a fixation process 206. The fixation process 206 includes adjusting the pH of the pre-finishing treatment solution to a pH suitable for fixing the dyes. In one example, the fixation process is an acid fixing process that includes decreasing the pH of the pre-finishing treatment solution. Non-limiting examples of acids suitable for acid fixing include acetic acid and formic acid. For example, acetic acid can be used to decrease the pH of the exemplary pre-finishing treatment solution described above to a pH of 3.15±1.0.

At step 210, the mycelium material can be soaked in the pH adjusted pre-finishing treatment solution and flattened in a manner similar to that described above with regard to step 204. The soaking and pressing process at step 210 can be repeated one or more times (e.g., 1, 2, 3, 4, 5 or more times).

Step 212 includes a final, extended soak of the material in the pH adjusted pre-finishing treatment solution. The material can be inverted about halfway through the extended soak period. The extended soak period can be from about 30 minutes to 1 hour or more. When the extended soak time period is complete, at 214 the material can be processed through a final pressing process. The final pressing process can be the same or different than that described above with regard to steps 204 and 210.

Following the fixation process 206, at step 216 the material can be dried with or without heating. The material can be held generally vertically, horizontally, or any orientation therebetween during the drying step 216. The material may optionally be restrained during the drying step. For example, one or more clamps may be used to restrain all or a portion of the material during drying. In some examples, the drying step 216 is conducted at ambient conditions.

Mechanical Properties of Composite Mycelium Material

Various methods of the present disclosure may be combined to provide processed cultivated or composite mycelium material that has a variety of mechanical properties. In such embodiments, the mycelium material includes a mechanical property, e.g., a wet tensile strength, an initial modulus, an elongation percentage at the break, a thickness, and/or a slit tear strength. Other mechanical properties include, but are not limited to, elasticity, stiffness, yield strength, ultimate tensile strength, ductility, hardness, toughness, creep resistance, and other mechanical properties known in the art.

In various embodiments, the processed mycelium material may have a thickness that is less than 1 inch, less than ½ inch, less than ¼ inch or less than ⅛ inch. In some embodiments, the composite mycelium material has a thickness of about 0.5 mm to about 3.5 mm, inclusive, e.g., about 0.5 mm to about 1.5 mm, about 1 mm to about 2.5 mm, and about 1.5 mm to about 3.5 mm. The thickness of the material within a given piece of material may have varying coefficients of variance. In some embodiments, the thickness is substantially uniform to produce a minimal coefficient of variance.

In some embodiments, the mycelium material can have an initial modulus of at least 20 MPa, at least 25 MPa, at least 30 MPa, at least 40 MPa, at least 50 MPa, at least 60 MPa, at least 70 MPa, at least 80 MPa, at least 90 MPa, at least 100 MPa, at least 110 MPa, at least 120 MPa, at least 150 MPa, at least 175 MPa, at least 200 MPa, at least 225 MPa, at least 250 MPa, at least 275 MPa, or at least 300 MPa. In some embodiments, the mycelium material may have an initial modulus of about 0.5 MPa to about 300 MPa, inclusive, for example about 0.5 MPa to about 10 MPa, about 1 MPa to about 20 MPa, about 10 MPa to about 30 MPa, about 20 MPa to about 40 MPa, about 30 MPa to about 50 MPa, about 40 MPa to about 60 MPa, about 50 MPa to about 70 MPa, about 60 MPa to about 80 MPa, about 70 MPa to about 90 MPa, about 80 MPa to about 100 MPa, about 90 MPa to about 150 MPa, about 100 MPa to about 200 MPa, and about 150 MPa to about 300 MPa. In specific embodiments, the mycelium material has an initial modulus of 0.8 MPa. In one aspect, the mycelium material has an initial modulus of 1.6 MPa. In another aspect, the mycelium material has an initial modulus of 97 MPa.

In some embodiments, the mycelium material can have a wet tensile strength of about 0.05 MPa to about 50 MPa, inclusive, e.g., about 1 MPa to about 5 MPa, about 5 MPa to about 20 MPa, about 10 MPa to about 30 MPa, about 15 MPa to about 40 MPa, and about 20 MPa to about 50 MPa. In specific embodiments, the mycelium material may have a wet tensile strength of about 5 MPa to about 20 MPa. In one aspect, the mycelium material has a wet tensile strength of about 7 MPa. In a specific embodiment, the wet tensile strength will be measured by ASTM D638.

In some embodiments, the mycelium material can have a breaking strength ("ultimate tensile strength") of at least 1.1 MPa, at least 6.25 MPa, at least 10 MPa, at least 12 MPa, at least 15 MPa, at least 20 MPa, at least 25 MPa, at least 30 MPa, at least 35 MPa, at least 40 MPa, at least 45 MPa, at least 50 MPa.

In some embodiments, the mycelium material has an elongation at the break of less than 2%, less than 3%, less than 5%, less than 20%, less than 25%, less than 50%, less than 77.6%, or less than 200%. For example, the mycelium material may have an elongation at the break of about 1% to about 200%, inclusive, e.g., about 1% to about 25%, about 10% to about 50%, about 20% to about 75%, about 30% to about 100%, about 40% to about 125%, about 50% to about 150%, about 60% to about 175%, and about 70% to about 200%.

In some embodiments, the initial modulus, ultimate tensile strength, and elongation at the break are measured using ASTM D2209 or ASTM D638. In a specific embodiment, the initial modulus, ultimate tensile strength, and elongation at the break are measured using a modified version ASTM D638 that uses the same sample dimension as ASTM D638 with the strain rate of ASTM D2209.

In some embodiments, the mycelium material can have a single stitch tear strength of at least 15N, at least 20N, at least 25N, at least 30N, at least 35N, at least 40N, at least 50N, at least 60N, at least 70N, at least 80N, at least 90N, at least 100N, at least 125N, at least 150N, at least 175N, or at least 200N. In a specific embodiment, the tongue tear strength will be measured by ASTM D4786.

In some embodiments, the mycelium material can have a double stitch tear strength of at least 20N, at least 40N, at least 60N, at least 80N, at least 100N, at least 120N, at least 140N, at least 160N, at least 180N, or at least 200N. In a specific embodiment, the tongue tear strength will be measured by ASTM D4705.

In some embodiments, the mycelium material can have a tongue tear strength (also referred to as slit tear strength) of at least 1.8N, at least 15N, at least 25N, at least 35N, at least 50N, at least 75N, at least 100N, at least 150N, or at least 200N, as measured by ISO-3377. In a specific embodiment, the tongue tear strength will be measured by ASTM D4704. In some embodiments, the mycelium material may have a slit tear strength of at least 1N, at least 20N, at least 40N, at least 60N, at least 80N, at least 100N, at least 120N, at least 140N, at least 160N, at least 180N, or at least 200N, as measured by ISO-3377-2. In one aspect, the mycelium material has a slit tear strength of about 1N to about 200N, inclusive, e.g., about 10N to about 30N, about 20N to about 40N, about 30N to about 50N, about 40N to about 60N, about 50N to about 70N, about 60N to about 80N, about 70N to about 90N, about 80N to about 100N, about 90N to about 110N, about 100N to about 120N, about 110N to about 130N, about 120N to about 140N, about 130N to about 150N, about 140N to about 160N, about 150N to about 170N, about 160N to about 180N, about 170N to about 190N, and about 180N to about 200N, as measured by ISO-3377-2.

In some embodiments, the mycelium material has a flexural modulus (Flexure) of at least 0.2 MPa, at least 1 MPa, at least 5 MPa, at least 20 MPa, at least 30 MPa, at least 50 MPa, at least 80 MPa, at least 100 MPa, at least 120 MPa, at least 140 MPa, at least 160 MPa, at least 200 MPa, at least 250 MPa, at least 300 MPa, at least 350 MPa, at least 380 MPa. In a specific embodiment, the compression will be measured by ASTM D695. In some embodiments, the mycelium material has a flexural modulus of about 5-10 MPa. In some embodiments, the mycelium material has a flexural modulus of about 10-20 MPa. In some embodiments, the mycelium material has a flexural modulus of about 20-30 MPa. In some embodiments, the mycelium material has a flexural modulus of about 30-40 MPa. In some embodiments, the mycelium material has a flexural modulus of about 10-11 MPa. In some embodiments, the mycelium material has a flexural modulus of about 10 MPa.

In various embodiments of the present disclosure, the mycelium material has different absorption properties measured as a percentage mass increase after soaking in water. In some embodiments, the percent mass increase after soaking in water for 1 hour is less than 1%, less than 5%, less than 25%, less than 50%, less than 74%, or less than 92%. In a specific embodiment, the percent mass increase after soaking in water after 1 hour is measured using ASTM D6015.

Methods of Producing a Mycelium Material

Also provided is a method of producing a mycelium material as described herein. According to one embodiment of the disclosure, a mycelium material can be produced by generating a cultivated mycelium material including one or more masses of branching hyphae; disrupting the cultivated mycelium material including the one or more masses of branching hyphae; and adding a bonding agent to the cultivated mycelium material (e.g., by contacting the disrupted cultivated mycelium material with a solution comprising a bonding agent); thus producing the composite mycelium material. In some embodiments, the cultivated mycelium material includes one or more masses of disrupted branching hyphae. In some embodiments, the one or more masses of disrupted branching hyphae has a length. In such embodiments, the one or more masses of disrupted branching hyphae has a length of about 0.1 mm to about 5 mm.

In another aspect, a mycelium material ca be produced by generating a cultivated mycelium material; pressing the cultivated mycelium material; and adding a bonding agent to the cultivated mycelium material (e.g., by contacting the pressed cultivated mycelium material with a solution comprising a bonding agent), thus producing the composite mycelium material.

In some embodiments, the generating comprises generating cultivated mycelium material on a solid substrate. In some embodiments, the method further comprises incorporating a supporting material into the mycelium material. In some embodiments, the supporting material is a reinforcing material. In some embodiments, the supporting material is a base material. In some embodiments, the disrupting comprises disrupting the one or more masses of branching hyphae by a mechanical action. In some embodiments, the method further comprises adding one or more proteins that are from a species other than a fungal species from which the cultivated mycelium material is generated. In some embodiments, the method further comprises adding a dye to the cultivated mycelium material or the mycelium material. In some embodiments, the method further comprises adding a plasticizer to the cultivated mycelium material or the mycelium material. In some embodiments, the method further comprises adding a tannin to the cultivated mycelium material or the mycelium material. In some embodiments, the method further comprises adding a finishing agent to the mycelium material. In some embodiments, the method further comprises determining a mechanical property of the mycelium material, wherein the mechanical property includes, but is not limited to, wet tensile strength, initial modulus, elongation percentage at the break, thickness, slit tear strength, elasticity, stiffness, yield strength, ultimate tensile strength, ductility, hardness, toughness, creep resistance, and the like. For example, the mycelium material has a wet tensile strength of about 0.05 MPa to about 50 MPa, an initial modulus of about 0.5 MPa to about 300 MPa, an elongation percentage at the break of about 1% to about 200%, a thickness of about 0.5 mm to about 3.5 mm, and/or a slit tear strength of about 1 N to about 200 N.

In some embodiments, the cultivated mycelium material or composite mycelium material is produced using traditional paper milling equipment.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

The following material and methods were used in the Examples.

Composite Mycelium Material Samples

For each of the samples described below, components were blended together in a blender (Vitamix or Blendtec). The resulting slurry was poured into a mold resting on a paper-making screen or forming cloth that lets water pass through. After waiting approximately 1-15 minutes, the mold was removed from the slurry. The material was then pressed via a hand press to about 0.25 inches. The resulting material was then removed from the screen and dried in front of a fan. The sample was dried and then pressed in a heated press. A scaffold was optionally included in the composite mycelium material as described below.

The following samples were used:

HM1-1-1: 15 g dry cultivated mycelium material, 375 mL water, and 3 g pea protein (Nutribiotic) were blended together. 3.75 g transglutaminase from BDF (BDF TG) was added. The blend was mixed with a spatula and incubated for 30 min at room temperature (RT), and then poured into a 6×6 inch mold, pressed to ¼" thick, dried, and labeled HM1-1-1. A third of this material was rubbed with 3 g of epoxidized soybean oil and the sample was then pressed at 120° C. for 1 min at 1 metric ton of pressure and labeled HM1-1-11_120 p.

HM1-1-7: 15 g dry cultivated mycelium material, 375 mL water, 3 g pea protein (Nutribiotic), and 3 g leather glue were blended together. 3.75 g BDF TG was added. The blend was mixed with a spatula and incubated for 30 min at RT, and then poured into a 6×6 inch mold, pressed to ¼" thick, dried, and labeled HM1-1-7.

HM1-1-9: 2.5 g dry cultivated mycelium material, 75 mL water, and 0.5 g pea protein (Nutribiotic) were blended together, and poured into a 6×6 inch mold, pressed to ¼" thick, dried, and labeled HM1-1-9.

HM1-1-11: 10 g dry cultivated mycelium material, 400 mL water, 4 g pea protein (Nutribiotic), and 7.5 g epoxidized soybean oil were blended together, and poured into a 6×6 inch mold, pressed to ¼" thick, dried, and labeled HM1-1-11. Half the sample was then pressed at 120° C. for 1 min at 1 metric ton of pressure.

HM0 referred to a blended sample made with 15 g dry cultivated mycelium material, 3 g pea protein and 5% glycerol in 400 mL of water.

HM25: 5 g dry cultivated mycelium material, 125 mL water, 125 mL of 1.5% polyamide epichlorohydrin resin (PAE resin, Polycup 9200 from Solenis) in 40 mM phosphate buffer at pH=7, and 1 g pea protein were blended together. Two 2×2 inch squares were made. One was heated for 5 minutes at 105° C. (Labeled: HM25_5 min) and one was heated for 10 minutes at 105° C. (Labeled: HM25_10).

HM1-3-1: 5 g cultivated mycelium material, 125 mL of 1.5% PAE in 50 mM phosphate buffer (pH=7.4), and 1 g pea protein were blended together. Two 2×2 inch mats were made. The mats were heated at 105° C. for 5 min; it took 5 min for the oven to reach 105° C. after putting the mats in. Then, one mat was soaked in 5% glycerol for 10 minutes and dried in the fume hood, the other was wet tensile tested as is.

HM1-3-2: 5 g cultivated mycelium material, 125 mL of 1.5% PAE in 50 mM phosphate buffer (pH=7.4), 2.5 g leather glue from Eco-Flo®, and 1 g pea protein were blended together. Two 2×2 inch mats were made and they were heated at 105° C. for 5 min; it took 5 min for the oven to reach 105° C. after putting the mats in. Then, one mat was soaked in 5% glycerol for 10 minutes and dried in the fume hood, the other was wet tensile tested as is.

HM1-3-3: 15 g cultivated mycelium material, 400 mL of 1.5% PAE in 50 mM phosphate buffer (pH=7.4), and 3 g pea protein were blended together. After drying, salt crystals formed on the outside of the homogenized mycelia panel. One 6×6 inch mat was made and heated at 105° C. for 5 min; it took 5 min for the oven to reach 105° C. after putting the mats in. Then, the mat was soaked in 5% glycerol for 10 minutes and dried in the fume hood.

HM1-3-4: 5 g cultivated mycelium material, 125 mL of 1.5% PAE in 25 mM phosphate buffer (pH=7.4), and 1 g pea protein were blended together. Two 2×2 inch mats were made; the mats were poured into a 2×2 inch mold and then rolled with a baking pin unidirectionally between two paper-making screens. The orientation with the pin was parallel to the longer side of the rectangular panels.

HM1-3-5: 5 g cultivated mycelium material, 125 mL of 3.0% PAE in 25 mM phosphate buffer (pH=7.4), and 1 g pea protein were blended together. Two 2×2 inch mats were made. These mats were heated at 105° C. for 5 min; it took 5 min for the oven to reach 105° C. after putting the mats in.

HM1-3-6: 5 g cultivated mycelium material, 125 mL of 1.5% PAE in 25 mM phosphate buffer (pH=7.4), 2.5 g leather glue from Eco-Flo®, and 1 g pea protein were blended together. A cotton textile scaffold (scaffold2) was incorporated in the center of two 2×2 inch mats. One panel was pressed to 1 metric ton at 105° C. for 2 min, the other panel was heated at 105° C. for 5 min, after waiting 5 minutes for the oven to reach 105° C. A 1.54 mm spacer was used to limit the degree to which the panel was pressed.

HM1-3-7: 5 g cultivated mycelium material, 125 mL of 1.5% PAE in 25 mM phosphate buffer (pH=7.4), 5 g leather glue from Eco-Flo®, and 1 g pea protein were blended together. A cotton textile scaffold (scaffold2) was incorporated in the center of two 2×2 inch mats. One panel was pressed to 1 metric ton at 105° C. for 2 min, the other panel was heated at 105° C. for 5 min, after waiting 5 minutes for the oven to reach 105° C. A 1.54 mm spacer was used to limit the degree to which the panel was pressed.

HM1-3-8: 5 g cultivated mycelium material and 125 mL of 1.5% PAE in 25 mM phosphate buffer (pH=7.4) were blended together. Two 2×2 inch mats were made. These mats were heated at 105° C. for 5 min; it took 5 min for the oven to reach 105° C. after putting the mats in.

HM1-3-9: 5 g cultivated mycelium material, 125 mL of 1.5% PAE in 25 mM phosphate buffer (pH=7.4), and 1 g pea protein were blended together. Two 2×2 inch mats were made. These mats were pressed at 1 metric ton at 105° C. for 2 minutes to a height of 1.45 mm.

HM1-3-10: 5 g cultivated mycelium material, 125 mL of 1.5% PAE in 25 mM phosphate buffer (pH=7.4), and 1 g pea protein were blended together. A textile scaffold (Scaffold2) was incorporated into one 2×2 inch mat. The scaffold was coated in dried cultivated mycelium material that had been poured over the scaffold in a dilute slurry the day before and allowed to dry. The panel was then pressed to 1.5 mm at 105° C. for 2 min at 1 metric ton of pressure.

HM1-3-11: 5 g cultivated mycelium material, 125 mL of 1.5% PAE in 25 mM phosphate buffer (pH=7.4), and 1 g pea protein were blended together. Two 2×2 inch mats were made. The mats and a cotton textile scaffold (scaffold) with ⅛ inch pores were coated with Weldwood contact cement and pressed at room temperature with 2 L of water in a beaker for 2.5 h. Then, the material was pressed to 2.54 mm for 4 min at 105° C. to 1 metric ton of pressure.

HM1-3-12: 2.5 g cultivated mycelium material, 62.5 mL of 1.5% PAE in 25 mM phosphate buffer (pH=7.4), and 0.5 g pea protein were blended together. A papermaking scaffold (Scaffold3, black, non-textile, plastic) was incorporated into one 2×2 inch mat. The panel was then pressed to 1.5 mm at 105° C. for 2 min at 1 metric ton of pressure.

HM1-3-13: 2.5 g cultivated mycelium material, 62.5 mL of 1.5% PAE in 25 mM phosphate buffer (pH=7.4), and 0.5 g pea protein were blended together. One 2×2 inch mat was made with a scaffold 4 incorporated inside that had had mycelia slurry poured over it the night before. The panel was then pressed to 1.5 mm at 105° C. for 2 min at 1 metric ton of pressure.

HM1-3-14: 2.5 g cultivated mycelium material, 62.5 mL of 1.5% PAE in 25 mM phosphate buffer (pH=7.4), and 0.5 g pea protein were blended together. One 2×2 inch mat with a clean scaffold 4 was incorporated inside. The panel was then pressed to 1.5 mm at 105° C. for 2 min at 1 metric ton of pressure.

HM1-3-15: 5 g cultivated mycelium material, 125 mL of 1.5% PAE in 25 mM phosphate buffer (pH=7.4), and 1 g pea protein were blended together. Two 2×2 inch mats were made. The mats and a cotton textile scaffold (scaffold4) with ⅛ inch pores were coated with leather tack glue from Springfield Leather Company and pressed at room temperature with 2 L of water in a beaker for 2.5 h. Then, the material was pressed to 2.54 mm for 4 min at 105° C. to 1 metric ton of pressure.

HM1-4-1: 5 g cultivated mycelium material, 125 mL of 1.5% PAE in 25 mM phosphate buffer (pH=7.4), 1 g pea protein, 1 g iron (III) oxide black or 1 g of cobalt blue, and 5% glycerol were blended together. A cotton textile scaffold (scaffold4) was incorporated inside. Two 2×2 inch mats were made. These mats were pressed and heated at 105° C. for 2 min at 1 metric ton of pressure.

HM1-4-2: 5 g cultivated mycelium material, 125 mL of 1.5% PAE in 25 mM phosphate buffer (pH=7.4), 1 g pea protein, 0.125 g brown acid dye, and 5% glycerol were blended together. A cotton textile scaffold (scaffold4) was incorporated inside. Two 2×2 inch mats were made. These mats were pressed and heated at 105° C. for 2 min at 1 metric ton of pressure.

HM1-4-3: 15 g cultivated mycelium material, 400 mL of 1.5% PAE in 25 mM phosphate buffer (pH=7.4), 3 g pea protein, 5 g iron (III) oxide black, and 5% glycerol were blended together. Two 6×6 inch mats were made. These mats were pressed and heated at 105° C. for 2 min at 1 metric ton of pressure.

HM1-4-4: Same as HM1-4-3.

HM1-4-5: Same as HM1-4-3 and HM1-4-4, except that 8 g of leather glue from Eco-Flo® was also blended together.

HM3: 15 g dry cultivated mycelium material, 500-600 mL water, and 3 g pea protein (Nutribiotic) were blended together. 3.75 g BDF TG was added, mixed with a spatula, poured half the mold into a 6×6 inch mold, pressed a pre-wetted scaffold1 into the material, and poured the other half of the material into the mold. The mixture was incubated for 30 min, then pressed to ¼" thick, and dried. This sample was cut in half, and 3 g of epoxidized soybean oil was rubbed into half the sample. The sample was then heat pressed at 1 metric ton of pressure at 120° C. for 2 min.

HM22: 15 g dry cultivated mycelium material, 550 mL water, and 3 g pea protein were blended together. One cheesecloth (scaffold1) was incorporated inside through crochet needling. Scaffold1 was not evenly placed in the middle of the material.

Wet Tensile Testing

The standard test method for tensile testing of composite mycelium materials was performed according to the ASTM D638 protocol. Samples were conditioned at 65±2% RH for 24 hours. In some embodiments, samples were soaked in water for 1 hour at room temperature prior to testing. ASTM standard dies such as an ASTM D638 type IV dogbone was used to punch out samples. Each sample's thickness, width, and mass were measured. The appropriate tensile test method was then run on a universal testing machine from Zwick (zwikiLine Materials Testing Machine Z5.0 TH).

Slit Tear Testing

The standard test method for slit tear testing of composite mycelium materials was performed according to the ISO 3377-2 protocol, using the universal testing system from Zwick. Samples were conditioned at 65±2% RH for 24 h. In some embodiments, samples were equilibrated at 65% relative humidity for 16 h at room temperature prior to testing. The ISO 3377-2 die was used to cut out 1"×2" specimens with a center slit. Each specimen's thickness and mass were measured. The appropriate slit tear test method was then run on the universal mechanical tester from Zwick.

Drafting of Mycelium Materials

The mycelium hyphae were aligned by manually drafting a thin sheet of material along direction. The drafting force applied to the material did not exceed the breaking force.

Scanning Electron Microscopy (SEM) Imaging and Fourier Transform (FT) Analysis

Scanning electron microscopy (SEM) used a focus electron beam to assess the morphology of materials through the secondary electrons. The electron beam was scanned in a raster pattern to collect micrographs at scales between 1 mm and 10 nm or between 10× and 100,000× magnification. The SEM method used low vacuum (1 to 10 ton), avoiding the need for dehydrating or sputter coating biological samples.

SEM micrographs were then cropped to a square size and analyzed using Fourier transform (FT). The FT of an image represented a sum of complex exponentials of varying magnitudes (i.e. intensity), frequencies, and phase angle. The resulting frequency domain revealed the periodicity in the image as a function of the angle. Because aligned fibers gave rise to a periodicity orthogonal to the fiber axis, the frequency domain was used to quantity the preferential fiber alignment. The polar coordinate frequency domain image was then transformed into Cartesian coordinates to extract the profile of the azimuthal distribution. The azimuthal distribution was then fitted with a Gaussian peak to calculate the full-width at half-maximum and the maximum angular position.

Polarized Fourier Transform Infrared (FTIR) Spectroscopy

Fourier Transform Infrared (FTIR) spectra were used to assess the secondary and tertiary structures of composite mycelium materials. Depending on the embodiment, FTIR spectra at different wavenumbers ($cm^{-1}$) may be used to assess the different chemical functions present in the chitin of mycelium hypha. The wavenumbers corresponding to the methyl deformation mode of the N-acetyl group was found to be about 1410 $cm^{-1}$ while the ether vibration mode was found to be about 950 $cm^{-1}$.

In attenuated total reflection mode, the infrared light beam was internally reflected inside the internal reflection element. The light absorbance arose from the attenuation of the evanescent wave at the interface.

In polarized FTIR, the light was polarized along with the s (perpendicular to the reflection plane). The sample was either angularly positioned along the polarized light s vector (0 degrees) or perpendicular (90 degrees). The ratio of the absorbance at 0 and 90 degrees defined the dichroic ratio (R) from which the second Legendre order parameter could be calculated $<P2>=(R-1)/(R-2)$.

Example 1: Tensile Properties of the Composite Mycelium Material

As shown in the following results, by incorporating a bonding agent such as the crosslinker polyamide-epichlorohydrin (PAE) and optionally a textile scaffold, the wet tensile strength and the tear strength of the material improved dramatically. PAE is a crosslinker that is traditionally used in the paper industry, but is also found in sausage casings. Stiffer textile scaffolds performed better in the composite mycelium materials than less-stiff, more stretchy scaffolds. Without intending to be bound by any particular theory, it is proposed that less-stiff scaffolds did not end up bearing any load when incorporated into the materials. Also, less-stiff scaffolds were more likely to delaminate upon breaking than stiffer scaffolds. Water-based latex adhesives provided further benefits for the material in terms of both strength and plastic deformation.

In some samples including PAE, the composite mycelium materials had a higher wet tensile strength and a higher slit tear than intact cultivated mycelium material. In some samples having PAE, the composite mycelium materials had a lower elongation at the break (plastic deformation) than intact cultivated mycelium material.

Adding a Bonding Agent

Table 1 depicts wet tensile strength (MPa), initial modulus (MPa), and elongation at the break (%) of various composite mycelium materials.

TABLE 1

| n | Sample | Wet Tensile strength (MPa) | | Initial Modulus (MPa) | | Elongation at the break (%) | |
|---|---|---|---|---|---|---|---|
| | | Average | Std. Dev. | Average | Std. Dev | Average | Std. Dev |
| 3 | No PAE control (HM1-1-9) | 0.11 | 0.00 | 1.97 | 0.78 | 8.20 | 0.11 |
| 5 | PAE (HM1-3-8) | 0.86 | 0.17 | 3.48 | 0.74 | 14.46 | 1.81 |
| 3 | PAE, pea protein (HM25_5 min) | 0.99 | 0.05 | 5.56 | 0.50 | 14.37 | 1.69 |
| 5 | PAE, pea protein, latex (HM1-3-2) | 1.18 | 0.22 | 5.50 | 0.35 | 20.53 | 2.33 |
| 5 | PAE, pressed (HM1-3-9p) | 1.80 | 0.22 | 15.26 | 3.21 | 12.70 | 1.66 |
| 4 | PAE, Scaffold3, pressed (HM1-3-12) | 7.38 | 1.71 | 96.98 | 14.53 | 10.39 | 3.45 |
| 4 | PAE, Scaffold4, pressed (HM1-3-13) | 2.15 | 0.57 | 13.38 | 1.30 | 17.77 | 12.28 |
| 4 | PAE, Scaffold4, glue, pressed (HM1-3-15) | 5.91 | 1.48 | 39.68 | 3.53 | 20.20 | 1.85 |
| 6 | Drafted mycelium polyurethane (PU) composite | 4.11 | 0.45 | 59.72 | 11.59 | 278.5 | 407.7 |

Adding a bonding agent such as PAE or polyurethane and in some samples, a textile scaffold, the tensile properties of the composite mycelium materials improved dramatically. The wet tensile strength increased from 0.11 MPa to at least 0.86 MPa, and up to 7.38 MPa. The initial modulus increased from 1.97 MPa to at least 3.48 MPa, and up to 96.98 MPa. The elongation at the break increased from 8.20% to at least 10.39%, and up to 278.5%. Thickness of the composite mycelium material ranged from 0.5 mm to 3.5 mm. Sub-network size, e.g., length, of the disrupted mycelium material ranged from 0.5 mm to 2 mm.

PAE Crosslinking

Figure 2:
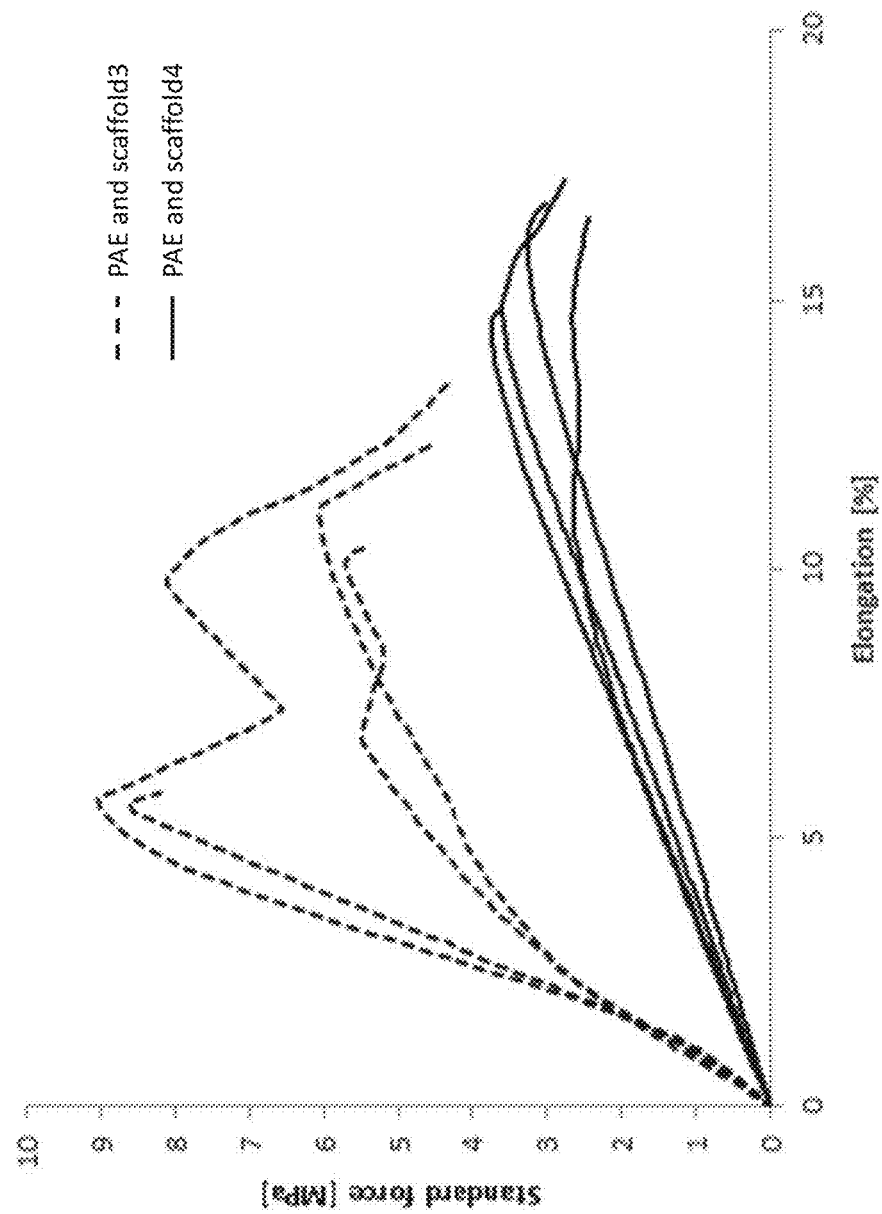
FIG. 2 depicts stress-strain curves of a pressed sample with polyamide-epichlorohydrin resin (PAE) and scaffold3 (dashed lines), and a pressed sample with PAE and scaffold4 (solid lines). Standard stress (MPa) is plotted against elongation (%).

The presence of pea protein did not impact the PAE crosslinking. Sample HM1-3-8 was crosslinked with 1.5% PAE and no pea protein (Table 2). Increasing the concentration of PAE from 1.5% to 3% did not increase the wet tensile strength significantly (Table 2). FIG. 2 illustrates the stress-strain curves of a mycelia panel containing PAE and Scaffold3 that was heat-pressed (HM1-3-12) (dashed lines), and a mycelia panel containing PAE and Scaffold4 that was heat-pressed (HM1-3-13) (solid lines).

Table 2 depicts the wet tensile strength (MPa), initial modulus (MPa), and elongation at the break (%) of various composite mycelium materials. Samples were made comparing PAE crosslinked samples at 1.5% dry weight percent in the panel with PAE crosslinked samples at 3% dry weight percent, and comparing PAE+pea protein crosslinked samples with samples crosslinked without pea protein.

TABLE 2

| n = ? | Sample | Wet Tensile Strength (MPa) | | Initial Modulus (MPa) | | Elongation at the break (%) | |
|---|---|---|---|---|---|---|---|
| | | Average | Std. Dev. | Average | Std. Dev. | Average | Std. Dev. |
| 3 | 1.5% PAE, pea protein (HM25_5 min) | 0.99 | 0.05 | 5.56 | 0.50 | 14.37 | 1.69 |
| 3 | 1.5% PAE, pea protein (HM25_10 min) | 0.87 | 0.23 | 4.40 | 0.53 | 16.10 | 2.61 |
| 4 | 1.5% PAE, pea protein (HM1-3-1) | 0.65 | 0.06 | 3.56 | 0.56 | 13.58 | 1.42 |
| 5 | 3% PAE, pea protein (HM1-3-5) | 1.03 | 0.30 | 5.64 | 1.12 | 12.88 | 0.90 |
| 5 | 1.5% PAE, no pea protein (HM1-3-8) | 0.86 | 0.17 | 3.48 | 0.74 | 14.46 | 1.81 |

Additive Strengthening

Latex adhesive (leather glue) improved wet tensile strength and elongation at the break and did not impact the ability of PAE to crosslink mycelia (Table 3).

Table 3 depicts wet tensile strength (MPa), initial modulus (MPa), and elongation at the break (%) of various composite mycelium materials, comparing PAE crosslinked mycelia samples without glue with a PAE crosslinked mycelia sample with glue.

TABLE 3

| n = ? | Sample | Wet Tensile Strength (MPa) | | Initial Modulus (MPa) | | Elongation at the break (%) | |
|---|---|---|---|---|---|---|---|
| | | Average | Std. Dev. | Average | Std. Dev. | Average | Std. Dev. |
| 3 | 1.5% PAE, pea protein (HM25_5 min) | 0.99 | 0.05 | 5.56 | 0.50 | 14.37 | 1.69 |
| 3 | 1.5% PAE, pea protein (HM25_10 min) | 0.87 | 0.23 | 4.40 | 0.53 | 16.10 | 2.61 |
| 4 | 1.5% PAE, pea protein (HM1-3-1) | 0.65 | 0.06 | 3.56 | 0.56 | 13.58 | 1.42 |
| 4 | 1.5% PAE, leather glue, pea protein (HM1-3-2) | 1.18 | 0.22 | 5.50 | 0.35 | 20.53 | 2.33 |
| 5 | 3% PAE, pea protein (HM1-3-5) | 1.03 | 0.30 | 5.64 | 1.12 | 12.88 | 0.90 |
| 5 | 1.5% PAE, no pea protein (HM1-3-8) | 0.86 | 0.17 | 3.48 | 0.74 | 14.46 | 1.81 |

Samples HM1-4-1 through HM1-4-5 included a dye, plasticizer, and scaffold, and were all pressed to about 1.4 mm.

Heat Pressing

Heat pressing the samples at 105° C. instead of crosslinking the samples in an oven at 105° C. resulted in a two-fold increase in wet tensile strength (Table 4).

Table 4 depicts wet tensile strength (MPa), initial modulus (MPa), and elongation at the break (%) of various composite mycelium materials. Samples were made comparing heat pressed samples at 105° C. (HM1-3-9p) with samples crosslinked at 105° C. in an oven.

TABLE 4

| n = ? | Sample | Wet Tensile Strength (MPa) | | Initial Modulus (MPa) | | Elongation at the break (%) | |
|---|---|---|---|---|---|---|---|
| | | Average | Std. Dev. | Average | Std. Dev. | Average | Std. Dev. |
| 3 | 1.5% PAE, pea protein (HM25_5 min) | 0.99 | 0.05 | 5.56 | 0.50 | 14.37 | 1.69 |
| 4 | 1.5% PAE, pea protein (HM1-3-1) | 0.65 | 0.06 | 3.56 | 0.56 | 13.58 | 1.42 |
| 5 | 3% PAE, pea protein (HM1-3-5) | 1.03 | 0.30 | 5.64 | 1.12 | 12.88 | 0.90 |

TABLE 4-continued

| n = ? | Sample | Wet Tensile Strength (MPa) | | Initial Modulus (MPa) | | Elongation at the break (%) | |
|---|---|---|---|---|---|---|---|
| | | Average | Std. Dev. | Average | Std. Dev. | Average | Std. Dev. |
| 4 | 1.5% PAE, leather glue, pea protein (HM1-3-2) | 1.18 | 0.22 | 5.50 | 0.35 | 20.53 | 2.33 |
| 5 | 1.5% PAE, pea protein, pressed (HM1-3-9p) | 1.80 | 0.22 | 15.26 | 3.21 | 12.70 | 1.66 |

Incorporating a Supporting Material

Figure 3:
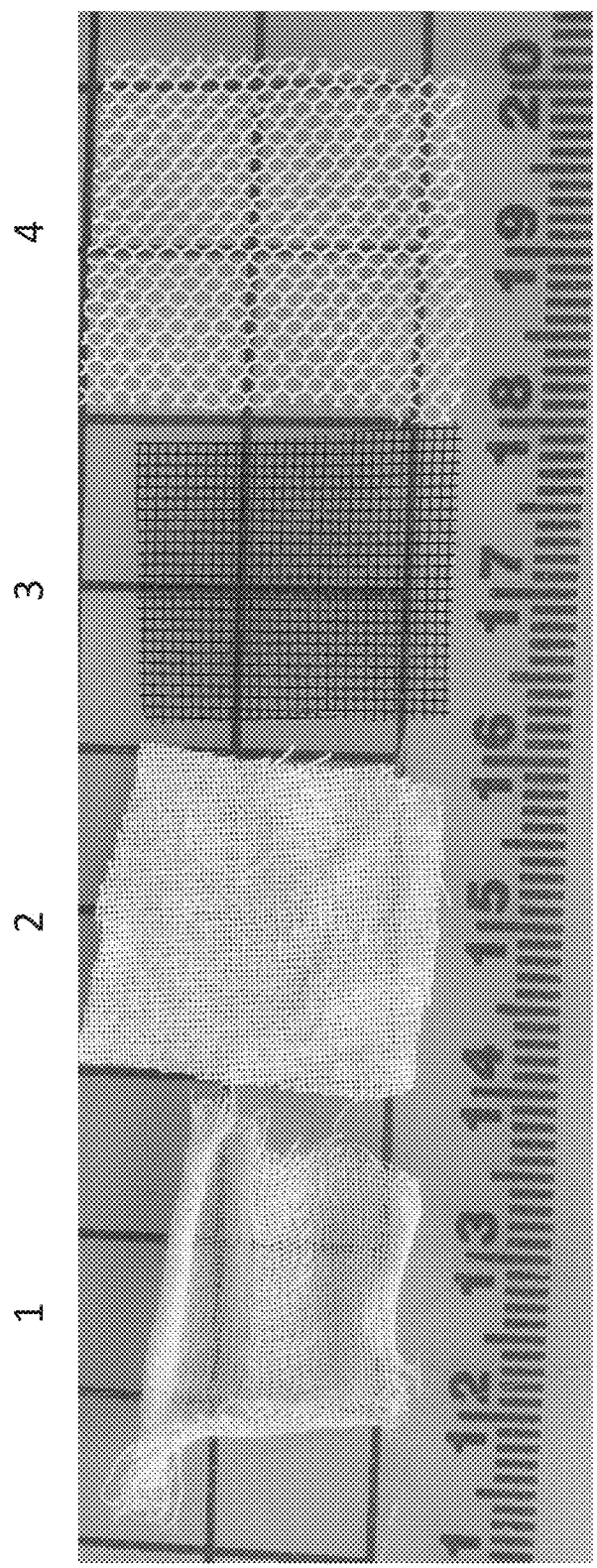
FIG. 3 depicts different scaffold materials. From left to right: scaffold1, a cheesecloth scaffold with pores slightly smaller than 1/16th of an inch; scaffold2, a cotton textile scaffold with pores smaller than 1/32nd of an inch; scaffold3, a non-textile scaffold with pores 1/16th of an inch in size; and scaffold4 a cotton textile scaffold with large pores 1/8th of an inch in size.
Figure 4:
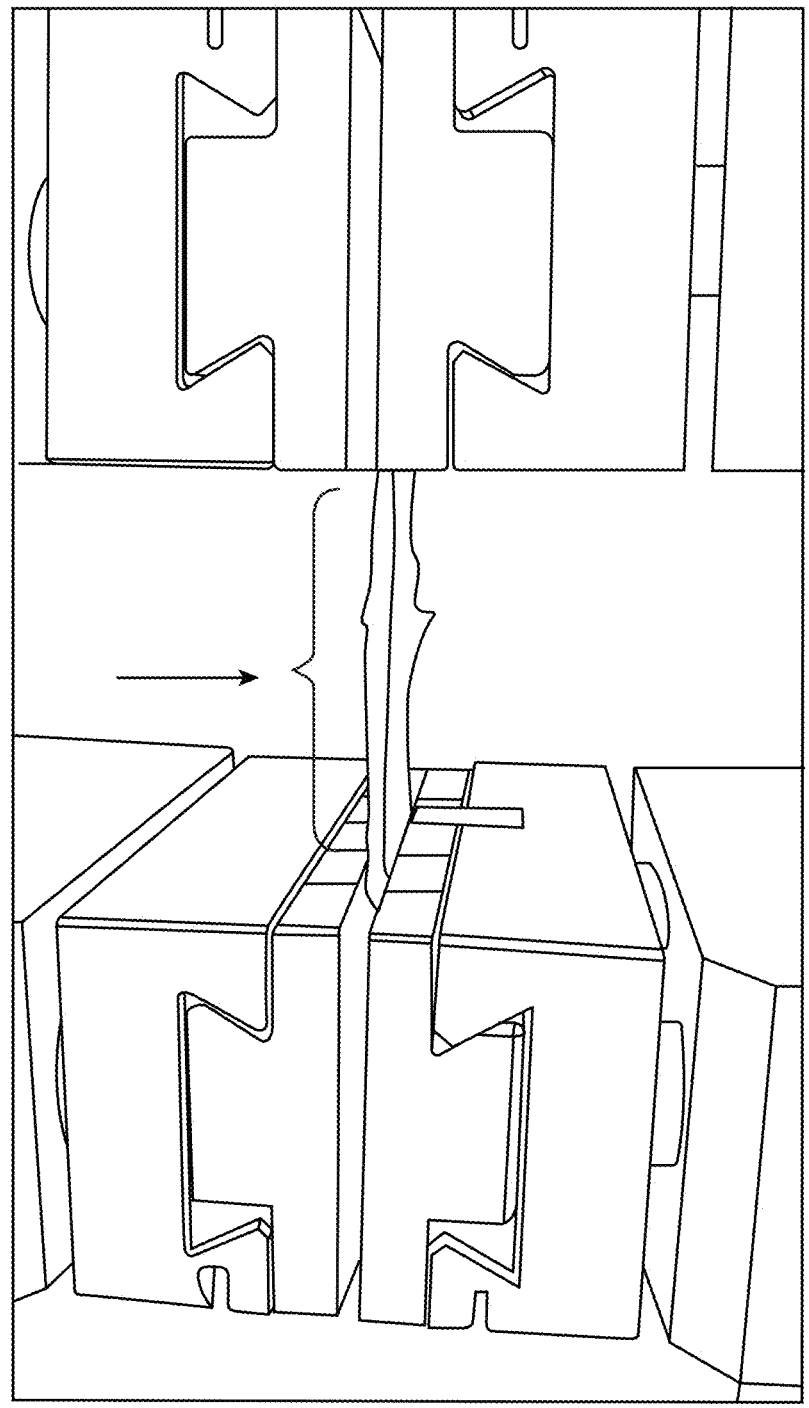
FIG. 4 depicts a sample containing 5 g cultivated mycelium material (indicated by an arrow), 125 mL of 1.5% PAE in 25 mM phosphate buffer (pH=7.4), 1 g pea protein, scaffold4, and weldwood adhesive after a wet tensile test.

Incorporated supporting materials increased the wet tensile strength of composite mycelium materials, with stiffer supporting materials such as scaffolds yielding a higher initial modulus than less stiff supporting materials. In some samples, incorporated supporting materials increased the wet tensile strength of the overheat pressed PAE samples about a two to five-fold increase. FIG. 3 shows different supporting materials incorporated inside the composite mycelium materials used herein. From left to right, FIG. 3 depicts a cheesecloth scaffold with pores slightly smaller than 1/16th of an inch (scaffold1); a cotton textile scaffold with pores smaller than 1/32 of an inch (scaffold2); a non-textile scaffold with pores 1/16th of an inch in size (scaffold 3); and a cotton textile scaffold with large pores 1/8th of an inch in size (scaffold4). FIG. 4 depicts scaffold 4 with Weldwood adhesive after a wet tensile test.

Table 5 depicts the exemplary mechanical properties of four scaffolds used herein. Mechanical properties were tested on the Zwick system.

TABLE 5

| n = ? | Sample | Tensile Strength (MPa) | Initial Modulus (MPa) | Elongation at the break (%) |
|---|---|---|---|---|
| 1 | Scaffold1 | 7.32 | 3.44 | 20.6 |
| 1 | Scaffold2 | 2.53 | 0.1 | 49 |
| 1 | Scaffold3 | 51.7 | 1110 | 4.96 |
| 1 | Scaffold4 | 8.7 | 2.32 | 31.1 |

An incorporated supporting material increased the wet tensile strength of one or more composite mycelium material samples, with stiffer supporting materials such as scaffolds taking more of the load prior to the disrupted mycelia breaking than less stiff scaffolds (e.g., scaffold3, non-textile, compared to scaffold2, cotton textile). Since one or more composite mycelium materials were relatively stiff, with a fairly low elongation at the break, a scaffold that was relatively stiff turned out to be more effective in yielding tensile property values comparable to bovine leather. It is desired for the supporting material to have a higher initial modulus than the composite mycelium material and optionally a lower elongation at the break so that the scaffold would initially take the strain from any tensile force and then break before the composite mycelium material breaks.

Scaffold3 (non-textile scaffold) met these desired requirements. Scaffold2 had a low initial modulus and high elongation at the break. Scaffold4 was made out of natural materials (cotton) and had a fair tensile strength and initial modulus. It was harder to tear Scaffold 4 as compared to Scaffold1.

Table 6 depicts the mechanical properties of pressed, crosslinked composite mycelium materials with and without an incorporated supporting material such as a scaffold. Mechanical properties of upholstery leather are used as a comparison.

TABLE 6

| n = ? | Sample | Wet Tensile Strength (MPa) | | Initial Modulus (MPa) | | Elongation at the break (%) | |
|---|---|---|---|---|---|---|---|
| | | Average | Std. Dev. | Average | Std. Dev. | Average | Std. Dev. |
| 3 | Upholstery leather | 15.60 | 1.21 | 0.87 | 0.53 | 86.97 | 4.10 |
| 3 | Cultivated mycelium material, split | 0.82 | 0.12 | 1.43 | 0.04 | 82.32 | 8.70 |
| 5 | PAE, pea protein, pressed (HM1-3-9p) | 1.80 | 0.22 | 15.26 | 3.21 | 12.70 | 1.66 |
| 3 | PAE, Scaffold2, pressed (HM1-3-10) | 2.97 | 0.10 | 16.97 | 4.05 | 13.47 | 1.61 |
| 3 | PAE, Scaffold2, glue, pressed (HM1-3-6) | 3.48 | 0.48 | 18.90 | 1.71 | 14.27 | 0.93 |
| 3 | PAE, Scaffold2, glue, pressed (HM1-3-7) | 4.46 | 0.43 | 15.33 | 4.80 | 18.20 | 1.01 |
| 4 | PAE, Scaffold4, glue, pressed (HM1-3-11) | 3.32 | 0.48 | 30.93 | 5.04 | 16.25 | 1.20 |
| 4 | PAE, Scaffold3, pressed (HM1-3-12) | 7.38 | 1.71 | 96.98 | 14.53 | 10.39 | 3.45 |
| 4 | PAE, Scaffold4, pressed (HM1-3-13) | 2.15 | 0.57 | 13.38 | 1.30 | 17.77 | 12.28 |
| 4 | PAE, Scaffold4, glue, pressed (HM1-3-15) | 5.91 | 1.48 | 39.68 | 3.53 | 20.20 | 1.85 |

Example 2: Slit Tear Strength of the Composite Mycelium Material

Slit tear strength of composite mycelium materials was compared to that of intact cultivated mycelium material.

Table 7 depicts slit tear strength (N) and thickness (mm) of various composite mycelium materials.

TABLE 7

| n = ? | Sample | Plasticized? | Slit tear strength (N) Average | Std. Dev. | Thickness (mm) Average | Std. Dev |
|---|---|---|---|---|---|---|
| 10 | Cultivated mycelium material, intact | Yes | 22 | 4 | 2.1 | 0.2 |
| 10 | Bovine leather | Yes | 106 | 9 | 1.29 | 0.02 |
| 2 | HM1-1-1 | No | 29 | 3 | 2.4 | 0.1 |
| 2 | HM1-1-7 | No | 51 | 4 | 3.22 | 0.07 |
| 1 | HM1-1-11 | Yes | 13 | | 1.75 | |
| 1 | HM1-1-11_120p | Yes | 18 | | 0.96 | |
| 1 | HM0 | Yes, 5% glycerol | 7 | | 2.2 | |
| 2 | HM1-4-3 | Yes, 5% glycerol | 42 | 2 | 1.4 | 0.2 |

Figure 5:
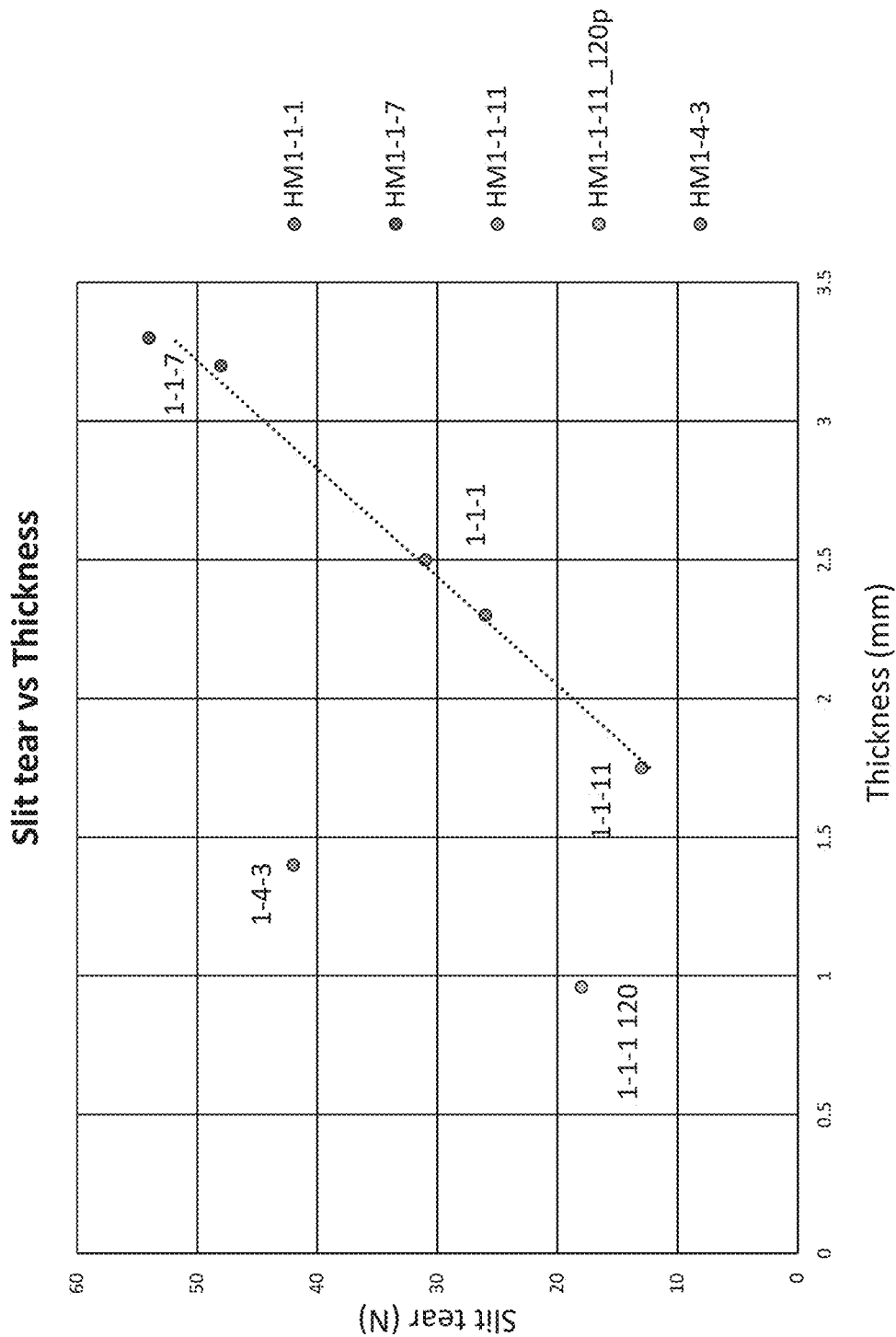
FIG. 5 depicts a plot of slit tear (N) versus thickness (mm) of pressed samples (HM1-4-3 and HM1-1-11_120 p) and unpressed samples (HM1-1-1, HM1-1-7, and HM1-1-11).

The slit tear strength of various composite mycelium materials ranged from about 7N to about 50N. FIG. 5 depicts a plot of slit tear versus thickness of various composite mycelium materials, including pressed samples (HM1-4-3 and HM1-1-11_120 p) and unpressed samples. The slit tear strength of pressed samples was far stronger than that of unpressed samples. HM1-4-3 was pressed in the presence of 1.5% PAE and HM1-1-11_120 p was pressed in the presence of epoxidized soybean oil. Unpressed samples without PAE had slit tear strengths that behaved linearly with thickness.

Example 3: Alignment of Mycelium Hypha from *Ganoderma sessile*

Figure 6:
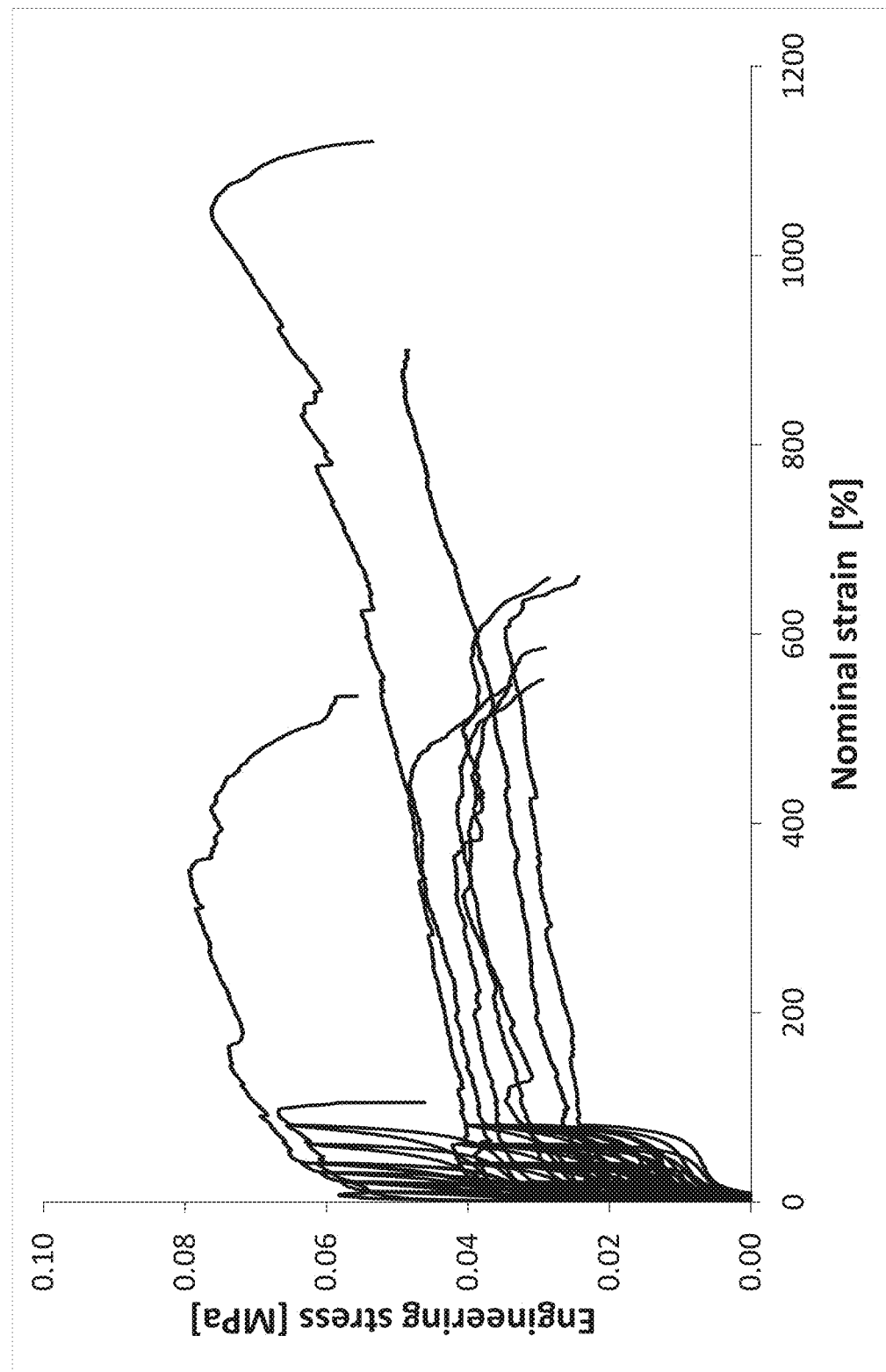
FIG. 6 depicts a stress-strain curve plotting engineering stress (MPa) against nominal strain (%). The strain cycles from 10% to 80% in increments of 10% before drafting to the maximum elongation until break.

Next, the cultivated mycelium material or composite mycelium material was disrupted by physically aligning branching hyphae in one or more directions. FIG. 6 shows a stress-strain curve plotting through-thickness drafting stress as a function of the strain to aligned mycelium. The strain cycles were performed from 10% to 80%, in increments of 10%, before drafting to the maximum elongation. The force was measured while the masses of branching hyphae were being aligned. The curves illustrated a proportional limit followed by a maximum in the curve at which necking takes place.

Table 8 depicts the drafting maximum alignment stress and elongation range for the through-thickness drafting illustrated in FIG. 6.

TABLE 8

| | Minimum | Maximum |
|---|---|---|
| Maximum alignment stress (MPa) | 0.035 | 0.079 |
| Elongation at the break (%) | 105.3 | 1120.5 |

Figure 7B:
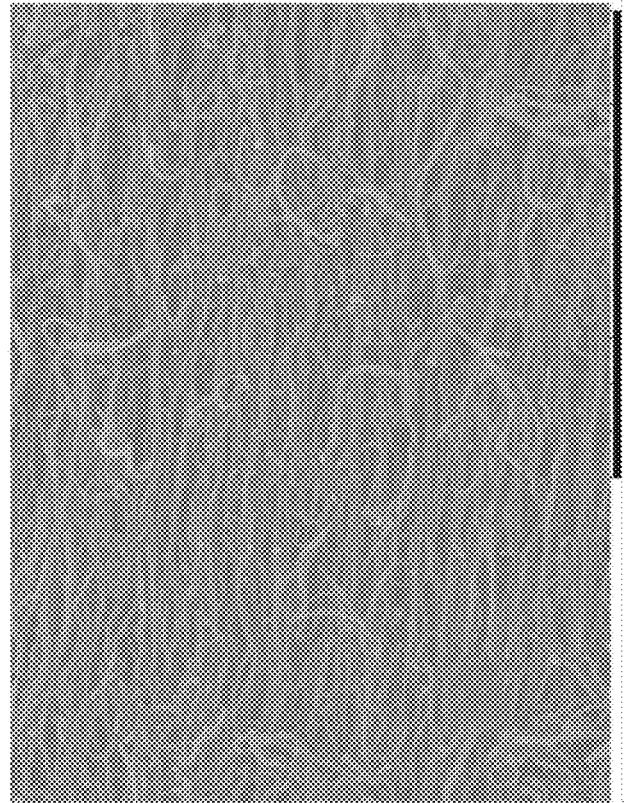
FIG. 7B depict SEM micrographs of mycelium hyphae after drafting. Scale bar of FIG. 7A=50 μm; scale bar of FIG. 7B=200 μm.
Figure 7A:
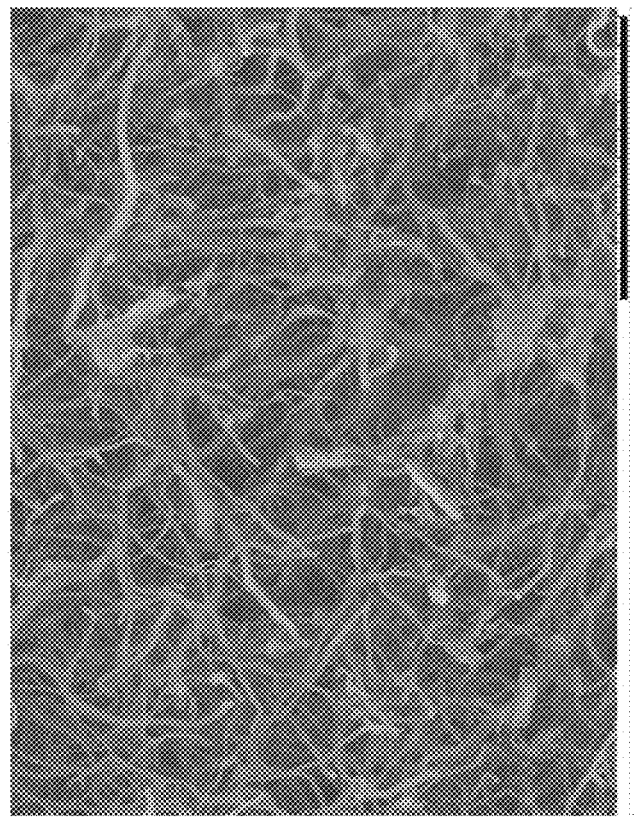
FIG. 7A depict SEM micrographs of mycelium hyphae before drafting.

FIGS. 7A and 7B show SEM micrographs of mycelium hyphae before drafting (FIG. 7A) and after drafting (FIG. 7B). In this embodiment, the fibers were aligned along the stress direction. The lamina included three successive layers.

Figure 8:
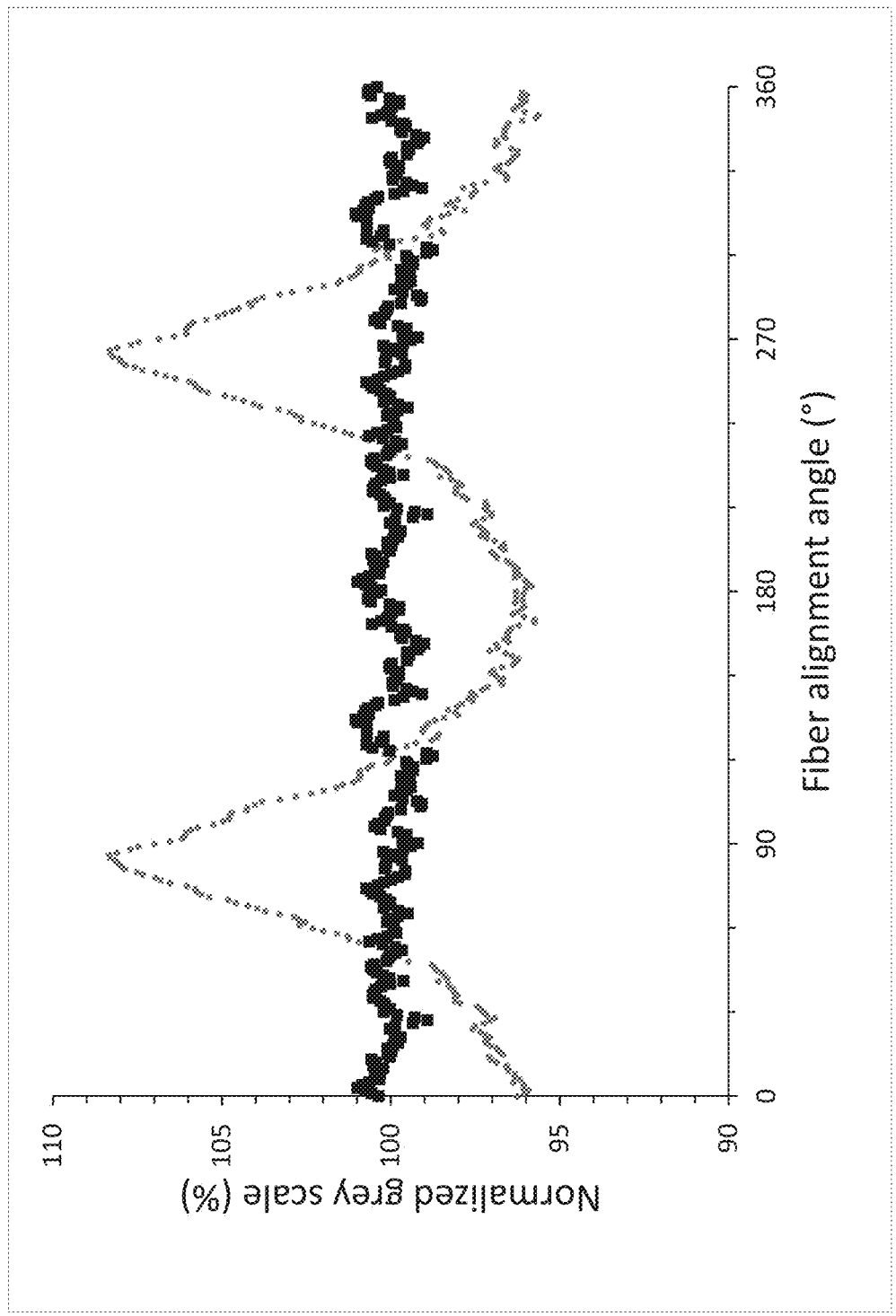
FIG. 8 shows a Fourier transform graph of a mycelium SEM image before drafting (black squares) and after drafting (grey circles).
Figure 9:
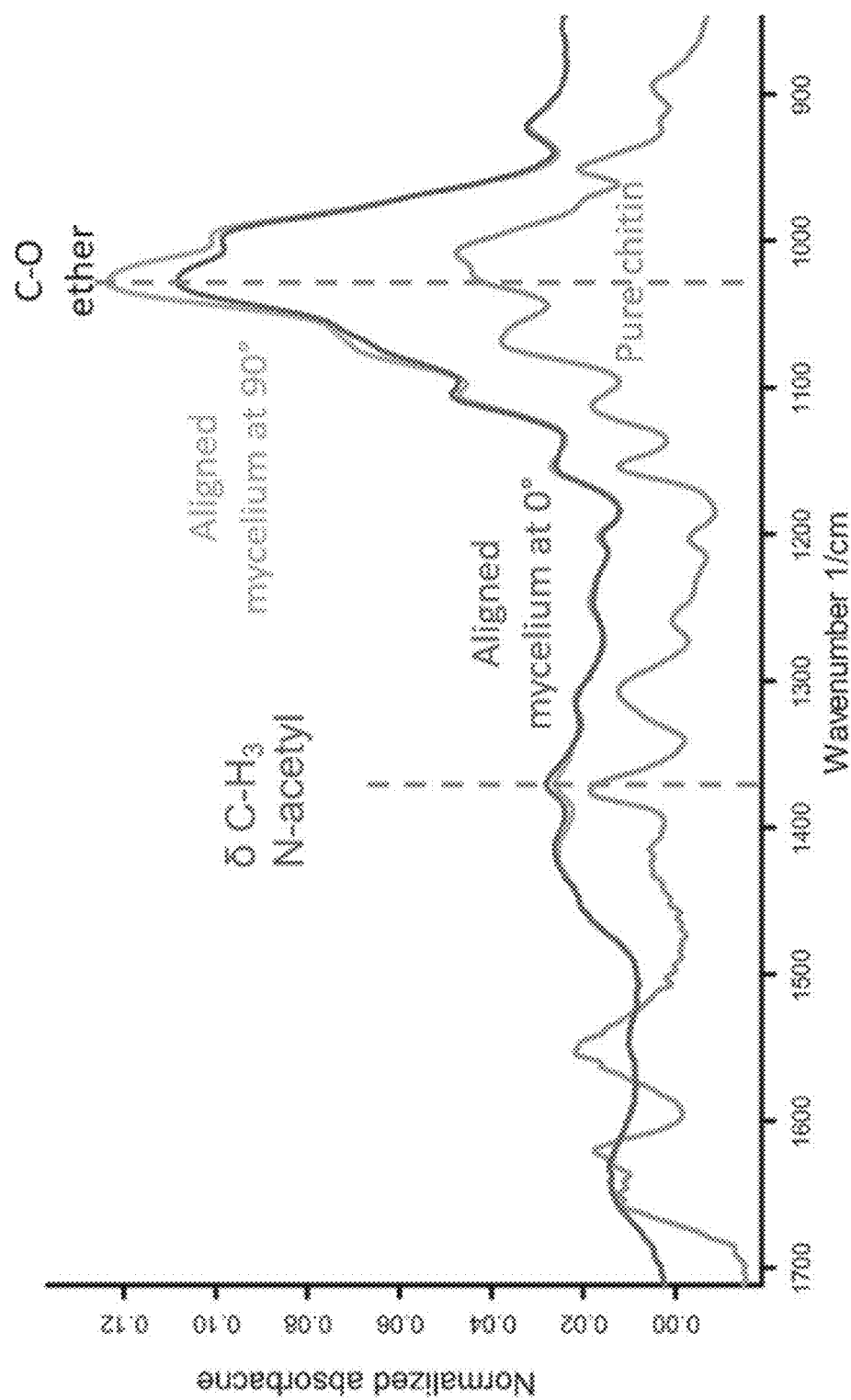
FIG. 9 shows a polarized Fourier transform infrared spectroscopy (FTIR) spectra graph of normalized absorbance versus wavenumber 1/cm of aligned mycelium hypha along with the polarization (0 degrees) and perpendicular to the polarization (90 degrees). A spectrum of pure chitin is shown for comparison.
Figure 10:
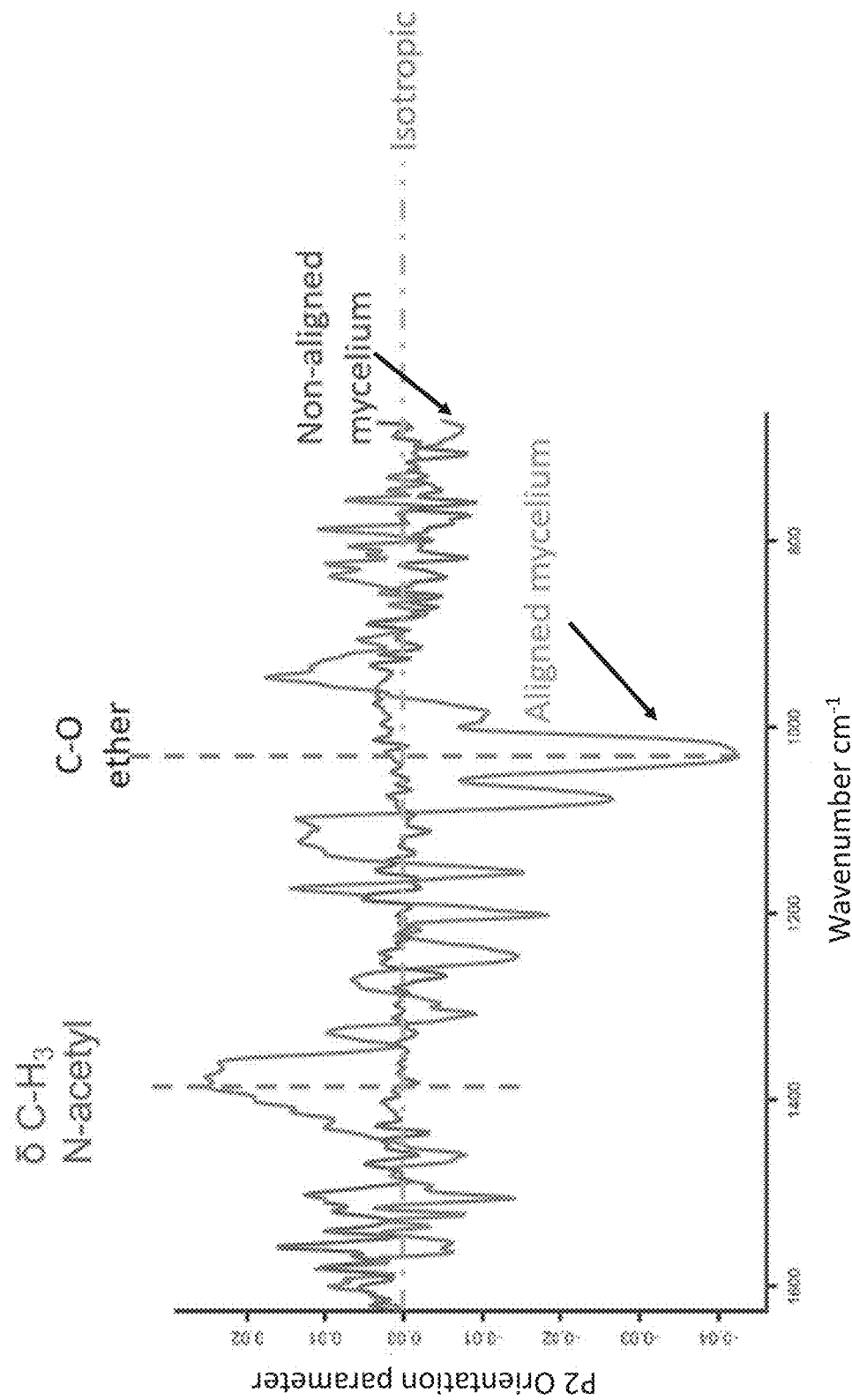
FIG. 10 depicts a polarized FTIR spectra graph of normalized absorbance versus wavenumber 1/cm of a second Legendre order parameter (<P2>) as a function of the wavenumber for non-aligned and aligned mycelium hypha.

FIG. 8 shows a Fourier transform graph of the mycelium SEM image before drafting (black squares) and after drafting (grey circles). The graph illustrated normalized grey scale (%) as a function of fiber alignment angle. FIG. 9 shows polarized FTIR spectra of aligned mycelium hyphae along with the polarization (0 degrees) and perpendicular to the polarization (90 degrees). A spectrum of pure chitin is shown as a comparison. FIG. 10 shows a second Legendre order parameter (<P2>) as a function of the wavenumber for non-aligned and aligned mycelium hyphae. The graph demonstrated there was an alignment of hyphae at particular frequencies. FIGS. 11A and 11B show SEM micrographs of two laminae of aligned mycelium bonded with polyurethane hot melt adhesive at 150× (FIG. 11A) and 500× (FIG. 11B) magnification. The surface of the layer was measured. FIGS. 12A and 12B show stress-strain curves for aligned mycelium and aligned mycelium bonded with polyurethane hot melt adhesive tested after conditioning at 65% RH at a dry state (FIG. 12A) and a wet state (FIG. 12B).

Table 9 depicts tensile properties of aligned mycelium and aligned mycelium bonded with polyurethane (PU) hot melt adhesive tested after conditioning at 65% relative humidity (RH) and after a one-hour water submersion.

TABLE 9

| | | Thickness (mm) | | Initial modulus (MPa) | | Yield strength 0.2% (MPa) | | Strength (MPa) | |
|---|---|---|---|---|---|---|---|---|---|
| | | Min | Max | Min | Max | Min | Max | Min | Max |
| Drafted mycelium PU laminate | Dry | 0.546 | 0.688 | 49.266 | 63.05 | 0.9505 | 1.538 | 5.750 | 8.804 |
| | Wet | 0.440 | 0.500 | 41.094 | 74.94 | 0.8054 | 1.791 | 3.298 | 4.549 |
| Drafted mycelium lamina | Dry | 0.066 | 0.162 | 0.253 | 47.04 | 0.0562 | 7.940 | 4.195 | 10.730 |
| | Wet | 0.141 | 0.148 | 7.956 | 9.801 | 0.2942 | 0.328 | 0.857 | 0.935 |

Dry tensile strength of composite mycelium material was measured against wet tensile strength. For instance, drafted mycelium PU laminate yielded dry tensile strength of 5.750 MPa to 8.804 MPa and a wet tensile strength of 3.298 MPa to 4.549 MPa. It was observed that initial modulus dropped due to wetting. There was likewise a larger decrease in values that occurred for non-bonded laminate as compared to bonded laminate. In the drafted mycelium lamina samples without PU, absence of a bonding agent did not change the tensile strength. In addition, using polyurethane yielded a material that was four times stronger when wet. Without intending to be bound by any particular theory, the tensile strength properties may be dependent on the specific type of manipulations of hyphae.

Example 4: Hydroentanglement of the Composite Mycelium Material

The components for the materials were disrupted in a blender and the resulting slurry included at least cultivated mycelium material and water. Water was directed at the mycelia slurry at about 750-1000 psi through pores with a diameter of about 50 microns. The mycelia slurry was submerged within a solution including one or more bonding agents. Without intending to be bound by any particular theory, it is proposed that the one or more masses of branching hyphae of the composite mycelium material entangled effectively via hydroentanglement, leading to certain mechanical property improvements in performance, e.g., wet tensile strength, an initial modulus, an elongation percentage at the break, a thickness, and/or a slit tear strength. Results are included herein, e.g., Example 15.

Example 5: Permeation of the Mycelium Material with Processing Solutions

Figure 15:
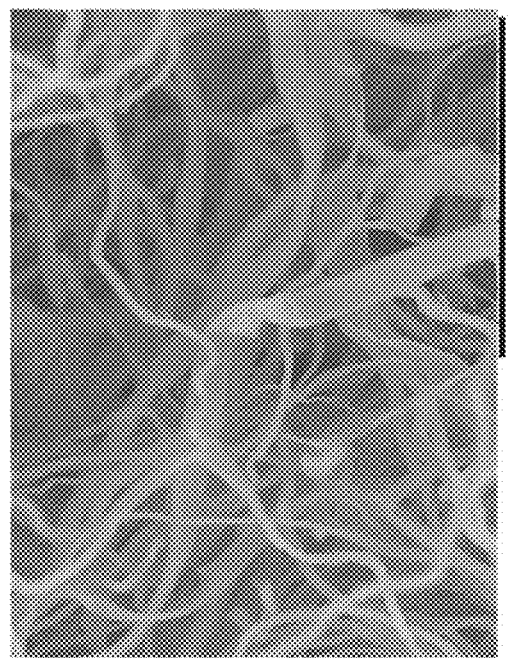
FIG. 15 shows mycelium hyphae form a 3D network that contains open pores between the hyphae structure.

Mycelium panels are porous materials made of entangled hyphae. The hyphae entangle to form a 3D network that contains open pores between the hyphae structure as shown in FIG. 15. These hyphae pore diameters can be between several hundred nanometers to several micrometers. When making mycelium materials, it can be beneficial to use chemical compounds that can bind the mycelium hyphae together, which helps with improving the structural integrity and lamination of the mycelium material. However, such compounds must also be able to permeate the mycelium material in order to efficiently act as a material binder.

Figure 16:
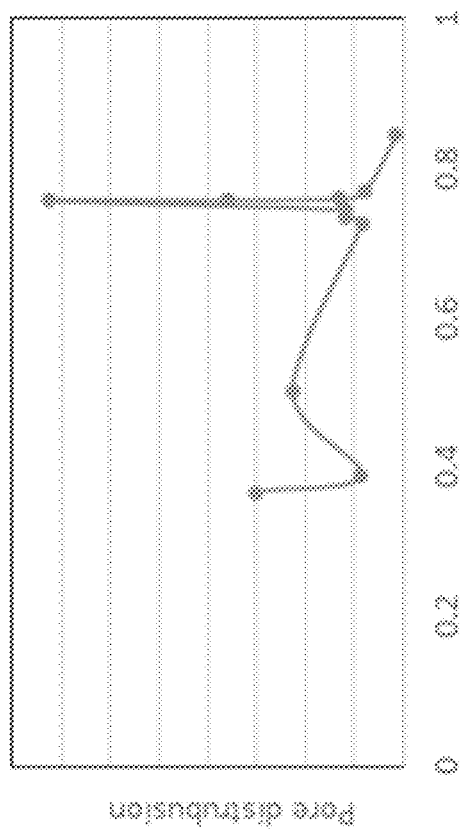
FIG. 16 shows that most pore diameters fall into the range between 0.36 and 0.84 micrometers, with a sharp peak of very high pore size distribution between 0.72 and 0.78 micrometers.

Pore size distribution inside mycelium materials was characterized using a capillary flow porometer (Porous Materials Inc., Ithaca N.Y.) following ASTM standard F316-03. FIG. 16 shows that most pore diameters fall into the range between 0.36 and 0.84 micrometers, with a sharp peak of very high pore size distribution between 0.72 and 0.78 micrometers. The largest pore size was approximately 2.2 micrometers, as determined by bubble point which is the pressure at which the first continuous gas bubbles are detected. Therefore, solutions with particle size above this range may be retained or blocked by the mycelium material surface and will not penetrate to the center of the mycelium material.

Mimosa Tannin, Fatliquor, and Dye Solutions Particle Size

Figure 18:
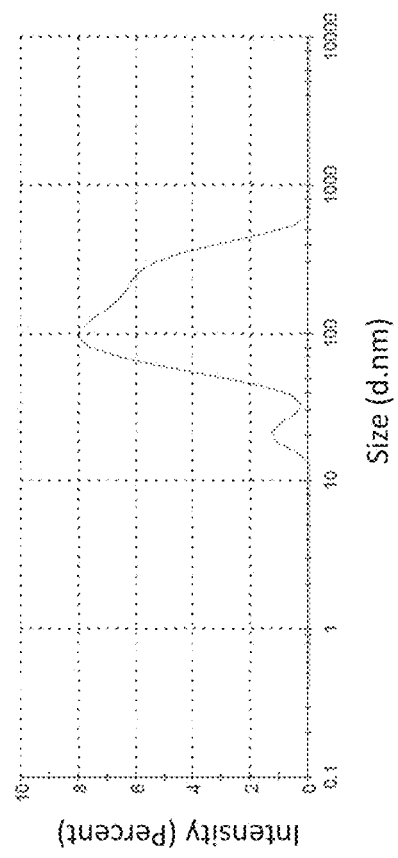
FIG. 18 shows the particle size of 5% wt/wt fatliquor (DXV/LEX=3:1) emulsion.
Figure 17:
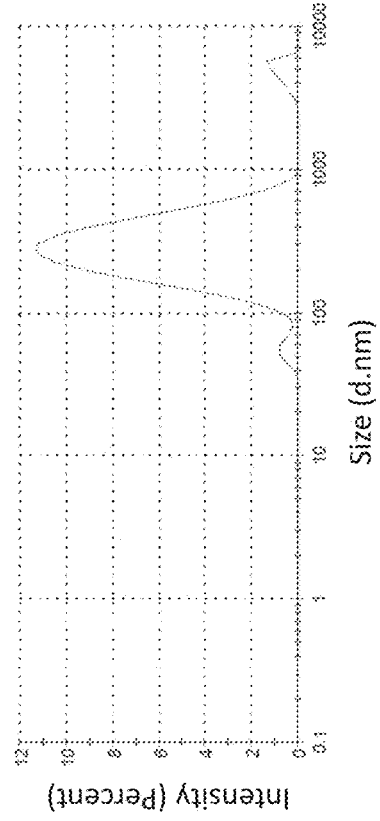
FIG. 17 shows the particle size of a mimosa tannin 5% aqueous solution

Next, the particle size of various processing solutions was determined. A Malvern Zetasizer Nano-S was used to measure the particle size in selected solutions and emulsions. This equipment can measure particles between 0.1 nanometers and 5 micrometers. Exemplary solutions included mimosa tannin, fatliquor, and dye. The particle size of a mimosa tannin 5% aqueous solution is shown in FIG. 17 and the particle size of a fatliquor 5 wt % aqueous solution (Trupon DVX:Truposol LEX=3:1) is shown FIG. 18.

Most particles were between 100 nm and 1 μm in the mimosa tannin solution, while most particles were between 50 and 500 nm in the fatliquor solution. Thus, mimosa tannin and fatliquor particles are expected to penetrate through the mycelium materials.

Gum Arabic, Tannin, and Fatliquor Solution Particle Size

Figure 20:
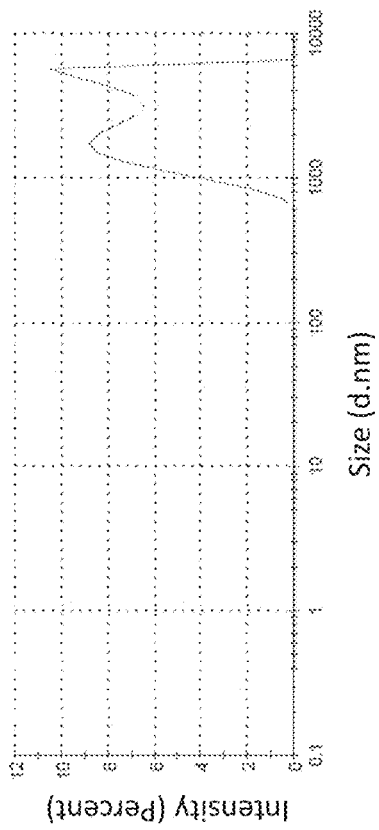
FIG. 20 shows particle size of crust solution that contains gum arabic, mimosa tannin and fatliquor

Gum Arabic is a natural gum consisting of hardened sap and can be used as a binder material, considered a candidate for mycelium treatment. However, processing of gum arabic with materials showed that only a superficial impregnation occurred. Measurement of the particle size distribution in a gum arabic solution showed that the particle size of gum arabic in aqueous solution is relatively large, likely causing the particles to be filtered by the mycelium and sit at the mycelium surface, generating a crusty surface layer. The particles size of gum arabic in 10% wt/wt aqueous solution (FIG. 19), and gum arabic (10% wt/wt) with tannin and fatliquor in crust solution are shown (FIG. 20).

Figure 19:
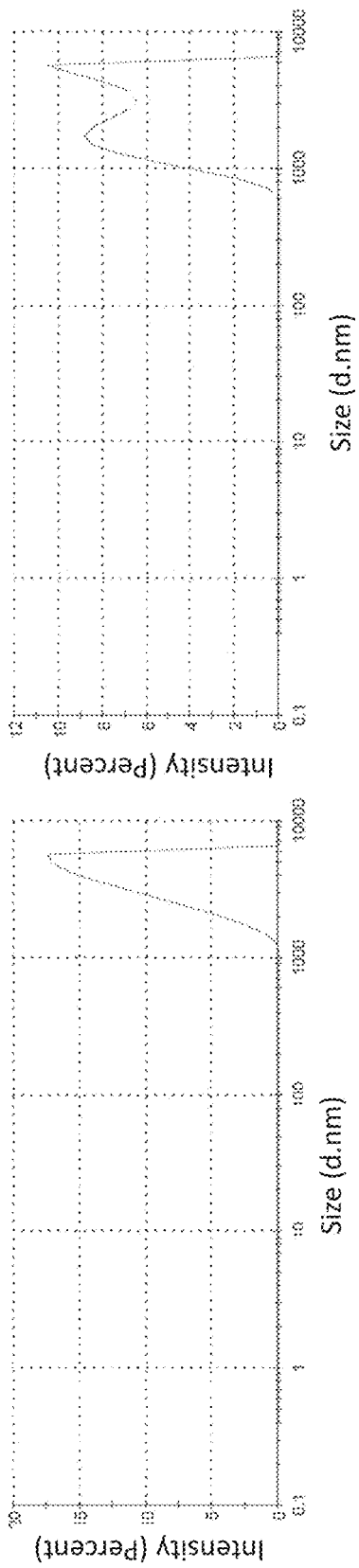
FIG. 19 shows the particle size distribution of 10 wt % gum arabic solution.

Gum arabic aqueous solution particles ranged between 1 μm and more than 5 μm (FIG. 19). Since the Malvern equipment measures particles smaller than 5 μm, the peak at the right edge of the chart was truncated. It was unexpected that the gum arabic/tannin/fatliquor combined solution had no particles between 50 nm and 1000 nm as would be expected from the particles of the mimosa tannin and fatliquors. Instead, a peak at around 2 μm was observed next to the gum arabic signal peak. Since fatliquor is a mixture of softening oil, surfactant, defoamer, and other ingredients, adding mimosa tannin and gum arabic, which both contains large quantities of hydroxyl groups, may have affected the surface energy. This may change the particle size, especially the micelle particle size, in such a solution.

Polymer Solution Particle Size

Figure 22:
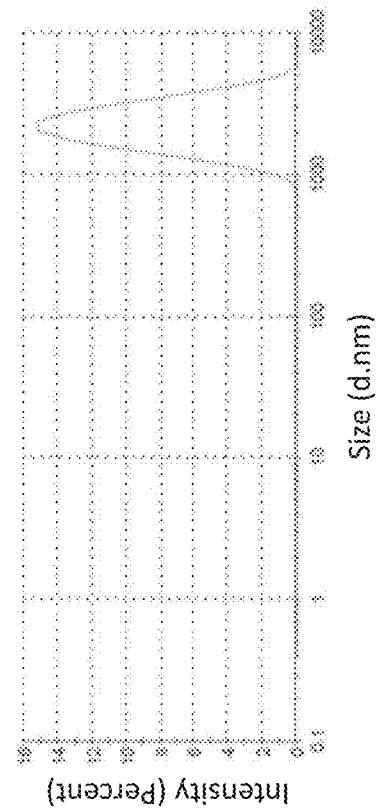
FIG. 22 shows the particle size distribution of VAE S-10 emulsion (US Adhesive).
Figure 21:
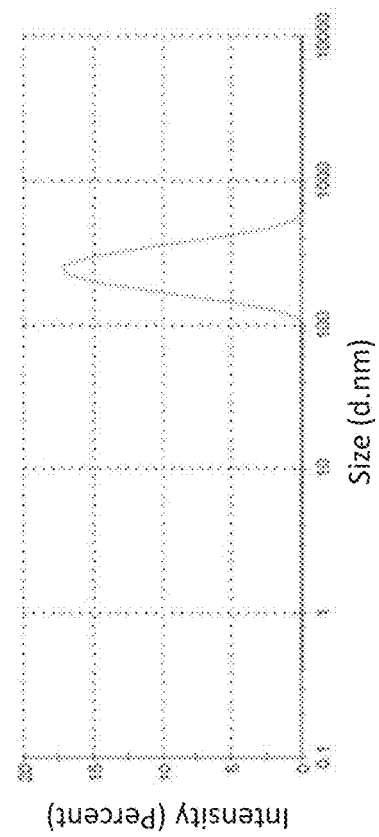
FIG. 21 shows the particle size distribution of 10 wt % X-LINK® 2833 emulsion (Celanese).

The particle size of various self-crosslinking co-polymers was also assessed. Vinyl acetate-acrylic and vinyl acetate-ethylene are self-crosslinking polymers that can bind to the mycelium material and to themselves, and thus function as both a binder and a crosslinker. Additional particle size test results showed vinyl acetate-ethylene (VAE) from different manufacturers have 10× different micelle particle size (0.23 μm vs 2.2 μm) in emulsion. FIG. 21 shows the particle size distribution of 10 wt % X-LINK® 2833emulsion (Celanese). FIG. 22 shows the particle size distribution of VAE S-10 emulsion (US Adhesive). Thus, even similar polymer solutions show a range of particle size depending on the manufacturer source.

Example 6: Treatment of Mycelium with Crosslinkers and Gum Arabic Binders

PAE and APS Crosslinkers

Polymer crosslinkers PAE and APS were investigated to improve the mechanical strength of the mycelium material. These crosslinkers act to crosslink the mycelium hyphae and can be used with additional polymer binders such as gum arabic or latex. The crosslinkers used were polyamide epichlorohydrin (PAE) and ammonium persulfate (APS). Polyamide epichlorohydrin resin is a water soluble, cationic resin with azetidinium groups that can be used to crosslink polysaccharides with carboxyl groups, such as cellulose.

The anion radical generated from APS decomposition can crosslink polymer chains that contain hydroxyl groups. Mycelium is mainly composed of polysaccharides, which have numerous hydroxyl groups on their side chains.

PAE Crosslinker

For the PAE samples, two sets of four 10% (w/w) mycelial slurry in water were prepared. In each set two samples were mixed with PAE to a final 1.5% (w/w) PAE concentration, one sample was mixed with PAE to a final 3% (w/w) PAE concentration, and one sample was not mixed with PAE as a control. The resulting mixtures were allowed to sit for 10 minutes, filtered and pressed into mats of 0.25 inches, then dried at room temperature. The control sample, one 1.5% PAE sample, and the 3% PAE sample were heated at 105° C. for 10 minutes. The other 1.5% PAE sample was left un-heat treated. One set of samples was tested dry, and the other was wet. ISO 3377-2 double edge tear, ASTM D2209 tensile, and ASTM D4704 tongue tear tests were then performed on a ZwickiLine Materials Testing Machine Z5.0 to determine relative strength of each PAE-treated sample as compared to the heat-only control sample.

Figure 23:
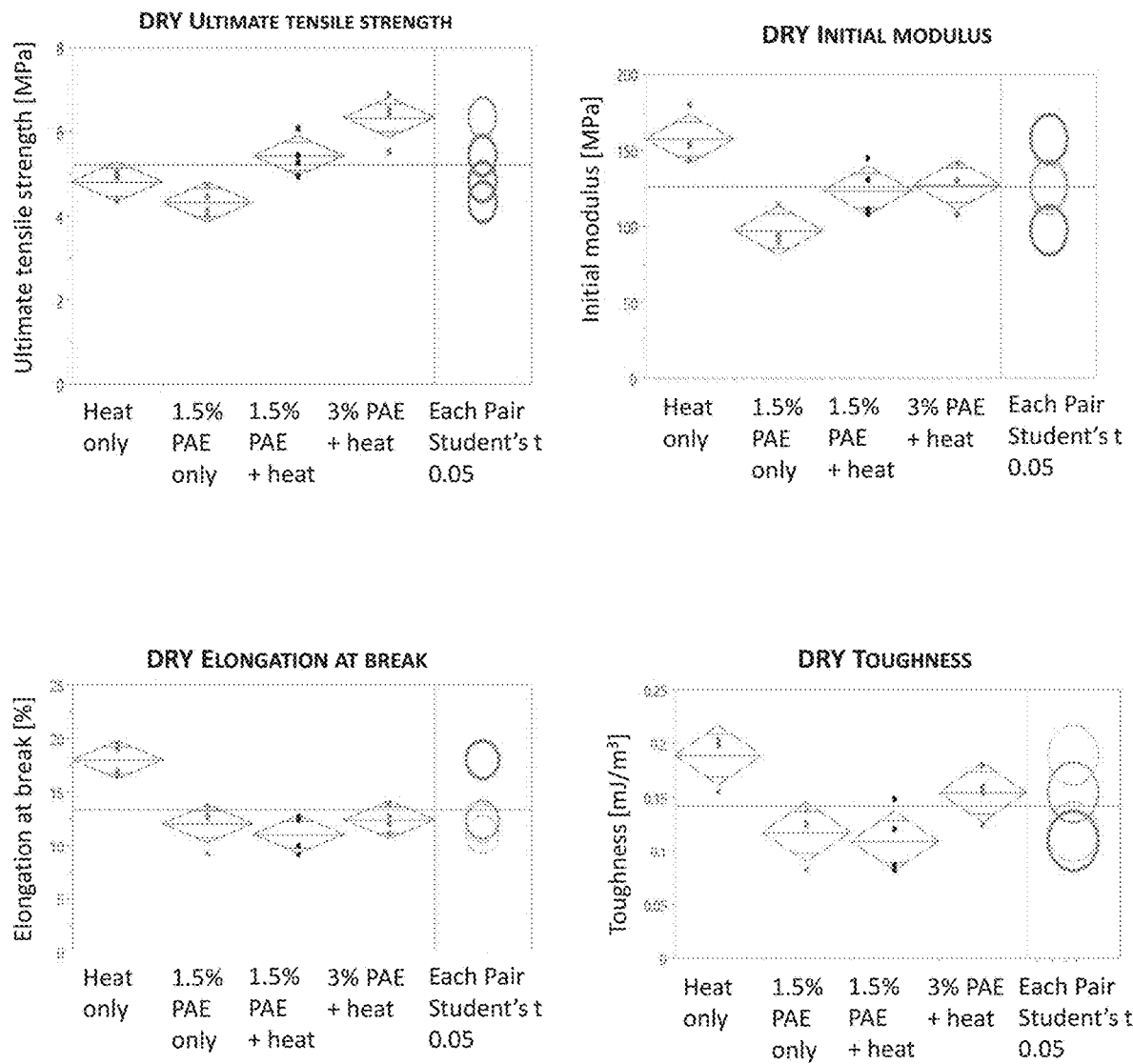
FIG. 23 shows the tensile strength results of the PAE crosslinked samples.
Figure 23:
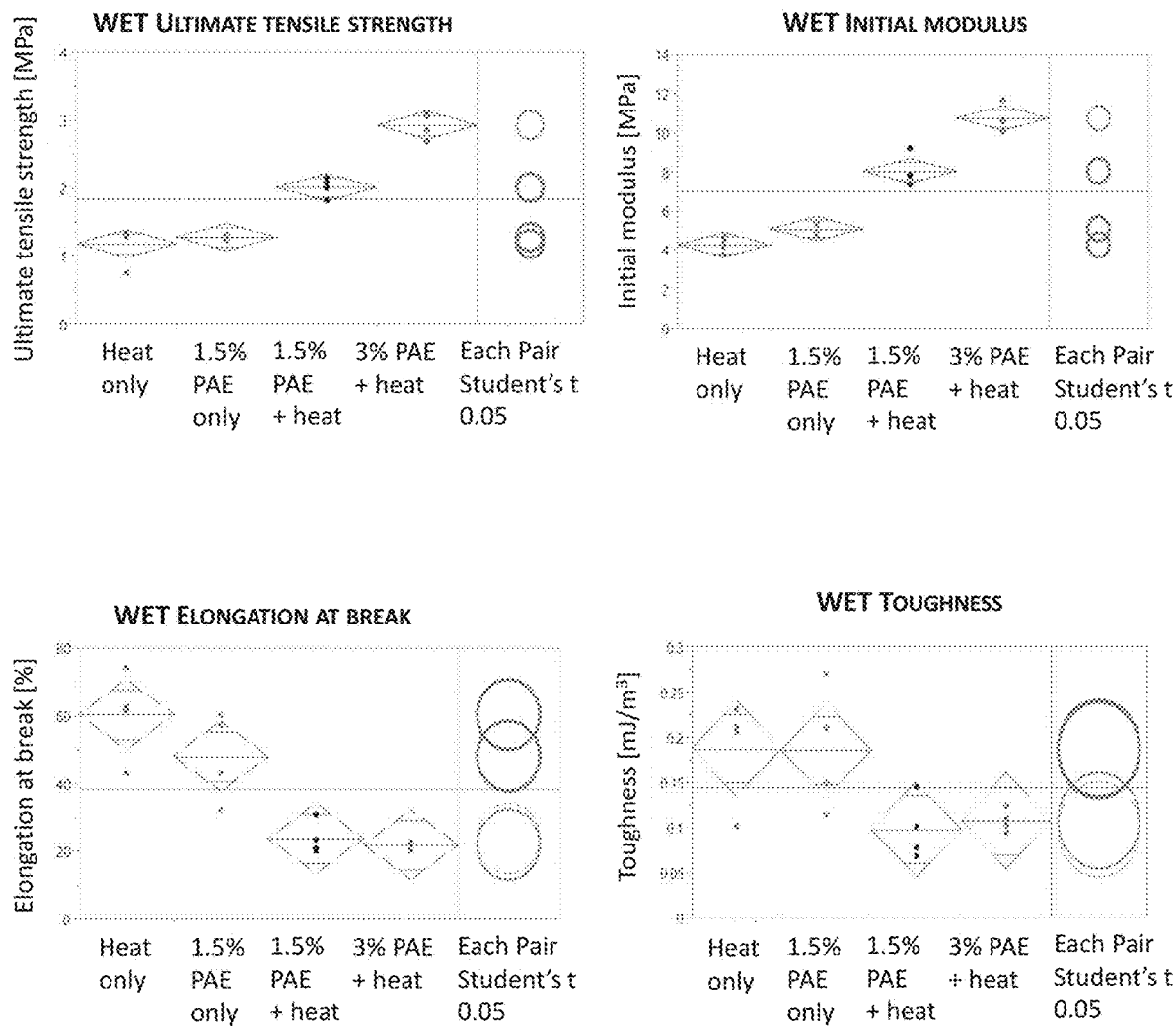

The tensile strength results of the PAE crosslinked samples are shown in FIG. 23. In both the wet and dry conditions, the 3% PAE and heat-treated sample had the highest stress strength and the 1.5% PAE and heat-treated sample had the second highest stress strength. In the wet conditions, the 1.5% PAE and no heat sample had the third highest strength, while in the dry conditions the 1.5% PAE and no heat sample and the heat only sample had similar strength. Thus, adding PAE and heating the samples increased the strength of the mycelium material in a concentration dependent manner, and the application of heat was required for full effectiveness of the PAE crosslinking. The addition of PAE and heat to crosslink the mycelium material improved the mechanical qualities of the mycelium panel.

APS Crosslinker

For the APS samples, dried mycelial mats were soaked in a 1% (w/w) solution of ammonium persulfate in deionized water or phosphate buffered saline (PBS) and brought to 80° C. with slight agitation for 3.5 hours. The resulting mats were rinsed in deionized water and dried at 40° C. for 3 hours. ISO 3377-2 double edge tear, ASTM D2209 tensile, and ASTM D4704 tongue tear tests were then performed on a ZwickiLine Materials Testing Machine Z5.0 to determine relative strengths versus control samples.

The results of the tear and tensile strength tests are shown in Table 13 and Table 14.

TABLE 13

Wet tensile strength, initial modulus, and elongation at break.

| n | Sample | Wet Tensile strength (MPa) Average | Std. Dev. | Initial Modulus (MPa) Average | Std. Dev | Elongation at break (%) Average | Std. Dev |
|---|--------|------------------------------------|-----------|-------------------------------|----------|---------------------------------|----------|
| 4 | PBS | 1.60 | 0.57 | 1.79 | 0.89 | 54.48 | 9.66 |
| 4 | PBS + APS | 3.32 | 0.71 | 3.92 | 1.13 | 63.30 | 4.67 |

TABLE 14

Slit tear test

| n | Sample | Slit tear strength (N) Average | Std. Dev. | Thickness (mm) Average | Std. Dev |
|---|--------|-------------------------------|-----------|------------------------|----------|
| 4 | PBS | 15 | 4 | 1.4 | 0.3 |
| 4 | PBS + APS | 22 | 7 | 1.4 | 0.2 |

The APS treated samples had significantly increased wet tensile strength, initial modulus, elongation, and slit tear strength as compared to the control samples. Thus, the addition of APS to crosslink the mycelium material improved the mechanical qualities of the mycelium panel.

Gum Arabic and Latex or APS

The ability of gum arabic to improve the mechanical strength of mycelium was also investigated. In addition, ammonium persulfate (APS) was added to crosslink the gum arabic and the mycelium.

Three samples of mycelium and gum arabic were tested. In the first two, gum arabic (AEP Colloids Division, Sarcom Inc) was crosslinked using 3% wt/wt and 5% wt/wt APS to gum arabic mass. In the third sample, latex was mixed with gum arabic at a 30:70 ratio. Latex contains monomers with unsaturated C=C bonds and can self-polymerize and/or crosslink. Samples were also treated with mimosa tannin and fatliquors.

Table 15 provides details of the samples and treatment conditions.

TABLE 15

| Sample | Composition |
|--------|-------------|
| 1: Gum Arabic with 3% APS | 7.5 g Mycelium<br>270 g water<br>30 g gum Arabic<br>4.5 g mimosa tannin<br>5.625 g Trupon DXV<br>1.875 g Truposol LEX<br>0.9 g APS |
| 2: Gum Arabic with 5% APS | 7.2 g Mycelium<br>270 g water<br>30 g gum Arabic<br>4.5 g mimosa tannin<br>5.625 g Trupon DXV<br>1.875 g Truposol LEX<br>1.5 g APS |
| 3: Gum Arabic: Latex 70:30 | 6.8 g Mycelium<br>270 g water<br>21 g Gum Arabic<br>9 g latex<br>4.5 g mimosa tannin<br>5.625 g Trupon DXV<br>1.875 g Truposol LEX |

All three samples were processed by soaking in the solution for 1 minute, followed by a rolling step. The soak and roll cycle was performed four times. Processed mycelial panels were dried in a convection oven at 90° C. for 2 hours. The panels were removed from the oven, and dried in a fume hood at room temperature overnight. Panels were cut and the cross section imaged using a Hitachi™-3030 Plus environmental scanning electron microscope at an accelerating voltage of 15 kV.

Figure 24:
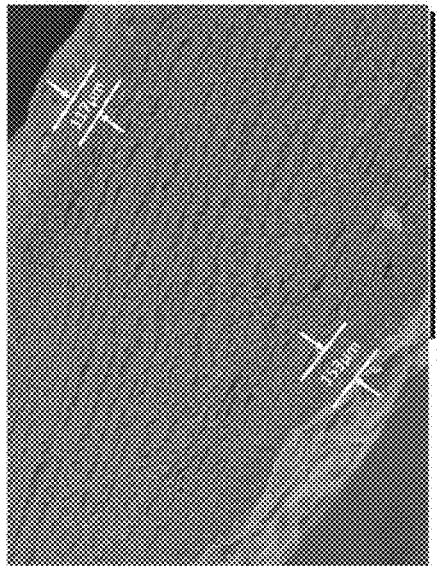
FIG. 24 shows a cross section SEM image of a processed mycelium panel treated with gum arabic with latex.

In the cross-section SEM image of gum arabic with latex, two dense layers can be observed on both surfaces of a processed mycelium panel (FIG. 24). The gum arabic binder penetrated approximately 100 to 150 µm in from the surface.

Figure 25:
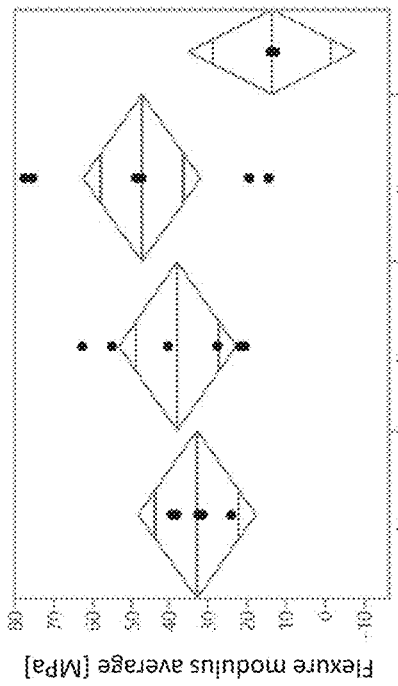
FIG. 25 shows the normalized flexural modulus of gum arabic and APS or latex treated mycelium panels.

FIG. 25 shows that gum arabic and latex treated samples have similar stiffness as the gum arabic and APS treated samples, and they were both slightly stiffer than the mycelium panels only treated with fatliquors (2.5% w/w in aqueous solution), as indicated by the higher flexural modulus. A higher flexural modulus indicates an increased stiffness and a reduced flexibility of the material. This increase in stiffness may be caused by the denser surface layer on the gum arabic/latex treated sample, which was observed in the SEM images. The data was normalized to unit sample thickness of untreated samples, calculated by dividing force by thickness, having units of N/mm.

Figure 26:
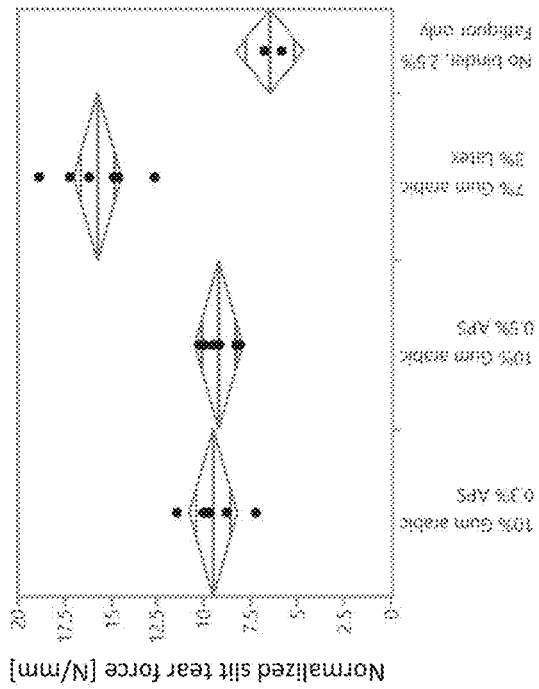
FIG. 26 shows the normalized slit tear maximum strength of gum arabic and APS or latex treated mycelium panels.

The normalized slit tear maximum strength of gum arabic and APS treated mycelium panels were slightly higher than the untreated panels (FIG. 26). The gum arabic and latex treated panel showed significant higher slit tear strength than the gum arabic and APS treated samples. Latex treated mycelium samples showed high slit tear strength indicating that the 30% latex in the binder mixture contributed to the improvement of slit tear strength. However, gum arabic and latex had a low permeation of the solution particles and increased flexural modulus in the material.

Example 7: Improvement of Mycelium Mechanical Properties with Self-Crosslinking Polymer Binders Permeation of Mycelium Material with Polymer Binder Emulsions Mycelium mats were incubated with solutions containing various concentrations of polymer emulsion binders to assess the effect on mechanical properties. Vinyl acetate-ethylene and vinyl acetate-acrylic are self-crosslinking co-polymers. Such co-polymers can act as a binder polymer and bind to both the mycelium material and/or themselves, allowing for a single molecule to act as both a binder and crosslinker.

First, an aqueous solution containing vegetable tannins, fatliquors, and dye was prepared according to the composition described in Table 17. The amount of water used to prepare the solution was 20 times based on the input mycelium sample mass.

TABLE 17

| Component | Product name | Supplier | Concentration in water (g/L) |
|---|---|---|---|
| Vegetable tannins | Mimosa FS powder | Forestal Mimosa | 25.00 |
| Fatliquor | Truposol LEX | Trumpler | 6.25 |
| Fatliquor | Trupon DXV | Trumpler | 18.75 |
| Dye | Acid brown 14 | Fisher | 1.00 |

A binder was then added to the solution to achieve a specific binder solids content. The binders and concentration ranges used for each binder are described in Table 18. Tear mender latex was used as a control.

TABLE 18

| Binder name | Supplier | Description | Conc range (solids g/L in solution) | Glass Transition Temp |
|---|---|---|---|---|
| Tear Mender | LHB Industries/ Tear Mender | Natural rubber latex | 3–205 | −70° C.[1] |
| S-10 | US Adhesives | Vinyl acetate-ethylene copolymer emulsion | 3–121 | <0° C.[2] |
| X-LINK ® 2833 | Celanese | Vinyl acetate-acrylic copolymer emulsion | 0–50 | −15° C. |
| Dur-O-Set ® Elite 22 | Celanese | Vinyl acetate-ethylene copolymer emulsion | 0–25 | −15° C. |

[1]Glass transition temperature for natural rubber latex is −70° C.
[2]Approximate glass transition temperature.

Dry mycelium samples were immersed in each of the solutions for one minute, and then passed through a roller to force the solution through the material. The soaking and rolling process was repeated until the sample appeared to be evenly saturated with solution. Samples were dried at ambient conditions and then calendar rolled to a final thickness of 1.3-1.7 mm. Sample masses were recorded before and after processing to determine the change in mass relative to its starting mass and the final mycelium content.

Figure 27:
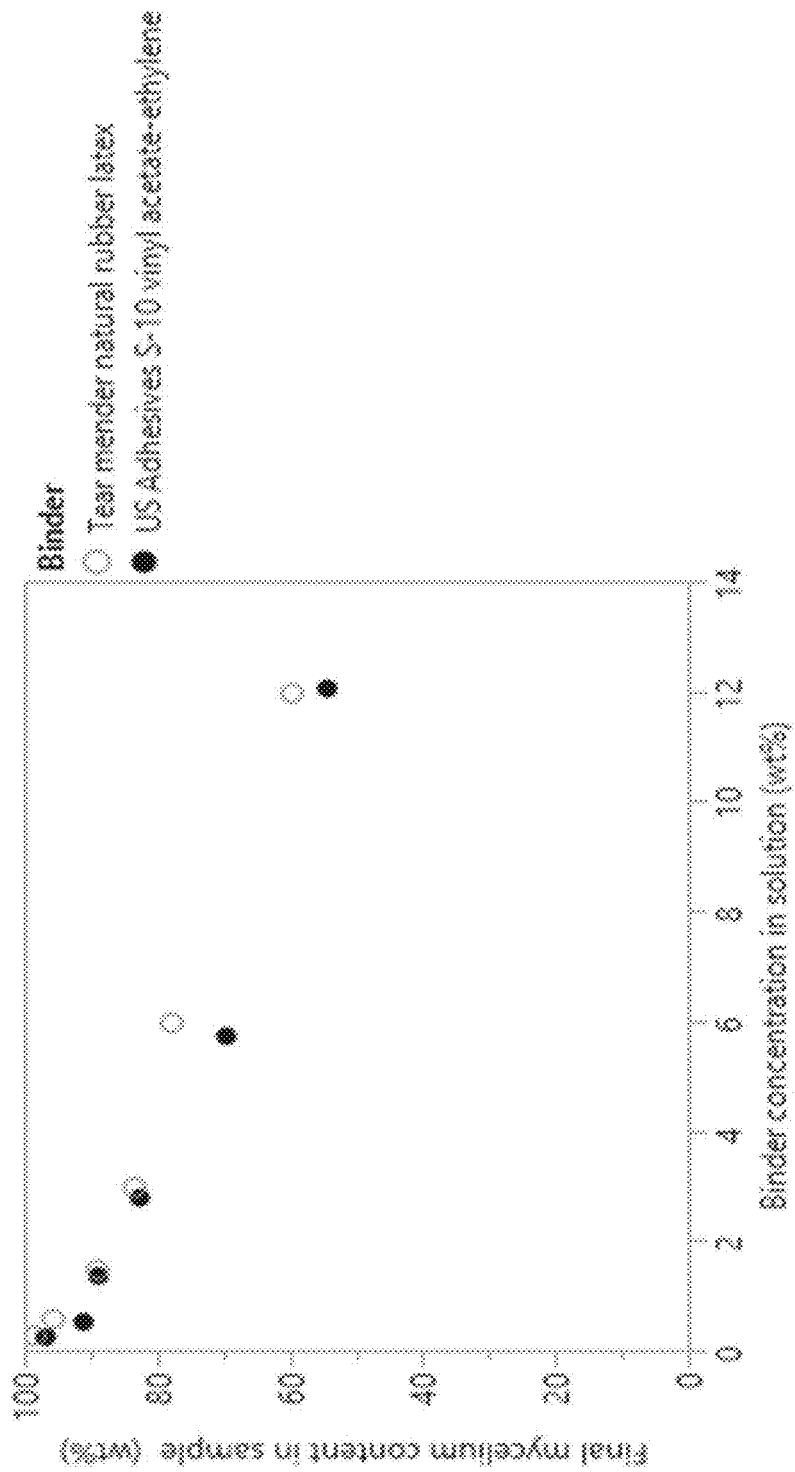
FIG. 27 shows the mycelium content of samples as a function of the binder concentration in solution for samples impregnated with natural rubber latex and S-10 vinyl acetate-ethylene.

For some experiments, the tannins, fatliquors, and dye were omitted to understand the effect of binder concentration alone on mass uptake in the final sample. FIG. 27 shows the mycelium content of samples as a function of the binder concentration in solution for samples impregnated with natural rubber latex (Tear Mender) and S-10 vinyl acetate-ethylene.

As shown in FIG. 27, the binder uptake in a final sample is proportional to the binder concentration in the solution and inversely proportional to the final mycelium content in the sample. Thus, the decreasing mycelium content in a final sample in FIG. 27 together with the increasing binder solution concentration suggests that more of the final sample total mass comprises of binder. Therefore, to achieve a desired final mycelium content, the binder concentration in the solution can be adjusted according to the relationship shown.

Figure 30:
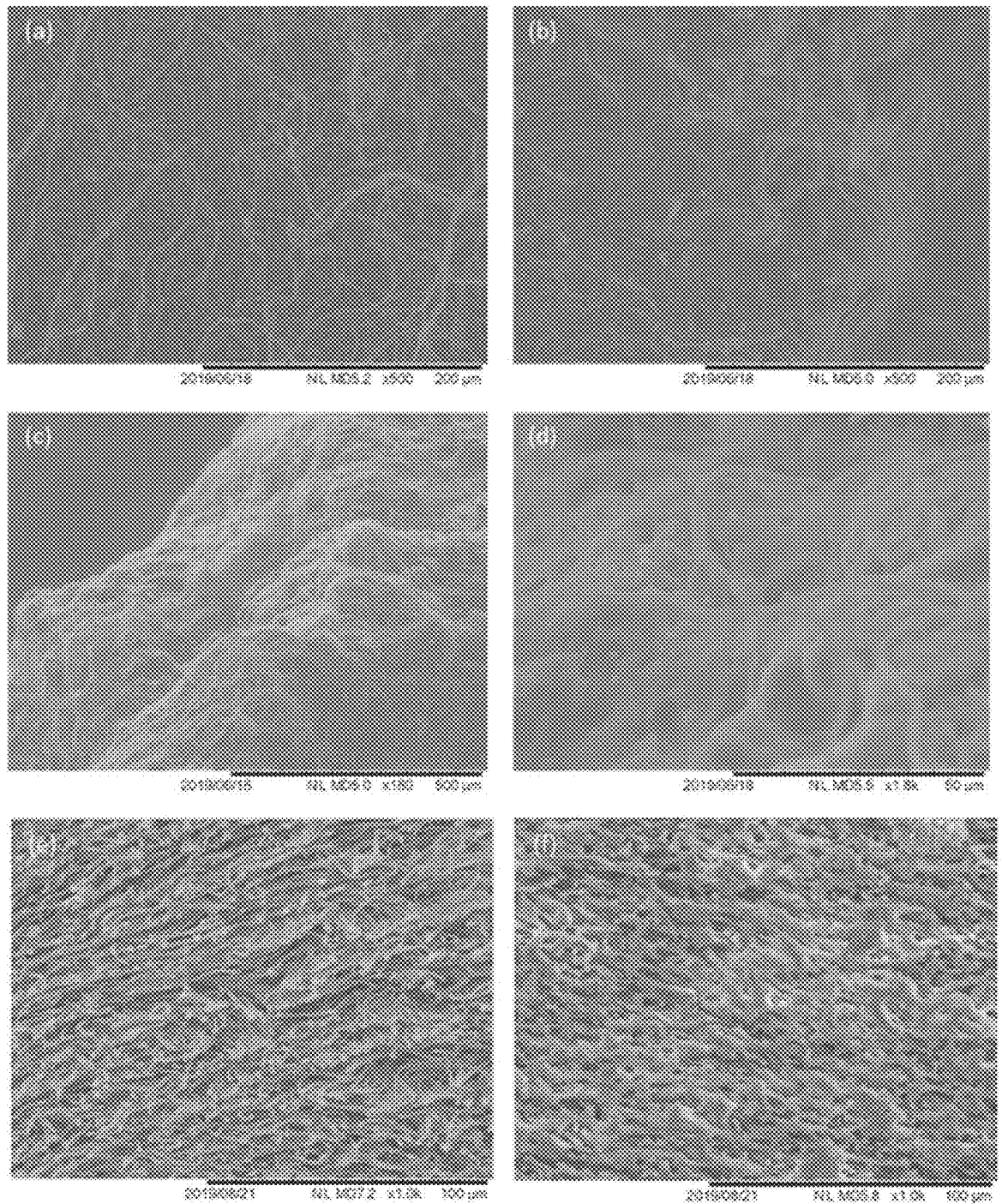
FIG. 30 shows representative scanning electron micrographs of untreated mycelium samples and mycelium samples impregnated with either natural rubber latex or S-10 vinyl acetate-ethylene.

The surface and interior of impregnated mycelium samples were examined with scanning electron microscopy (SEM) to qualitatively assess the degree of impregnation. SEM was performed using a Hitachi™-3030 Plus environmental scanning electron microscope at an accelerating voltage of 15 kV. FIG. FIG. 30 shows representative scanning electron micrographs of untreated mycelium samples and mycelium samples impregnated with either natural rubber latex or S-10 vinyl acetate-ethylene. As shown in FIG. 30, there was the effective impregnation of binder S-10 vinyl acetate-ethylene and natural rubber latex into the mycelial network, as evidenced by the filled voids in the cross sections and tear surfaces (panels b, c, d, f) compared to the empty spaces between the hyphae in the untreated samples (panels a and e).

Assessment of Mechanical Properties

To assess the delamination resistance of binder-impregnated mycelium samples, T-peel testing was performed following ASTM D1876 using a Zwick Proline universal testing system with a 500N load cell. Prior to testing, samples were conditioned at 65% relative humidity until their masses were stable to within 0.25 wt % for one hour.

Figure 29:
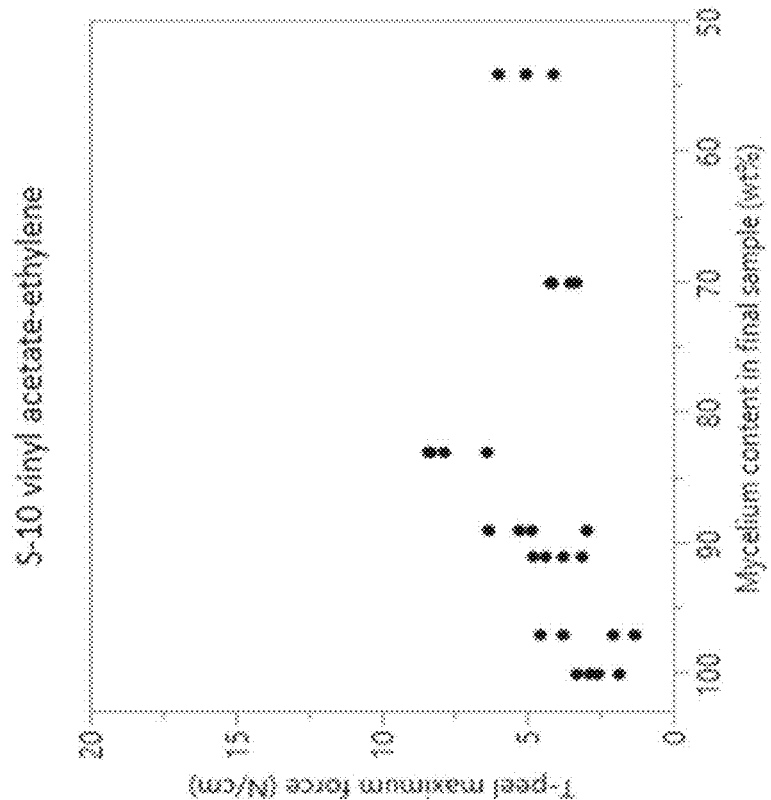
FIG. 29 shows the maximum T-peel force for mycelium samples impregnated with S-10 vinyl acetate-ethylene over a range of concentrations. Points denote individual T-peel tests.
Figure 28:
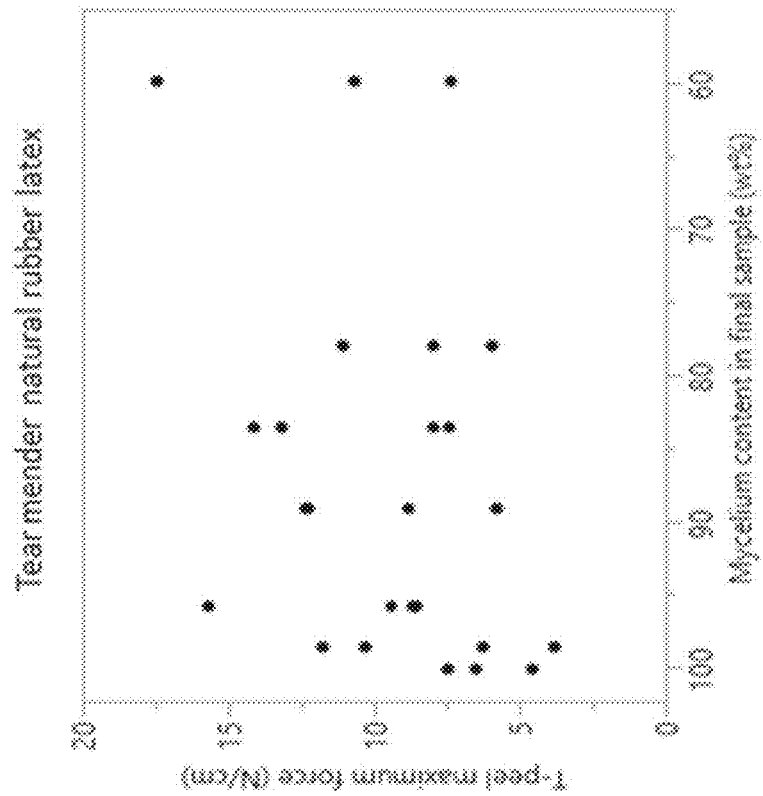
FIG. 28 shows the maximum T-peel force for mycelium samples impregnated with Tear mender natural rubber latex. Points denote individual T-peel tests.

FIG. 28 shows the maximum T-peel force for mycelium samples impregnated with Tear mender natural rubber latex. FIG. 29 shows the maximum T-peel force for mycelium samples impregnated with S-10 vinyl acetate-ethylene over a range of concentrations. Points denote individual T-peel tests. For these samples, fatliquors, dye, and tannins were omitted.

Figure 31:
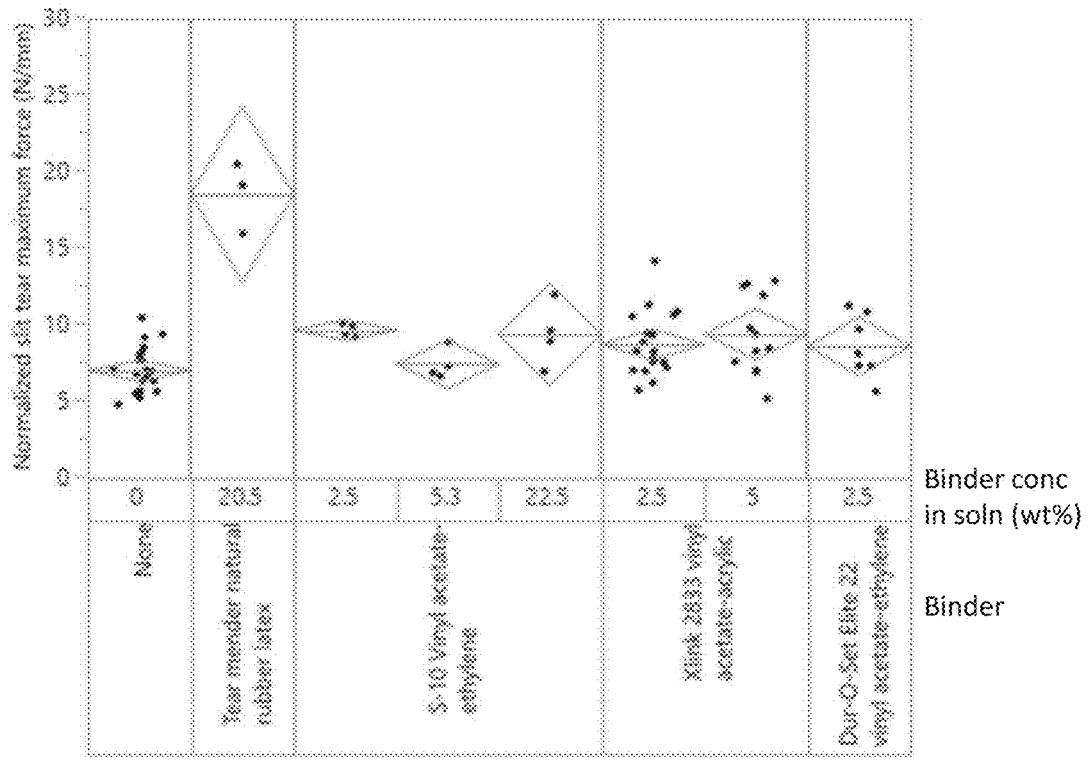
FIG. 31 shows normalized slit tear maximum force of samples impregnated with various binders at various concentrations. Points denote individual slit tear tests. Diamonds denote the upper and lower 95% confidence interval of the mean normalized slit tear force in each group.
Figure 32:
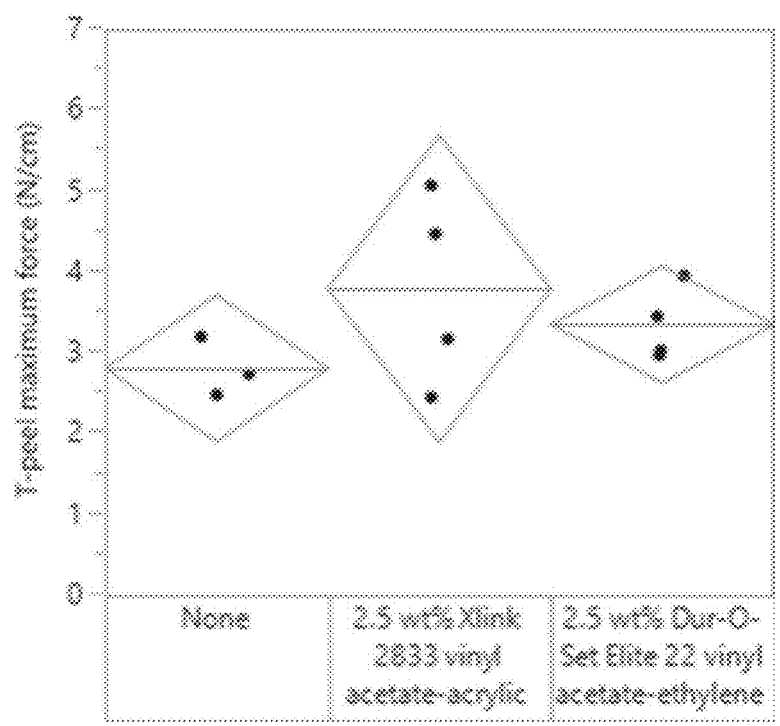
FIG. 32 shows the maximum T-peel force for mycelium samples impregnated with either X-LINK® 2833 vinyl acetate-acrylic or Dur-O-Set Elite 22 vinyl acetate-ethylene at the same binder concentration.

To assess the slit tear resistance of binder-impregnated mycelium samples, slit tear testing was performed according to ISO 3377-2 using a Zwickiline universal testing system. Prior to testing, samples were conditioned at 65% relative humidity until their masses were stable to within 0.25 wt % for one hour. FIG. 31 shows the slit tear maximum force normalized to the sample thickness for samples impregnated with various binders at various concentrations. Specifically, the maximum force was divided by the sample thickness for units of N/mm FIG. 32 shows the maximum T-peel force for mycelium samples impregnated with either X-LINK® 2833 vinyl acetate-acrylic or Dur-O-Set Elite 22 vinyl acetate-ethylene at the same binder concentration. Maximum T-peel force for mycelium samples impregnated with either X-LINK® 2833 vinyl acetate-acrylic or Dur-O-Set Elite 22 vinyl acetate-ethylene at the same binder concentration. Points denote individual T-peel tests. Diamonds denote the upper and lower 95% confidence interval of the mean maximum T-peel force.

As shown in FIGS. 31 and 32, the delamination resistance of mycelium can be affected by the choice of binder used for impregnation and its concentration. In general, the average maximum T-peel force of impregnated samples was greater than unimpregnated samples for both binders investigated.

Thus, the slit tear resistance of mycelium can be affected by the choice of binder used for impregnation and its concentration.

Example 8: Processing Methods to Improve Mycelium Permeating Efficiency

Sonication-Assisted Solution Permeation Process with Optional Heating

Sonication is a mechanical method to help solution infiltration, and thus may make the impregnation process more efficient. A mycelium panel (wet or dry) was soaked in a bag with a processing solution (a "crust" solution, for example, a dye, fatliquor, and/or tannin solution, and optionally a binder) and rolled with a roller to help the solution penetrate the mycelium material. Next, the bagged mycelium material and processing solution was sonicated in a bath sonicator or with a probe sonicator. The mycelium material was rolled again in the processing solution, removed from the solution, and dried. The mycelium was finally mechanically softened with additional rolling to smooth and soften the material.

Figure 33:
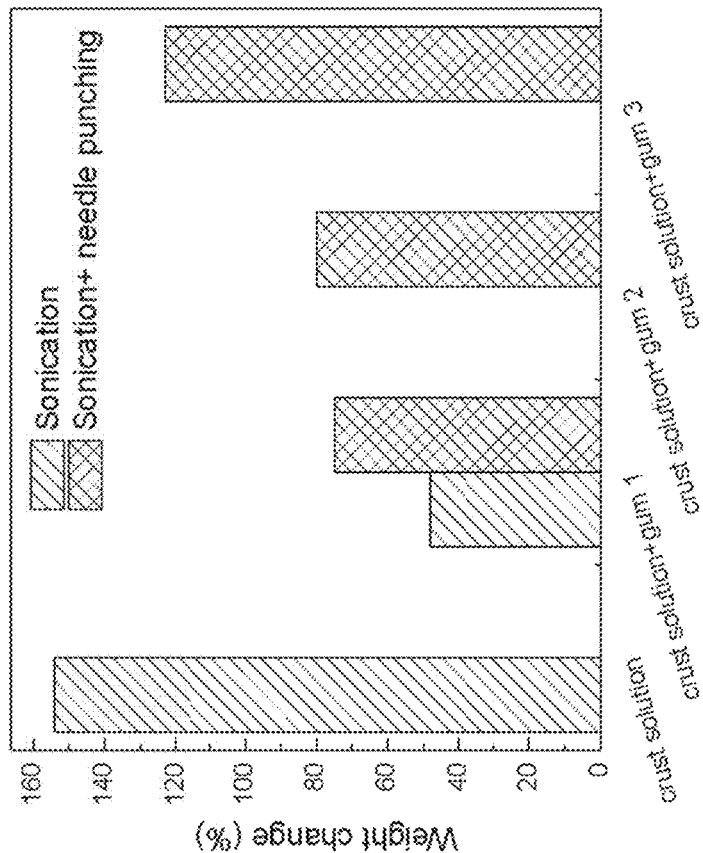
FIG. 33 shows the weight change percentage of the binder-permeated mycelium panel after sonication and soaking.

To study the effectiveness of sonication, three solutions representing different viscosity levels were used: low viscosity crust solution, medium viscosity crust solution with 7 wt % latex, and high viscosity crust solution with 10 wt % gum arabic. Water alone was used as a baseline control. Control samples were soaked in the test solutions for 24 hours. The sonication was done in a bath sonicator. The sample weight change from dry intact mycelium panel to infiltrated panel after drying is shown in FIG. 33. Sonication of the mycelium panel with the low, medium, and high viscosity crust solutions resulted in significant increases in the mycelium panel weight, as compared to soaking alone. The medium viscosity crust solution with 7% wt latex resulted in the greatest increase in weight. Thus, sonication improved the permeation of the processing solutions in each solution condition tested.

A modified sonication bath with heating function can also be used, as (1) heated solutions help particles move faster due to Brownian motion; (2) heated solutions strengthen mycelium material simultaneously and (3) sonicating the mycelium in the processing solution in a sonication bath directly can skip the bagging step.

Sonication with Perforation Permeation

Mechanical perforation of the mycelium material was investigated to determine if it improved solution permeation, for example by creating through-thickness micro-channels. Two punching media were evaluated: needle and water. Air-punching can also be used. For the needle-punching method, a roller with 3 mm needle length (perforating depth) was used. For water-perforation method, a high-pressure water with 50 μm diameter spinneret was used. Sonication was used in addition to the mechanical perforation step. Percent weight change of a crust solution as described in Table 17 with 5% gum arabic concentration was compared to crust solution alone with sonication only. Mycelium panels were weighed before soaking and after soaking and the increase in weight of the final panel is shown as the percentage weight change of the starting panel weight.

Figure 34:
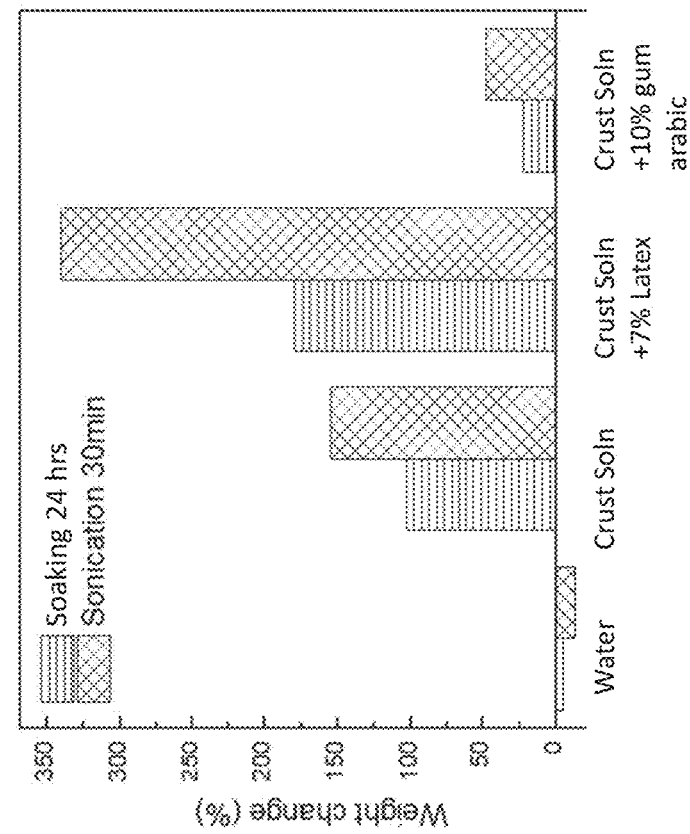
FIG. 34 shows the weight change percentage of the binder-permeated mycelium panel in the samples perforated with the needle-perforation method and sonicated as compared to sonication only.
Figure 35:
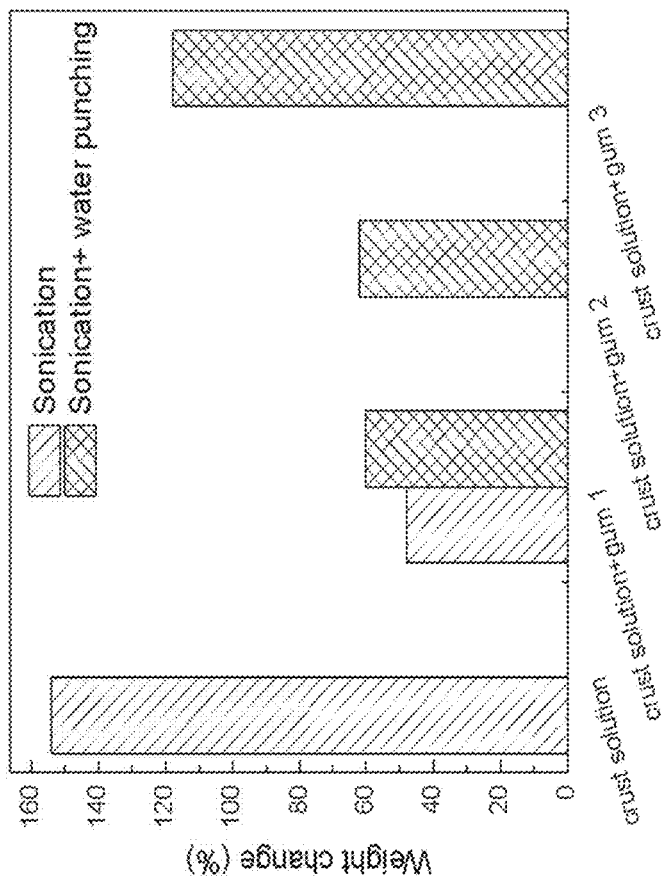
FIG. 35 shows the weight change percentage of the binder-permeated mycelium panel in the samples perforated with the water-perforation method and sonicated as compared to sonication only.

FIG. 34 shows the weight change percentage of the binder-permeated mycelium panel in the samples perforated with the needle-perforation method and sonicated as compared to sonication only. FIG. 35 shows the weight change percentage of the binder-permeated mycelium panel in the samples perforated with the water-perforation method and sonicated as compared to sonication only. Mechanically perforating holes on the mycelium panel surface was found to improve solution infiltration for the solutions containing gum arabic.

Vacuum-Assisted Solution Permeation

Due to the high porosity (up to 95 vol %) of mycelium panels, vacuum was used to remove the air before solution infiltration. This allowed for the determination of the ability of vacuum to compact the porous mycelium panel in order to minimize the air volume and increase the solution transfer by vacuum force. A vacuum machine setup was built from a solution tank, a one-sided mold, a vacuum bag, a solution trap and a vacuum pump. Panels were incubated with various solutions under vacuum, removed from the vacuum and allowed to dry, and then mechanically softened.

Three solutions representing different viscosity levels were used: crust solution as described in Table 17 (low viscosity), crust solution with 7 wt % latex (medium viscosity) and crust solution with 10 wt % cold soluble starch A (high viscosity) (Cargill, USA) were used. Mycelium panels were weighed before soaking in the crust solution and after soaking and the increase in weight of the final panel is shown as the percentage weight change of the starting panel weight.

Figure 36:
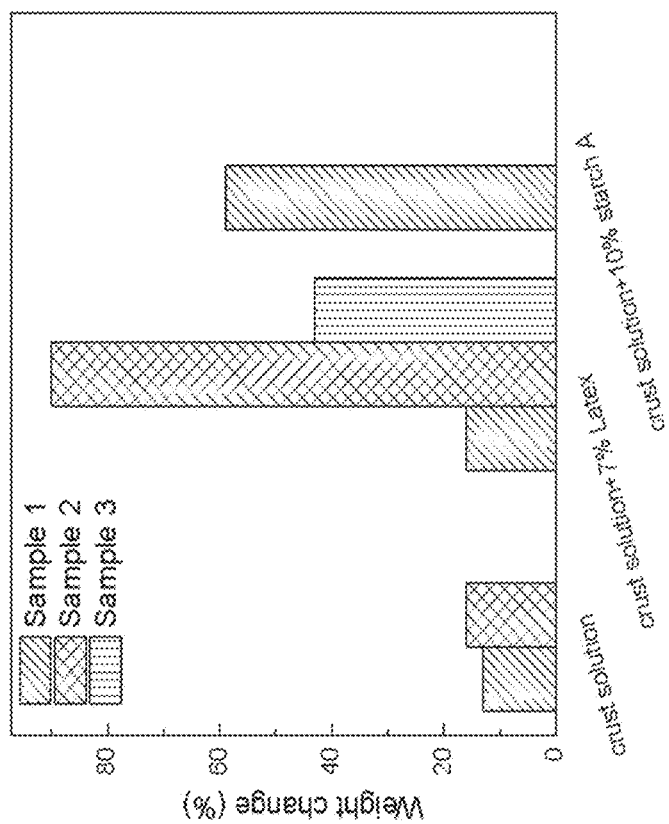
FIG. 36 shows the weight change percentage of the binder-permeated mycelium panel in samples 1, 2, and 3 after vacuum-assisted permeation.

The sample weight change from dry intact mycelium panel to infiltrated panel after drying is illustrated in FIG. 36. The effectiveness of vacuum-assisted infiltration process is dependent on the vacuum condition, as shown by the higher vacuum levels leading to a higher sample weight increase in the crust solution with 7 wt % latex samples.

Example 9: Lamination of Mycelium Material with Binders and Adhesives

In addition to improving the internal bonding strength of mycelium materials, binders can also be used as adhesives to construct mycelium-based composites. Lamination using binders and adhesives can be used to produce mycelium materials with improved mechanical properties.

The slit tear and tensile properties of the mycelium materials can also be improved by adding a textile scrim without sacrificing the flexibility of the material. Depending on the type of textile scrim used, e.g. a fabric or a plastic scrim, the slit tear and tensile properties can be adjusted at will to match given specifications. The scrim can be added at the back side of the mycelium materials by using an adhesive or binder such as latex, or laminated in between two layers Lamination and Scrims Mycelium samples were first prepared as described in Example 7. Briefly an aqueous solution containing vegetable tannins, fatliquors, and dye was prepared according to the composition described in Table 17 and the mycelium material was soaked and rolled as previously described. After drying, samples were laminated by spreading a thin layer of Tear Mender natural rubber latex on the faces of two mycelium samples, pressed together, and passed through a roller to improve bonding and remove excess solution. This resulted in a laminated double layer mycelium material. In some samples, a textile scrim was laminated in between the two layers. A piece of textile scrim material cut to the same size as the crust samples was placed in between the two samples before the laminate was passed through a roller. Samples were left to dry at ambient conditions for 96 hours before testing.

Figure 37:
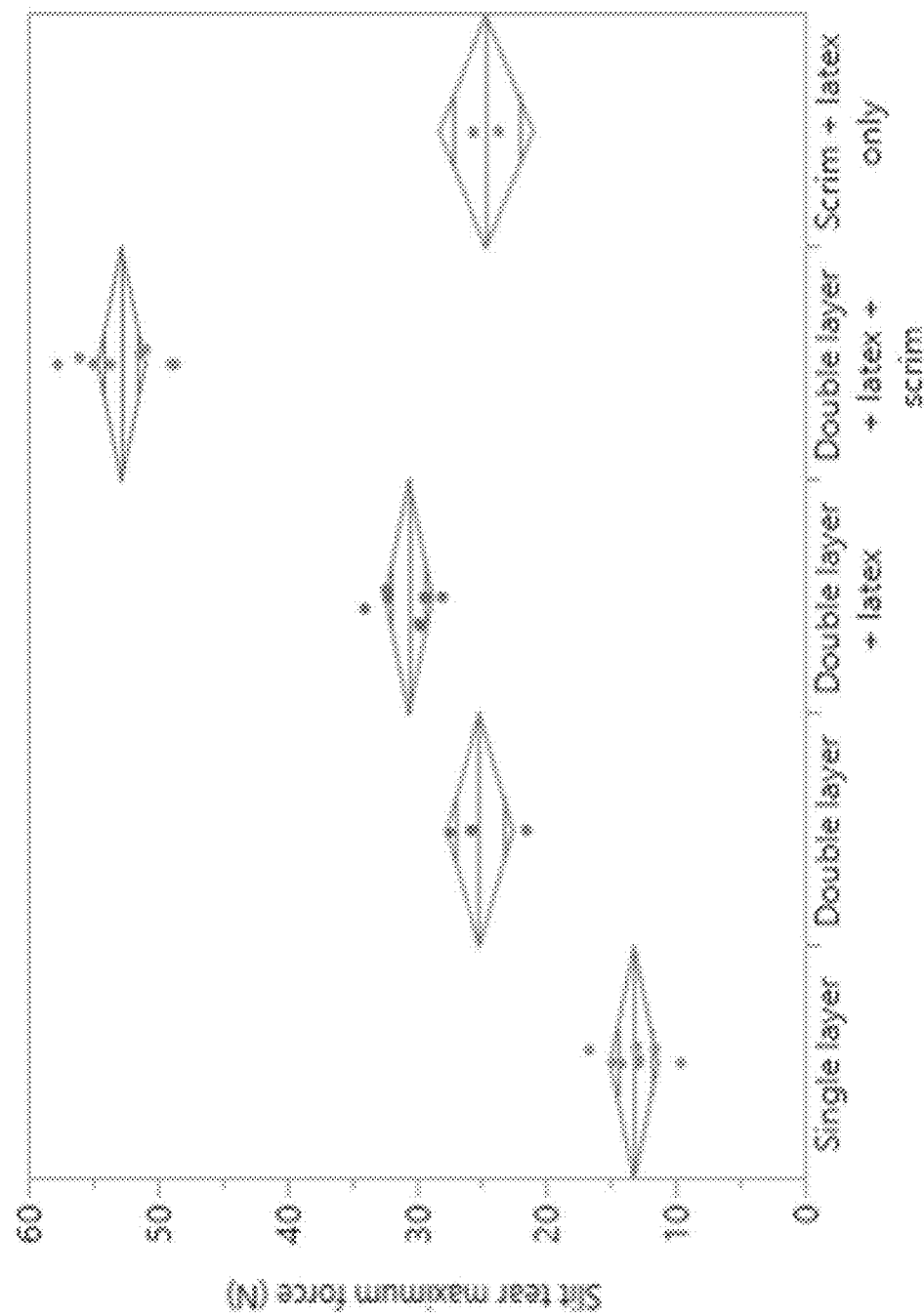
FIG. 37 shows the slit tear maximum force for various mycelium samples and composites: single layer mycelium sample; two layers of mycelium tested simultaneously; two layers of mycelium laminated using natural rubber latex; two layers of mycelium laminated using natural rubber latex with a textile scrim between them; the same textile scrim coated with natural rubber latex (no mycelium).

Slit tear force was tested as previously described. FIG. 37 shows the maximum slit tear force for mycelium samples laminated with and without a scrim. A laminated double layer only of mycelium and a double layer of mycelium with latex were also tested. A scrim coated in latex was tested as a control. Points denote individual slit tear tests. Diamonds denote the upper and lower 95% confidence interval of the mean maximum slit tear force.

As shown in FIG. 37, the maximum slit tear force of mycelium composites can be substantially increased using lamination. Each additional lamination step (doubling and pressing, adding a latex layer, adding a scrim) increased the slit tear force required to tear the material.

Figure 38:
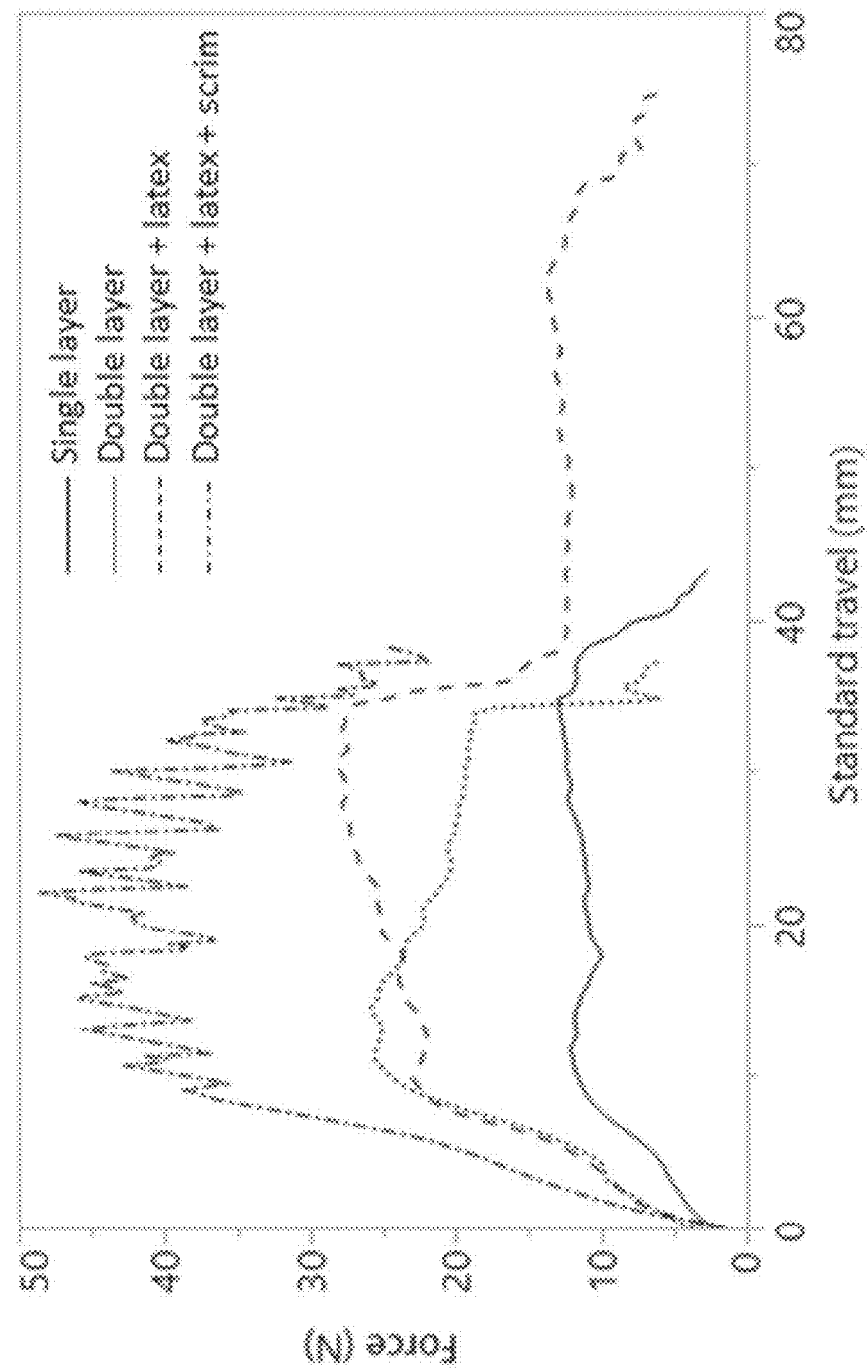
FIG. 38 shows representative slit tear force-travel curves for the indicated mycelium composite samples.

FIG. 38 shows representative slit tear force-travel curves for various mycelium samples and composites: single layer mycelium sample; two layers of mycelium tested simultaneously; two layers of mycelium laminated using natural rubber latex; two layers of mycelium laminated using natural rubber latex with a textile scrim between them.

FIGS. 37 and 38 show that while lamination alone is a useful approach to create a stronger material, the incorporation of a textile scrim during lamination offers two advantages over lamination alone. First, the maximum force can be increased to that of the scrim rather than relying on the strength of the mycelium and adhesive alone. Second, the scrim inhibits tear propagation through the material, as seen by the successive peaks in force after the yield point, which arise from the successive loading and rupture of the scrim yarns. Conversely, in the sample laminated without a scrim, tear propagation proceeded uninhibited until the mycelium was completely torn.

To construct another type of mycelium-based composite, lamination was performed concurrently with the solution permeation process as described in Example 7 by pressing two mycelium samples together with a layer of latex after the first soak cycle, and completing the rest of the process with the samples adhered together. The unlaminated sample (single layer+latex) was made as described in Example 7; a single piece of mycelium material was soaked in crust solution containing latex tear mender as the binder, and rolled through the pasta roller, with a total of 4 soak and roll cycles.

Figure 39:
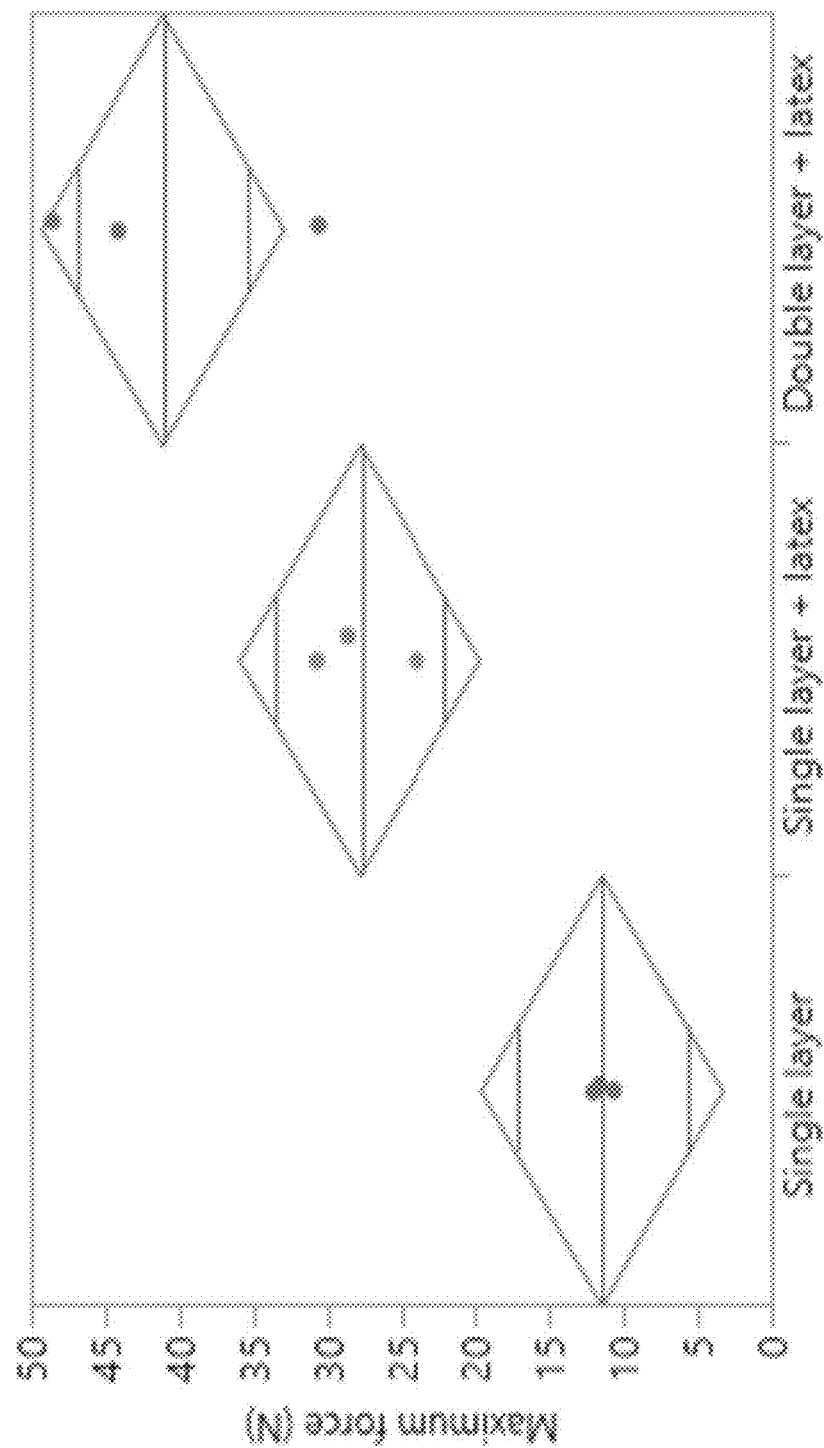
FIG. 39 shows the maximum slit tear force of concurrently laminated and impregnated mycelium samples ("Double layer+latex"), with unlaminated ("single layer+latex") and unimpregnated ("single layer") samples for comparison. Points denote individual slit tear tests. Diamonds denote the upper and lower 95% confidence interval of the mean maximum slit tear force.

FIG. 39 shows the maximum slit tear force of concurrently laminated and impregnated mycelium samples, with unlaminated (single layer+latex) and unimpregnated (single layer) samples for comparison. The double layer and latex laminated sample had a higher slit tear force compared to the unlaminated and unimpregnated samples. Points denote individual slit tear tests. Diamonds denote the upper and lower 95% confidence interval of the mean maximum slit tear force. Thus, improved slit tear resistance can be achieved with a lamination process that is performed concurrently with the impregnation process, rather than performing lamination as a separate process.

In addition to improving tear resistance, the design and processing of the composite can also be chosen to tune the flexibility of the material. The "Scrim+latex binding" sample and "Scrim+Latex adhered" samples were prepared as previously described in Example 7 and Example 8 above. "Scrim+latex binding" refers to the process of adding a scrim during the lamination/crusting process. "Scrim+latex adhered" refers to the process of adding a scrim after the crusting process is finished and the samples are dry. The gum arabic and APS sample was prepared as previously described in Example 6 with 10% gum arabic and 3% APS. To prepare the Half crust with scrim sample, a dry mycelium sample was first cut to be approximately 0.5 inches thick, and then impregnated with crust solution as described in Table 17 using the same soaking and rolling process described in Example 7 but without the addition of a binder.

Figure 40:
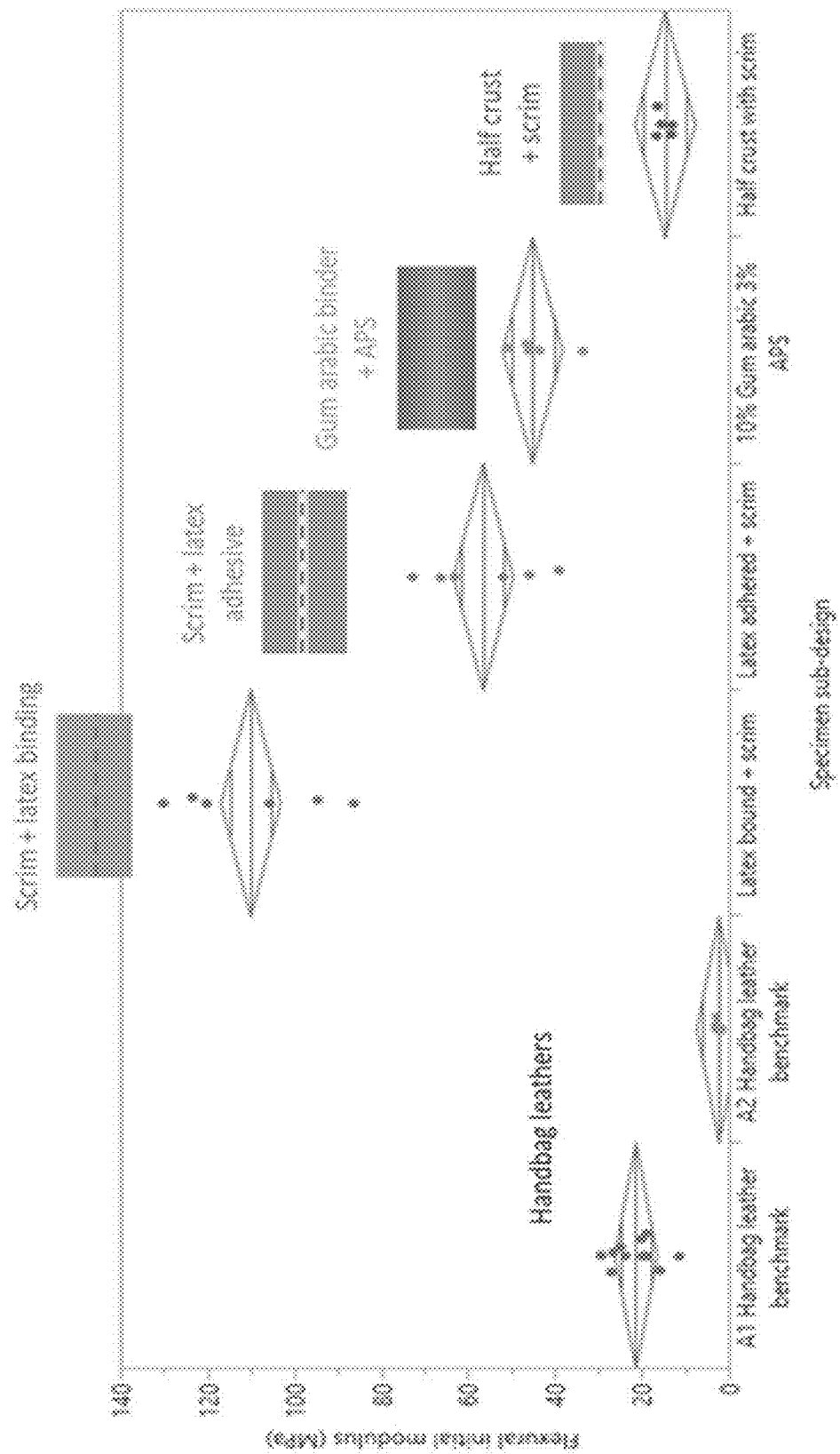
FIG. 40 shows the flexural initial modulus of the indicated samples: a two-play sample laminated with latex (thickness t); a two-ply sample laminated with a scrim and latex (thickness t+the scrim thickness); a one ply sample (thickness 2t) treated with gum arabic and APS; and a one-ply sample with a scrim adhered to one side (thickness 0.5 t+the scrim thickness). Bovine handbag leather samples are shown for reference. Dots represent individual measurements. Diamonds denote the upper and lower 95% confidence intervals of the mean.

To measure the flexural initial modulus, samples were subjected to a 3-point bending test according to ASTM D790 but with the strain rate increased from 1% per min to 10% per min. FIG. 40 shows the flexural modulus of a double layer with latex, a double layer with a scrim and latex, a double layer treated with gum arabic and APS, and a single layer with a scrim adhered to one side. The double layer treated with gum arabic and APS sample was made taking a single mycelium layer, splitting it in half, and then laminating the halves back together. As shown in FIG. 40, different material designs and processing approaches can be selected to tune the flexural initial modulus over an order of magnitude, which can be used to design products with varying hand and aesthetic. In this case, the flexibility of the material is controlled based on whether the material is impregnated with a latex emulsion or a gum arabic solution; whether the latex binder is impregnated throughout the thickness of the material or used only as an adhesive; and by controlling the thickness of the input mycelium material. A1 and A2 bovine handbag leather samples were used as comparison. The double layer with latex was the stiffest at about 110 MPa, while the single layer with the adhered scrim had a similar flexural modulus as that of the A1 handbag leather benchmark at about 15 MPa. Thus, the selection of lamination, binder, and scrim can be chosen to provide more tear resistance or more or less flexibility of the resulting material.

Hot-Pressing of Mycelium Materials

The mechanical properties of mycelium materials such as the resistance to tear and delamination can be improved by the addition of a binder and also by hot-pressing. Hot-pressing increases the areal density and fuses the mycelium hyphae together which results in improved mechanical properties.

20 mm thick mycelium panels were treated with crust solution as described in Table 17 and were hot-pressed at 70° C. for 2 min to achieve a panel thickness of 1.5 mm. Prior to testing the samples were conditioned at 65% relative humidity for 24 hours. Parallel samples were also incubated with 0.5% S-10 vinyl acetate-ethylene prior to hot pressing. T-peel testing was performed according to ASTM D1876 and the slit tear properties were tested according to ISO 3377-2 using universal tensile tester.

Figure 41:
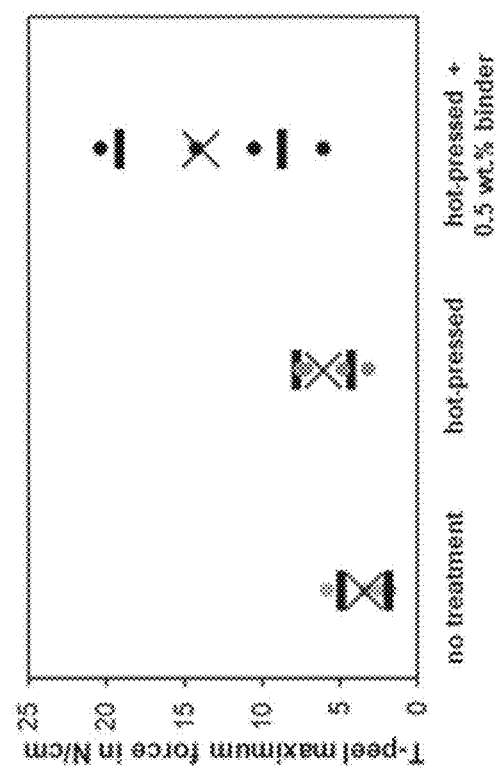
FIG. 41 shows the T-peel maximum force for untreated, hot-pressed as well as hot-pressed and bound mycelium materials. Hot-pressing was done at 70° C. for 2 min. For the hot-pressed and bound sample, 0.5 wt % S-10 vinyl acetate-ethylene binder was added to the crust solution. The crosses mark the average value and the bars represent the standard deviation.

As shown in FIG. 41, the resistance to delamination (T-peel maximum force) is increased by hot-pressing. Further improvements in the T-peel maximum force were achieved by combining hot-pressing with the addition of the S-10 vinyl acetate-ethylene binder.

Figure 42:
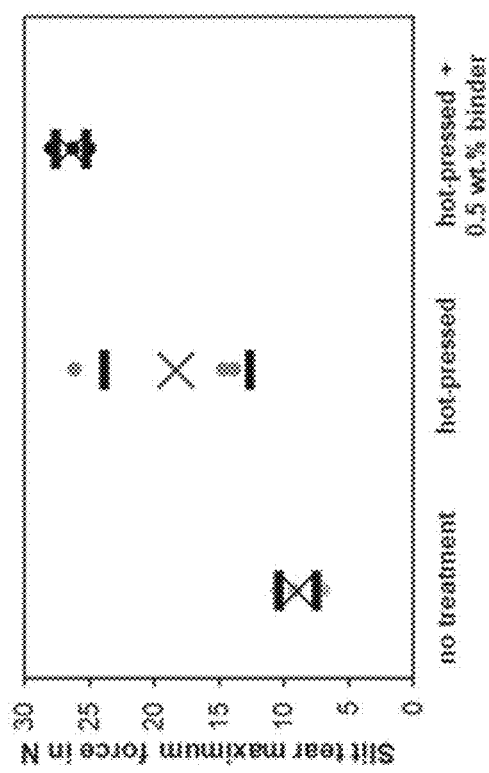
FIG. 42 shows the slit tear maximum force for untreated, hot-pressed as well as hot-pressed and bound mycelium materials. Hot-pressing was done at 70° C. for 2 min. For the hot-pressed and bound sample, 0.5 wt % S-10 vinyl acetate-ethylene binder was added to the crust solution. The crosses mark the average value and the bars represent the standard deviation.

FIG. 42 shows that hot-pressing significantly increases the slit tear maximum force of the treated mycelium panel. The combination of hot-pressing and the S-10 vinyl acetate-ethylene binder further improved the tear resistance.

Example 10: Treatment of Mycelium Material with Plasticizers

Fatliquor, Fabric Softeners, or Sorbitol
Materials and Methods

Several different types of chemicals were tested to improve the softness of the processed panels after treatment with fatliquors, binders, and/or crosslinkers. Softening agents were also assessed for changes in the panel mechanical strength, as a reduction in mechanical strength is unfavorable.

Mycelium panels were treated with a crust solution that contained a total 2.5 wt % fatliquors at a 3:1 ratio of Trupon DXV to Truposol LEX (Trumpler Gmbh) and dried. The dried panels were then soaked in deionized water for 1 minute, then passed through a dip roller with gap setting 1. The soaking and rolling steps were repeated 8 times, to ensure the mycelium panel was fully wet, and that any soluble debris or chemicals were removed. Next, various plasticizers shown in Table 19 were diluted in water.

TABLE 19

Plasticizer type and concentration in aqueous solution

| Sample description | Plasticizer Concentration |
|---|---|
| None (water only) | N/A |
| Fatliquor | 1:3 LEX:DXV, 50 g/L |
| Downy* (fabric softener) | 75 g/L |
| Sorbitol | 50 g/L |
| Sorbitol 2X | 100 g/L |

*Diethyloxyester dimethyl ammonium chloride (DEEDMAC) is an effective ingredient in Downy fabric softener.

Samples were treated with 200 mL of the plasticizer solutions shown in Table 19 for about 10 min to one hour depending on the volume of water. A control sample was incubated with water only. After treatment, the samples were dried at ambient condition for 24 hours, then conditioned at 65% relative humidity, calculated by dividing partial pressure of water vapor to the equilibrium vapor pressure of water at a given temperature, overnight before mechanical testing.

Results

Figure 43:
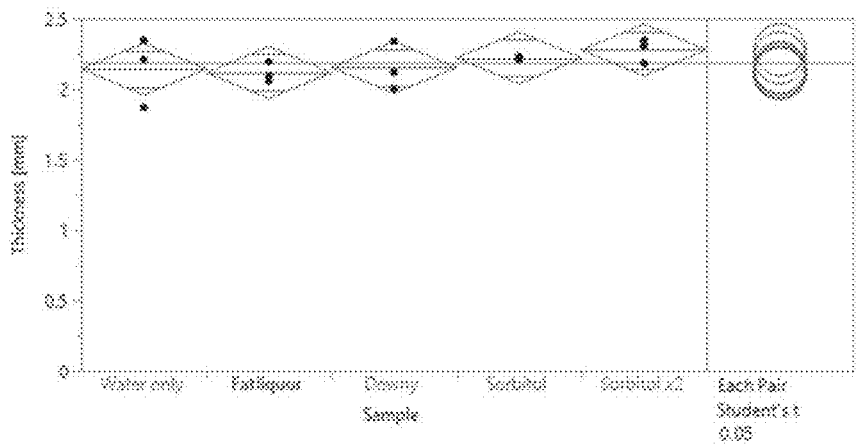
FIG. 43 shows the sample thickness after the indicated plasticizer treatment.
Figure 44:
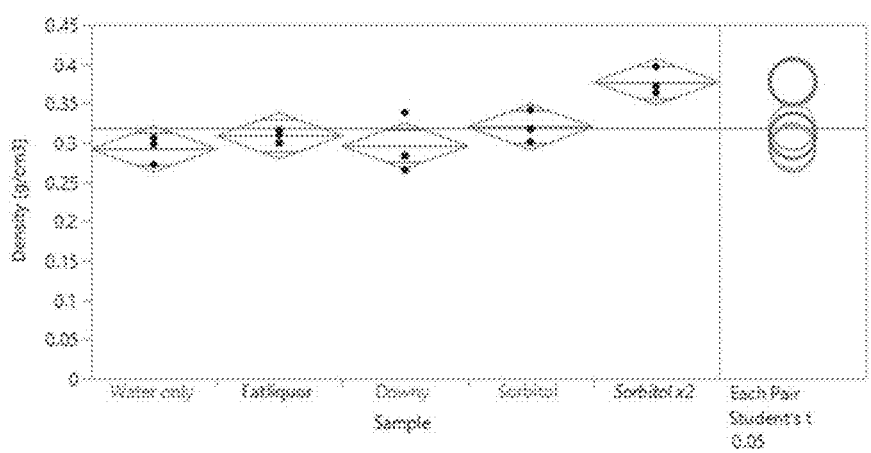
FIG. 44 shows the sample density after the indicated plasticizer treatment.

The material thickness was constant across all treated samples (FIG. 43). The final density of the treated samples was assessed as well by dividing mass over volume. Density changes indicate uptake of plasticizers. The sorbitol 2x sample had a higher final density as compared to the other samples, which may due to the higher concentration of sorbitol in the solution (FIG. 44).

Figure 45:
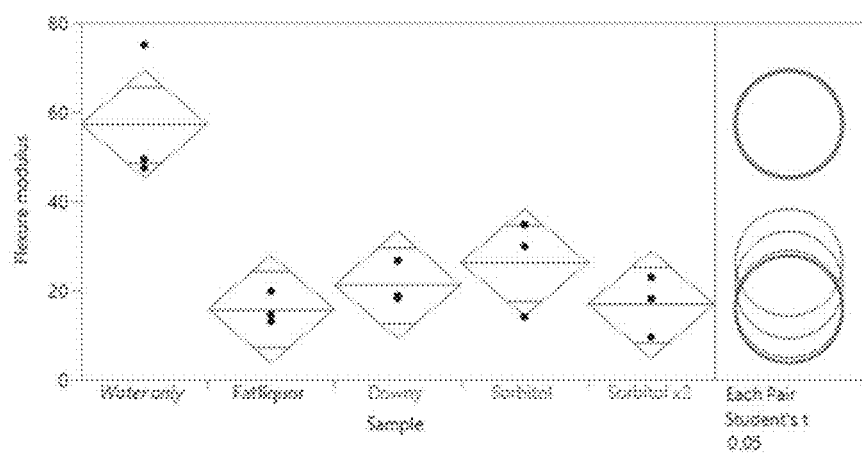
FIG. 45 shows the highest flexural modulus for each sample after the indicated plasticizer treatment.

The flexural modulus of each sample was determined (FIG. 45). All plasticizers tested resulted in a similar range of mycelium panel flexural modulus, and a significant decrease in the flexural modulus as compared to water-only treated mycelium. The samples treated with Downy fabric softener and sorbitol had a slightly stiffer hand feel compared to the fatliquor and sorbitol 2x treated samples. The sorbitol 2x and fatliquor treated samples had the same hand feel.

Figure 46:
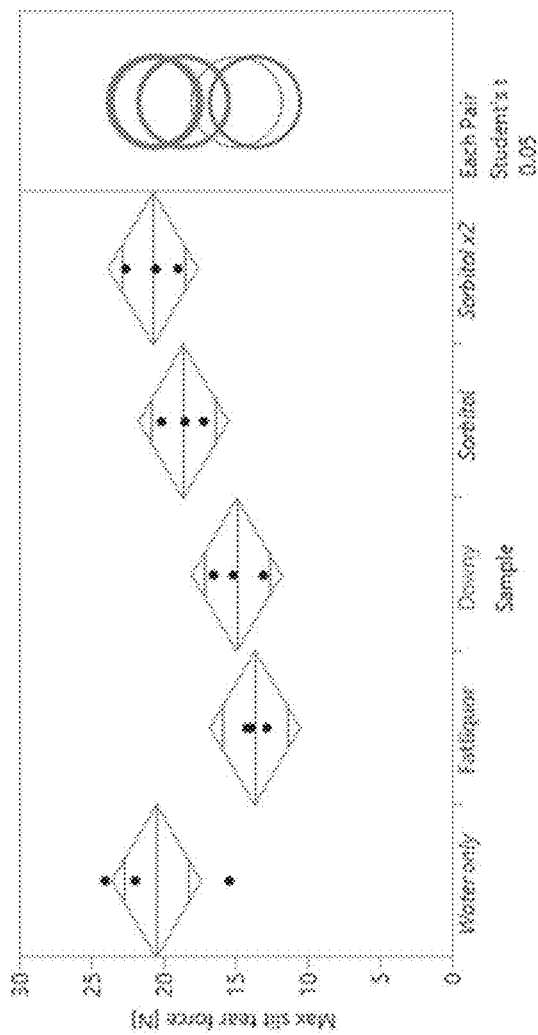
FIG. 46 shows maximum slit tear force for each sample after the indicated plasticizer treatment.
Figure 47:
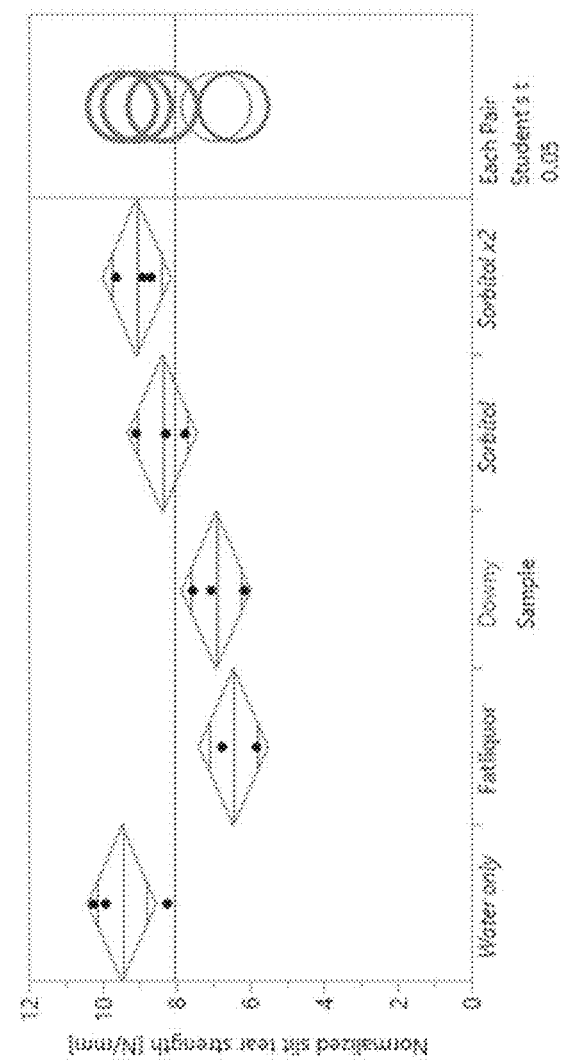
FIG. 47 shows normalized slit tear force for each sample after the indicated plasticizer treatment.

The slit tear of the treated panels was also determined as previously described. The maximum slit treat strength for each panel is shown in FIG. 46. Fatliquors produced the lowest slit tear strength of all the conditions. The sorbitol 2x sample had a slit tear strength comparable to the untreated mycelium panel, even though the panel was as flexible as the fatliquor sample. The maximum slit tear force was normalized to each panels' thicknesses as well (FIG. 47). The normalized (by dividing force with sample thickness, with unit of N/mm) maximum slit tear strength showed the same trend in tear strength for the samples as compared to the raw maximum strength force, indicating that the improvement in tear strength observed in the sorbitol 2x sample was not simply due to the increased material thickness or density.

Tween 20 and Tween 80

Sorbitol is a sugar alcohol that can be used as a plasticizer or softener with mycelium panels to reduce the flexural modulus while maintaining the slit tear strength. Polysorbates (Tween 20, Tween 80) are oily liquids derived from ethoxylated sorbitan (a derivative of sorbitol) esterified with fatty acids. Polysorbates are nonionic surfactants with variety of well-understood molecular structures. The ability of polysorbates to act as plasticizers was assessed.

Untreated mycelium panels were pre-weighed and cut such that each panel had the same dry weight of 3.2 g. Tween 20 and Tween 80 solutions were prepared by dissolving 0.5 g or 1.5 g weight of Tween 20 or Tween 80 in 20 ml of DI water. The amounts and concentrations of the Tween solutions are shown in Table 20. Three drops of food coloring were added to the solution too to help identifying solution penetration.

TABLE 20

Plasticizer type and amount

| Treatment description | Tween Solution Concentration |
|---|---|
| Tween 20, 0.5 g | 0.5 g Tween 20 in 20 mL of water, applied to 3.2 g dry mycelia mass (25 mg/ml Tween 20, 0.16 g/g). |
| Tween 20, 1.5 g | 1.5 g Tween 20 in 20 mL of water, applied to 3.2 g dry mycelia mass (75 mg/ml Tween 20, 0.47 g/g). |
| Tween 80, 0.5 g | 0.5 g Tween 80 in 20 mL of water, applied to 3.2 g dry mycelia mass (25 mg/ml Tween 80, 0.16 g/g). |
| Tween 80, 1.5 g | 1.5 g Tween 80 in 20 mL of water, applied to 3.2 g dry mycelia mass (75 mg/ml Tween 80, 0.47 g/g). |

Each panel was soaked in deionized water and compressed by passing through a dip roller with gap setting 1. The soaking and rolling steps were repeated total 9 times, to ensure the mycelium panel was fully wet and that any soluble debris or chemicals were removed. Mycelium panel were then dried at ambient condition overnight inside a fume hood.

For plasticizer solution treatment, the compressed and dried mycelium panels were manually massaged in Tween solutions. Solution penetration was determined by observing the food coloring level inside mycelium panel and massaging the panel until the color penetrated through a cut cross-section. Samples were dried in a fume hood overnight. All samples were conditioned at 65% RH overnight before testing.

Results

Figure 48:
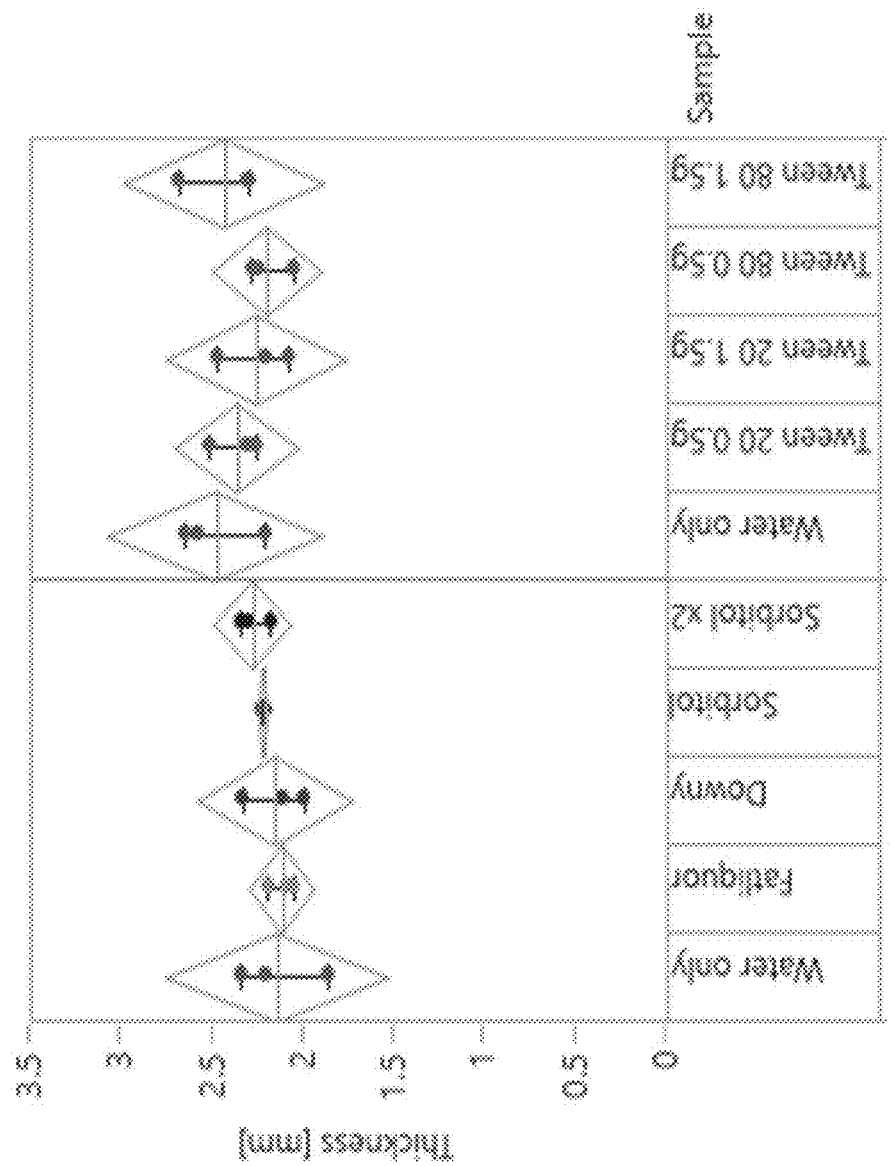
FIG. 48 shows the sample thickness after the indicated plasticizer treatment.
Figure 49:
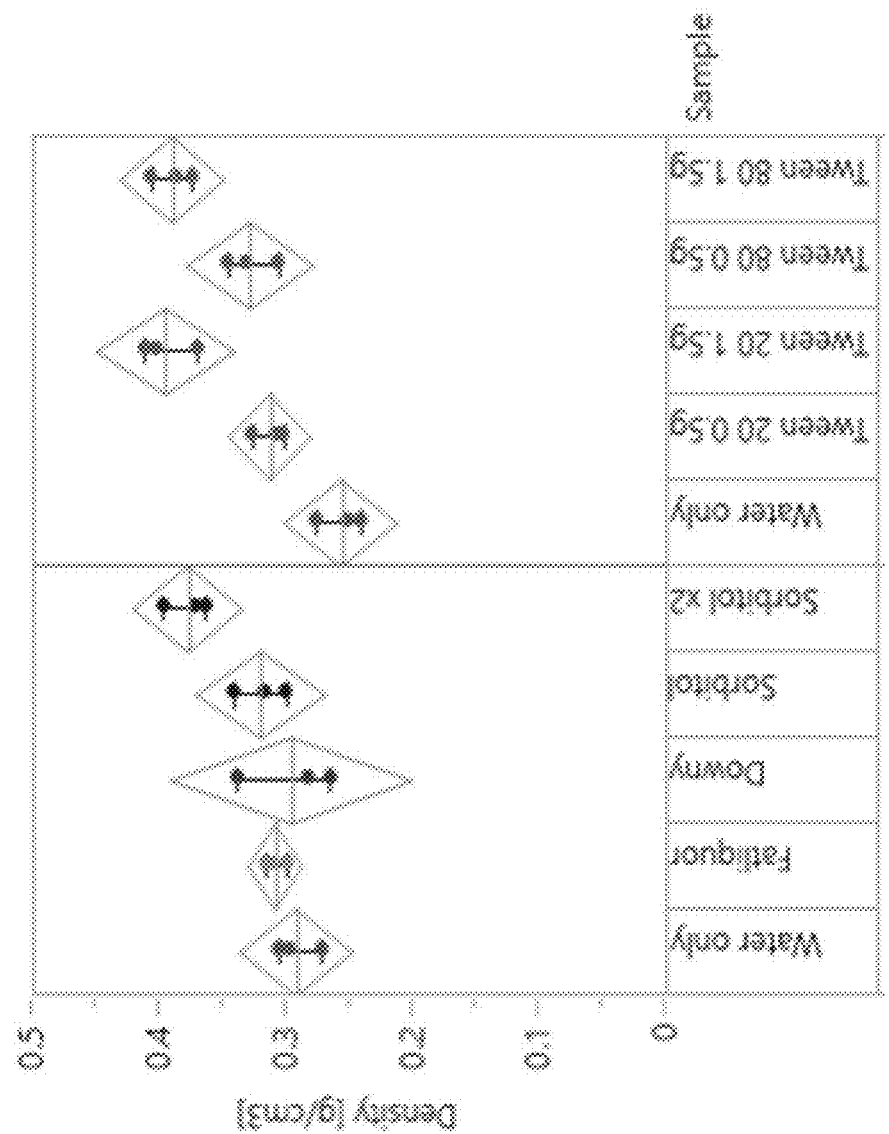
FIG. 49 shows the sample density after the indicated plasticizer treatment.

FIG. 48 shows the sample thickness after plasticizer treatment. FIG. 49 shows the sample density after plasticizer treatment. Comparison thickness and densities of the fatliquor, Downy, and sorbitol treated samples previously described are also shown. The Tween plasticizers did not alter the thickness of the mycelium material as compared to the control sample (FIG. 48). However, Tween 20 and Tween 80 did increase the density of the samples as compared to the control sample in a dose dependent manner (FIG. 49). Increasing the concentration of either Tween 20 or Tween 80 resulted in a comparable increase in the sample density, as seen by the higher densities in the 1.5 g treated samples compared to the 0.5 g treated samples.

Figure 50:
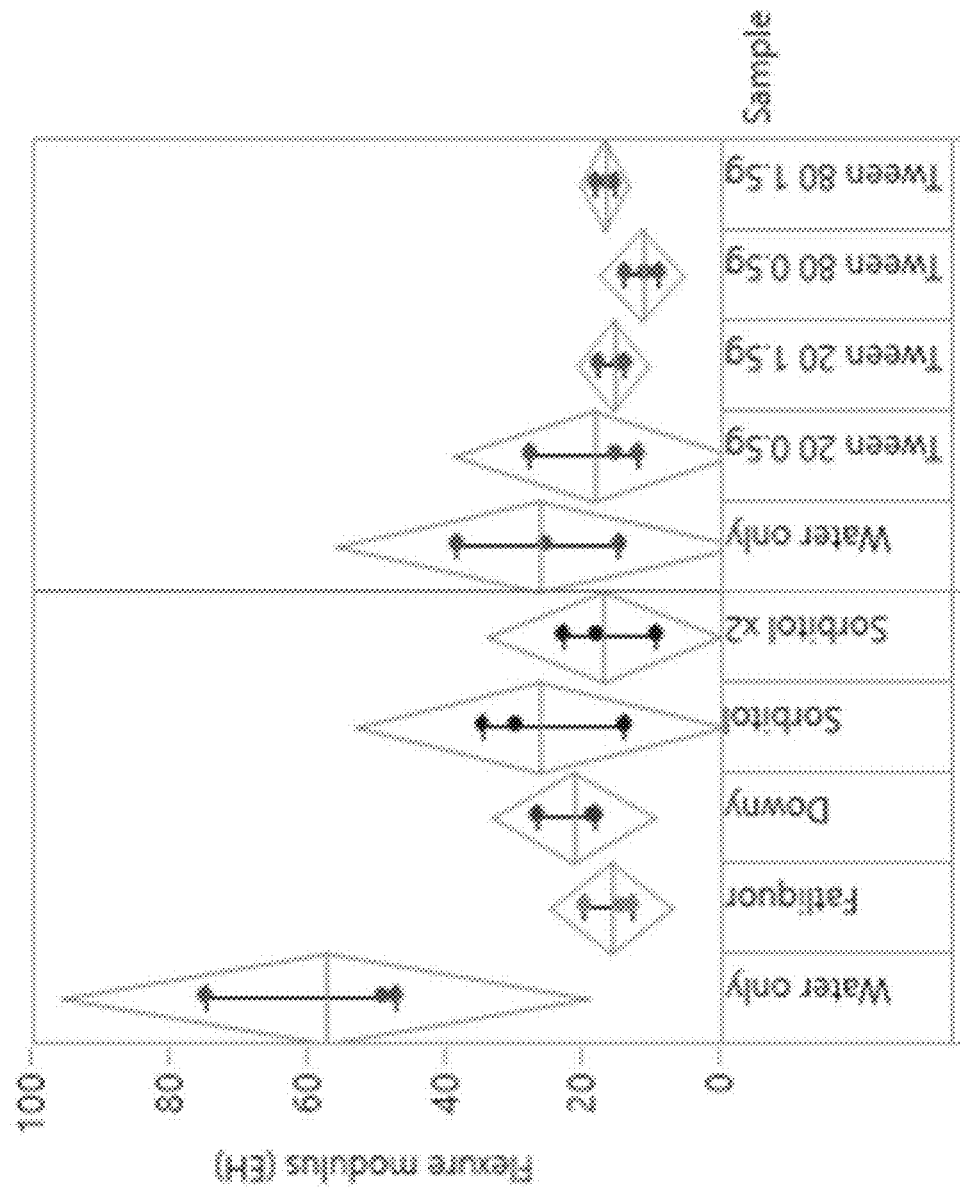
FIG. 50 shows the highest flexural modulus for each sample after the indicated plasticizer treatment.
Figure 51:
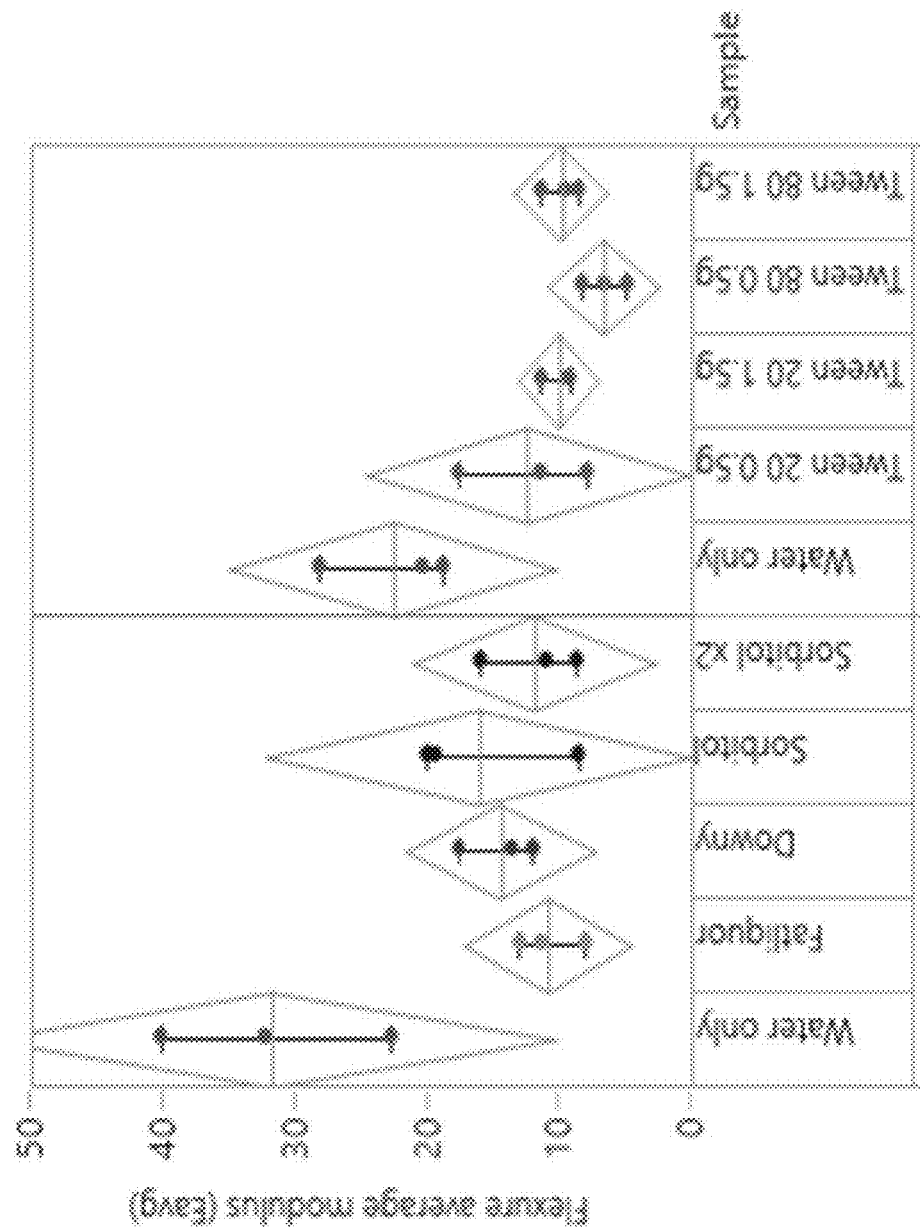
FIG. 51 shows the average flexural modulus for each sample after the indicated plasticizer treatment.

FIG. 50 shows the highest flexural modulus for each sample. FIG. 51 shows the average flexural modulus for each sample. Comparison flexural moduli for the fatliquor, Downy, and sorbitol treated samples previously described are also shown. The Tween surfactants had a plasticizing effect, as seen by the reduction in flexural total and average modulus (FIG. 50 and FIG. 51). The Tween flexural modulus absolute values were in a similar range as the fatliquors and sorbitol. However, the plasticizer concentration did not affect the flexural modulus. Both concentrations of both the Tween 20 and Tween 80 resulted in similar flexural moduli, although the 25 mg/ml (0.5 g) Tween 20 sample had a larger standard deviation in the measured flexural modulus.

Figure 52:
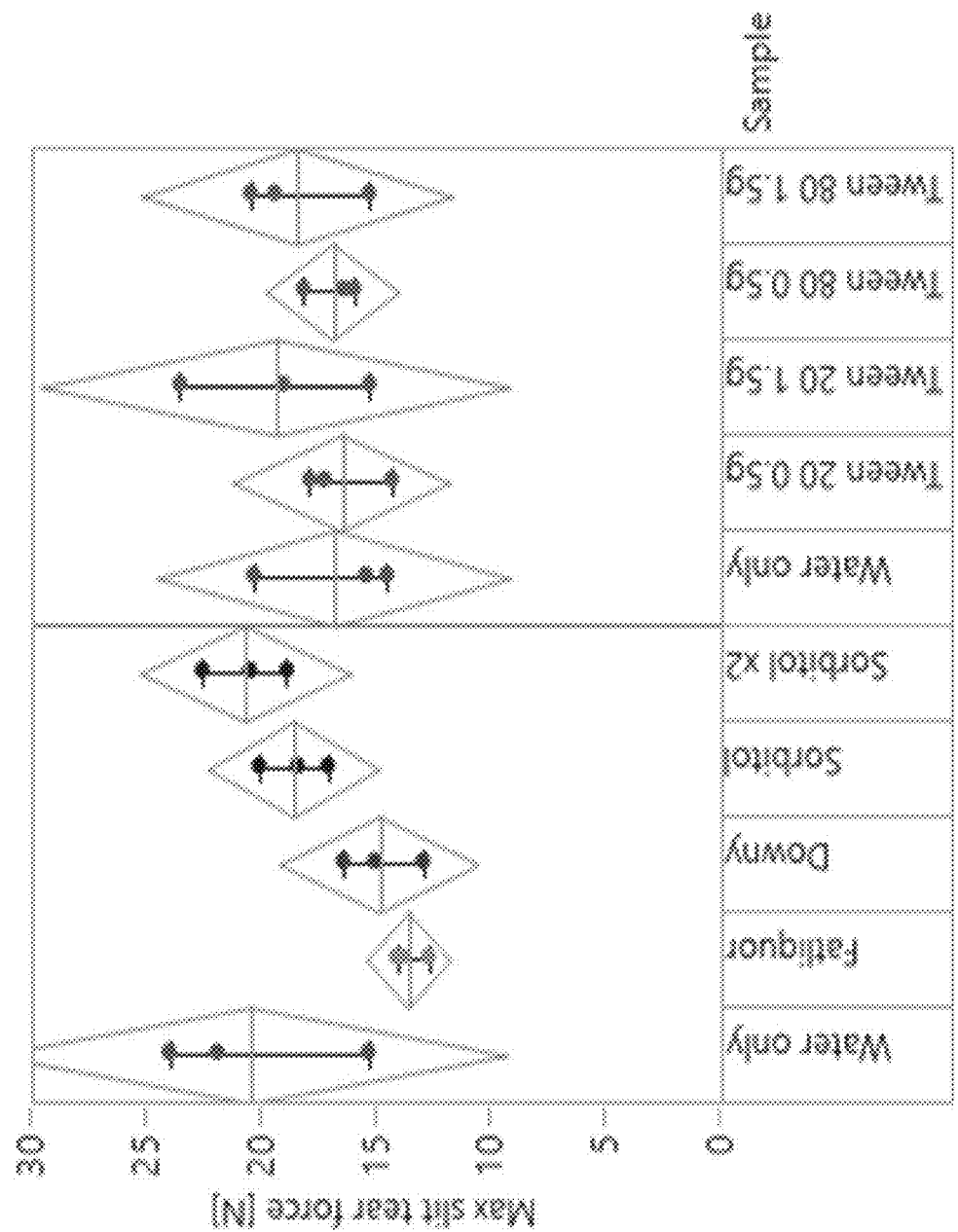
FIG. 52 shows maximum slit tear force for each sample after the indicated plasticizer treatment.
Figure 53:
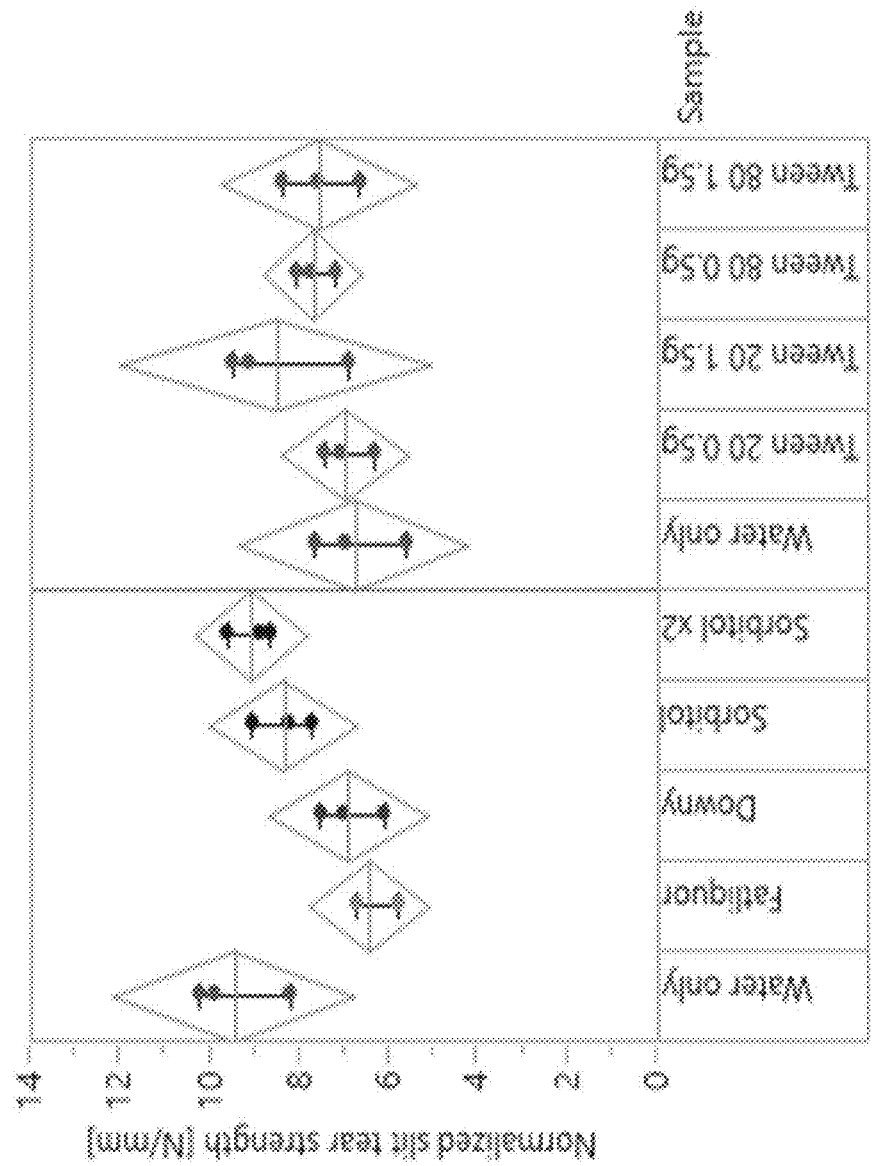
FIG. 53 shows normalized slit tear force for each sample after the indicated plasticizer treatment.

FIG. 52 shows the highest slit tear strength for each sample. FIG. 53 shows the normalized slit tear strength for each sample. Comparison flexural moduli for the fatliquor, Downy, and sorbitol treated samples previously described are also shown. The water control sample also shows lower slit tear strength than previous control sample, which may due to the different application method, or because of the heterogeneity of the starting panel. The slit tear strength does not appear to have been significantly reduced through Polysorbates solution treatment, or affected by the Tween type or the Tween concentration. 0.5 g of Tween into 3.2 g of mycelium panel (~15.1% weight pickup) may be sufficient.

The surface color evenness of the tween treated samples was also assessed (data not shown). The color was due to the food dye included in the Tween solutions. The samples treated with Tween had more even coloration, even after drying and conditioning. Thus, the use of Tween as a surfactant can be used to improve liquid penetration in the mycelium material and dye levelness.

M-Erythritol and Fatliquor Content

Mycelium panels were cut to 3"×5" size. Each panel was soaked in water and compressed by passing through a dip roller with gap setting 1. The soaking and rolling steps were repeated total 5 times. Mycelium panel were then dried in a convection oven at 40° C. overnight.

Two different plasticizer application methods were used. Plasticizer solutions are described in Table 21. Fatliquor control (treated with 100 ml 2.5% w/w fatliquor aqueous solution), and m-erythritol samples were treated using the regular soaking and rolling method. The amount of fatliquor used was based on previous examples. In parallel samples with fatliquors, the fatliquor was pre-weighed to 15% or 30% of the mycelium panel weight, diluted in small amount of water (4 times panel weight), and applied to the mycelium panels using gently manual massage. After the plasticizer application, mycelium panels were dried at ambient condition in a fume hood overnight. All mycelium samples were weighed before and after plasticizer application, so that the percentage increase of the panel weight due to permeation of the plasticizer could be determined. Table 21 provides the panel starting and end weights, and the calculated percent increase in weight due to plasticizer uptake.

TABLE 21

Plasticizer type and solution concentration

| Treatment description | Solution Concentration |
| --- | --- |
| Water control | No treatment |
| Fatliquor 2.5% | DXV:LEX = 3:1, 2.5% in 100 ml aqueous solution |
| m-erythritol | 5% in 100 ml aqueous solution |

TABLE 21-continued

Plasticizer type and solution concentration

| Treatment description | Solution Concentration |
| --- | --- |
| Fatliquor 15% | DXV:LEX = 3:1, 0.45 g dilute into 12 ml of water |
| Fatliquor 30% | DXV:LEX = 3:1, 0.83 g dilute into 11 ml of water |

TABLE 22

Plasticizer type and panel percent weight increase

| Description | Weight pre-treatment (g) | Weight post-treatment (g) | Panel weight increase (%) |
| --- | --- | --- | --- |
| Fatliquor 2.5% | 2.89 | 3.18 | 7.75 |
| 5% M-erythritol | 3.05 | 3.45 | 13.01 |
| Fatliquor 15% | 3.02 | 3.41 | 13.00 |
| Fatliquor 30% | 2.75 | 3.47 | 26.13 |

The 2.5% fatliquor concentration resulted in a 7.75% panel weight increase in mycelium panel. The mycelium panel treated with 5% m-erythritol had a 13% weight increase. For the 15% and 30% fatliquor samples applied with massaging, both panels increased in mass by almost an equal percentage (13% and 26%, respectfully), suggesting that most of the fatliquor substrate was absorbed into the mycelium panel and only had a small loss during processing.

Figure 54:
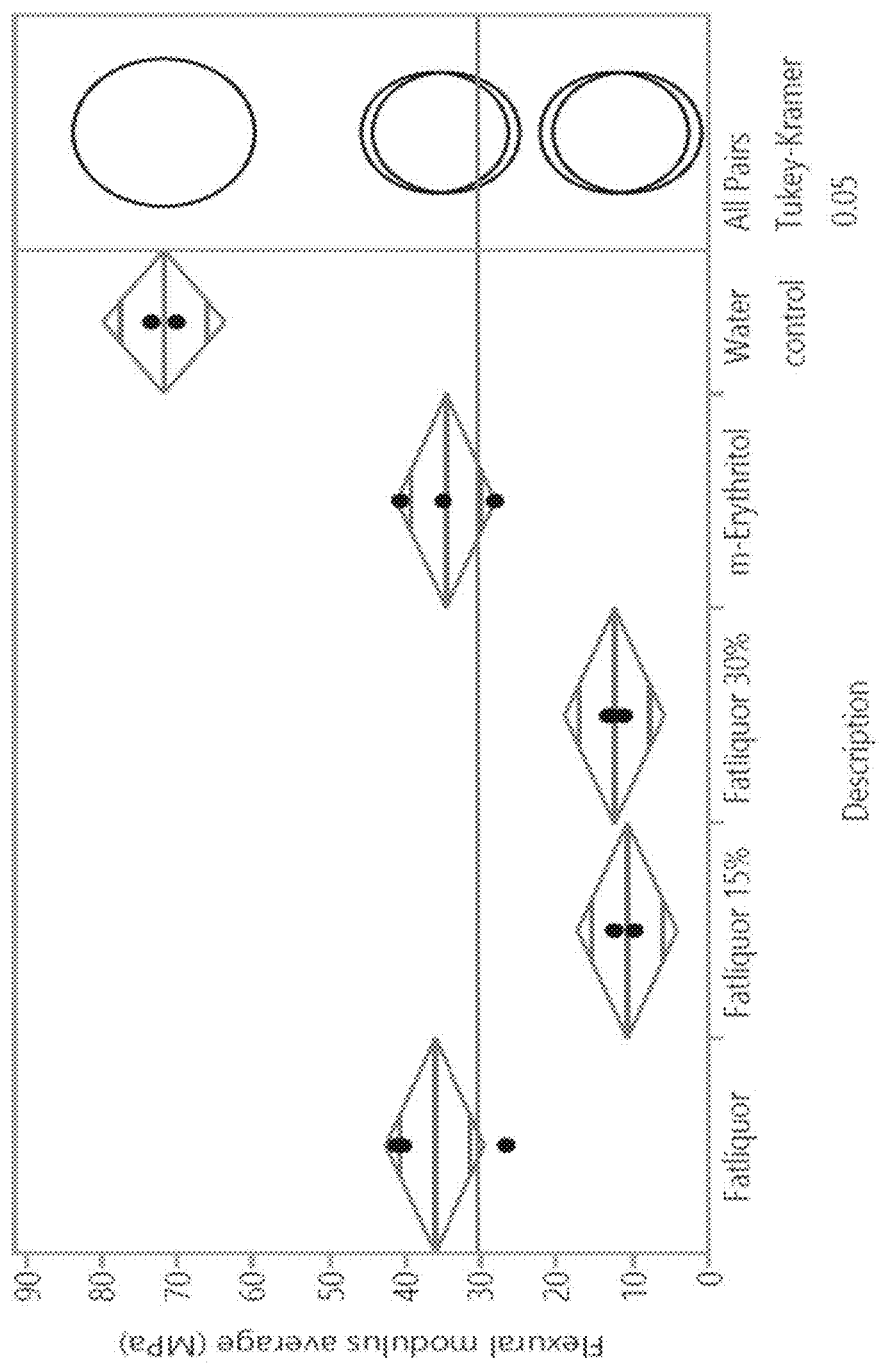
FIG. 54 shows the average flexural modulus for each sample after the indicated plasticizer treatment.

The flexural modulus of the mycelium panels was tested and is shown in FIG. 54. Increasing the fatliquor content in mycelium panel from 8% to 13% significantly reduced the flexural modulus (see the panel weight increase % of the 2.5% fatliquor sample compared to the 15% fatliquor sample shown in Table 22). The fatliquor 15% sample also felt softer than the fatliquor control sample. The fatliquor 30% sample had a slightly softer hand feel than the fatliquor 15% sample. However, the flexural modulus of both samples was almost identical, indicating that the 13% fatliquor uptake in the 15% fatliquor sample was sufficient. Thus, additional fatliquor loading may not improve the materials softness.

M-erythritol solution (5%) treatment also reduce the flexural modulus but was not as effective as the fatliquors (FIG. 54). Soaking and rolling treatment with 5% erythritol showed similar flexural modulus to a 2.5% fatliquor solution treatment.

Example 11: Acid Dyes and Reactive Dyes

After treatment for tear resistance and softness, the mycelium panels are dyed to color them. Previous dye development used acid dyes to color the mycelium panels. Acid dyes penetrate well into mycelium panel. However, the color fastness of acid dye in the mycelium panels was not satisfying, so alternative dyes were investigated. Reactive dyes are known to react with cellulose and polysaccharides that contains hydroxyl groups and forms covalent bonds, resulting in better color fastness. Jacquard Procion MX brown reactive dye was tested and compared to Acid Brown 14 dye for color fastness in mycelium material.

For the acid dye dying process, an aqueous solution of an acid dye (such as Acid Brown M (TCI America™, C.I. Acid Brown 14) or Lanasyn Black (C.I. Acid Black 194), vegetable tannin, and fatliquors was made and applied to the mycelium material via four rounds of soaking and rolling as previously described. A pH 3.15 solution was made with either formic or acetic acid. The panel was soaked and rolled three times in the acid solution for 1 minute, then soaked for 1 hour in fresh pH 3.15 fixation solution. The panel was rinsed in water and dried in a fume hood.

For the reactive dye dying process, an aqueous solution of less than 10 g/L reactive dye (Jacquard Procion MX) and 5-100 g/L of NaCl was made and applied to the mycelium material via four rounds of soaking for 30 min and rolling as previously described. Sodium carbonate was added to the solution at a final concentration of 20 g/L and the panels underwent six rounds of 10-minute soaking/roll cycles for a total of 1 hour. The panels were rinsed in water and rolled four times and dried in a fume hood. Two mycelia samples were treated with an acid dye and three mycelia samples were treated with a reactive dye. Each of the five samples had small sections cut out and soaked in water for approximately one hour. The soaking step was repeated until almost no dye was visually observed to be leaching out into the soak solution. This required five soaking steps for the acid dye samples and three soaking steps for the reactive dye samples. The water was collected after each soaking step and the UV/vis absorbance of the solutions were measured using the whole visible spectrum (360-740 nm) to assess the color of a sample. FIG. 55A-E shows the maximum absorbance of the water contained leached dye from the dyed mycelia samples after five rounds of progressive soaking in water. The two samples on the left are mycelium dyed with an acid dye, the three samples on the right are mycelium dyed with a reactive dye. FIG. 55A shows the light absorbance after 1 round of soaking. FIG. 55B shows the light absorbance after 2 rounds of soaking. FIG. 55C shows the light absorbance after 3 rounds of soaking. FIG. 55D shows the light absorbance after 4 rounds of soaking. FIG. 55E shows the light absorbance after 5 rounds of soaking.

The small sections of washed mycelia were then air dried to see how much color remained. The acid dye samples lost most of the color, while the reactive dye samples retained the color well against multiple rounds of washing (data not shown). Comparing with acid dye, reactive dye-treated mycelium panels had much better color fastness.

Example 12: Crust Solution Optimization of Mycelium Material

The processing solution ("crust solution") was also optimized to produce material of acceptable quality for downstream finishing procedures.

Table 23 provides a list of the variables, the ranges tested, and notes on the variables

| Variable | Range | Notes |
| --- | --- | --- |
| Pea protein concentration [g/L] | 0-7 | Pea protein may improve colorfastness and/or slit tear strength. |
| TG concentration [g/L] | 0-20 | Crosslinking between pea protein and TG may improve slit tear strength. |
| Fatliquor concentration [g/L] | 25-50 | Plasticizer needed for flexibility. Without fatliquors, material is too brittle for a slit tear test |
| Dye concentration [g/L] | 1-1.5 | Brown Acid dye for coloration |
| Tannin concentration [g/L] | 0-5 | May affect coloration, colorfastness, dye penetration. |
| Soak pH | 3.5-7.8 | An acid fixation step may be required for the use of acid dyes. Condition included to determine effect of pH on pea protein and/or TG. Enzyme TG is not active at pH 3.5 |
| Soak temperature [deg C.] | 20-35 | Higher temperatures may improve penetration. |
| # passes through rollers | 4-10 | Competing hypotheses: (1) more passes through the roller could improve pressing/alignment/strength, or (2) more passes could damage the material and reduce strength. |
| Roller spacing | Setting 1 (thicker) vs. 5 (wider) | Thinner spacings may improve penetration but may also cause more damage/decrease strength. |
| Incubation time [hours] | 0-18 | Vary incubation with TG enzyme |

Mycelium material panels from 5 different lots were used in the tests. The length, width, thickness, and mass of each raw starting sample were collected. Thus, the wet density and starting thickness could be used as additional input variables for the final analysis. Each sample was processed by making an aqueous solution of dye, vegetable tannin, fatliquor, pea protein, and TG in water. The pH of the solution was adjusted to 3.5, 5.5 or 7 using either formic acid or acetic acid. The mycelium material was soaked in the crust solution for 1 minute, then passed through a pasta roller 4 or 10 times. The soaked and rolled panels were then incubated for 0, 4, or 18 hours at 40° C. and dried.

The finished panels was assessed for the following properties: slit tear strength (mechanical testing—maximum force to tear, normalized tear strength); dye penetration via visual grading 1-5; colorfastness using an electronic crockmeter (SDLAtlas Company, USA), graded 1-5; and surface color analysis using a light box and ImageJ grayscale rating.

Results

Figure 56:
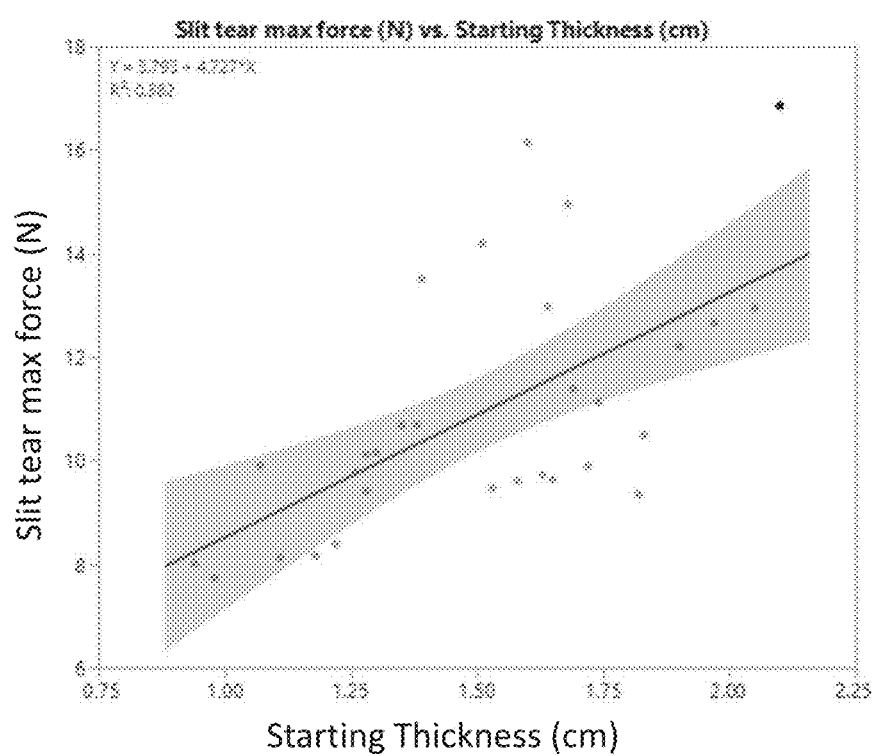
FIG. 56 shows the slit tear max force as compared to the starting thickness (cm) of the panel.
Figure 57:
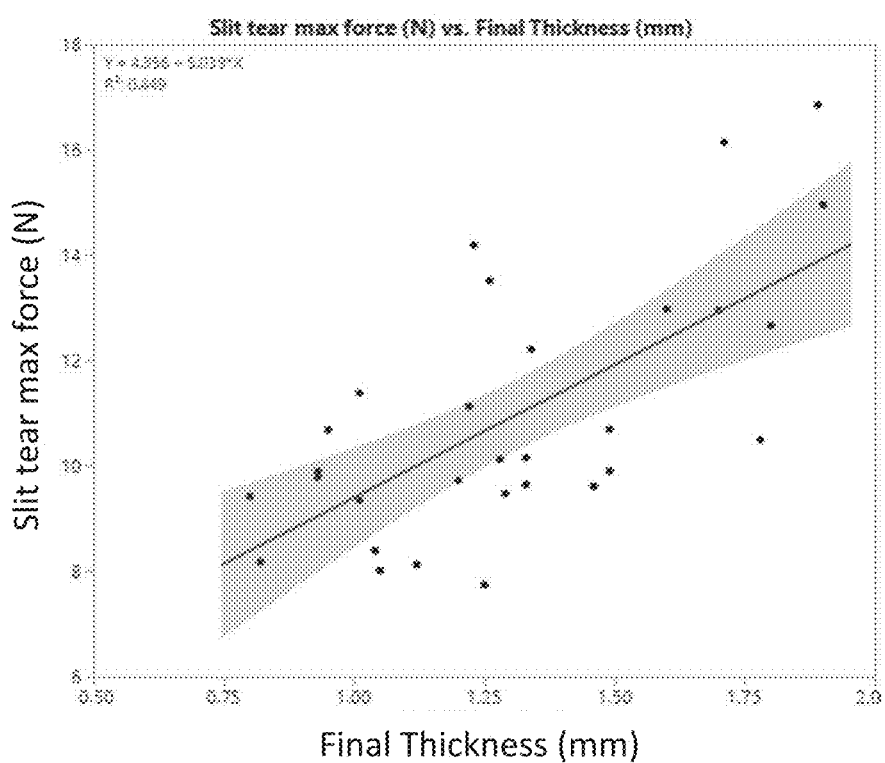
FIG. 57 shows the slit tear max force as compared to the final thickness (cm) of the panel.

The panel starting thickness or density had the largest effect on the slit tear strength. FIG. 56 shows the slit tear max force as compared to the starting thickness (cm) of the panel. FIG. 57 shows the slit tear max force as compared to the final thickness (cm) of the panel. Thicker starting or final panels had higher slit tear max forces.

Figure 58:
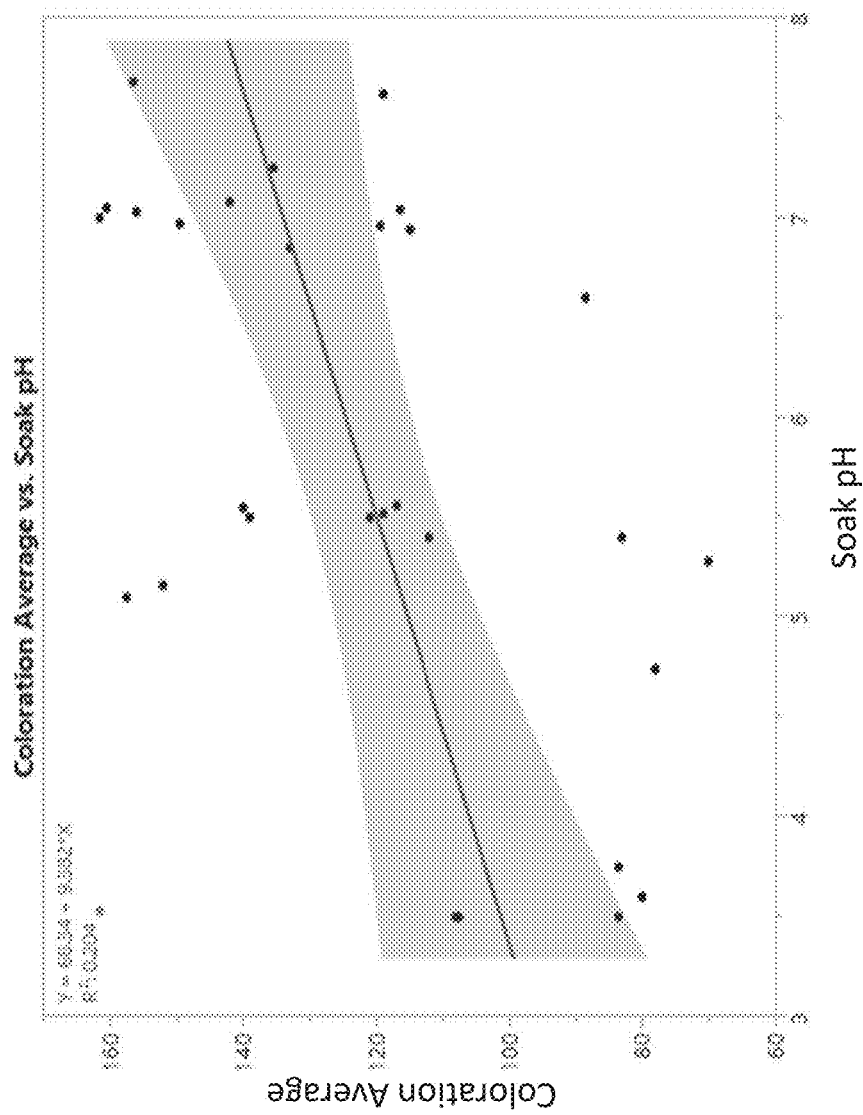
FIG. 58 shows the coloration average as compared to the soak pH.
Figure 59:
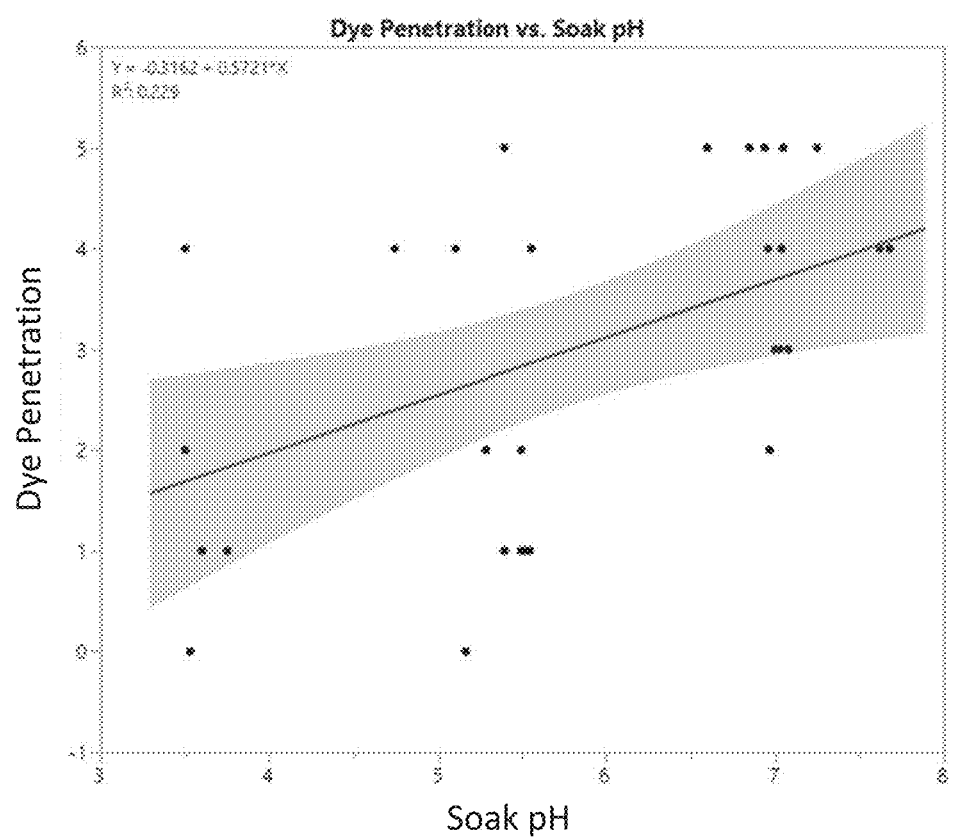
FIG. 59 shows the dye penetration as compared to the soak pH.
Figure 60:
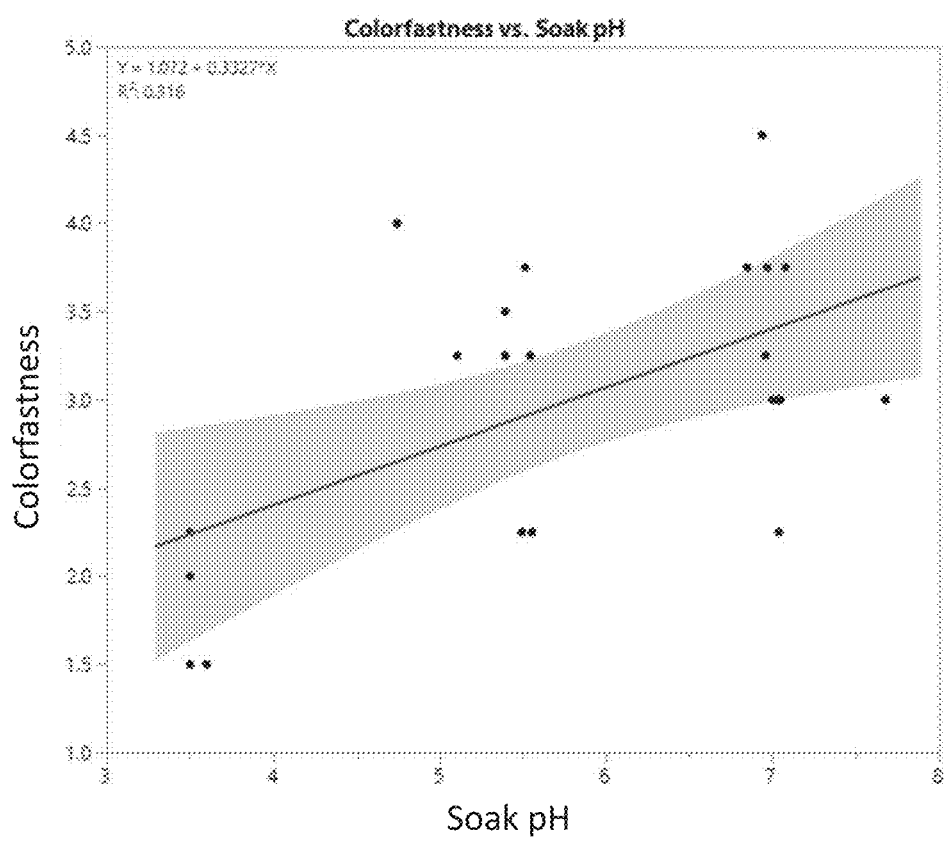
FIG. 60 shows the colorfastness as compared to the soak pH.

The soaking solution pH also had one of the most observable effects, as it affected the final coloration and dye penetration of the samples. FIG. 58 shows the coloration average as compared to the soak pH, lower coloration values indicate darker color. FIG. 59 shows the dye penetration as compared to the soak pH. FIG. 60 shows the colorfastness as compared to the soak pH.

The main trends observed were: a higher starting density resulted in a higher final density; a higher starting thickness resulted in a higher final thickness; roller settings affected the final thickness as a wide rolling spacer resulted in a thicker final material; a higher starting thickness resulted in a higher maximum tear force; low pH resulted in worse dye penetration; more pea protein resulted in a lighter coloration.

Additional slight trends observed were: TG increased final density; roller settings affected maximum and normalized tear force, as the material processed with a thinner roller spacing resulted in a lower tear force; a longer incubation resulted in a higher normalized tear strength; more pea protein or TG resulted in worse dye penetration; higher solution temperature resulted in higher dye penetration; and higher pH resulted in more colorfastness.

Thus, a higher thickness and/or density in the starting material resulted in a higher slit tear strength. For instance, to achieve a product specification of 20N, an exemplary starting panel should be at least 3.4 cm thick. However, simply increasing the panel thickness may not result in superior slit tear properties if the product specification force is higher. Thus, additional technologies such as composites (e.g., addition of scaffolds, scrims, adhesives, etc) or improved growth structures, such as hydroentanglement, should be explored.

In addition, low pH solutions adversely affected the panels with pea protein and TG. Therefore, if a low pH fixation step is used, it should be as a separate step.

for 30 minutes. It was again dried at 45° C. in a convection oven and submitted for testing.

Results

A range of different leather products was tested and the average peel force varied from 2.5 N/cm to greater than 23 N/cm.

Table 24 provides a list of average peel forces for different leather samples.

| Leather Sample | Average Peel Force (N/cm) |
|---|---|
| 1 | 2.5 |
| 2 | 14 |
| 3 | >23 |

Table 25 provides mechanical data of samples with Elite-Plus binder.

| ID | Low stimate of binder (%) | High estimate of Binder (%) | Ave. max peel force (N/cm) | Ave. peel force (N/cm) | Ave. width (mm) | Ave. thickness (mm) | Grams per square meter | Ave. max force (N) | Average first modulus (N/mm) |
|---|---|---|---|---|---|---|---|---|---|
| P1015 | 32.44 | 35.43 | 4.50 | 3.18 | 12.50 | 1.83 | 766 | 8.04 | 3.82 |
| P1016 | 32.91 | 35.92 | 4.89 | 3.18 | 12.48 | 1.51 | 723 | 9.38 | 5.57 |
| P1067 | 35.66 | 43.08 | 7.13 | 3.69 | 12.56 | 1.12 | 753 | 12.47 | 9.22 |
| P1068 | 35.66 | 43.08 | 7.39 | 3.74 | 12.56 | 1.24 | 786 | 9.01 | 5.30 |
| P1069 | 32.03 | 39.90 | 6.84 | 3.44 | 12.58 | 1.26 | 768 | 14.39 | 8.83 |
| P1070 | 32.03 | 39.90 | 6.56 | 3.90 | 12.69 | 1.34 | 793 | 12.87 | 8.35 |
| P1071 | 20.65 | 29.94 | 5.06 | 3.22 | 12.57 | 1.08 | 670 | 14.28 | 9.53 |
| P1072 | 20.65 | 29.94 | 4.77 | 3.16 | 12.56 | 1.09 | 706 | 10.08 | 5.48 |
| P1073 | 5.37 | 16.58 | 2.93 | 2.10 | 12.73 | 1.07 | 574 | 11.13 | 6.49 |
| P1074 | 5.37 | 16.58 | 5.69 | 2.07 | 12.52 | 1.03 | 570 | 9.08 | 4.23 |

Figure 61:
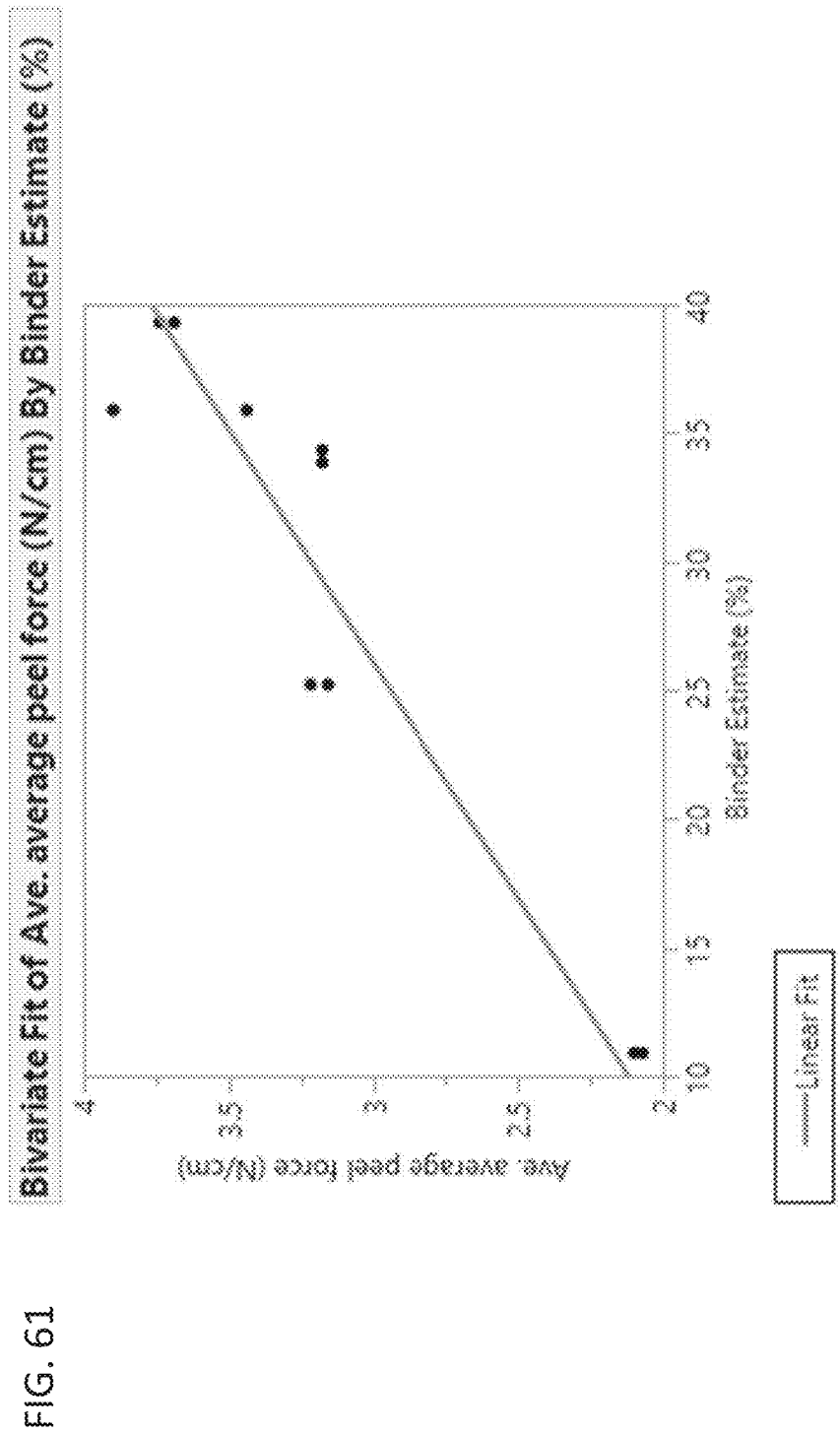
FIG. 61 shows the bivariate fit of average peel force (N/cm) against binder estimate (%).

Example 13: Treatment of Mycelium Material with Elite-Plus Binder and Other Additives Mechanical Properties of Mycelium Material with Elite-Plus Binder Materials and Methods Between 27 and 35 g dried mycelia was mechanically broken into cubes. 1.5-1.75 L water was added, and a slurry was disrupted using a low-shear rotary blender. The slurry was then dewatered before being redispersed in another 1.5-1.75 L water. It was dewatered a second time before being redispersed in another 1.5-1.75 L water. The specified amount of Dur-o-Set Elite Plus (Celanese Emulsions, U.S.A) was added to the slurry dispersion and mixed to homogeneity. The resulting slurry was then wet-laid onto a forming cloth and dewatered to form a panel. This panel was dried at 45° C. in a convection oven. The resulting panel was placed into a 7.5-15% fatliquor solution and allowed to soak FIG. 61 shows bivariate fit of average peel force (N/cm) against binder estimate (%). As the concentration of binder increases, so does the average max peel force. The panels were also subjected to Taber tests. For example, panel P1015 underwent 7000 cycles on Taber abrasion with 1000 g weights and a CS-10 abrasion disc. The sample showed even wear with a mass loss of about 6%. Binder samples also survived 30,000 cycles of Bally flex with minimal cracking or signs of damage.

Table 26 provides dry tensile strength data of samples with Elite-Plus binder.

TABLE 26 provides dry tensile strength data of samples with Elite-Plus binder.

| ID | Low estimate of binder (%) | High estimate of binder (%) | Ave. tensile strength (MPa) | Ave. initial modulus (MPa) | Ave. maximum force (N) | Ave. elong. at break (%) | Ave. toughness (MPa) |
|---|---|---|---|---|---|---|---|
| P1015 | 32.44 | 35.43 | 11.08 | 17.30 | 100.70 | 18.83 | 1.15 |
| P1016 | 32.91 | 35.92 | 9.61 | 18.61 | 128.50 | 19.45 | 1.00 |

Mechanical Properties of Mycelium Material with Elite-22 Binder and Abaca Fibers Materials and Methods Dried and disrupted mycelia were crusted in 10% Elite 22 with a 7.5% (1:3 LEX:DXV) fatliquor solution by soaking for 20-30 sec and abaca fibers were added before being passed through a pasta roller. The soak and pasta roller were performed 4 times and the mycelia were dried in an oven at 113° F. for 4-5 hours and hot-pressed at 80° C. for 1 min for smoothing the surface. The mycelia were conditioned in the humidity chamber at 50% moisture content overnight before testing.

Results

Figure 62:
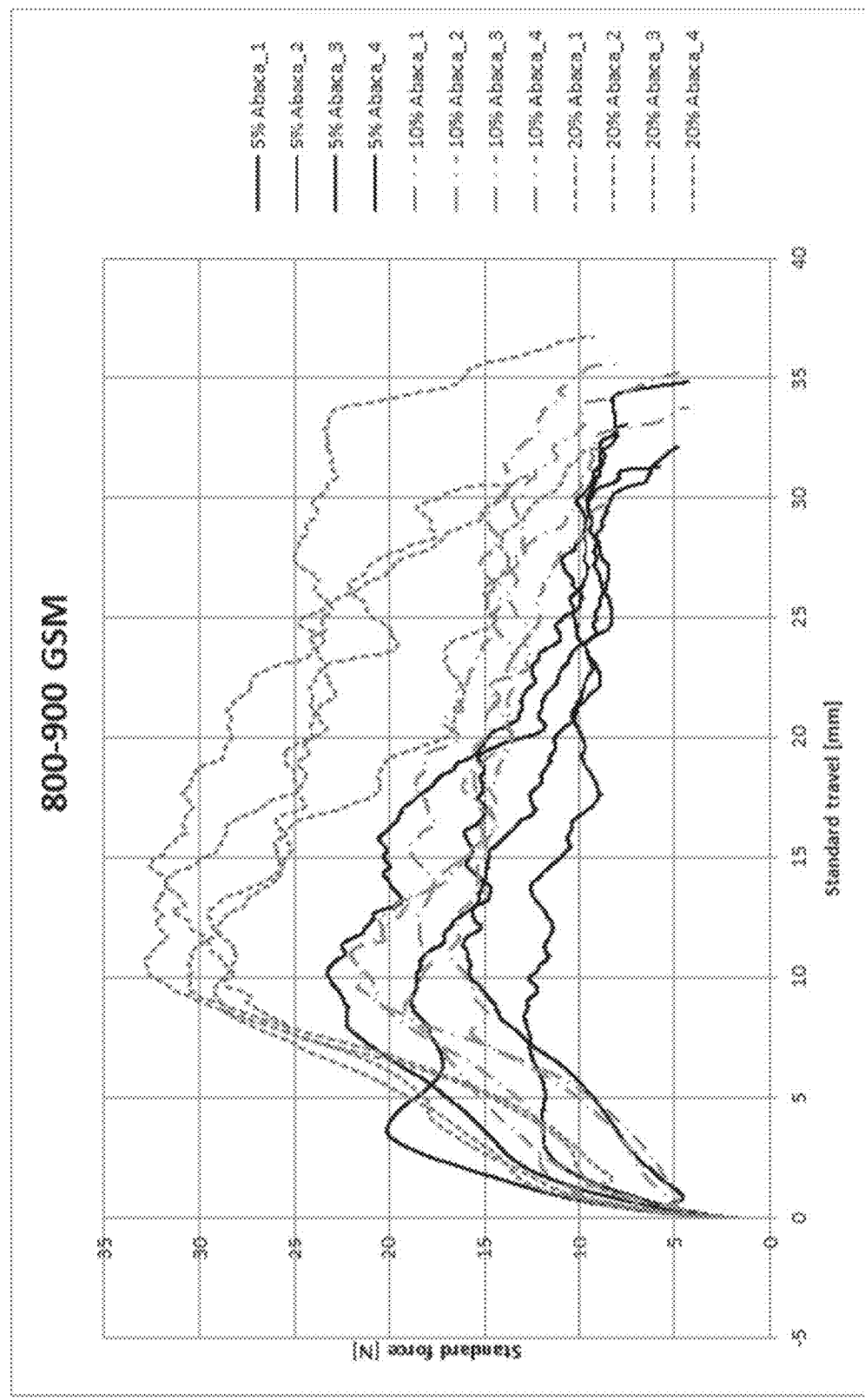
FIG. 62 illustrates the standard force values of mycelia samples with various concentrations of abaca fibers.
Figure 63:
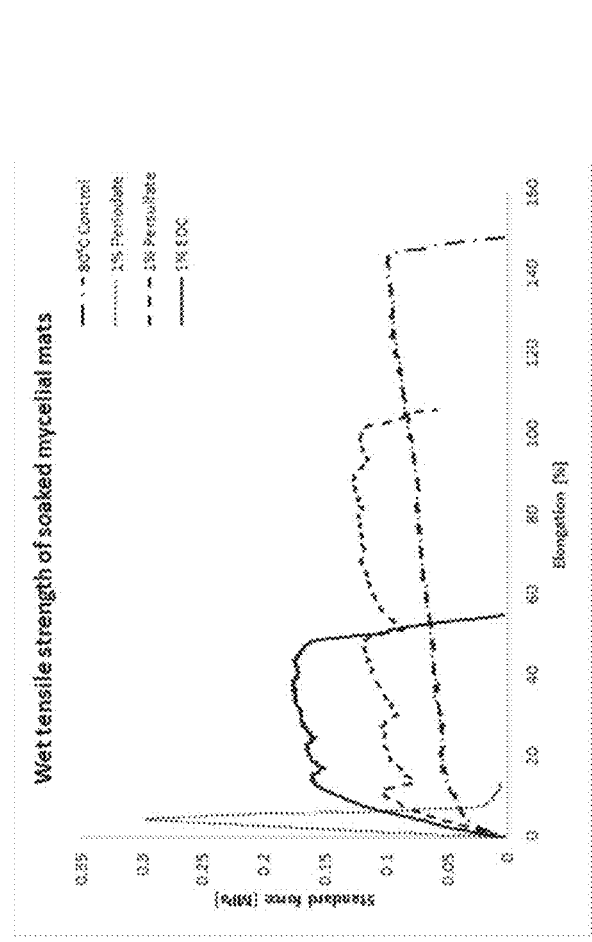
FIG. 63 shows the tensile strength results of disrupted mycelia samples crosslinked with sodium periodate, ammonium persulfate, or EDC.
Figure 64:
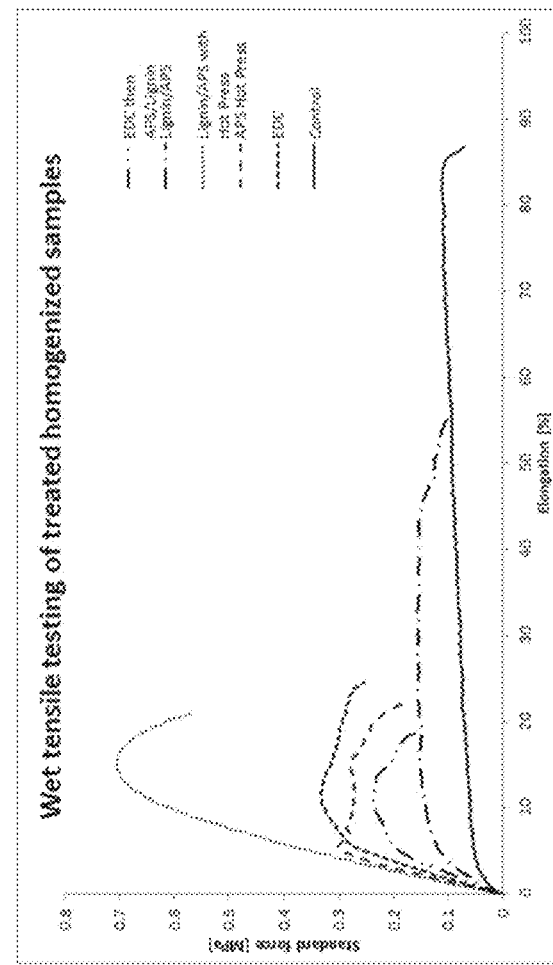
FIG. 64 shows the tensile strength results of disrupted mycelia samples crosslinked with combinations of EDC, APS/lignin, and hot pressing.

Samples were crusted via the procedure described above. Slit tear of samples increased as the percentage of abaca fibers in the samples increased. FIG. 62 illustrates the standard force values of samples with various concentrations of abaca fibers.

Table 27 provides thickness and slit tear data of various samples with abaca fibers.

|  | n | Thickness mm Avg. | Thickness mm Std. Dev | Slit Tear (N) Avg. | Slit Tear (N) Std. Dev | Slit Tear (N) normalized to 1.5 mm Avg. | Slit Tear (N) normalized to 1.5 mm Std. Dev |
|---|---|---|---|---|---|---|---|
| Control crust, no Abaca |  | 1.8 |  | 13.2 |  | 11 |  |
| 10% Abaca crust | 4 | 1.51 | 0.05 | 14.27 | 2.68 | 14.21 | 2.51 |
| 20% Abaca crust | 4 | 1.46 | 0.13 | 18.43 | 2.3 | 18.98 | 1.37 |
| 30% Abaca crust | 4 | 2.24 | 0.16 | 27.39 | 2.5 | 18.44 | 2.67 |
| 10% Abaca hydroentangled crust | 4 | 1.75 | 0.05 | 12.2 | 2.9 | 10.4 | 2.5 |
| 20% Abaca hydroentangled crust | 4 | 1.53 | 0.10 | 15.0 | 3.7 | 14.8 | 3.6 |
| 30% Abaca hydroentangled crust | 3 | 1.48 | 0.03 | 21.7 | 4.3 | 22.07 | 4.39 |

Example 14: Treatment of Mycelium Material with Other Additives

APS, EDC, Sodium Periodate, Ionic Liquid, and PAE resin

Ammonium persulfate (APS), ethyl-3(3-dimethylaminopropyl) carbodiimide (EDC), sodium periodate, ionic liquid, and PAE resin were investigated to improve the mechanical strength of the mycelium material. These crosslinkers act to crosslink the mycelium hyphae and can be used with additional polymer binders. Hot pressing was also used in some of the experiments. Mycelial mats were treated with APS crosslinker per the methods described in Example 6.

Materials and Methods

APS Crosslinker

For the APS samples, dried mycelial mats were soaked in a 1% (w/w) solution of ammonium persulfate in deionized water or phosphate buffered saline (PBS) and brought to 80° C. with slight agitation for 3.5 hours. In certain samples, 1% (w/w) solution of lignin in deionized water was also added. The resulting mats were rinsed in deionized water and dried at 40° C. for 3 hours. ISO 3377-2 double edge tear, ASTM D2209 tensile, and ASTM D4704 tongue tear tests were then performed on a ZwickiLine Materials Testing Machine Z5.0 to determine relative strengths versus control samples.

APS Crosslinker+Hot Pressing

For the APS samples, dried mycelial mats with or without a binder were soaked in a 1% (w/w) solution of ammonium persulfate in deionized water and brought to 80° C. with slight agitation for 1 hour. The mats were then transferred to a 80° C. hot press where they were pressed to 1.4-2.0 mm for 2.5 hours. The resulting mats were rinsed in deionized water and dried at 40° C. for 3 hours. ISO 3377-2 double edge tear, ASTM D2209 tensile, and ASTM D4704 tongue tear tests were then performed on a ZwickiLine Materials Testing Machine Z5.0 to determine relative strengths versus control samples.

EDC Crosslinker

Dried mycelial mats with or without a binder were soaked in a 1% (w/w) solution of 1-ethyl-3(3-dimethylaminopropyl) carbodiimide in deionized water at room temperature for six hours at a buffered pH of either 5.5, 7.4, 8.3, or 9.5. In certain samples, 1% (w/w) solution of lignin in deionized water was also added. The resulting mats were rinsed in deionized water and dried at 40° C. for 3 hours. ISO 3377-2 double edge tear, ASTM D2209 tensile, and ASTM D4704 tongue tear tests were then performed on a ZwickiLine Materials Testing Machine Z5.0 to determine relative strengths versus control samples.

Sodium Periodate

Dried mycelial mats were soaked in a 1% (w/w) solution of sodium periodate in deionized water. The solution was brought to 80° C. for 2 hours prior to being rinsed and dried at 40° C. for 3 hours. ASTM D2209 tensile tests were then performed on a ZwickiLine Materials Testing Machine Z5.0 to determine relative strengths versus control samples.

Ionic Liquid

Dried mycelial mats were soaked in the ionic liquid solution at room temperature for 5 min to 16 hours. The samples were then pressed at 80° C. for 5 min. Wet tensile tests were then performed via ASTM D2209.

PAE Resin

The samples were either heated at 105° C. for 5 minutes or 10 minutes. The samples were either at pH=5 (HM24) or pH=7 (HM25).

Results

The results of the mechanical property tests are shown in FIG. 63, FIG. 64, FIG. 65, FIG. 66, Table 28, and Table 29.

TABLE 28

Initial modulus, wet tensile strength, and elongation at break.

| Sample | Modulus (MPa) | Std. Dev (MPa) | Strength (MPa) | Std. Dev (MPa) | Elong at max stress (%) | Std. Dev (%) |
|---|---|---|---|---|---|---|
| EDC then APS/Lignin | 3.60 | 1.02 | 0.26 | 0.04 | 14.53 | 9.81 |
| Lignin/APS Hot Press | 6.83 | 2.76 | 0.61 | 0.11 | 24.06 | 15.84 |
| APS Hot Press | 7.41 | 1.53 | 0.32 | 0.07 | 5.55 | 0.86 |
| EDC | 5.07 | 0.23 | 0.39 | 0.05 | 12.06 | 3.46 |
| APS/Lignin | 2.45 | 0.82 | 0.18 | 0.02 | 35.49 | 26.02 |
| Control | 2.07 | 0.85 | 0.10 | 0.01 | 48.44 | 22.95 |

The treated samples had significantly increased wet tensile strength, initial modulus as compared to the control samples. Thus, the addition of APS to crosslink the mycelium material improved the mechanical qualities of the mycelium panel.

TABLE 29

Wet tensile strength and elongation at break.

| Sample | Strength (MPa) | Std. Dev (MPa) | Elongation at Max Stress (%) | Std. Dev (%) |
|---|---|---|---|---|
| Mycelial Control | 0.11 | 0.01 | 140.60 | 8.63 |
| Sodium Periodate | 0.22 | 0.06 | 5.12 | 0.82 |

TABLE 29-continued

Wet tensile strength and elongation at break.

| Sample | Strength (MPa) | Std. Dev (MPa) | Elongation at Max Stress (%) | Std. Dev (%) |
|---|---|---|---|---|
| Ammonium Persulfate | 0.11 | 0.01 | 77.01 | 42.71 |
| EDC | 0.17 | 0.02 | 21.91 | 11.41 |

The sodium periodate and EDC treated samples had significantly increased wet tensile strength as compared to the control sample. Thus, the addition of sodium periodate and/or EDC to crosslink the mycelium material improved at least one mechanical parameter of the mycelium panel.

Figure 65:
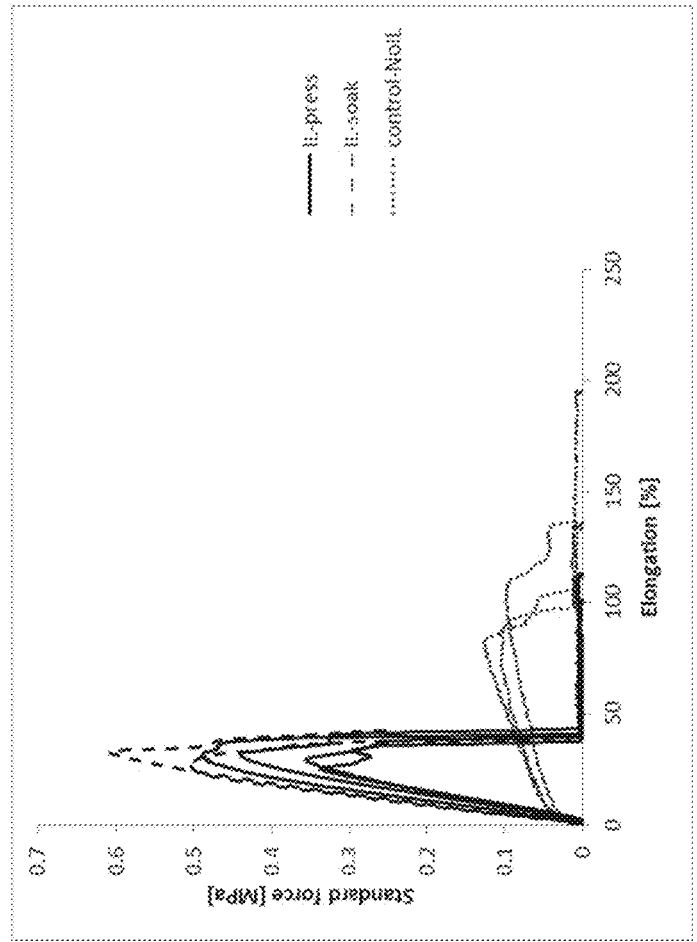
FIG. 65 shows the tensile strength results of ionic liquid treated samples versus a control.

FIG. 65 shows the tensile strength results of ionic liquid treated samples as compared to a control sample. IL-P0.75 mm-16 h indicates the sample was soaked in ionic liquid for 16 hours at room temperature and then pressed to 0.75 mm at 80° C. for 5 min. The elongation at break was around 50% for the crosslinked samples.

Figure 66:
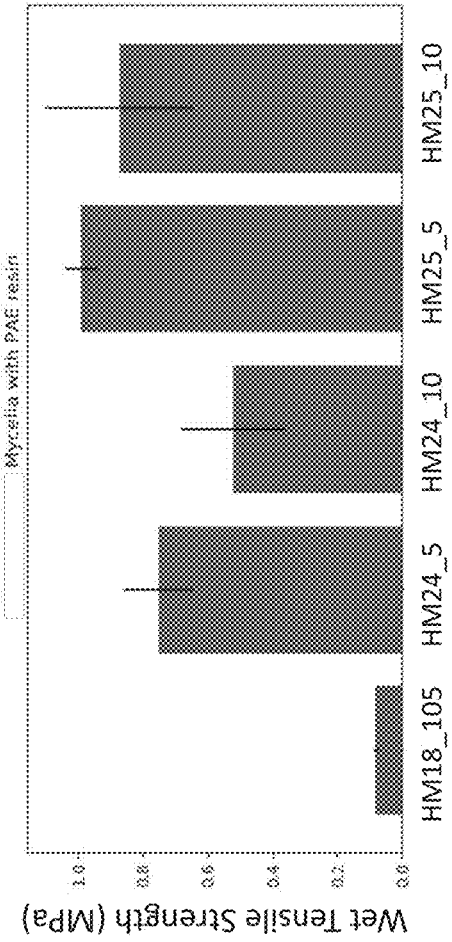
FIG. 66 shows the tensile strength results of disrupted mycelia crosslinked with PAE resin.

FIG. 66 shows the tensile strength results of PAE resin treated samples as compared to a control sample. HM18_105 did not contain PAE resin, but it did have epoxidized soybean oil and was heated at 105° C. for 4 hours, indicating that the heat treatment alone did not lead to increased wet tensile strength.

Example 15: Lamination, Scrim Addition, Heat Pressing, and Hydroentanglement of Mycelium Material Materials and Methods Slurry Preparation Mycelium slurry was prepared by blending dry mycelium in tap water using a Blendtec Pro 800 blender. The concentration of the slurry ranged from 0.5-2.5 w/v % depending on the experiment. The mycelium was blended to produce a uniform slurry, typically on setting 5 for 90 seconds. After blending, the slurry was sieved on a 500 micron sieve to remove fines and soluble components. The sieved mycelium was then resuspended back to 1 w/v %, stirred manually to disperse, and sieved/resuspended two more times. After the final resuspension, sodium dodecyl sulfate (SDS) solution in DI water was added and the slurry was blended on setting 5 for 10 seconds to create foam. The final concentration of sodium dodecyl sulfate in the slurry was typically 0.002 w/v %. The foam remained trapped in the slurry and helped to create porosity in the web after wetlaying.

Wetlaying

A bench scale wetlay apparatus was constructed to produce webs from slurry. The apparatus consisted of a 150 mm diameter Buchner funnel lined with a forming cloth, attached to a 4 L vacuum flask. The vacuum flask was attached to a vacuum pump (Vacuubrand VARIO PC 3001 Select) which allowed control over the vacuum setpoint with a precision of 1 ton. A 3-way valve in between the vacuum pump and the flask controlled whether the flask was under vacuum or vented to atmosphere. Wetlaying was accomplished by pouring the slurry into the Buchner funnel and subsequent vacuum filtration at a defined vacuum level (typically 600 ton) until no more water was observed dripping out of the funnel (typically 90 seconds). The resulting web had a moisture content between 75-80 wt %. The web was then manually peeled from the forming cloth and dried at 45° C. with convection until its mass reached a steady state (typically several hours).

Crusting

A crust solution containing a binder emulsion and fatliquors were prepared using a planetary centrifugal mixer (THINKY ARE—400 TWIN) with a typical composition as listed in Table 30. 100 ml of solution was sufficient to perform impregnation of a single web formed on a 150 mm diameter Buchner funnel as described above.

TABLE 30

Crust solution composition for impregnation.

| Component | Concentration (wt %) |
|---|---|
| DUR-O-SET Elite 22 VAE | 10 (based on binder emulsion solids content) |
| Trupon DXV fatliquor | 5.625 |
| Truposol LEX fatliquor | 1.875 |
| Water | Balance |

To perform the impregnation, a dried web was immersed in the crust solution for at least 1 minute to wet, and then passed between two rollers with approximately 2 mm spacing to remove air and force solution through the material. The immersion and rolling process was repeated until the web was evenly saturated with the crust solution, typically 4 iterations. Afterwards, the crust was dried at 45° C. with convection until its mass reached a steady state (typically several hours).

Lamination

Lamination, scrim incorporation, and heat pressing to compress the material and smooth the surface could be performed concurrently. To laminate two crusted webs together, a thin layer of DUR-O-SET Elite 22 VAE was first applied to one side of each web using a brush or roller. The typical application was approximately 9 mg/cm$^2$ on a wet basis. After application, the binder was exposed to ambient conditions for roughly 30 seconds, during which time it became tacky. The webs were then pressed together (binder side inward) using a manual heated press (Carver 4120) at 80° C. for 1 minute to a final thickness (controlled by placing shims in between the press platens) ranging from 1-3 mm. A scrim could be incorporated into the material (typically 95 gsm woven cotton) by placing it in between the two webs before pressing. After pressing, the laminate was dried at 45° C. with convection until its mass reached a steady state (typically several hours) to remove residual water from the binder before curing.

Curing

DUR-O-SET Elite 22 VAE contained self-crosslinking N-methylol acrylamide side chains which, once crosslinked, increased the initial modulus, ultimate tensile strength, and water resistance of the polymer (especially under elevated temperatures which could be encountered during aqueous dyeing processes). Before curing a crust or laminate, the sample was dried to remove residual water to prevent expanding vapor from delaminating the material. Curing was accomplished by placing the sample in an oven between 90 and 135° C. for 0.5 to 1 hour.

Hydroentanglement

Hydroentanglement of mycelia webs was performed according to the methods described in Example 4. Samples were hydroentangled with 50 micrometer water jets with 1000 psi. Each sample was hydroentangled with multiple passes in both the vertical and horizontal direction.

Results

Effect of a Scrim in Mycelium Materials

The mechanical properties of typical samples are shown in Table 31. Note that these samples were constructed with a scrim. The area density was calculated by dividing the mass of the sample by the sample area. The apparent volumetric density was calculated by dividing the mass of the sample by the product of the thickness of the sample as measured according to ASTM D1813 and the sample area.

TABLE 31

Mechanical performance and dimensional properties of typical samples.

| Property or Test | Testing standard (if applicable) | Test result (mean ± standard deviation if applicable) | n |
|---|---|---|---|
| Taber abrasion | ASTM D7255 | 90 wt % remaining after 7000 cycles | 1 |
| T-peel | ASTM D1876 | 4.3 ± 0.1 N/cm peak force, ~1.5 N/cm sustained force during tear propagation | 3 |
| Slit tear normalized maximum force | ISO 3377-2 | 21 ± 1 N/mm | 5 |
| Dry bally flexure | ISO 5402-1 | 30000 cycles without gross macroscopic failure, i.e. no holes or tears visible to the eye. Some creasing and internal delamination in the fold area. | 1 |
| Thickness | ASTM D1813 | 1.39 ± 0.04 mm | 3 |
| Area density | N/A | 1000 ± 30 g/cm$^2$ | 3 |
| Apparent volumetric density | N/A | 0.75 ± 0.03 g/cm$^3$ | 3 |

Effect of Heat Pressing on Mycelium Materials

Pressing mycelium materials at or above ambient temperature was performed to control the final thickness and surface roughness, which in turn affected downstream operations such as finishing and embossing as well as the flexibility and feel of the final product.

To investigate the effects of pressing time, temperature, and pressure on the final thickness of the material, samples were prepared according to the process described above, but without the curing step, and then the samples were pressed at various points in the time-temperature-pressure parameter space as denoted in Table 32. The thickness of the material before pressing was 2.2±0.1 mm. The thicknesses of the materials were measured before and after pressing according to ASTM D1813.

TABLE 32

Time-temperature-pressure parameter space investigated for heat pressing experiments.

| Factor | Levels |
|---|---|
| Pressing time (s) | 5, 60 |
| Pressing temperature (° C.) | 22, 50, 80 |
| Pressing pressure (MPa) | 0.34, 1.7 |

Figure 67:
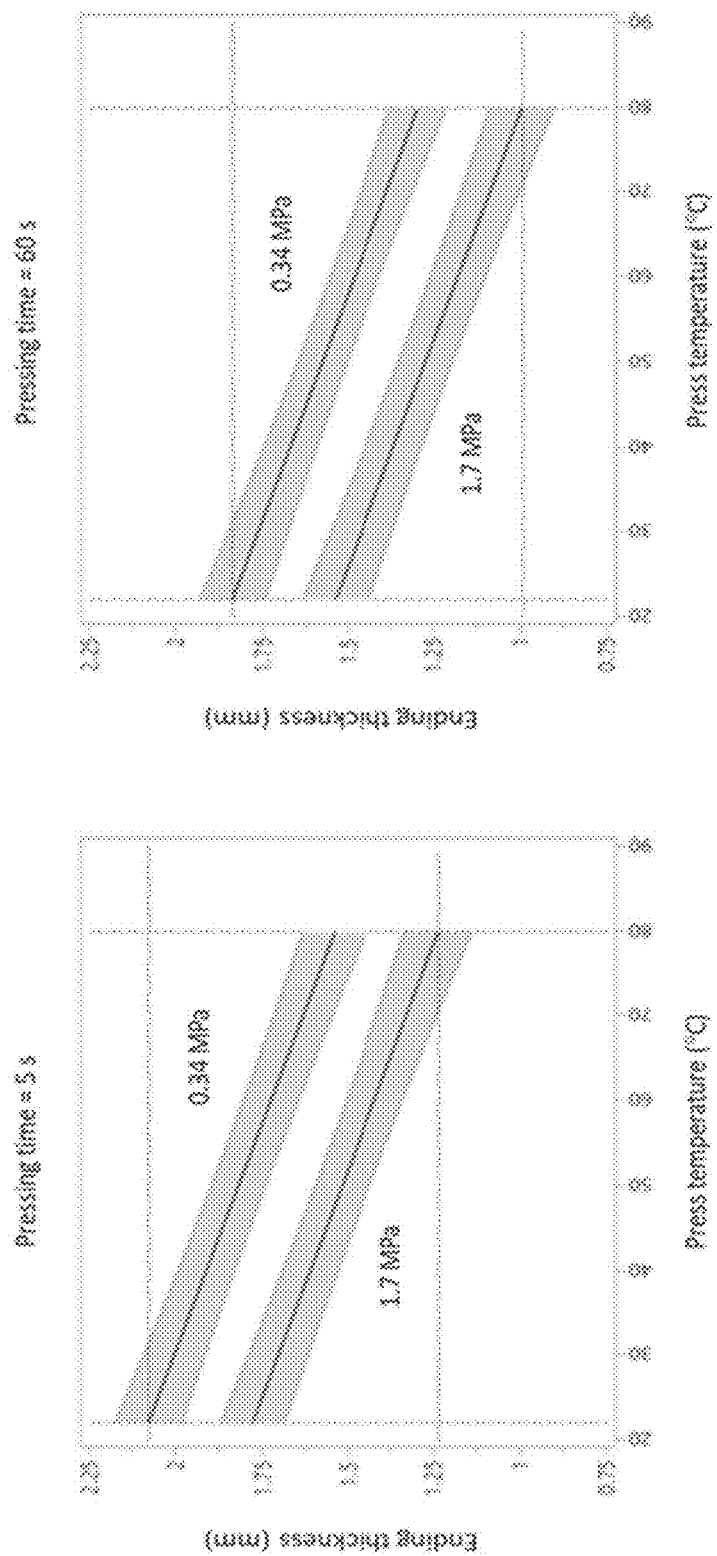
FIG. 67 shows a linear model describing the effect of pressing time, temperature, and pressure on the final thickness of the material. Solid lines represent the mean of the response. Shaded areas represent the 95% confidence interval of the mean. $R^2=0.96$.

FIG. 67 shows that the pressing temperature had the largest effect on final thickness, and pressing time and pressure had smaller effect sizes of comparable magnitude. Surface roughness was qualitatively directly proportional to final thickness. The results of this model could be used to tune the final thickness of the material as needed for downstream operations.

Effect of Wetlay Process Parameters on Web Porosity

The porosity of the web influenced several downstream properties, such as the area and volumetric density, compressibility, flexibility, through-thickness strength, and ability to be impregnated with solutions. Thus, understanding which factors influence web porosity and controlling them contributed to tuning the behavior of the intermediate material and the properties of the final product.

To investigate the effects of slurry volume, concentration, and vacuum treatment on web porosity, slurries were prepared as described in this example, but the sieving step, resuspension step, and the addition of sodium dodecyl sulfate were omitted. The slurries were then wetlaid using the bench scale web forming apparatus at various points in the parameter space described in Table 33. After drying as previously described, samples of the webs were cut using a scalpel so that the web cross section could be observed by scanning electron microscopy. Scanning electron microscopy was performed using a Hitachi™ 3030 Plus scanning electron microscope with an accelerating voltage of 15 kV.

TABLE 33

Parameter space investigated to determine the effects of wetlay parameters on web porosity.

| Factor | Levels |
|---|---|
| Slurry volume (L) | 0.5, 1 |
| Slurry concentration (w/v %) | 1, 2.5 |
| Vacuum setpoint (torr) | 35, 600 |

Figure 68:
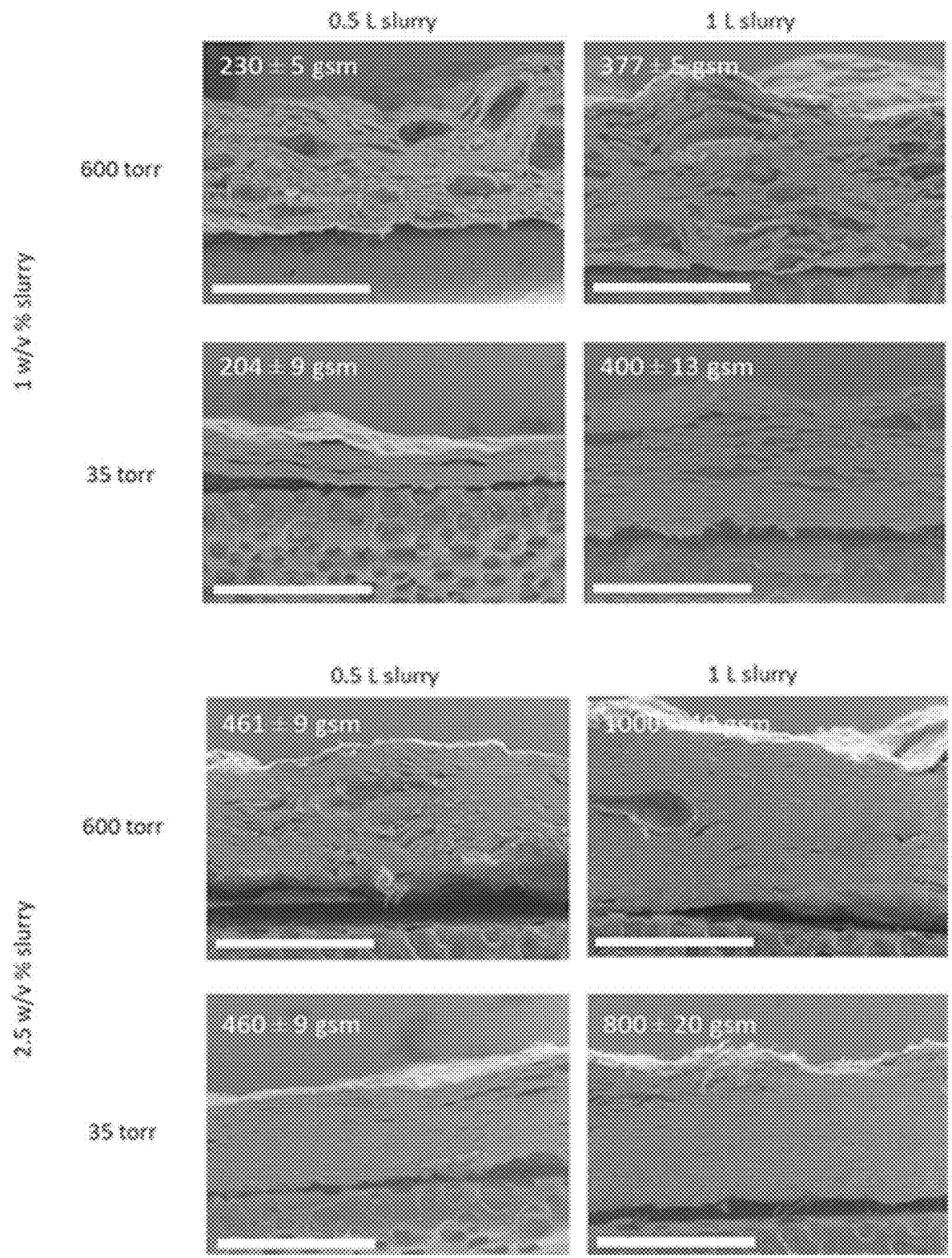
FIG. 68 shows representative scanning electron micrographs of webs produced at various points in the volume-concentration-vacuum parameter space, along with their corresponding area densities. Scale bars are 1.5 mm.

FIG. 68 shows representative scanning electron micrographs of webs produced at various points in the parameter space described in Table 33, along with their corresponding area densities. The relationships between the factors investigated and the thickness, qualitative porosity, and qualitative compressibility of the web are summarized in Table 34.

TABLE 34

Relationships between wetlay parameters investigated and the thickness, porosity, and compressibility of the resulting webs.

| Response | Significant parameter(s) | Relative effect strength | Description |
|---|---|---|---|
| Thickness | Vacuum setpoint | Strong | Higher vacuum leads to more compression and thinner web |
| | Slurry concentration | Moderate | Increased amount of mycelium increases web thickness |
| | Slurry volume | Moderate | |
| Porosity | Vacuum setpoint | Strong | Higher vacuum leads to more compression and less porosity |
| | Slurry concentration | Strong | Higher concentration produced less porous webs |
| Compressibility | Slurry concentration | Strong | Higher concentration produced harder webs |

The results of this experiment are generally applicable for tuning the thickness, porosity, and compressibility of the material, which in turn affect the downstream processing and final properties.

Figure 69:
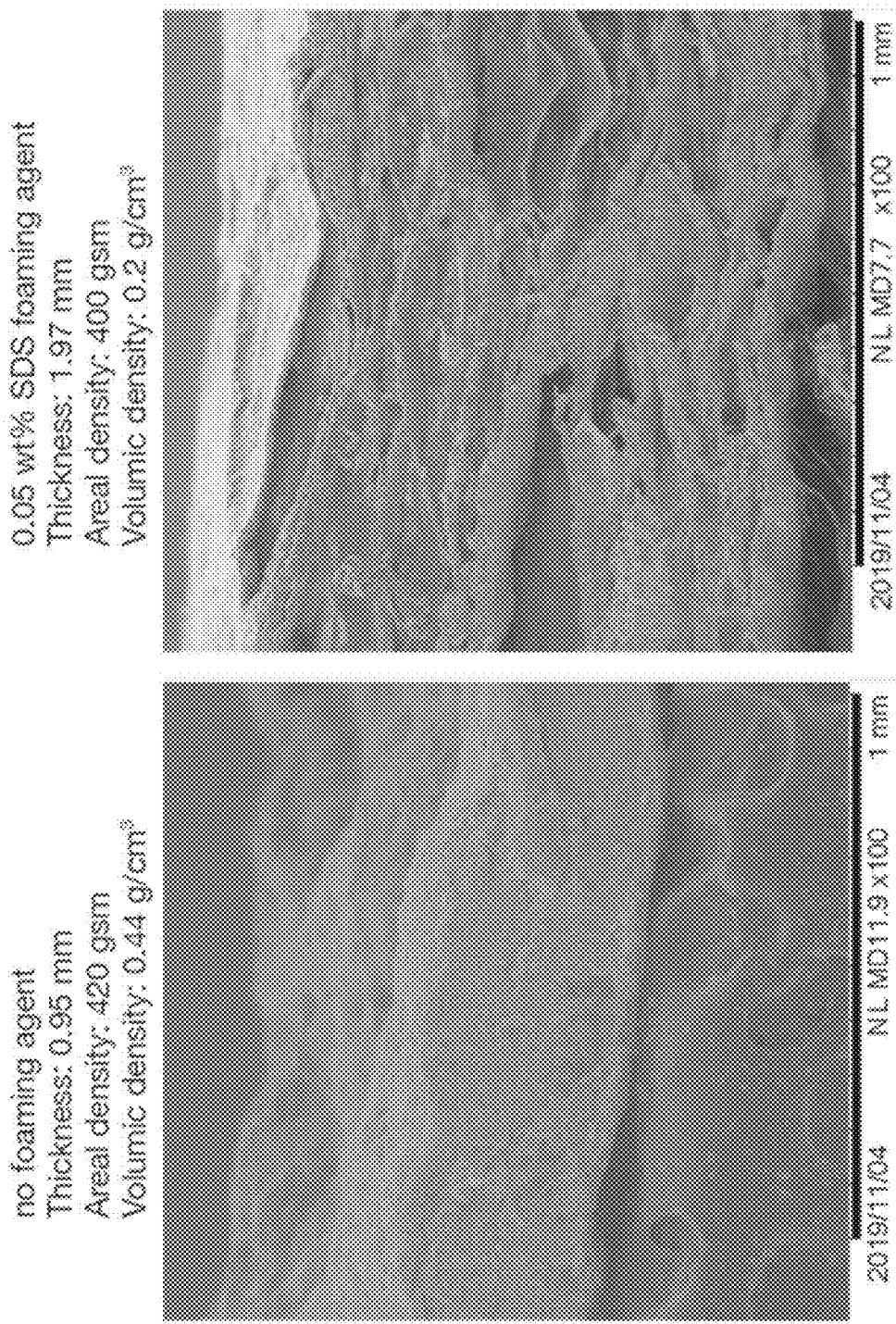
FIG. 69 shows scanning electron micrographs of webs prepared with and without 0.05 wt % sodium dodecyl sulfate (SDS) blended into the slurry.

The addition of a foaming agent into the slurry can also be used to tune the porosity of the web. To investigate the effect of a foaming agent, slurry was prepared as described in this example at the same concentration (0.75 w/v %) with or without 0.05 wt % sodium dodecyl sulfate (SDS) blended into the slurry. The slurries were then wetlaid using the bench scale wetlay apparatus as described in this example, but at a vacuum setpoint of 450 torr. FIG. 69 shows scanning electron micrographs of the two webs and their corresponding dimensional data.

The addition of a foaming agent such as SDS to the slurry significantly increased the porosity and decreased the apparent volumetric density of the web. With the addition of SDS into the slurry and subsequent blending, the foam generated became trapped within the slurry and created additional porosity after dewatering and drying.

In Situ Binder Addition

Table 35. This table shows wet-end Elite-Plus crust data. This table demonstrates how web volumetric density changes based on the presence or absence of vacuum during wet lay and the presence or absence of chemical defoamer. This change in web volumetric density impacts T-peel strength.

TABLE 35

In situ binder addition during web forming.

| Sample | Max. T-peel force (N/cm) | Avg. T-peel force (N/cm) | Min. T-peel force (N/cm) | Web vol. density (g/cm$^3$) | Crust width (mm) | Crust thickness (mm) | Vacuum during wet lay | Chemical defoamer added? |
|---|---|---|---|---|---|---|---|---|
| 1 | 5.13 | 3.23 | 2.01 | 0.12 | 13.53 | 1.212 | Gravity | No |
| 2 | 5.56 | 3.65 | 2.08 | 0.12 | 13.15 | 1.235 | Gravity | No |
| 3 | 7.85 | 4.58 | 2.65 | 0.16 | 13.14 | 1.325 | 600 Torr | No |
| 4 | 7.4 | 4.63 | 2.77 | 0.16 | 13.81 | 1.305 | 600 Torr | No |
| 5 | 7.98 | 4.91 | 2.36 | 0.21 | 13.98 | 1.313 | 600 Torr | Yes |
| 6 | 7.59 | 5.23 | 2.80 | 0.21 | 11.79 | 1.309 | 600 Torr | Yes |
| 7 | 7.39 | 5.03 | 3.73 | 0.29 | 13.80 | 1.195 | 600 Torr | Yes |

In situ binder addition during web forming is another method for binder incorporation, in addition to adding binder solution in the slurry or impregnating a dry web with binder solution. One possible advantage of this approach compared to other methods is that the amount of binder required may be less. Possible advantages over dry impregnation include not having to dry the web first before impregnation, and that loading of binder in the material may be better controlled and not limited by the ability of the binder to penetrate the dry web. Tuning the binder content in the final material affected the mechanical performance of the material as well as its hand feel and other aesthetic properties.

To investigate the effect of in situ binder addition process parameters, slurries were first prepared as described in this example. The bench scale wetlay apparatus was then modified by adding a valve between the Buchner funnel stem and the vacuum flask, so that the volume of liquid drained from the slurry could be controlled. Binder solutions were prepared by mixing DUR-O-SET Elite 22 VAE with water to obtain final solids content of either 2.5 or 5 wt %. Slurries were then wetlaid in the modified apparatus while varying the amount of water removed from the slurry before addition of binder solution, the amount of binder solution added, and the concentration of the binder solution added. After binder addition and vacuum filtration was complete, the webs were dried and the mass uptake relative to the input mycelium mass was recorded. In addition, Fourier transform infrared spectroscopy (FTIR) was used to semi-quantitatively assess the binder to mycelium ratio as a function of the Z position (through-thickness direction) of the material for each point in the volume-concentration parameter space. FTIR was performed using a Bruker Alpha II attenuated total reflectance (ATR) FTIR equipped with a diamond ATR element. Web samples were cut with a scalpel and their top, bottom, and core surfaces were placed on the internal reflection element (IRE) of the instrument. Spectra were recorded at 30° C. by averaging 32 scans from 4000-600 cm$^{-1}$ with 4 cm$^{-1}$ resolution. Spectra were then baseline corrected over the entire wavenumber region, and straight baselines were drawn from 1760-1700 cm$^{-1}$ (corresponding to the C═O bond of the acetate group in DUR-O-SET Elite 22 VAE) and 1180-880 cm$^{-1}$ (corresponding to the C—O bonds in saccharides, taken to be representative of the mycelium content). The regions were then integrated and the ratio of the peak areas was reported.

Table 36 summaries the parameter space investigated in this experiment.

| Factor | Levels |
|---|---|
| Amount of water removed from the slurry before applying binder solution (ml) | 300, 600 |
| Volume of binder solution added (ml) | 100, 200, 400 |
| Concentration of binder solution (wt %) | 2.5, 5 |

Figure 70:
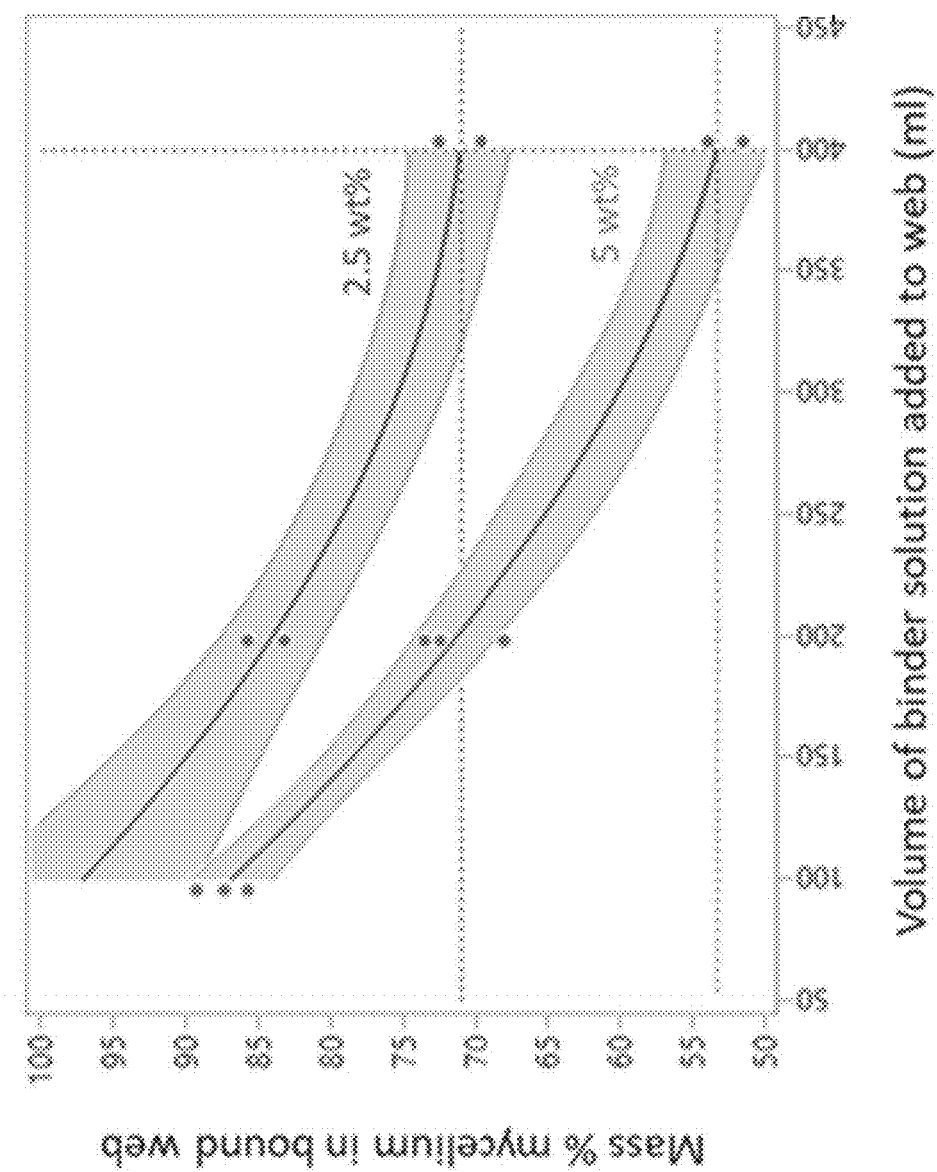
FIG. 70 shows a model relating the mass % of mycelium in the dry bound web as a function of the volume of binder solution added to the web and the concentration of the binder solution.

FIG. 70 shows a model relating the mass % of mycelium in the dry bound web as a function of the volume of binder solution added to the web and the concentration of the binder solution. Points denote individual measurements. Curves denote the mean and shaded areas denote the 95% confidence interval of the mean. $R^2$=0.97. The mass % calculation assumes a 25 wt % mass loss relative to the input mycelium mass due to fines and soluble loss during the sieving operation.

Figure 71:
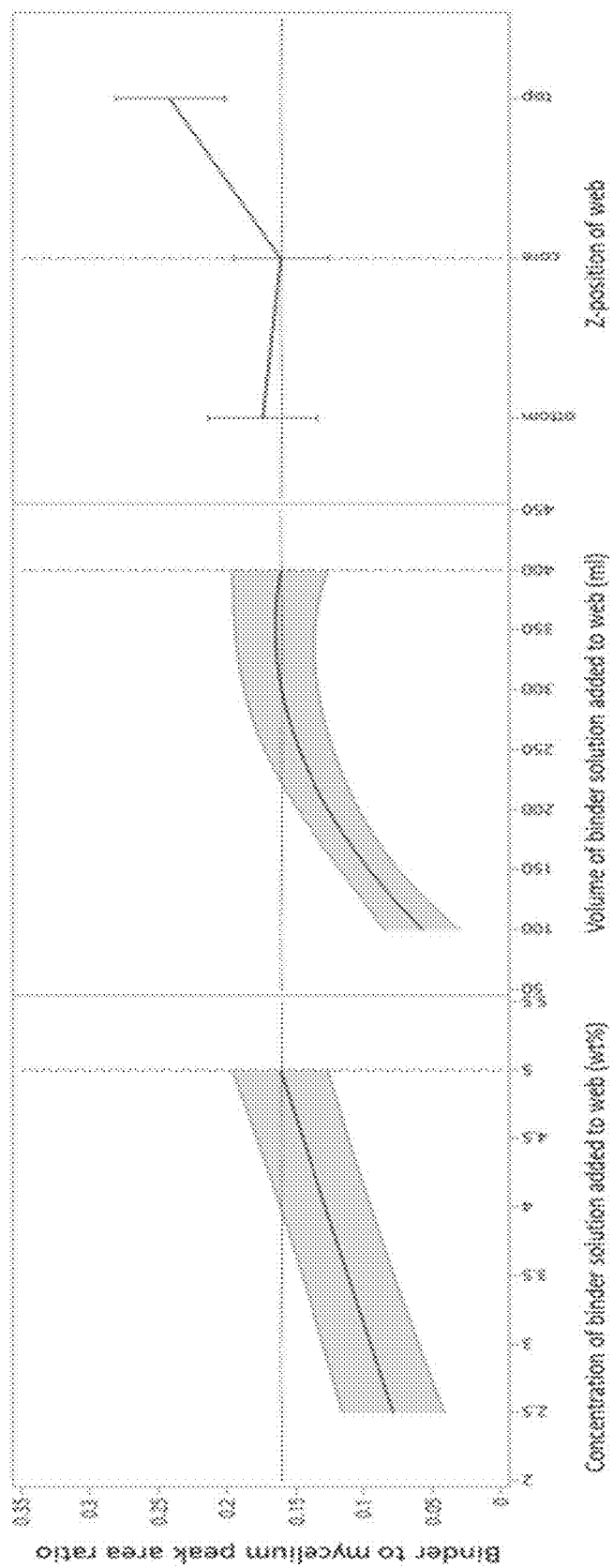
FIG. 71 shows a model describing the mean binder to mycelium peak area ratios over the concentration-volume-Z position parameter space.

The model shown in FIG. 71 describes how the binder content of the bound web can be tuned to a desired value by controlling the amount of binder solution added to the web and the concentration of that solution. In this experiment, the amount of water removed from the slurry before addition of the binder solution did not significantly affect the final binder content.

FIG. 71 shows a model describing the mean binder to mycelium peak area ratios over the concentration-volume-Z position parameter space. Lines and curves denote the mean of each response. Shaded areas and error bars denote the 95% confidence interval of the mean. $R^2$=0.77.

Figure 72:
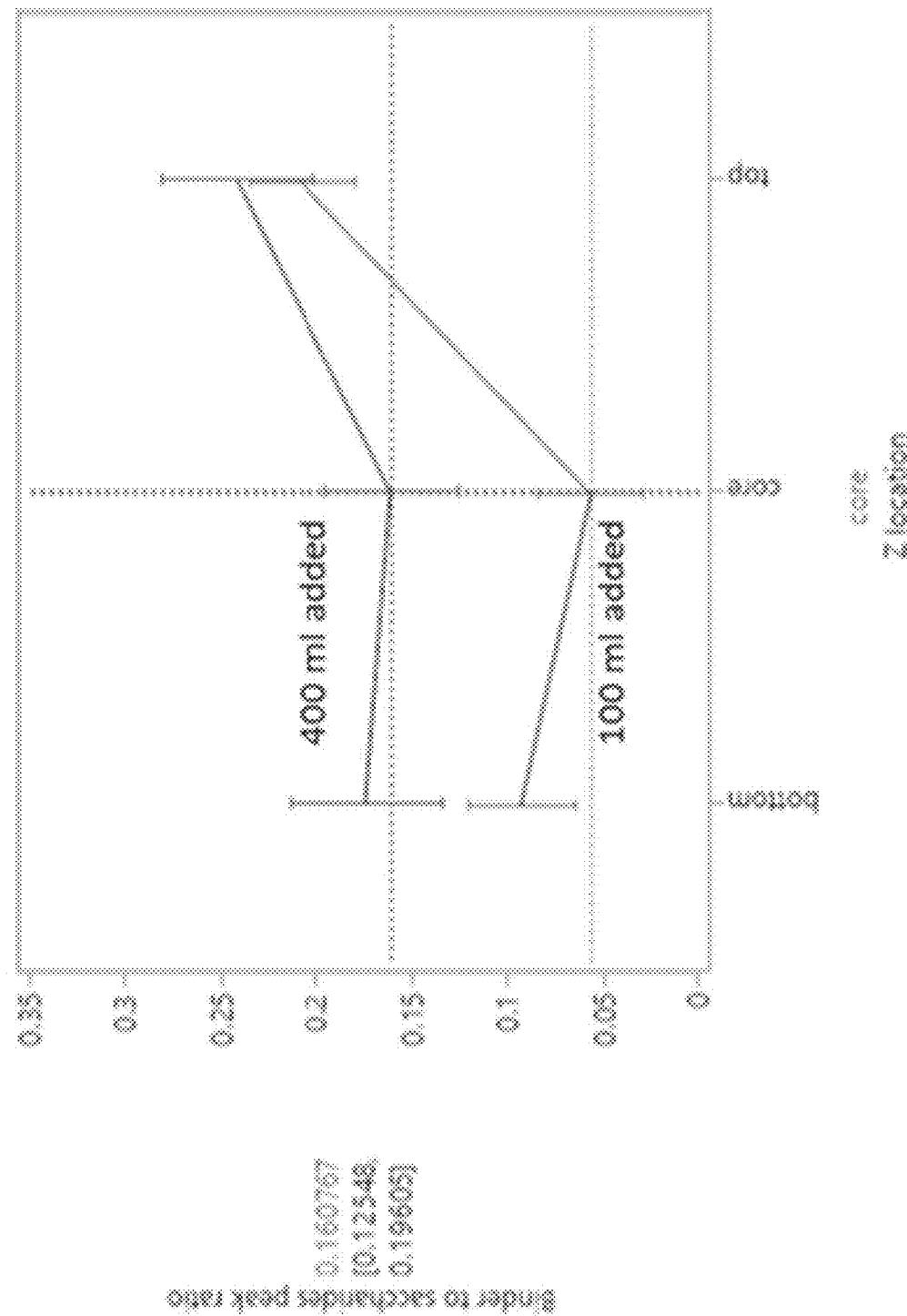
FIG. 72 shows the binder to mycelium ratio as a function of Z position in the web, for low and high binder addition volumes.

FIG. 72 shows binder to mycelium peak ratio as a function of Z position in the web, for low and high binder addition volumes. Error bars represent the 95% confidence interval of the mean. The binder to mycelium ratio increased with both the volume and concentration of the binder solution added. The model also predicted diminishing returns with increasing addition volume. In addition, the model showed that on average, the top of the bound web (where the binder was added) had a higher binder content than the core or the bottom. Finally, the model showed that the difference in binder content between the top of the web and the core/bottom was exacerbated in cases of low binder addition volume. Ensuring even distribution of binder throughout the thickness of the material contributed to mitigating internal delamination.

Effect of Hydroentanglement on Mycelium Materials

Figure 73:
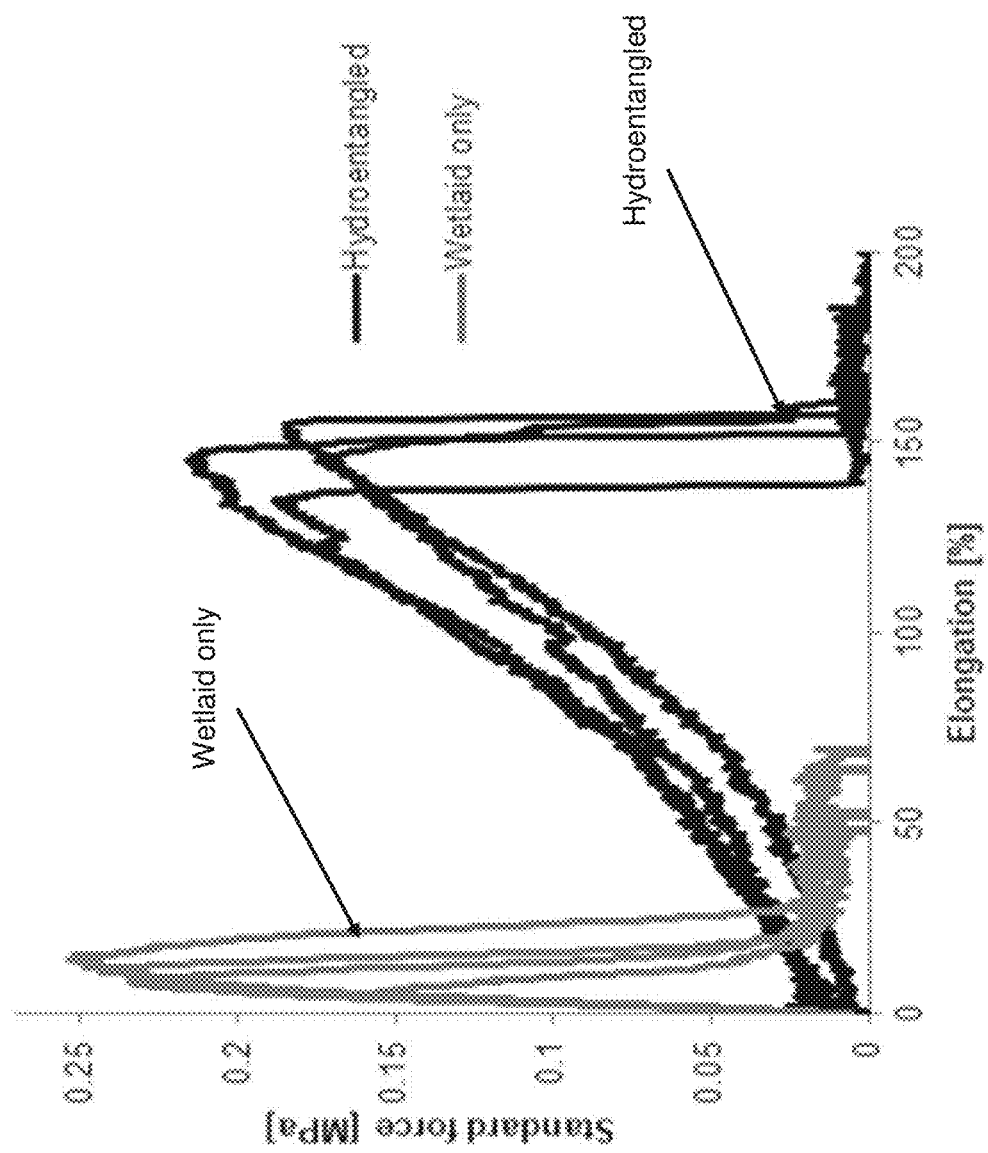
FIG. 73 shows the impact of hydroentanglement on the wet tensile curves of mycelium webs.

FIG. 73 shows the impact of hydroentanglement on the wet tensile curves of mycelium webs. The wet tensile results were determined from mycelium webs without binder fatliquor, or hot pressing. Hydroentanglement lowered the initial modulus and increased elongation-at-break of mycelium webs.

Example 16: Process Chemicals and their Effects on Mechanical Properties of Mycelium Material Binder Dur-O-Set Elite 22 Curing Conditions
    Materials and Methods
    Experiments were conducted on mycelium webs that have been hydroentangled, or "spunlace." Spunlaces were treated with a binder baseline solution, 10% Elite 22 solution, soaked for 15 minutes, rolled with hand roller twice to remove air bubbles inside the spunlace, then soaked again for 15 minutes. After binder application, spunlaces were dried under 45° C. overnight. After spunlaces were dried, fatliquors were applied using 7.5 wt % DXV/LEX solution (3:1 ration DXV to LEX), and underwent a soak for 15 minutes, one hand roll, and another soak for 15 minutes. After fatliquor application, spunlaces were again dried at 45° C. overnight. Spunlaces were then post-cured under various temperatures and time conditions.
    Results
    The results of the curing tests are shown in FIG. 74, FIG. 75, and Table 37.

TABLE 37

Sample description of curing experiments.

| Sample ID (Temp-time) | Dry weight (g) | Thickness (mm) | Binder dry loading (g) | Fatliquor solution loading (g) | Fatliquor dry loading (g) |
|---|---|---|---|---|---|
| 70-30 | 3.81 | 1.35 ± 0.13 | 1.26 | 17.23 | 0.84 |
| 90-30 | 3.90 | 1.31 ± 0.10 | 1.31 | 17.19 | 0.78 |
| 110-30 | 3.95 | 1.27 ± 0.12 | 1.30 | 14.45 | 0.64 |
| 135-15 | 3.82 | 1.34 ± 0.12 | 1.23 | 15.64 | 0.63 |
| 135-30 | 3.87 | 1.33 ± 0.14 | 1.36 | 15.07 | 0.59 |
| 135-45 | 3.84 | 1.38 ± 0.10 | 1.25 | 14.21 | 0.53 |
| 135-60 | 3.90 | 1.30 ± 0.16 | 1.24 | 12.17 | 0.47 |

As shown in FIG. 74, flexural modulus increased as curing temperature increased, indicating the spunlaces became harder during curing. When temperature reached 110° C. for 30 minutes, or 135° C. for 15 minutes, average flexural modules became stable.

However, as shown in FIG. 75, slit tear strength increased as temperature increased, and reached maximum when cured at 135° C. for 30 minutes. After that, extra curing temperature led to a decrease in slit tear strength. Elite 22 binder cured (crosslink) above 130° C., thus the mechanical strength increased as a result. The mechanical results suggest that the crosslinking started around 110° C. When cured at 135° C. for more than 30 mixtures, slit tear strength decreased, which may be due to some damage to the mycelium material itself.

Mechanical Strength of Mycelium Material Cured at Different Temperatures
    Materials and Methods
    Samples C116, C133 and C134 were spunlaces generated using the methods described herein. Each spunlace contained 30% Tencel fiber (8 mm length) in biomass, was wetlaid and hydroentangled. A 10% of Elite 22 binder solution using the baseline (soak-roll-soak) method was used, then each spunlace was dried at 45° C. overnight. Sample C116 was then cured at 135° C. for 2 hours. After curing, sample C116 was dyed, fatliquor was added, and sunlace dried. Samples C133 and C134 were first dyed, and then dried. Sample C133 was then cured at 135° C. for 2 hours, before fatliquor was added and spunlace dried. Fatliquors were added to Sample C134 without curing at 135° C., and the spunlace was dried after fatliquors were added.
    Results

TABLE 38

Slit tear strength of mycelium material cured at different temperatures.

| Sample ID | Thickness (mm) | Slit tear (N) | 95% CI | Test numbers |
|---|---|---|---|---|
| C116 (135 C.) | 2.6 | 21.3 | ±2.02 | 6 |
| C133 (135 C.) | 2.14 | 26.19 | ±2.20 | 8 |
| C134 (70 C.) | 2.06 | 15.52 | ±1.95 | 8 |

Figure 76:
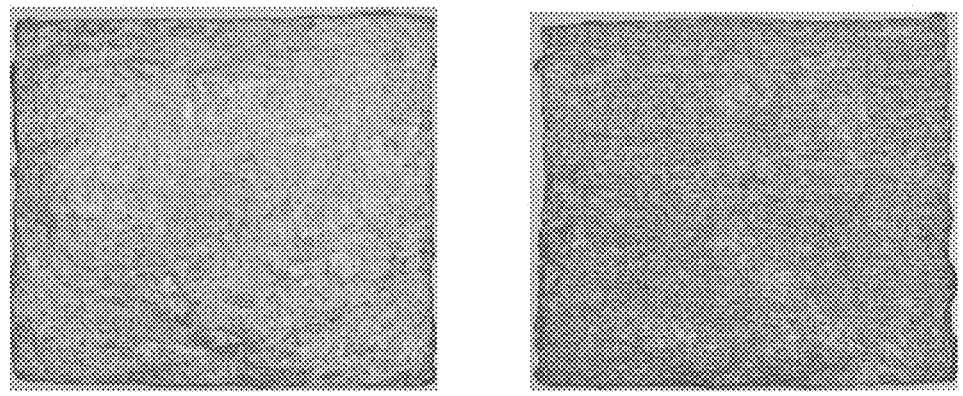
FIG. 76 shows the effects of curing and dyeing of a mycelium material sample.
Figure 77:
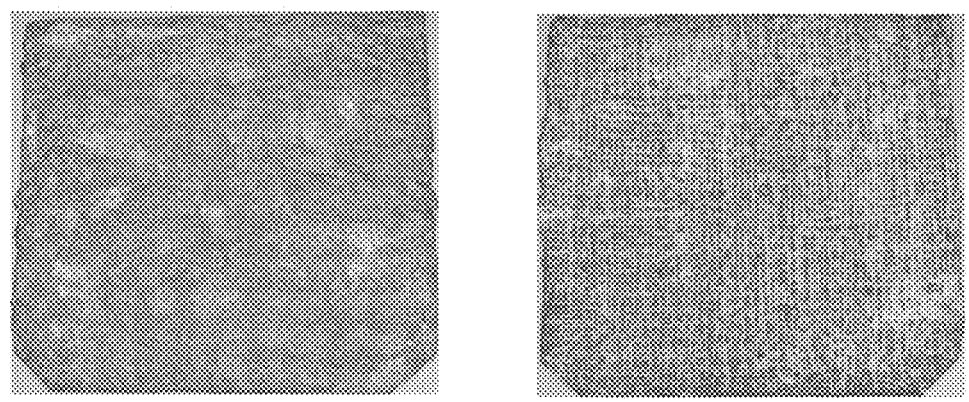
FIG. 77 shows the effects of curing and dyeing of a mycelium material sample.
Figure 78:
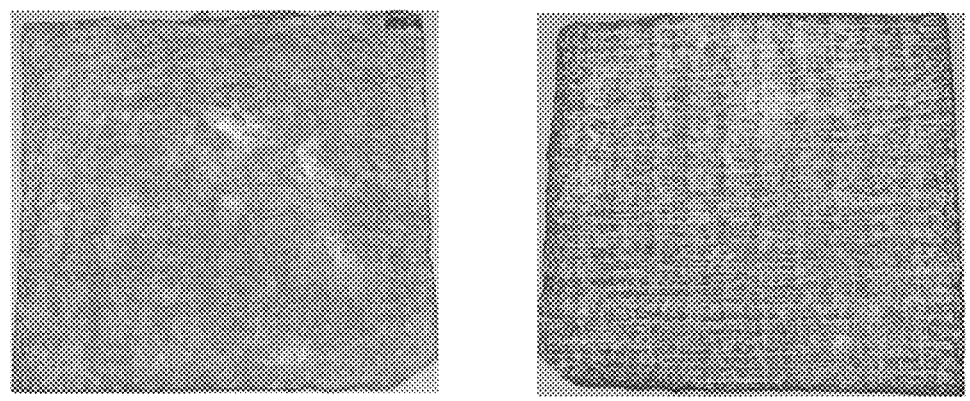
FIG. 78 shows the effects of dyeing without curing of a mycelium material sample.

Samples C116 (FIG. 76) and C133 (FIG. 77), which were cured at 135° C. showed significant higher slit tear strength than uncured sample C134 (FIG. 78). However, sample C116 experienced problems during dyeing, it seemed that the binder which had been cured at 135° C. could be dyed with reactive dye, leaving uneven dyeing patterns on the crust surface. Samples C133 and C134 did not have uneven dyeing problems. Sample C133 showed slightly more color-variation as compared to sample C134, but was uniformly dyed. It is suggested that a mycelium material having binder needed to be dyed first before fully cured at 135° C.

Figure 79:
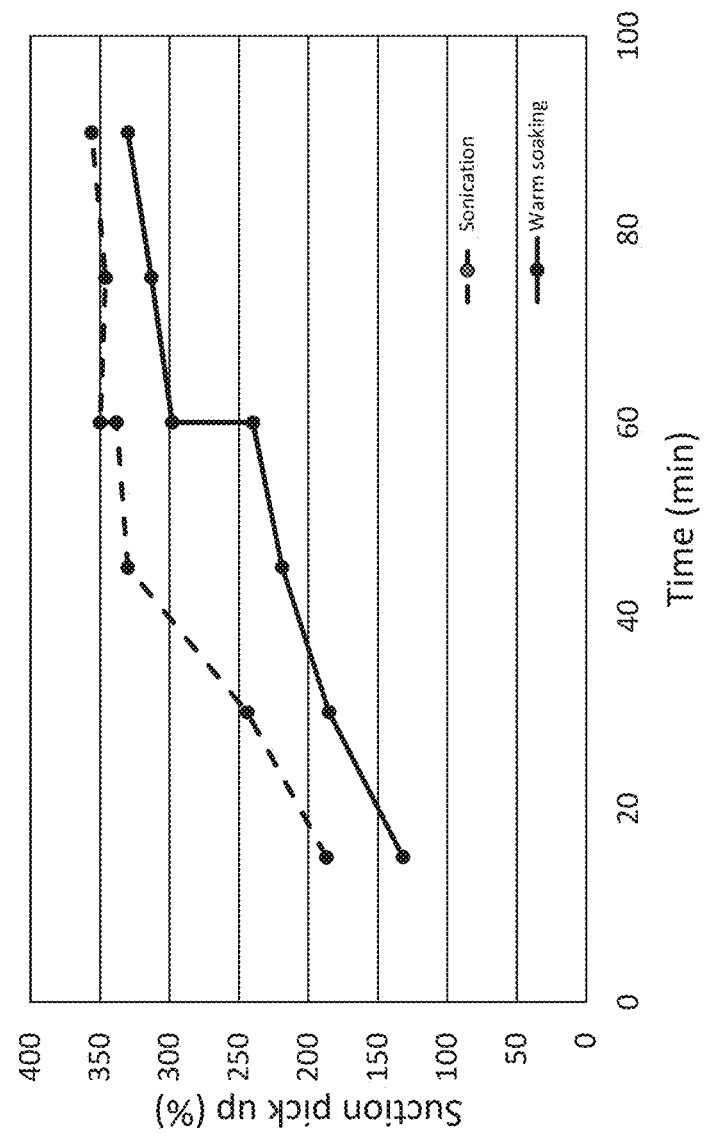
FIG. 79 shows binder solution pickup on mycelium webs over time using sonication and warm soaking methods.

Binder Application with Sonication and Warm Solution Soaking
    Different binder application methods were tested on mycelium webs that were wetlaid to identify a steady state binder loading.
    Materials and Methods
    For the warm solution soaking method, webs were subjected to a soak-roll-soak method using a 60° C. water bath, and then the webs were sonicated at 60° C. Specifically, each web was sealed in a Ziploc bag with a 10% Elite 22 binder solution, then the Ziploc bag was immersed in a 60° C. water bath heated by a sous vide cooker. The web, binder solution, and Ziploc bag were heated for 1 hour, and during that time, the wet weight of the web was measured every 15 minutes to monitor binder solution pickup. After warm soaking for one hour, the web was pressed or rolled using a hand roller, and air bubbles were pushed out of the web. The web was then soaked in warm binder solution in a Ziploc bag in a water bath for a few more minutes to reach a steady state.
    For the sonication method, a binder solution was directly put into an ultrasonic cleaner, and heated to 60° C. The web was then soaked in the 60° C. binder solution under ultrasonication. Wet weight of the web was measured every 15 minutes, and the web was rolled after 1 hour of soaking.
    Results
    FIG. 79 shows the binder solution pickup over time on webs using sonication and warm soaking methods.

Sonication methods reached to a steady state after 1.5 hours of processing, and rolling did not change the wet weight of the web, indicating there were almost no air bubbles in the web. Webs that underwent warm soaking increased wet weight after rolling, indicating that more air bubbles were squeezed out. However, after rolling and soaking for another 30 minutes, the two methods reached a similar binder loading.

TABLE 39

Binder pickup of mycelium webs using sonication and warm soaking methods.

| Sample ID | Original weight (g) | Binder concentration (%) | Original + binder solution weight (g) | Binder solution pickup (%) | Binder dry pickup (%) | Note |
| --- | --- | --- | --- | --- | --- | --- |
| P1012-P20W04-04-02 | 6.62 | 10 | 30.21 | 356 | 30.7 | Sonication |
| P1013-P20W04-04-02 | 11.73 | 10 | 50.46 | 330 | 28.0 | 60° C. sous vide soak |

Example 17: Salt Concentration and Dye Penetration

Reactive dye protocols provided by the manufacturers typically called for the addition of high concentrations of sodium sulfate (30-100 g/L: higher concentrations for darker shades) during the exhaustion phase of dyeing. This salt addition greatly hindered the penetration of the dye into mycelia wetlays or spunlace. Additionally, sodium carbonate was added to the dyebath in order to raise the pH and promote fixation. Manufacturers often recommended concentrations in the range of 8-20 g/L. This sodium carbonate addition may also affect the dye penetration. Concentrations around 1 g/L raised the pH to around 10 allowing for adequate fixation while not preventing dye penetration.

Sodium Sulfate Concentration

Figure 80:
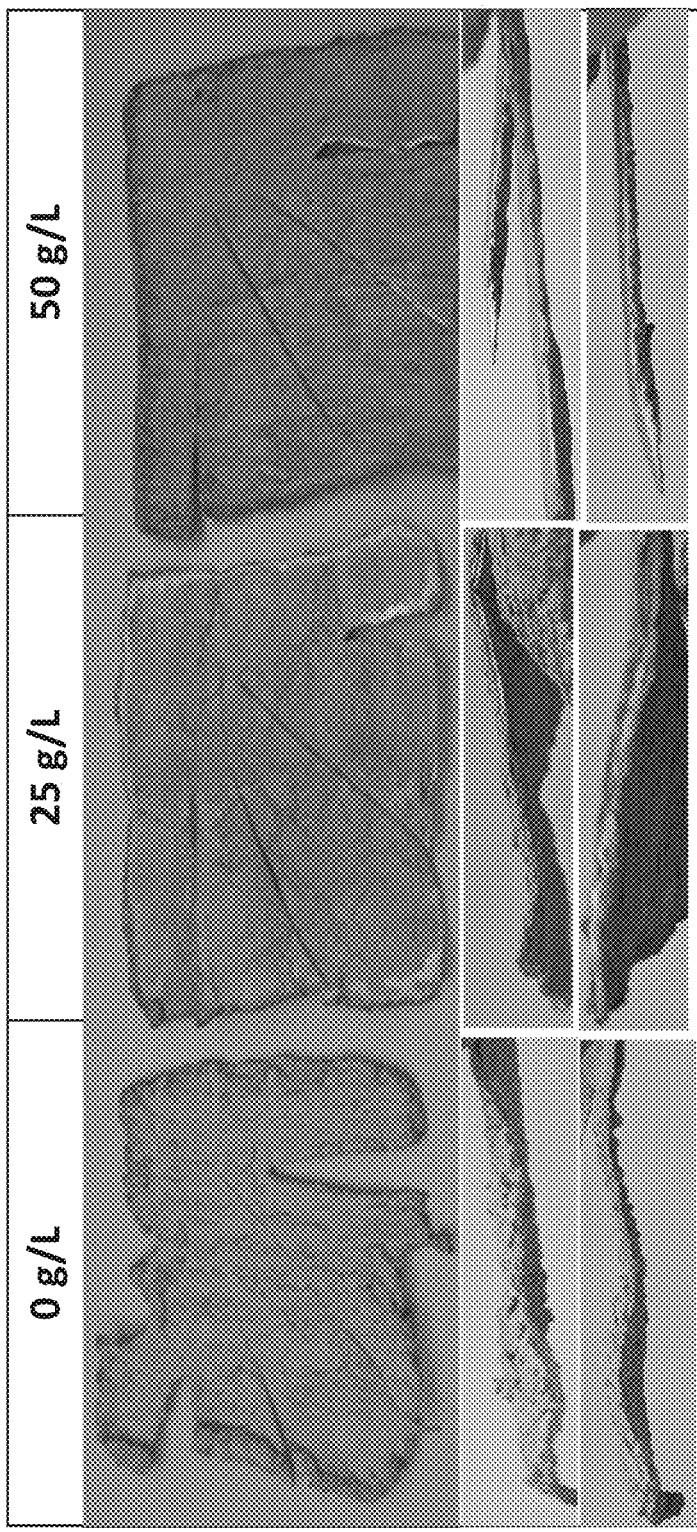
FIG. 80 shows images of samples dyed using 0 g/L, 25 g/L, and 50 g/L of sodium sulfate and 2 g/L Procion MX medium blue with no fixation or rinsing. The bottom two rows show the penetration of the dye into the interior of the samples.

Three spunlace samples were dyed at 60° C. for 2 h with 2 g/L Procion MX medium blue dye and a varying amount of sodium sulfate (0, 25, 50 g/L). These samples did not go through fixation or rinsing in order to focus the amount of dye that penetrated into the sample. As shown in FIG. 80, increasing salt concentration led to a darker surface color, but almost completely prevented any dye penetration. Spunlace samples with 0 g/L of sodium sulfate yielded good penetration, but samples with 50 g/L of sodium sulfate yielded bad penetration. Higher concentrations of sodium sulfate resulted in poorly dyed spunlaces.

Sodium Carbonate Concentration

Figure 82:
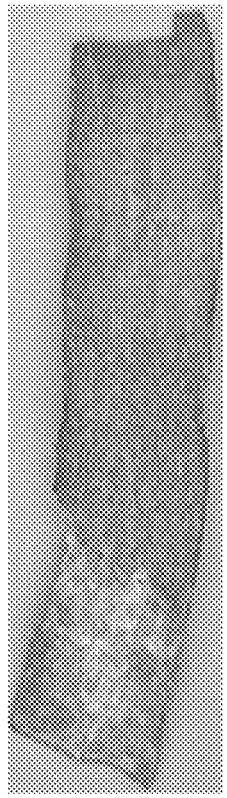
FIG. 82 shows images of dye solutions leached out of dyed mycelia samples after progressive soaking in water for over one hour and fixed with 1 g/L sodium carbonate.
Figure 81:
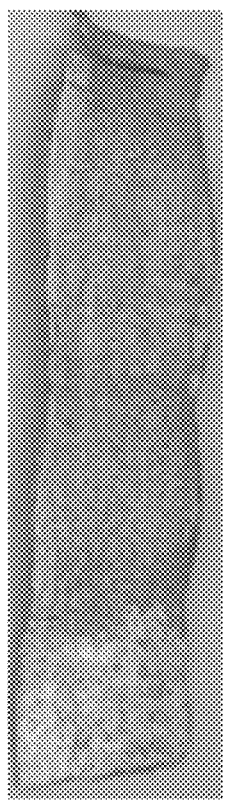
FIG. 81 shows images of dye solutions leached out of dyed mycelia samples after progressive soaking in water for over one hour and fixed with 0.5 g/L sodium carbonate.

Because the concentration of sodium sulfate decreased the penetration of dye, it was investigated whether lowering the sodium carbonate concentration during fixation affected fixation and penetration. A 1 g/L sodium carbonate solution was found to have a pH of 10 which should be in the proper range for fixing of dye to the fibers. Two spunlace samples were then dyed with 2 g/L of Drimaren® Navy HF dye at 60° C. for 90 min and then fixed with 0.5 and 1 g/L sodium carbonate at 60° C. for 60 min. As shown in FIG. 81 (0.5 g/L sodium carbonate) and FIG. 82 (1 g/L sodium carbonate), these samples had good penetration and the dye was still fixed to the substrate.

Effects of Dyeing Temperature and Times

Figure 83:
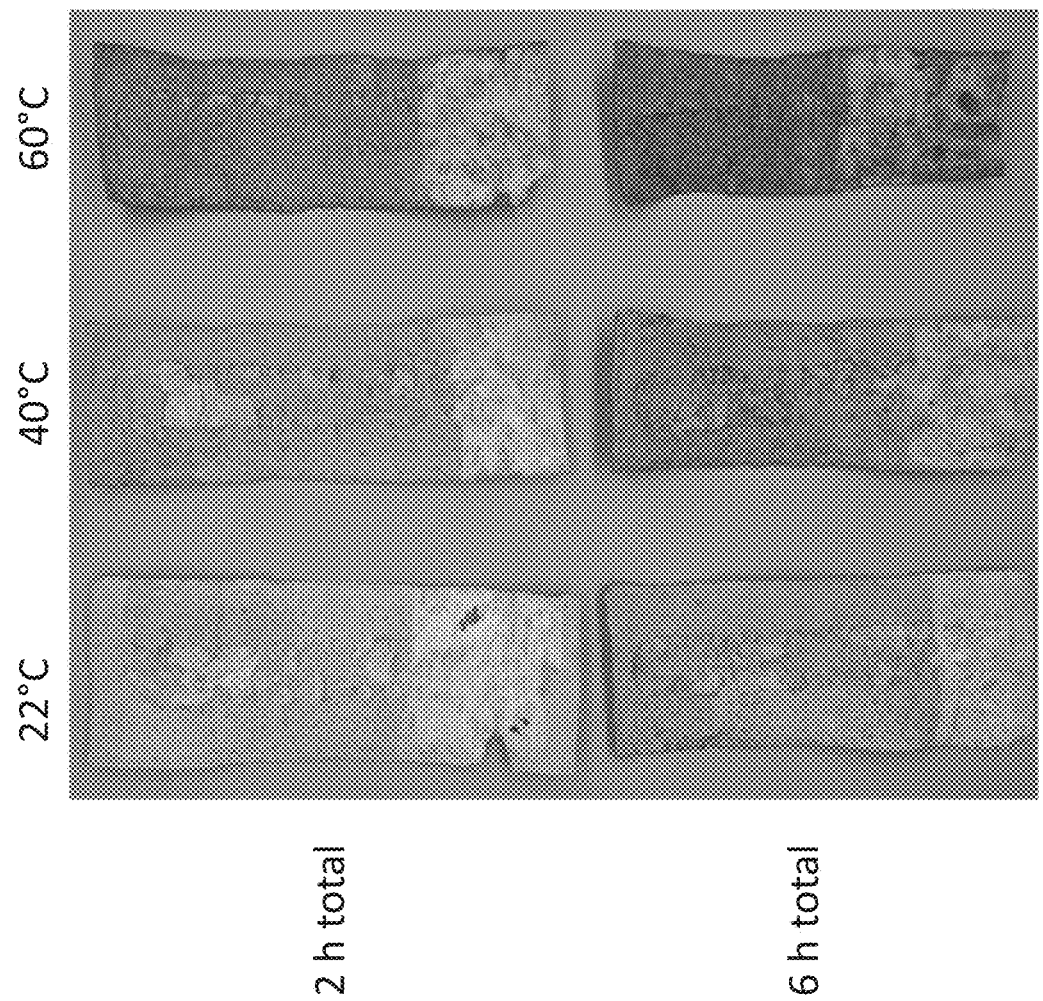
FIG. 83 shows images of spunlace samples dyed at 22° C., 40° C., and 60° C. for 2 and 6 h of total dyeing time. The bottom section of each sample was shaved off to show dye penetration.

Six spunlace samples were dyed with 2 g/L Drimaren® Navy HF dye at 22, 40, or 60° C. for 1 hour or 3 hours and then fixed by adding 1 g/L sodium carbonate. Fixing occurred at the same temperature for the same time as the dye exhaustion. As shown in FIG. 83, it can be seen qualitatively that longer times and higher temperatures led to darker colors on the surface and longer times led to better dye penetration.

Figure 84:
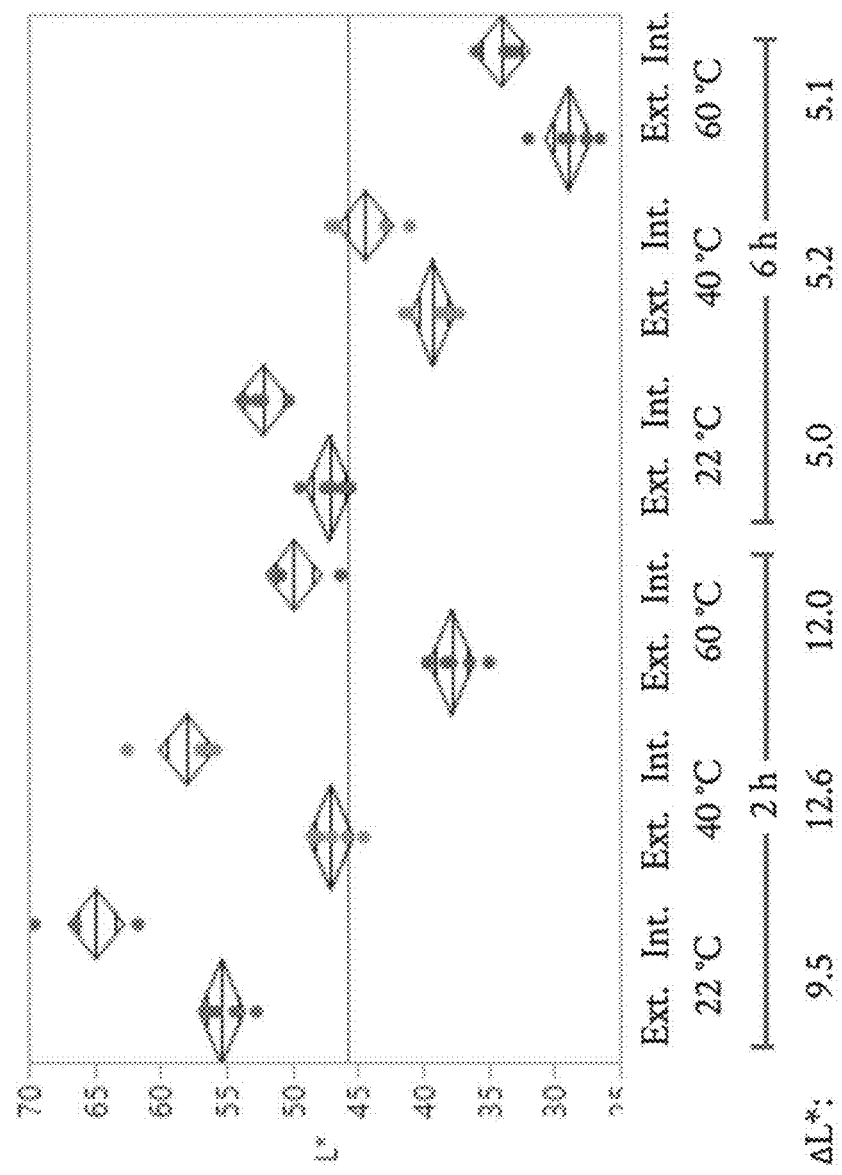
FIG. 84 shows quantitative measurements of spunlace samples using a Konica Minolta CM-5 Spectrophotometer.

Additionally, quantitative measurements using a Konica Minolta CM-5. As shown in FIG. 84, spectrophotometer in reflectance mode showed the same trends. In these measurements a lower L* value corresponds to darker colors.

Effects of Binder Cure Temperature and Time

A 10 wt % Elite 22 binder solution was applied to spunlace samples and then cured at different temperatures (70, 90, 110, 130° C.) and times (15-45 min) before dyeing. The samples were dyed at 60° C. for 2 h with 2 g/L Drimaren® Navy HF dye. As shown in FIG. 85, curing at 90° C. and above led to poor dyeing of the spunlace. This suggests that any dyeing procedure should be carried out before the final curing operation.

Additional Aspects of the Present Disclosure Include:

According to a first aspect of the present disclosure, a composite mycelium material, includes: a cultivated mycelium material including one or more masses of branching hyphae, wherein the one or more masses of branching hyphae is disrupted; and a bonding agent.

According to a second aspect of the present disclosure, the composite mycelium material of aspect 1, wherein the cultivated mycelium material has been generated on a solid substrate.

According to a third aspect of the present disclosure, the composite mycelium material of aspects 1 or 2, wherein the cultivated mycelium material includes one or more masses of disrupted branching hyphae.

According to a fourth aspect of the present disclosure, the composite mycelium material of any one of aspects 1 to 3, wherein the one or more masses of disrupted branching hyphae has a length of 0.1 mm to 5 mm.

According to a fifth aspect of the present disclosure, the composite mycelium material of aspect 4, wherein the one or more masses of disrupted branching hyphae has a length of 2 mm.

According to a sixth aspect of the present disclosure, composite mycelium material of any one of aspects 1 to 5, wherein the composite mycelium material further includes a supporting material.

According to a seventh aspect of the present disclosure, the composite mycelium material of aspect 6, wherein the supporting material has a pore size of ¹⁄₁₆th of an inch.

According to an eighth aspect of the present disclosure, the composite mycelium material of aspect 6, wherein the supporting material includes a reinforcing material.

According to a ninth aspect of the present disclosure, the composite mycelium material of aspect 8, wherein the reinforcing material is entangled within the composite mycelium material.

According to a tenth aspect of the present disclosure, the composite mycelium material of aspect 6, wherein the supporting material includes a base material.

According to an eleventh aspect of the present disclosure, the composite mycelium material of aspect 10, wherein the base material is positioned on one or more surfaces of the composite mycelium material.

According to a twelfth aspect of the present disclosure, the composite mycelium material of any one of aspects 1 to 11, wherein the supporting material is selected from the group consisting of a mesh, a cheesecloth, a fabric, a knit fiber, a woven fiber, a non-woven fiber, a knit textile, a woven textile, and a non-woven textile.

According to a thirteenth aspect of the present disclosure, the composite mycelium material of any one of aspects 1 to 12, wherein the one or more masses of branching hyphae is disrupted by a mechanical action.

According to a fourteenth aspect of the present disclosure, the composite mycelium material of aspect 13, wherein the mechanical action includes blending the one or more masses of branching hyphae.

According to a fifteenth aspect of the present disclosure, the composite mycelium material of aspect 13, wherein the mechanical action includes applying a physical force to the one or more masses of branching hyphae such that at least some of the masses of branching hyphae are aligned in a parallel formation.

According to a sixteenth aspect of the present disclosure, the composite mycelium material of aspect 15, wherein the physical force is a pulling force.

According to a seventeenth aspect of the present disclosure, the composite mycelium material of aspect 15, wherein the mechanical action includes applying the physical force in one or more directions such that the at least some of the masses of branching hyphae are aligned in parallel in one or more directions, wherein the physical force is applied repeatedly.

According to an eighteenth aspect of the present disclosure, the composite mycelium material of any one of aspects 1 to 17, wherein the one or more masses of branching hyphae is disrupted by chemical treatment.

According to a nineteenth aspect of the present disclosure, the composite mycelium material of aspect 18, wherein the chemical treatment includes contacting the one or more masses of branching hyphae with a base or other chemical agent in an amount sufficient to cause a disruption.

According to a twentieth aspect of the present disclosure, the composite mycelium material of aspect 19, wherein the base includes alkaline peroxide.

According to a twenty-first aspect of the present disclosure, the composite mycelium material of any one of aspects 1 to 20, wherein the bonding agent includes one or more reactive groups.

According to a twenty-second aspect of the present disclosure, the composite mycelium material of aspect 21, wherein the one or more reactive groups react with active hydrogen containing groups.

According to a twenty-third aspect of the present disclosure, the composite mycelium material of aspect 22, wherein the active hydrogen containing groups comprise amine, hydroxyl, and carboxyl groups.

According to a twenty-fourth aspect of the present disclosure, the composite mycelium material of any one of aspects 1 to 23, wherein the bonding agent includes an adhesive, a resin, a crosslinking agent, and/or a matrix.

According to a twenty-fifth aspect of the present disclosure, the composite mycelium material of any one of aspects 1 to 23, wherein the bonding agent is selected from the group consisting of transglutaminase, polyamide-epichlorohydrin resin (PAE), citric acid, genipin, alginate, a natural adhesive, and a synthetic adhesive.

According to a twenty-sixth aspect of the present disclosure, the composite mycelium material of any one of aspects 1 to 23, wherein the bonding agent is PAE.

According to a twenty-seventh aspect of the present disclosure, the composite mycelium material of aspect 26, wherein the PAE includes cationic azetidinium groups that react with active hydrogen containing groups including amine, hydroxyl, and carboxyl groups, in the one or more branches of hyphae.

According to a twenty-eighth aspect of the present disclosure, the composite mycelium material of aspect 25, wherein the natural adhesive includes a natural latex-based adhesive.

According to a twenty-ninth aspect of the present disclosure, the composite mycelium material of aspect 28, wherein the natural latex-based adhesive is leather glue or weld.

According to a thirtieth aspect of the present disclosure, the composite mycelium material of any one of aspects 1 to 29, wherein the composite mycelium material includes one or more proteins that are from a species other than a fungal species from which the cultivated mycelium material is generated.

According to a thirty-first aspect of the present disclosure, the composite mycelium material of aspect 30, wherein the one or more proteins is from a plant source.

According to a thirty-second aspect of the present disclosure, the composite mycelium material of aspect 31, wherein the plant source is a pea plant.

According to a thirty-third aspect of the present disclosure, the composite mycelium material of aspect 31, wherein the plant source is a soybean plant.

According to a thirty-fourth aspect of the present disclosure, the composite mycelium material of any one of aspects 1 to 33, wherein the composite mycelium material further includes a dye.

According to a thirty-fifth aspect of the present disclosure, the composite mycelium material of aspect 34, wherein the dye is selected from the group including an acid dye, a direct dye, a synthetic dye, a natural dye, and a reactive dye.

According to a thirty-sixth aspect of the present disclosure, the composite mycelium material of aspect 34, wherein the composite mycelium material is colored with the dye and the color of the composite mycelium material is substantially uniform on one or more surfaces of the composite mycelium material.

According to a thirty-seventh aspect of the present disclosure, the composite mycelium material of aspect 34, wherein the dye is present throughout the interior of the composite mycelium material.

According to a thirty-eighth aspect of the present disclosure, the composite mycelium material of any one of aspects 1 to 37, wherein the composite mycelium material further includes a plasticizer.

According to a thirty-ninth aspect of the present disclosure, the composite mycelium material of aspect 38, wherein the plasticizer is selected from the group including oil, glycerin, fatliquor, water, glycol, triethyl citrate, water, acetylated monoglycerides, and epoxidized soybean oil.

According to a fortieth aspect of the present disclosure, the composite mycelium material of aspect 38, wherein the composite mycelium material is flexible.

According to a forty-first aspect of the present disclosure, the composite mycelium material of any one of aspects 1 to 40, wherein an external element is applied to the cultivated mycelium material.

According to a forty-second aspect of the present disclosure, the composite mycelium material of aspect 41, wherein the external element is applied via heating and/or pressing.

According to a forty-third aspect of the present disclosure, the composite mycelium material of any one of aspects 1 to 42, wherein the composite mycelium material further includes a tannin.

According to a forty-fourth aspect of the present disclosure, the composite mycelium material of any one of aspects 1 to 43, wherein the composite mycelium material further includes a finishing agent.

According to a forty-fifth aspect of the present disclosure, the composite mycelium material of aspect 44, wherein the finishing agent is selected from the group consisting of urethane, wax, nitrocellulose, and a plasticizer.

According to a forty-sixth aspect of the present disclosure, the composite mycelium material of any one of aspects 1 to 45, wherein the composite mycelium material includes a mechanical property.

According to a forty-seventh aspect of the present disclosure, the composite mycelium material of any one of aspects 1 to 46, wherein the mechanical property includes a wet tensile strength, an initial modulus, an elongation percentage at the break, a thickness, and/or a slit tear strength.

According to a forty-eighth aspect of the present disclosure, the composite mycelium material of any one of aspects 1-46, wherein the composite mycelium material has a wet tensile strength of 0.05 MPa to 10 MPa.

According to a forty-ninth aspect of the present disclosure, the composite mycelium material of any one of aspects 1 to 46, wherein the composite mycelium material has a wet tensile strength of 5 MPa to 20 MPa.

According to a fiftieth aspect of the present disclosure, the composite mycelium material of any one of aspects 1 to 46, wherein the composite mycelium material has a wet tensile strength of 7 MPa.

According to a fifty-first aspect of the present disclosure, the composite mycelium material of any one of aspects 1 to 46, wherein the composite mycelium material has an initial modulus of 1 MPa to 100 MPa.

According to a fifty-second aspect of the present disclosure, the composite mycelium material of any one of aspects 1 to 46, wherein the composite mycelium material has an elongation percentage at the break of 1% to 25%.

According to a fifty-third aspect of the present disclosure, the composite mycelium material of any one of aspects 1 to 46, wherein the composite mycelium material has a thickness of 0.5 mm to 3.5 mm.

According to a fifty-fourth aspect of the present disclosure, the composite mycelium material of any one of aspects 1 to 46, wherein the composite mycelium material has a thickness of 2 mm.

According to a fifty-fifth aspect of the present disclosure, the composite mycelium material of any one of aspects 1 to 46, wherein the composite mycelium material has a slit tear strength of 5 N to 100 N.

According to a fifty-sixth aspect of the present disclosure, the composite mycelium material of any one of aspects 1 to 46, wherein the composite mycelium material has a slit tear strength of 50 N.

According to a fifty-seventh aspect of the present disclosure, the composite mycelium material of any one of aspects 1 to 56, wherein the composite mycelium material is produced using traditional paper milling equipment.

According to a fifty-eighth aspect of the present disclosure, a method of producing a composite mycelium material, the method includes: generating a cultivated mycelium material including one or more masses of branching hyphae; disrupting the cultivated mycelium material including the one or more masses of branching hyphae; and adding a bonding agent to the cultivated mycelium material; thus producing the composite mycelium material.

According to a fifty-ninth aspect of the present disclosure, the method of aspect 58, wherein the generating includes generating cultivated mycelium material on a solid substrate.

According to a sixtieth aspect of the present disclosure, the method of aspect 58 or 59, wherein the cultivated mycelium material includes one or more masses of disrupted branching hyphae.

According to a sixty-first aspect of the present disclosure, the method of any one of aspects 58 to 60, wherein the one or more masses of disrupted branching hyphae has a length of 0.1 mm to 5 mm.

According to a sixty-second aspect of the present disclosure, the method of aspect 61, wherein the one or more masses of disrupted branching hyphae has a length of 2 mm.

According to a sixty-third aspect of the present disclosure, the method of any one of aspects 58 to 62, further including incorporating a supporting material into the composite mycelium material.

According to a sixty-fourth aspect of the present disclosure, the method of aspect 63, wherein the supporting material has a pore size of ¹⁄₁₆th of an inch.

According to a sixty-fifth aspect of the present disclosure, the method of aspect 63, wherein the supporting material includes a reinforcing material.

According to a sixty-sixth aspect of the present disclosure, the method of aspect 65, wherein the reinforcing material is entangled within the composite mycelium material.

According to a sixty-seventh aspect of the present disclosure, the method of aspect 63, wherein the supporting material includes a base material.

According to a sixty-eighth aspect of the present disclosure, the method of aspect 67, wherein the base material is positioned on one or more surfaces of the composite mycelium material.

According to a sixty-ninth aspect of the present disclosure, the method of any one of aspects 58 to 68, wherein the supporting material is selected from the group consisting of a mesh, a cheesecloth, a fabric, a knit fiber, a woven fiber, a non-woven fiber, a knit textile, a woven textile, and a non-woven textile.

According to a seventieth aspect of the present disclosure, the method of any one of aspects 58 to 69, wherein the disrupting includes disrupting the one or more masses of branching hyphae by a mechanical action.

According to a seventy-first aspect of the present disclosure, the method of aspect 70, wherein the mechanical action includes blending the one or more masses of branching hyphae.

According to a seventy-second aspect of the present disclosure, the method of aspect 70, wherein the mechanical action includes applying a physical force to the one or more masses of branching hyphae such that at least some of the masses of branching hyphae are aligned in a parallel formation.

According to a seventy-third aspect of the present disclosure, the method of aspect 72, wherein the physical force is a pulling force.

According to a seventy-fourth aspect of the present disclosure, the method of aspect 72, wherein the mechanical action includes applying the physical force in one or more directions such that the at least some of the masses of branching hyphae are aligned in parallel in one or more directions, wherein the physical force is applied repeatedly.

According to a seventy-fifth aspect of the present disclosure, the method of any one of aspects 58 to 74, wherein the one or more masses of branching hyphae is disrupted by chemical treatment.

According to a seventy-sixth aspect of the present disclosure, the method of aspect 75, wherein the chemical treatment includes contacting the one or more masses of branching hyphae with a base or other chemical agent in an amount sufficient to cause a disruption.

According to a seventy-seventh aspect of the present disclosure, the method of aspect 76, wherein the base includes alkaline peroxide.

According to a seventy-eighth aspect of the present disclosure, the method any one of aspects 58 to 77, wherein the bonding agent includes one or more reactive groups.

According to a seventy-ninth aspect of the present disclosure, the method of aspect 78, wherein the one or more reactive groups react with active hydrogen containing groups.

According to an eightieth aspect of the present disclosure, the method of aspect 79, wherein the active hydrogen containing groups comprise amine, hydroxyl, and carboxyl groups.

According to an eighty-first aspect of the present disclosure, the method of any one of aspects 58 to 80, wherein the bonding agent includes an adhesive, a resin, a crosslinking agent, and/or a matrix.

According to an eighty-second aspect of the present disclosure, the method of any one of aspects 58 to 80, wherein the bonding agent is selected from the group consisting of transglutaminase, polyamide-epichlorohydrin resin (PAE), citric acid, genipin, alginate, a natural adhesive, and a synthetic adhesive.

According to an eighty-third aspect of the present disclosure, the method of any one of aspects 58 to 80, wherein the bonding agent is PAE.

According to an eighty-fourth aspect of the present disclosure, the method of aspect 83, wherein the PAE includes cationic azetidinium groups that react with active hydrogen containing groups including amine, hydroxyl, and carboxyl groups, in the one or more branches of hyphae.

According to an eighty-fifth aspect of the present disclosure, the method of aspect 82, wherein the natural adhesive includes a natural latex-based adhesive.

According to an eighty-sixth aspect of the present disclosure, the method of aspect 85, wherein the natural latex-based adhesive is leather glue or weld.

According to an eighty-seventh aspect of the present disclosure, the method of any one of aspects 58 to 86, further including adding one or more proteins that are from a species other than a fungal species from which the cultivated mycelium material is generated.

According to an eighty-eighth aspect of the present disclosure, the method of aspect 87, wherein the one or more proteins is from a plant source.

According to an eighty-ninth aspect of the present disclosure, the method of aspect 88, wherein the plant source is a pea plant.

According to a ninetieth aspect of the present disclosure, the method of aspect 88, wherein the plant source is a soybean plant.

According to a ninety-first aspect of the present disclosure, the method of any one of aspects 58 to 90, further including adding a dye to the cultivated mycelium material or the composite mycelium material.

According to a ninety-second aspect of the present disclosure, the method of aspect 91, wherein the dye is selected from the group including an acid dye, a direct dye, a synthetic dye, a natural dye, and a reactive dye.

According to a ninety-third aspect of the present disclosure, the method of aspect 91, wherein the composite mycelium material is colored with the dye and the color of the composite mycelium material is substantially uniform on one or more surfaces of the composite mycelium material.

According to a ninety-fourth aspect of the present disclosure, the method of aspect 91, wherein the dye is present throughout the interior of the composite mycelium material.

According to a ninety-fifth aspect of the present disclosure, the method of any one of aspects 58 to 94, further including adding a plasticizer to the cultivated mycelium material or the composite mycelium material.

According to a ninety-sixth aspect of the present disclosure, the method of aspect 95, wherein the plasticizer is selected from the group including oil, glycerin, fatliquor, water, glycol, triethyl citrate, water, acetylated monoglycerides, and epoxidized soybean oil.

According to a ninety-seventh aspect of the present disclosure, the method of aspect 95, wherein the composite mycelium material is flexible.

According to a ninety-eighth aspect of the present disclosure, the method of any one of aspects 58 to 97, further including applying an external element to the cultivated mycelium material.

According to a ninety-ninth aspect of the present disclosure, the method of aspect 98, wherein the external element is applied via heating and/or pressing.

According to a one hundredth aspect of the present disclosure, the method of any one of aspects 58-99, further including adding a tannin to the cultivated mycelium material or the composite mycelium material.

According to a one hundred first aspect of the present disclosure, the method of any one of aspects 58 to 100, further including adding a finishing agent to the composite mycelium material.

According to a one hundred second aspect of the present disclosure, the method of aspect 101, wherein the finishing agent is selected from the group consisting of urethane, wax, nitrocellulose, and a plasticizer.

According to a one hundred third aspect of the present disclosure, the method of any one of aspects 58 to 102, further including determining a mechanical property of the composite mycelium material.

According to a one hundred fourth aspect of the present disclosure, the method of any one of aspects 58 to 103, wherein the mechanical property includes a wet tensile strength, an initial modulus, an elongation percentage at the break, a thickness, and/or a slit tear strength.

According to a one hundred fifth aspect of the present disclosure, the method of any one of aspects 58 to 103, wherein the composite mycelium material has a wet tensile strength of 0.05 MPa to 10 MPa.

According to a one hundred sixth aspect of the present disclosure, the method of any one of aspects 58 to 103, wherein the composite mycelium material has a wet tensile strength of 5 MPa to 20 MPa.

According to a one hundred seventh aspect of the present disclosure, the method of any one of aspects 58 to 103, wherein the composite mycelium material has a wet tensile strength of 7 MPa.

According to a one hundred eighth aspect of the present disclosure, the method of any one of aspects 58 to 103, wherein the composite mycelium material has an initial modulus of 1 MPa to 100 MPa.

According to a one hundred ninth aspect of the present disclosure, the method of any one of aspects 58 to 103, wherein the composite mycelium material has an elongation percentage at the break of 1% to 25%.

According to a one hundred tenth aspect of the present disclosure, the method of any one of aspects 58 to 103, wherein the composite mycelium material has a thickness of 0.5 mm to 3.5 mm.

According to a one hundred eleventh aspect of the present disclosure, the method of any one of aspects 58 to 103, wherein the composite mycelium material has a thickness of 2 mm.

According to a one hundred twelfth aspect of the present disclosure, the method of any one of aspects 58 to 103, wherein the composite mycelium material has a slit tear strength of 5 N to 100 N.

According to a one hundred thirteenth aspect of the present disclosure, the method of any one of aspects 58 to 103, wherein the composite mycelium material has a slit tear strength of 50 N.

According to a one hundred fourteenth aspect of the present disclosure, the method of any one of aspects 58 to 113, wherein the composite mycelium material is produced using traditional paper milling equipment.

It will be understood by one having ordinary skill in the art that construction of the described disclosure and other components is not limited to any specific material. Other exemplary embodiments of the disclosure disclosed herein may be formed from a wide variety of materials, unless described otherwise herein.

It is also important to note that the construction and arrangement of the elements of the disclosure as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. Accordingly, all such modifications are intended to be included within the scope of the present disclosure. Other substitutions, modifications, changes, and omissions may be made in the design, operating conditions, and arrangement of the desired and other exemplary embodiments without departing from the spirit of the present disclosure.

It will be understood that any described processes or steps within processes described herein may be combined with other disclosed processes or steps to form structures within the scope of the present disclosure. The exemplary structures and processes disclosed herein are for illustrative purposes and are not to be construed as limiting.

The invention claimed is:

1. A composite mycelium material, comprising:
    a. a cultivated mycelium material comprising one or more masses of branching hyphae, wherein the one or more masses of branching hyphae is disrupted; and
    b. a bonding agent; and
    c. a dye.

2. The composite mycelium material of claim 1, wherein the bonding agent is selected from the group consisting of a vinyl acetate-ethylene (VAE) copolymer, a vinyl acetate-acrylic copolymer, a polyamide-epichlorohydrin resin (PAE), a copolymer, transglutaminase, citric acid, genipin, alginate, gum arabic, latex, a natural adhesive, and a synthetic adhesive.

3. The composite mycelium material of claim 2, wherein the bonding agent is a copolymer with a property selected from the group consisting of: a particle size of less than or equal to 1 μm, a sub-zero glass transition temperature, and self-crosslinking function.

4. The composite mycelium material of claim 2, wherein the bonding agent is a vinyl acetate-ethylene (VAE) copolymer.

5. The composite mycelium material of claim 2, wherein the bonding agent is a vinyl acetate-acrylic copolymer.

6. The composite mycelium material of claim 1, wherein the composite mycelium material further comprises a supporting material.

7. The composite mycelium material of claim 6, wherein the supporting material comprises a reinforcing material.

8. The composite mycelium material of claim 6, wherein the supporting material is selected from the group consisting of a mesh, a cheesecloth, a fabric, a knit textile, a woven textile, and a non-woven textile.

9. The composite mycelium material of claim 1, wherein the one or more masses of branching hyphae is disrupted by a mechanical action.

10. The composite mycelium material of claim 9, wherein the mechanical action comprises blending the one or more masses of branching hyphae.

11. The composite mycelium material of claim 9, wherein the mechanical action comprises breaking the one or more masses of branching hyphae.

12. The composite mycelium material of claim 1, wherein the dye is selected from the group consisting of an acid dye, a direct dye, a synthetic dye, a natural dye, and a reactive dye.

13. The composite mycelium material of claim 12, wherein the dye is a reactive dye.

14. The composite mycelium material of claim 1, wherein the composite mycelium material is colored with the dye and the color of the composite mycelium material is substantially uniform on one or more surfaces of the composite mycelium material.

15. The composite mycelium material of claim 1, wherein the dye is present throughout the interior of the composite mycelium material.

16. The composite mycelium material of claim 1, wherein the composite mycelium material further comprises a plasticizer.

17. The composite mycelium material of claim 16, wherein the plasticizer is selected from the group consisting of oil, glycerin, fatliquor, sorbitol, diethyloxyester dimethyl ammonium chloride, Tween 20, Tween 80, m-erythritol, water, glycol, triethyl citrate, water, acetylated monoglycerides, and epoxidized soybean oil.

18. The composite mycelium material of claim 17, wherein the plasticizer is a fatliquor.

19. The composite mycelium material of claim 1, wherein the composite mycelium material further comprises a finishing agent.

20. The composite mycelium material of claim 19, wherein the finishing agent is selected from the group consisting of urethane, wax, nitrocellulose, and a plasticizer.

21. The composite mycelium material of claim 1, wherein the composite mycelium material comprises a mechanical property.

22. A method of producing a composite mycelium material, the method comprising:
   a. generating a cultivated mycelium material comprising one or more masses of branching hyphae;
   b. disrupting the cultivated mycelium material comprising the one or more masses of branching hyphae; and
   c. adding a bonding agent to the cultivated mycelium material; thus producing the composite mycelium material.

23. A method, comprising:
   a. generating a cultivated mycelium material;
   b. pressing the cultivated mycelium material; and
   c. contacting the pressed cultivated mycelium material with a solution comprising a bonding agent.

* * * * *